(12) United States Patent
Finlay

(10) Patent No.: US 10,611,838 B2
(45) Date of Patent: Apr. 7, 2020

(54) C-KIT ANTIBODIES

(71) Applicant: ULTRAHUMAN FIVE LIMITED, Sandwich (GB)

(72) Inventor: William James Jonathan Finlay, Sandwich (GB)

(73) Assignee: ULTRAHUMAN FIVE LIMITED, Sandwich (GB)

( * ) Notice: Subject to any disclaimer, the term of this patent is extended or adjusted under 35 U.S.C. 154(b) by 0 days.

(21) Appl. No.: 16/521,793

(22) Filed: Jul. 25, 2019

(65) Prior Publication Data

US 2020/0010548 A1  Jan. 9, 2020

Related U.S. Application Data

(63) Continuation of application No. PCT/EP2019/053331, filed on Feb. 11, 2019.

(30) Foreign Application Priority Data

Feb. 9, 2018 (GB) .................................. 1802201.2
Apr. 20, 2018 (GB) .................................. 1806468.3

(51) Int. Cl.

| | | |
|---|---|---|
| *C07K 16/28* | (2006.01) |
| *A61K 39/395* | (2006.01) |
| *C07K 19/00* | (2006.01) |
| *C07H 21/04* | (2006.01) |
| *C12N 15/09* | (2006.01) |
| *C12N 15/63* | (2006.01) |
| *A61K 47/51* | (2017.01) |
| *C07K 14/715* | (2006.01) |
| *A61K 45/06* | (2006.01) |

(52) U.S. Cl.
CPC ........ *C07K 16/2803* (2013.01); *A61K 39/395* (2013.01); *A61K 47/51* (2017.08); *C07H 21/04* (2013.01); *C07K 16/2866* (2013.01); *C07K 19/00* (2013.01); *C12N 15/09* (2013.01); *C12N 15/63* (2013.01); *A61K 45/06* (2013.01); *C07K 14/715* (2013.01); *C07K 2317/21* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

2014/0271688 A1  9/2014 Abrams et al.

FOREIGN PATENT DOCUMENTS

| WO | WO 2006/096653 A2 | 9/2006 |
| WO | WO 2008/009545 A1 | 1/2008 |
| WO | WO 2012/092374 A2 | 7/2012 |
| WO | WO 2012/103165 A2 | 8/2012 |
| WO | WO 2014/018625 A1 | 1/2014 |
| WO | WO 2015/050959 A1 | 4/2015 |
| WO | WO 2015/067667 A1 | 5/2015 |
| WO | WO 2015/166484 A1 | 11/2015 |
| WO | WO 2016/020791 A1 | 2/2016 |

OTHER PUBLICATIONS

International Search Report and Written Opinion dated May 21, 2019 for International Application No. PCT/EP2019/053331, 10 pages.
UKIPO Search Report dated May 9, 2019 for GB Application No. GB1806468.3, 5 pages.
Townsend, S. et al., "Augmented binary substitution: single-pass CDR germ-lining and stabilization of therapeutic antibodies," PNAS, 112(50):15354-15359 (2015).

*Primary Examiner* — Zachary C Howard
(74) *Attorney, Agent, or Firm* — Cooley LLP; Ivor Elrifi

(57) ABSTRACT

Disclosed herein are antibody molecules binding specifically to C-KIT, antigen-binding portions thereof and medical uses therefor.

24 Claims, 53 Drawing Sheets
Specification includes a Sequence Listing.

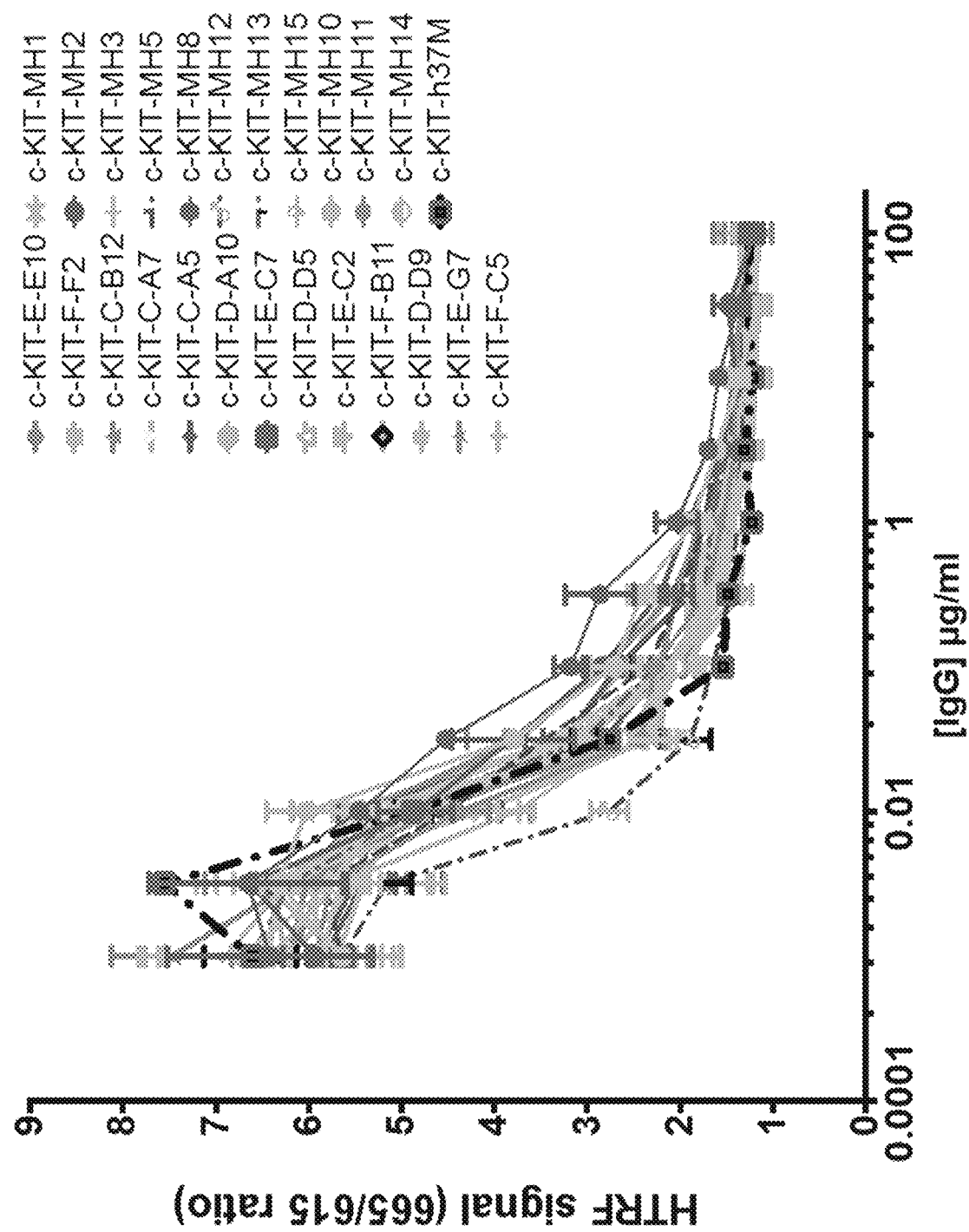

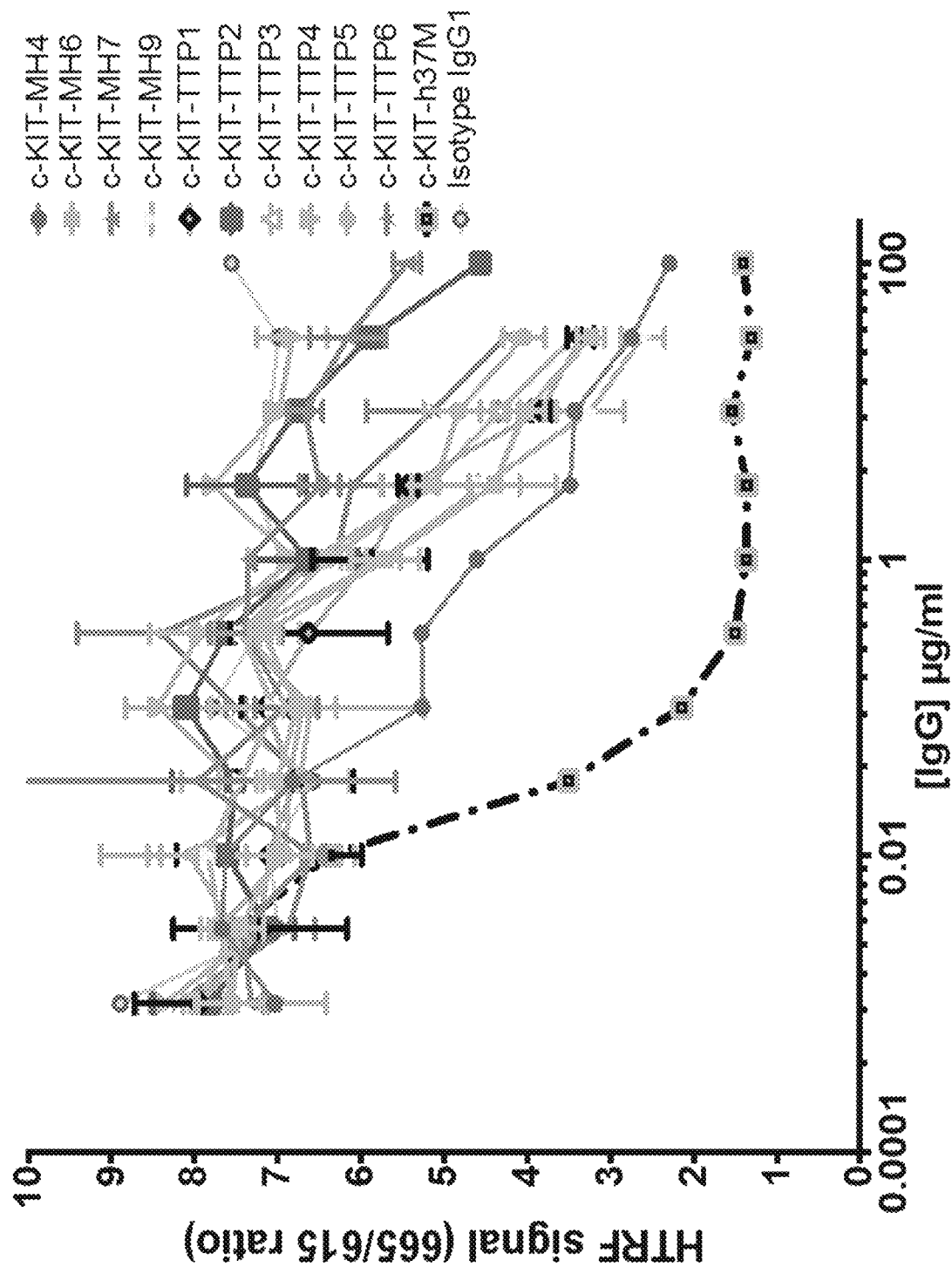

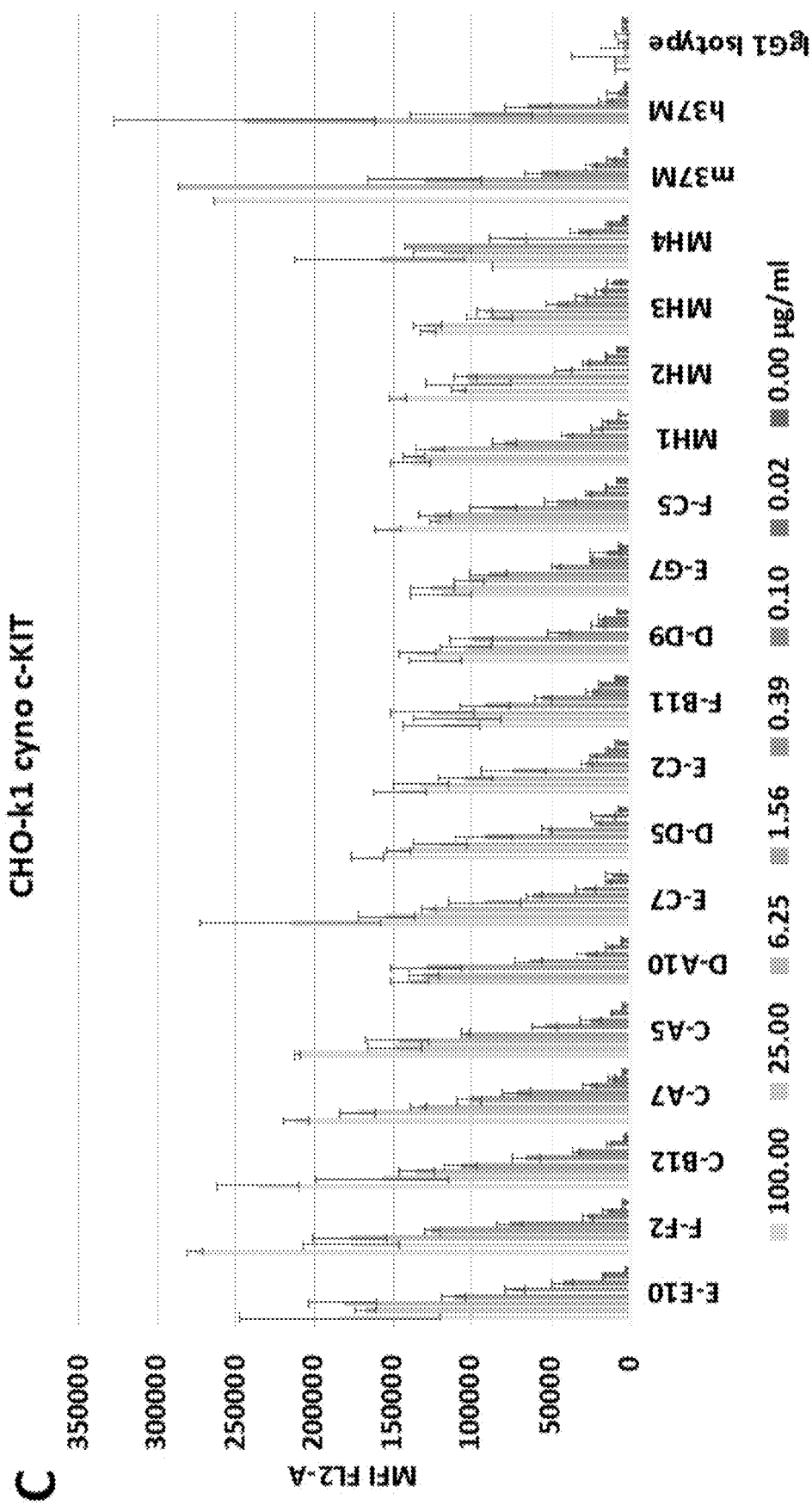

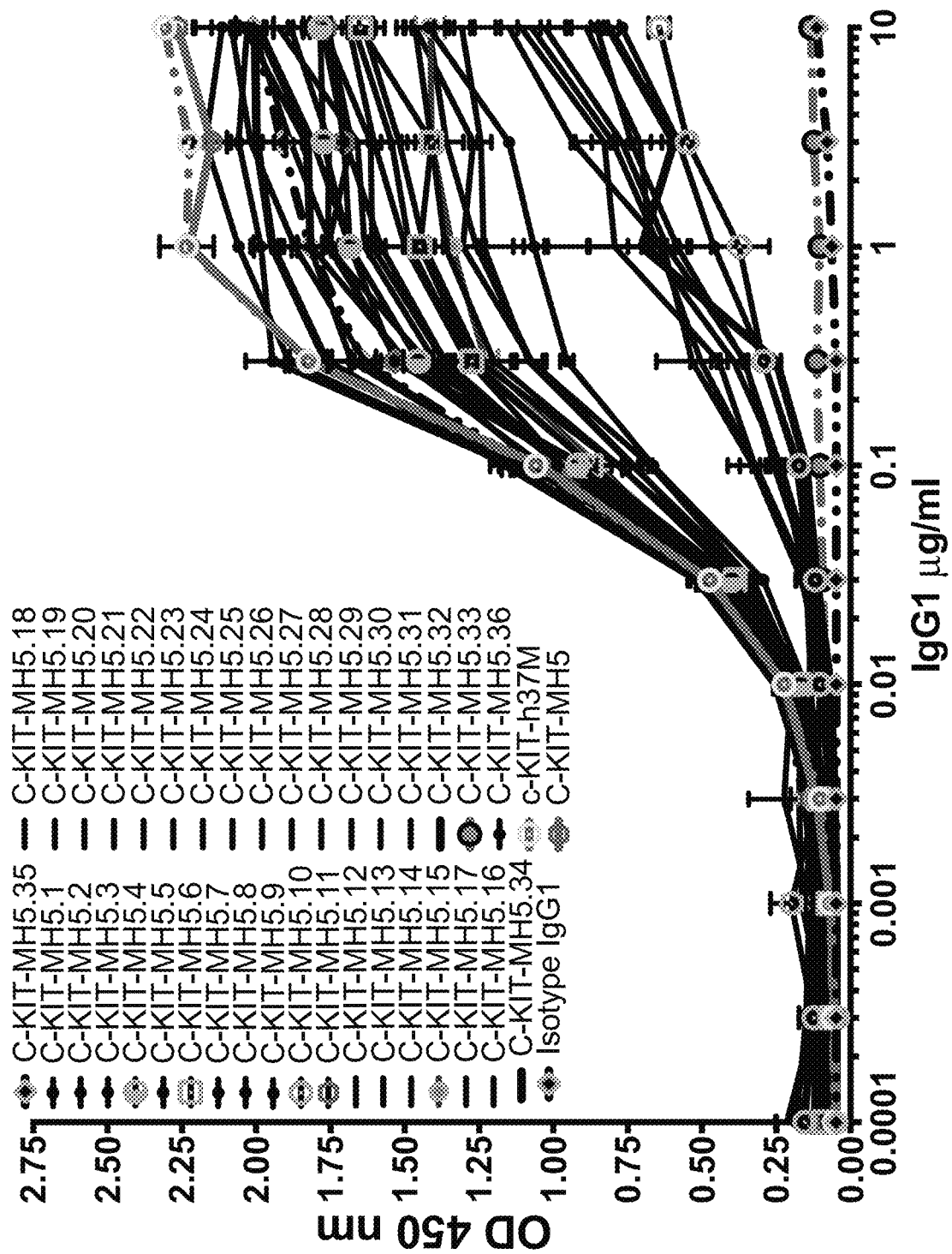

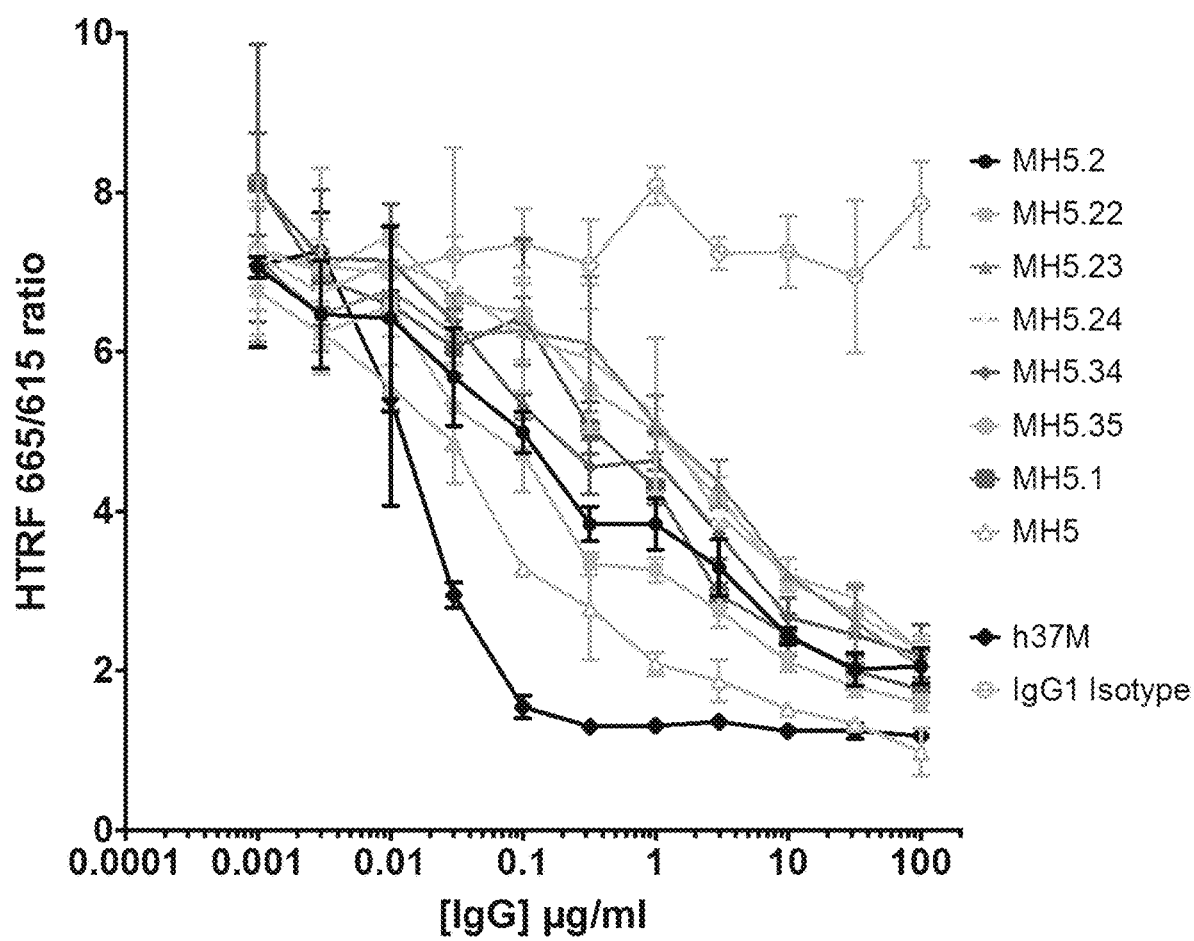

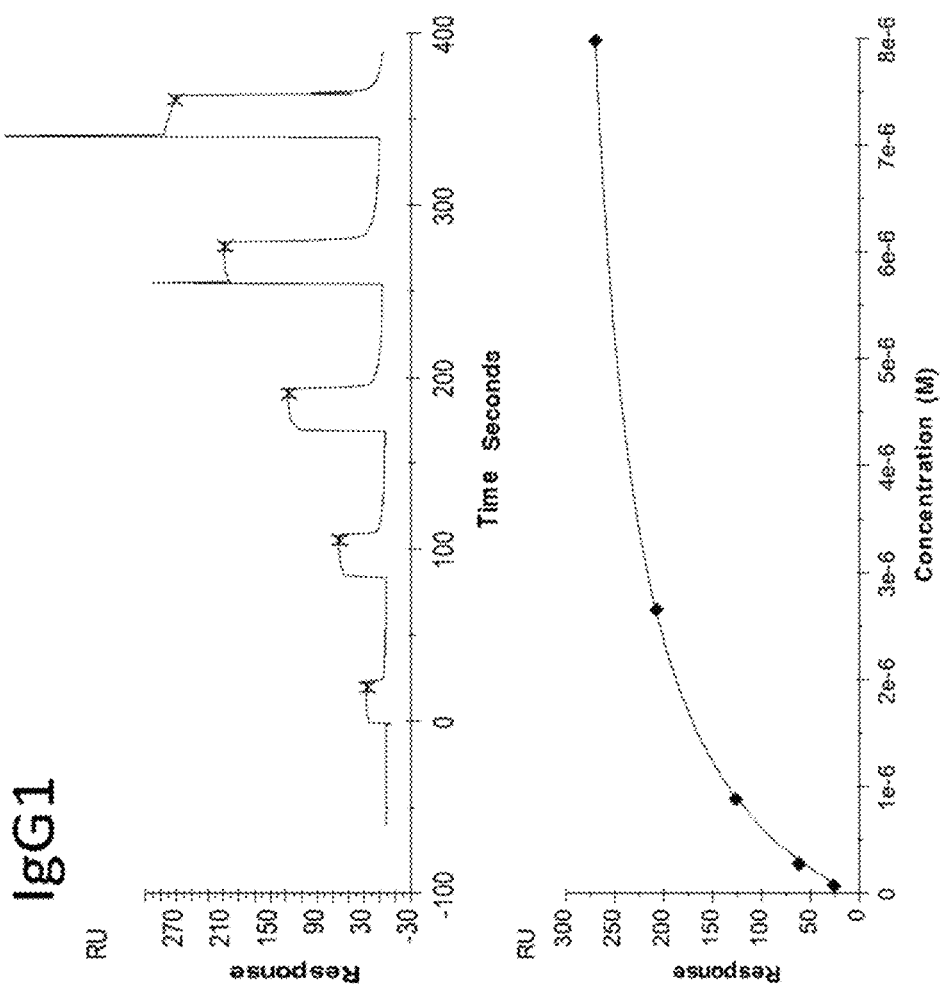

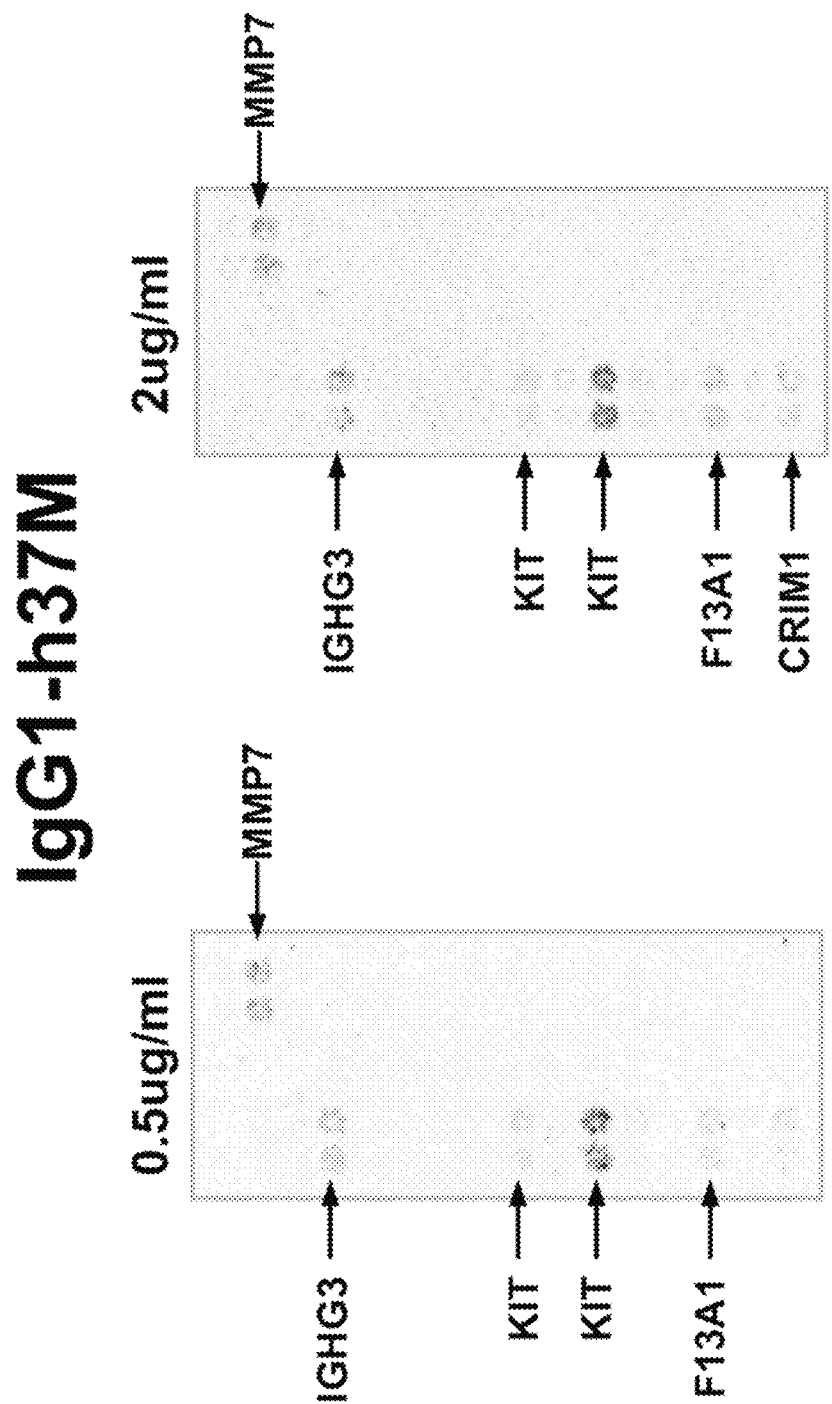

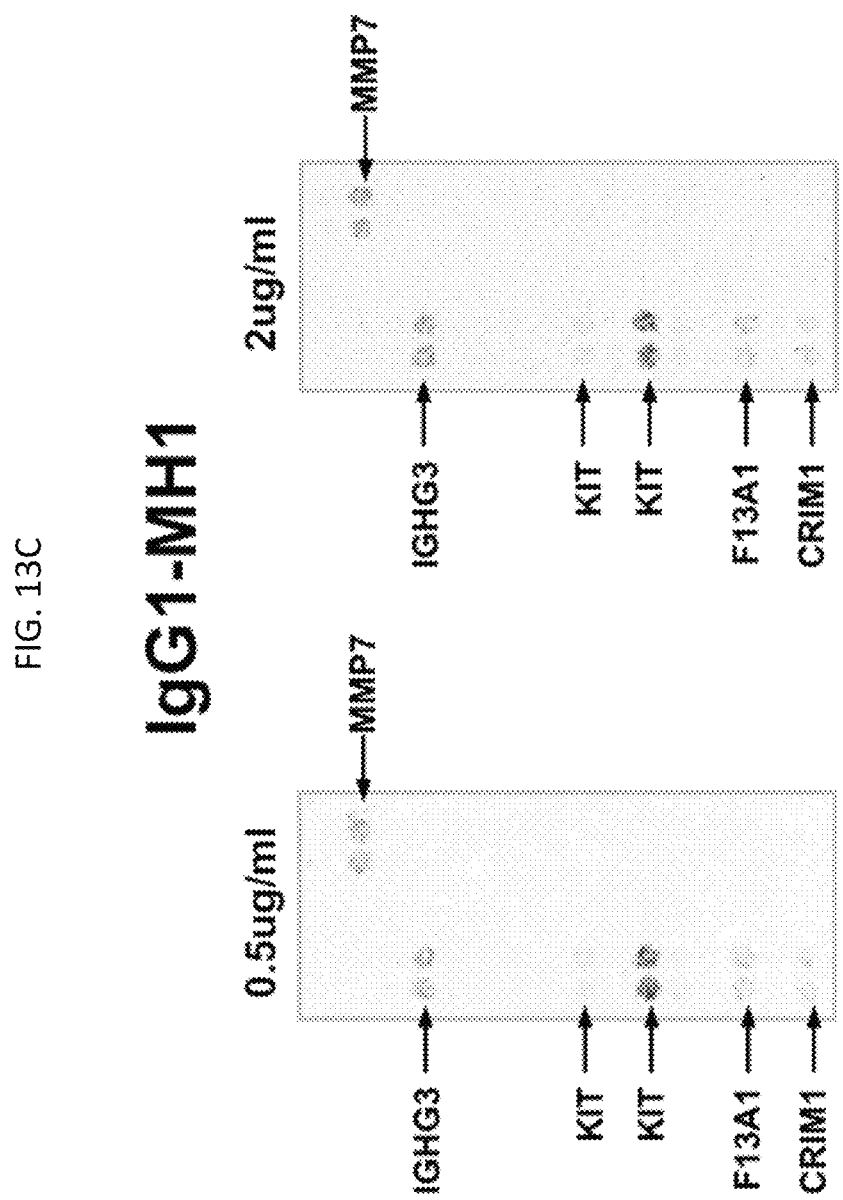

C-KIT ANTIBODIES

CROSS-REFERENCE TO RELATED APPLICATIONS

This application is a continuation of International Patent Application No. PCT/EP2019/053331, filed on Feb. 11, 2019, which claims the benefit of GB Patent Application No. 1806468.3, filed on Apr. 20, 2018, and GB Patent Application No. 1802201.2, filed on Feb. 9, 2018, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: UHFL_001_02US_SeqList_ST25.txt, date recorded: Jul. 23, 2019, file size 101,317 bytes).

FIELD OF THE INVENTION

The invention relates to antibody molecules binding specifically to C-KIT (also known as KIT, Cluster of Differentiation 117 (CD117), PBT, SCFR, KIT proto-oncogene receptor tyrosine kinase) and medical uses therefor.

BACKGROUND OF THE INVENTION

C-KIT (also known as KIT, Cluster of Differentiation 117 (CD117), PBT, SCFR, KIT proto-oncogene receptor tyrosine kinase) is a transmembrane protein that belongs to the immunoglobulin superfamily and binds to the soluble factor SCF (stem cell factor). C-KIT is a receptor tyrosine kinase type III that is highly expressed by hematopoietic stem cells as well as multiple other cell types, such as mature Mast Cells, where SCF signalling acts as a cytokine. On binding to SCF, this receptor dimerises, activating its tyrosine kinase activity. This kinase activation leads to further downstream activation of signal transduction molecules that play known roles in cell survival, proliferation, and differentiation.

Altered forms of C-KIT, such as constitutively active mutants, are strongly associated with the progression of several important types of cancer, such as Gastrointestinal Stromal Tumours (GIST), Acute Myeloid Leukaemia (AML), Mast Cell tumours and Melanoma. Preclinical and clinical evidence suggests that blocking C-KIT-SCF signalling can have clear therapeutic benefit in multiple cancers, but this has predominantly been achieved using small molecule inhibitors of C-KIT kinase function. Resistance mutations commonly develop after treatment, causing the therapeutic efficacy of the small molecule kinase inhibitor to be lost. Therapeutic antibodies that antagonise KIT signalling by blocking the ability of the receptors to dimerise have the potential to overcome kinase inhibitor resistance and mediate anti-tumour effects, via two mechanisms: 1. Potent inhibition of the KIT signalling pathway by locking the receptors into a non-activating monomeric form. 2. Antibody effector-function mediated engagement of immune cells. Importantly, it has recently been recognised in preclinical studies that C-KIT-SCF signalling in mast cells found in the tumour microenvironment (via SCF produced by stromal cells), can promote downstream cytokine signalling that recruits myeloid cells such as Myeloid-Derived Suppressor Cells (MDSCs). As MDSCs are believed to be a key cell population that suppress immune responses against tumours, the indirect inhibition of their tumour infiltration via KIT signalling antagonism may be an attractive therapeutic strategy.

The majority of currently approved antibody therapeutics are derived from immunized rodents. Many of those antibodies have undergone a process known as "humanization", via the "grafting" of murine Complementarity-Determining Regions (CDRs) into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized antagonistic anti-C-KIT antibody would therefore have as many residues as possible in the v-domains that are identical to those found in both the frameworks and CDRs of well-characterized human germline sequences. This high level of identity to high-stability germlines that are highly expressed in the maximum number of potential patients minimises the risk of a therapeutic antibody having unwanted immunogenicity in the clinic, or unusually high 'cost of goods' in manufacturing.

Townsend et al. (2015; PNAS 112: 15354-15359) describe a method for generating antibodies in which CDRs derived from rat, rabbit and mouse antibodies were grafted into preferred human frameworks and then subject to a human germ-lining approach termed "Augmented Binary Substitution". Although the approach demonstrated a fundamental plasticity in the original antibody paratopes, in the absence of highly accurate antibody-antigen co-crystal structural data, it is still not possible to reliably predict which individual residues in the CDR loops of any given antibody can be converted to human germline, and in what combination. Additionally, the Townsend et al. study did not address the addition of mutagenesis beyond the residues found in the human germline at positions where the removal of development risk motifs might be beneficial. This is a technological limitation which renders the process inherently unsatisfactory as it allows the retention of development liability motifs in CDRs.

CDR germ-lining is thus a complex, multifactorial problem, as multiple functional properties of the molecule should preferably be maintained, including in this instance: target binding specificity, affinity to C-KIT from both human and animal test species (e.g. cynomolgus monkey, also known as the crab-eating macaque, i.e. *Macaca fascicularis*), v-domain biophysical stability and/or IgG yield from protein expression platforms used in research, clinical and commercial supply. Antibody engineering studies have shown that mutation of even single residue positions in key CDRs can have dramatic effects on all of these desired molecular properties.

WO2014018625A1 describes an antagonistic murine anti-C-KIT IgG molecule termed "37M", and also the preparation of humanized forms of 37M. Those humanized forms of 37M were produced using classical humanization techniques, i.e. by grafting of Kabat-defined murine CDRs into human heavy and light chain framework sequences, with some of the human framework residues being potentially back-mutated to the correspondingly positioned 37M murine residues. For reasons noted above, such humanized forms of 37M described in WO2014018625A1 are not ideal.

The present invention provides a number of optimized anti-C-KIT antibodies and medical uses thereof.

SUMMARY OF THE INVENTION

According to one aspect of the invention, there is provided an antibody molecule which specifically binds to human C-KIT, and optionally also to cynomolgus monkey C-KIT, or an antigen-binding portion thereof, wherein the antibody molecule or antigen-binding portion comprises a heavy chain variable region with:
  an HCDR1 having amino acids in sequence in the following order: G-Y-T-F-T-D or a conservative substitution of D-Y or a conservative substitution of Y-Y-M or a conservative substitution of M-N(SEQ ID NO: 1);
  an HCDR2 having amino acids in sequence in the following order: M or a conservative substitution of M (for example, I)-G or a conservative substitution of G (for example, A)-R-I-Y-P-G or a conservative substitution of G (for example, A)-S or a conservative substitution of S (for example, A or T)-G-N-T-Y-Y-A-Q-K-F-Q-G (SEQ ID NO: 2); and
  an HCDR3 having amino acids in sequence in the following order: G-V-Y or any amino acid (for example, W or F)-Y or any amino acid (for example, E or H)-F or any amino acid (for example, Y, Q or L)-D or any amino acid (for example, G, N or S)-Y or any amino acid (for example, A, D, E, F, G, H, I, K, L, M, N, P, Q, R, S, T, V) (SEQ ID NO: 3).

In aspects of the invention, the HCDR1 of the antibody molecule or antigen-binding portion may exclude the sequence GYTFTDYYIN (SEQ ID NO: 4; 37M murine/humanized antibody HCDR1 disclosed in WO2014018625A1), the HCDR2 of the antibody molecule or antigen-binding portion may exclude the sequence IARIYPGSGNTYYNEKFKG (SEQ ID NO: 5; 37M murine/humanized antibody HCDR2 disclosed in WO2014018625A1), and/or the HCDR3 of the antibody molecule or antigen-binding portion may exclude the sequence GVYYFDY (SEQ ID NO: 6; 37M murine/humanized antibody HCDR3 disclosed in WO2014018625A1).

The antibody molecule or antigen-binding portion may further comprise a light chain variable region with:
  an LCDR1 having amino acids in sequence in the following order: R-A-S-Q-G-I or a conservative substitution of I-R or a conservative substitution of R-T or any amino acid (such as N)-N or any amino acid (for example, Y)-L-A (SEQ ID NO: 7);
  an LCDR2 having amino acids in sequence in the following order: A or any amino acid (for example, S, Y)-A-S-S or any amino acid (for example, Y)-L or any amino acid (for example, R)-Q or any amino acid (for example, Y)-S (SEQ ID NO: 8); and
  an LCDR3 having amino acids in sequence in the following order: Q-Q-Y-N or any amino acid (for example, A)-S or any amino acid (for example, N or D)-Y-P-R-T (SEQ ID NO: 9).

In aspects of the invention, the LCDR1 of the antibody molecule or antigen-binding portion may exclude the sequence KASQNVRTNVA (SEQ ID NO: 10; 37M murine/humanized antibody LCDR1 disclosed in WO2014018625A1), and/or the LCDR2 of the antibody molecule or antigen-binding portion may exclude the sequence SASYRYS (SEQ ID NO: 11; 37M murine/humanized antibody LCDR2 disclosed in WO2014018625A1). In some embodiments, the LCDR1 of the antibody molecule or antigen-binding portion may exclude the sequence KASQNVRTNVA (SEQ ID NO: 10; 37M murine/humanized antibody LCDR1 disclosed in WO2014018625A1), and/or the LCDR2 of the antibody molecule or antigen-binding portion may exclude the sequence SASYRYS (SEQ ID NO: 11; 37M murine/humanized antibody LCDR2 disclosed in WO2014018625A1) and/or the LCDR3 of the antibody molecule or antigen-binding portion may exclude the sequence QQYNSYPRT (SEQ ID NO: 12; 37M murine/humanized antibody LCDR3 disclosed in WO2014018625A1).

In some aspects, disclosed herein is an anti-C-KIT antibody or an antigen-binding portion thereof, wherein the antibody comprises a heavy chain variable (VH) region and a light chain variable (VL) region, wherein
  (a) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of AASSLQS (SEQ ID NO: 24) and LCDR3 of QQYNSYPRT (SEQ ID NO: 12);
  (b) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of AASSLQS (SEQ ID NO: 24) and LCDR3 of QQYANYPRT (SEQ ID NO: 25);
  (c) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of SASSLQS (SEQ ID NO: 17) and LCDR3 of QQYANYPRT (SEQ ID NO: 25);
  (d) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of SASSLQS (SEQ ID NO: 17) and LCDR3 of QQYNSYPRT (SEQ ID NO: 12);
  (e) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYLDY (SEQ ID NO: 18); and the VL region amino acid sequence comprises LCDR1 of RASQGIRTNVA (SEQ ID NO: 19), LCDR2 of SASYRQS (SEQ ID NO: 20) and LCDR3 of QQYNSYPRT (SEQ ID NO: 12);

(f) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYFDE (SEQ ID NO: 21); and the VL region amino acid sequence comprises LCDR1 of RASQGVRTNLA (SEQ ID NO: 22), LCDR2 of AASSRQS (SEQ ID NO: 23) and LCDR3 of QQYN-SYPRT (SEQ ID NO: 12); or (g) the VH region amino acid sequence comprises HCDR1 of GYTFTDFYMN (SEQ ID NO: 180), HCDR2 of MGRIYPASGNTYYAQKFQG (SEQ ID NO: 26) and HCDR3 of GVWYYDY (SEQ ID NO: 27); and the VL region amino acid sequence comprises LCDR1 of RASQGIRTNLA (SEQ ID NO: 16), LCDR2 of AASSLQS (SEQ ID NO: 24) and LCDR3 of QQYANYPRT (SEQ ID NO: 25).

In some aspects, disclosed herein is an anti-C-KIT antibody or an antigen-binding portion thereof, wherein the antibody comprises a heavy chain variable (VH) region and a light chain variable (VL) region, wherein the VH region amino acid sequence comprises:
(a) HCDR1 of SEQ ID NO: 13;
(b) HCDR2 of SEQ ID NO: 14; and
(c) HCDR3 of SEQ ID NO: 15, SEQ ID NO: 18 or SEQ ID NO: 21; and the VL region amino acid sequence comprises:
(a') LCDR1 of SEQ ID NO: 16, SEQ ID NO: 19 or SEQ ID NO: 22;
(b') LCDR2 of SEQ ID NO: 24, SEQ ID NO: 17, SEQ ID NO: 20 or SEQ ID NO: 23 and
(c') LCDR3 of SEQ ID NO: 12 or SEQ ID NO: 25.

In some aspects, disclosed herein is an anti-C-KIT antibody or an antigen-binding portion thereof, wherein the antibody comprises a heavy chain variable (VH) region and a light chain variable (VL) region, wherein (a) the VH region amino acid sequence comprises SEQ ID NO:185 and the VL region amino acid sequence comprises SEQ ID NO:186;
(b) the VH region amino acid sequence comprises SEQ ID NO:187 and the VL region amino acid sequence comprises SEQ ID NO:188;
(c) the VH region amino acid sequence comprises SEQ ID NO:189 and the VL region amino acid sequence comprises SEQ ID NO:190;
(d) the VH region amino acid sequence comprises SEQ ID NO:191 and the VL region amino acid sequence comprises SEQ ID NO:192;
(e) the VH region amino acid sequence comprises SEQ ID NO:193 and the VL region amino acid sequence comprises SEQ ID NO:194; or
(f) the VH region amino acid sequence comprises SEQ ID NO:195 and the VL region amino acid sequence comprises SEQ ID NO:196.

In some aspects, disclosed herein is an anti-C-KIT antibody or an antigen-binding portion thereof, wherein the antibody comprises a heavy chain variable (VH) region and a light chain variable (VL) region, wherein (a) the HCDR1 comprises the amino acid sequence G-Y-T-F-T-$X_1$-$X_2$-Y-$X_3$-N, wherein $X_1$ is D or a conservative substitution of D, $X_2$ is Y or a conservative substitution of Y and $X_3$ is M or a conservative substitution of M (SEQ ID NO: 1);
(b) the HCDR2 comprises $X_1$-$X_2$-R-I-Y-P-$X_3$-$X_4$-G-N-T-Y-Y-A-Q-K-F-Q-G, wherein $X_1$ is M or a conservative substitution of M, $X_2$ is G or a conservative substitution of G, $X_3$ is G or a conservative substitution of G and $X_4$ is S or a conservative substitution of S (SEQ ID NO: 2);
(c) the HCDR3 comprises G-V-$X_1$-$X_2$-$X_3$-$X_4$-$X_5$, wherein $X_1$ is Y or any other amino acid, $X_2$ is Y or any other amino acid, $X_3$ is F or any other amino acid, $X_4$ is D or any other amino acid and $X_5$ is Y or any other amino acid (SEQ ID NO: 3);
(d) the LCDR1 comprises R-A-S-Q-G-$X_1$-$X_2$-$X_3$-$X_4$-L-A, wherein $X_1$ is I or a conservative substitution of I, $X_2$ is R or a conservative substitution of R, $X_3$ is T or any other amino acid and $X_4$ is N or any other amino acid (SEQ ID NO: 7);
(e) the LCDR2 comprises $X_1$-A-S-$X_2$-$X_3$-$X_4$-S, wherein $X_1$ is A or any other amino acid, $X_2$ is S or any other amino acid, $X_3$ is L or any other amino acid and $X_4$ is Q or any other amino acid (SEQ ID NO: 8); and
(f) the LCDR3 comprises Q-Q-Y-$X_1$-$X_2$-Y-P-R-T, wherein $X_1$ is N or any other amino acid and $X_2$ is S or any other amino acid (SEQ ID NO: 9).

Also provided according to the invention is an immunoconjugate comprising the antibody molecule or antigen-binding portion thereof as defined herein linked to a therapeutic agent.

In another aspect the invention provides nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-C-KIT antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The autoimmune disease or inflammatory disease may be selected in all aspects from the group consisting of: arthritis, asthma, multiple sclerosis, psoriasis, Crohn's disease, inflammatory bowel disease, lupus, Grave's disease and Hashimoto's thyroiditis, and ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Further provided herein is an antibody molecule or antigen-binding portion thereof as defined herein, or the immunoconjugate as defined herein, or the nucleic acid molecule as defined herein, or the vector as defined herein, or the pharmaceutical composition as defined herein, for use as a medicament. Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease, an inflammatory disease or a fibrotic disease.

The cardiovascular disease in any aspect of the invention may for example be coronary heart disease or atherosclerosis.

The fibrotic disease in any aspect of the invention may be selected from the group consisting of myocardial infarction, angina, osteoarthritis, pulmonary fibrosis, cystic fibrosis, bronchitis and asthma.

The invention also provides a method of producing an antibody molecule which specifically binds to human C-KIT and optionally also to cynomolgus monkey C-KIT, or an antigen-binding portion thereof, comprising the steps of:

(1) grafting anti-C-KIT CDRs from a non-human source into a human v-domain framework to produce a humanized anti-C-KIT antibody molecule or antigen-binding portion thereof;

(2) generating a phage library of clones of the humanized anti-C-KIT antibody molecule or antigen-binding portion thereof comprising one or more mutations in the CDRs;

(3) screening the phage library for binding to human C-KIT and optionally also to cynomolgus monkey C-KIT;

(4) selecting clones from the screening step (3) having binding specificity to human C-KIT and optionally also to cynomolgus monkey C-KIT; and (5) producing an antibody molecule which specifically binds to human C-KIT and optionally also to cynomolgus monkey C-KIT, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

BRIEF DESCRIPTION OF THE DRAWINGS

FIG. 4A-FIG. 4E. HTRF-based solution-phase, high-sensitivity, C-KIT epitope competition assay. HTRF binding signal for the h37M IgG to human or cyno C-KIT was examined in the presence of titrated competitor IgGs including library-derived and designer leads, plus Isotype IgG1 as a negative control and unlabelled h37M IgG1 as a positive control. All library-derived and multiple designer IgGs exhibited full concentration-dependent inhibition of h37M binding to human (FIG. 4A) and cyno (FIG. 4C, FIG. 4D) c-KIT, similar to unlabelled h37M IgG, suggesting maintenance of a shared epitope and binding affinity. All TTP clones, plus MH clones 4, 6, 7 and 9 were found to have reduced ability to inhibit h37M binding to either human (FIG. 4B) or cyno (FIG. 4E) C-KIT.

FIG. 5A-FIG. 5F. Flow cytometric binding to human and cyno C-KIT+ CHO-K1 cells for library-derived and primary designer leads. Anti-C-KIT controls m37M and h37M, library-derived and designer leads in IgG1 format were examined for specific binding on human C-KIT-transfected CHO-K1 cells (FIG. 5A, FIG. 5B), cyno C-KIT-transfected CHO-K1 cells (FIG. 5C, FIG. 5D), and wild type (WT, i.e. untransfected) CHO-K1 cells (FIG. 5E, FIG. 5F). IgGs were tested at concentrations ranging from 0.02-100 µg/ml. Concentration-dependent binding was observed against both human and cyno cell lines for all C-KIT-specific antibodies but not isotype controls. No binding signals above background were observed against wild type CHO-K1 cells.

FIG. 6A-FIG. 6B. Direct titration ELISA for second-generation designer IgGs binding to human and cyno C-KIT-Fc proteins. Anti-C-KIT h37M, MH5 and second-generation designer clones in human IgG1 format were titrated (in µg/ml) in a direct binding ELISA against human (FIG. 6A) and cyno (FIG. 6B) C-KIT-Fc proteins. The h37M and MH5 clones demonstrated binding activity against both orthologs of C-KIT. All designer clones other than MH5.33 retained human and cyno C-KIT binding, but only clones MH5.1, 5.2, 5.3, 5.22, 5.23, 5.24, 5.34 and 5.35 exhibited binding comparable to clone h37M on both orthologs.

FIG. 7A-FIG. 7B. HTRF-based C-KIT epitope competition assay for key second-generation designer leads. HTRF binding signal for the h37M IgG to human or cyno C-KIT was examined in the presence of titrated competitor second-generation designer leads in IgG1 format, plus isotype IgG1 as a negative control and unlabelled h37M IgG1 as a positive control. All IgGs (other than the Isotype control IgG1) exhibited full concentration-dependent inhibition of h37M binding to human (FIG. 7A) and cyno (FIG. 7B) C-KIT, similar to unlabelled h37M IgG.

FIG. 12A-FIG. 12C. Affinity analyses for IgG1 Fc engineered variants on human FcγRIIb. Purified anti-KIT IgGs were analysed for binding affinity to FcγRIIb in a 'steady state' affinity measurement on a BIACORE® T200 instrument. Clones h37M-IgG1 (FIG. 12A), h37M-IgG1-3M (FIG. 12B) and MH1-IgG-4M (FIG. 12C) all exhibited measurable binding to FcγRIIb, with MH1-IgG-4M showing the lowest overall binding signal across the full concentration range. In A-C, the raw data for chip interaction is shown in each upper panel and the plotted curves for Response Units (RU) per concentration are shown in the lower panel.

FIG. 13A-FIG. 13C. Human proteome re-array analyses. After a full screen of 5528 unique proteins, analyses of binding specificity were performed on chips in which plasmids encoding potentially relevant targets were arrayed and used to transfect HEK293 cells. Transfection of all plasmids was confirmed by screening for the co-encoded marker ZS green (FIG. 13A). Separate chips were then probed using Rituximab analog and secondary labelled antibody only (FIG. 13A), h37M at 0.5 and 2 µg/ml (FIG. 13B) and MH1 at 0.5 and 2 µg/ml (FIG. 13C). These analyses confirmed that h37M and MH1 both exhibited highly specific binding to C-KIT. Binding signals to MMP7, CRIM1 and F13A1 on all chips were found to be an artefact of the secondary antibody (FIG. 13A).

DETAILED DESCRIPTION OF THE INVENTION

Figure 1A:
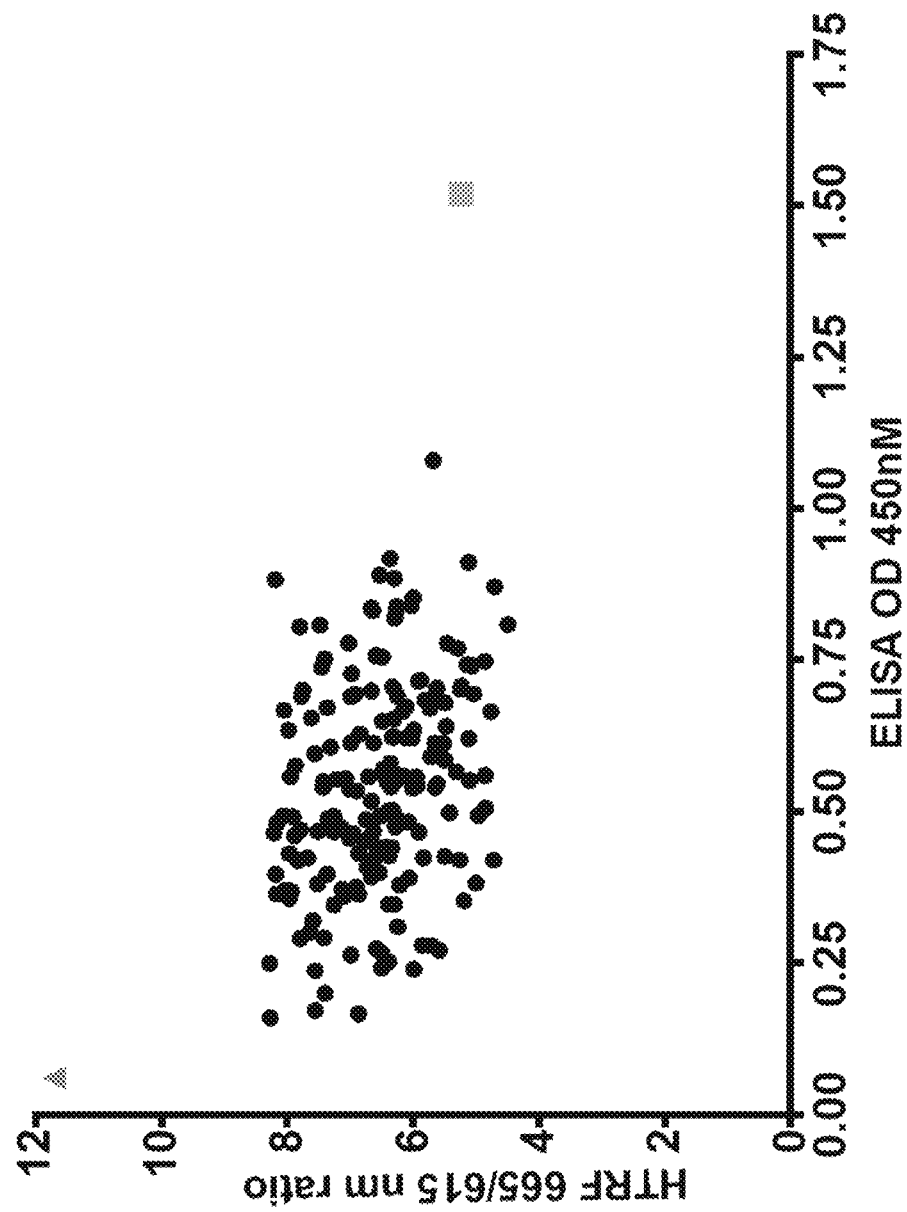
FIG. 1A-FIG. 1B. Direct binding ELISA and HTRF competition screening of library-derived anti-C-KIT scFvs against human and cyno C-KIT-Fc proteins. Clones were derived from separate phage selection branches on biotinylated human and/or cynomolgus monkey C-KIT-Fc proteins in each round. After multiple rounds of selection, library-derived clones (black circles) were screened for binding against both human (FIG. 1A) and cyno (FIG. 1B) C-KIT-Fc and epitope blocking of h37M IgG1 against both orthologs. Negative control (non-C-KIT-binding) and positive control h37M scFvs are represented in grey triangles and squares, respectively.

According to a first aspect of the invention, there is provided an antibody molecule which specifically binds to human C-KIT and optionally also to cynomolgus monkey C-KIT, or an antigen-binding portion thereof, wherein the antibody molecule or antigen-binding portion comprises a heavy chain variable region with:

an HCDR1 (heavy chain complementarity determining region 1) having amino acids in sequence in the following order: G-Y-T-F-T-D or a conservative substitution of D-Y or a conservative substitution of Y-Y-M or a conservative substitution of M-N(SEQ ID NO: 1);

an HCDR2 (heavy chain complementarity determining region 2) having amino acids in sequence in the following order: M or a conservative substitution of M (for example, I)-G or a conservative substitution of G (for example, A)-R-I-Y-P-G or a conservative substitution of G (for example, A)-S or a conservative substitution of S (for example, A or T)-G-N-T-Y-Y-A-Q-K-F-Q-G (SEQ ID NO: 2); and an HCDR3 (heavy chain complementarity determining region 3) having amino acids in sequence in the following order: G-V-Y or any amino acid (for example, W or F)-Y or any amino acid (for example, E or H)-F or any amino acid (for example, Y, Q or L)-D or any amino acid (for example, G, N or S)-Y or any amino acid (for example, A, D, E, F, G, H, I, K, L, M, N, P, Q, R, S, T, V) (SEQ ID NO: 3).

In some aspects an anti-C-KIT antibody or antigen-binding portion provided herein specifically binds to a C-KIT protein comprising or consisting of SEQ ID NO:208. In some aspects an anti-C-KIT antibody or antigen-binding portion provided herein specifically binds to a C-KIT protein having an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:208. In some aspects an anti-C-KIT antibody or antigen-binding portion provided herein specifically binds to a C-KIT protein encoded by a nucleic acid molecule comprising or consisting of SEQ ID NO:209 or SEQ ID NO:210.

In aspects of the invention, the HCDR1 of the antibody molecule or antigen-binding portion may exclude the sequence GYTFTDYYIN (SEQ ID NO: 4; 37M murine/humanized antibody HCDR1 disclosed in WO2014018625A1), the HCDR2 of the antibody molecule or antigen-binding portion may exclude the sequence IARIYPGSGNTYYNEKFKG (SEQ ID NO: 5; 37M murine/humanized antibody HCDR2 disclosed in WO2014018625A1), and/or the HCDR3 of the antibody molecule or antigen-binding portion may exclude the sequence GVYYFDY (SEQ ID NO: 6; 37M murine/humanized antibody HCDR3 disclosed in WO2014018625A1).

The antibody molecule or antigen-binding portion may further comprise a light chain variable region with:

an LCDR1 (light chain complementarity determining region 1) having amino acids in sequence in the following order: R-A-S-Q-G-I or a conservative substitution of I-R or a conservative substitution of R-T or any amino acid (such as N)-N or any amino acid (for example, Y)-L-A (SEQ ID NO: 7);

an LCDR2 (light chain complementarity determining region 2) having amino acids in sequence in the following order: A or any amino acid (for example, S, Y)-A-S-S or any amino acid (for example, Y)-L or any amino acid (for example, R)-Q or any amino acid (for example, Y)-S(SEQ ID NO: 8); and an LCDR3 (light chain complementarity determining region 3) having amino acids in sequence in the following order: Q-Q-Y-N or any amino acid (for example, A)-S or any amino acid (for example, N or D)-Y-P-R-T (SEQ ID NO: 9).

In some aspects of the invention, the LCDR1 of the antibody molecule or antigen-binding portion may exclude the sequence KASQNVRTNVA (SEQ ID NO: 10; 37M murine/humanized antibody LCDR1 disclosed in WO2014018625A1), and/or the LCDR2 of the antibody molecule or antigen-binding portion may exclude the sequence SASYRYS (SEQ ID NO: 11; 37M murine/humanized antibody LCDR2 disclosed in WO2014018625A1). In some embodiments, the LCDR1 of the antibody molecule or antigen-binding portion may exclude the sequence KASQNVRTNVA (SEQ ID NO: 10; 37M murine/humanized antibody LCDR1 disclosed in WO2014018625A1), and/or the LCDR2 of the antibody molecule or antigen-binding portion may exclude the sequence SASYRYS (SEQ ID NO: 11; 37M murine/humanized antibody LCDR2 disclosed in WO2014018625A1) and/or the LCDR3 of the antibody molecule or antigen-binding portion may exclude the sequence QQYNSYPRT (SEQ ID NO: 12; 37M murine/humanized antibody LCDR3 disclosed in WO2014018625A1).

In some aspects, disclosed herein is an anti-C-KIT antibody or an antigen-binding portion thereof, wherein the antibody comprises a heavy chain variable (VH) region and a light chain variable (VL) region, wherein (a) the HCDR1 comprises the amino acid sequence G-Y-T-F-T-$X_1$-$X_2$-Y-$X_3$-N, wherein $X_1$ is D or a conservative substitution of D, $X_2$ is Y or a conservative substitution of Y and $X_3$ is M or a conservative substitution of M (SEQ ID NO: 1);

(b) the HCDR2 comprises $X_1$-$X_2$-R-I-Y-P-$X_3$-$X_4$-G-N-T-Y-Y-A-Q-K-F-Q-G, wherein $X_1$ is M or a conservative substitution of M (for example, I), $X_2$ is G or a conservative substitution of G (for example, A), $X_3$ is G or a conservative substitution of G (for example, A) and $X_4$ is S or a conservative substitution of S (for example, A or T) (SEQ ID NO: 2);

(c) the HCDR3 comprises G-V-$X_1$-$X_2$-$X_3$-$X_4$-$X_5$, wherein $X_1$ is Y or any other amino acid (for example, W or F), $X_2$ is Y or any other amino acid (for example, E or H), $X_3$ is F or any other amino acid (for example, Y, Q or L), $X_4$ is D or any other amino acid (for example, G, N or S) and $X_5$ is Y or any other amino acid (for example, A, D, E, F, G, H, I, K, L, M, N, P, Q, R, S, T or V) (SEQ ID NO: 3);

(d) the LCDR1 comprises R-A-S-Q-G-$X_1$-$X_2$-$X_3$-$X_4$-L-A, wherein $X_1$ is I or a conservative substitution of I, $X_2$ is R or a conservative substitution of R, $X_3$ is T or any other amino acid (for example, N) and $X_4$ is N or any other amino acid (for example, Y) (SEQ ID NO: 7);

(e) the LCDR2 comprises $X_1$-A-S-$X_2$-$X_3$-$X_4$-S, wherein $X_1$ is A or any other amino acid (for example, S or Y), $X_2$ is S or any other amino acid (for example, Y), $X_3$ is L or any other amino acid (for example, R) and $X_4$ is Q or any other amino acid (for example, Y) (SEQ ID NO: 8); and (f) the LCDR3 comprises Q-Q-Y-$X_1$-$X_2$-Y-P-R-T, wherein $X_1$ is N or any other amino acid (for example, A) and $X_2$ is S or any other amino acid (for example, N or D) (SEQ ID NO: 9).

In some aspects, disclosed herein is an anti-C-KIT antibody or an antigen-binding portion thereof, wherein the antibody comprises a heavy chain variable (VH) region comprising, in amino-terminal to carboxyl-terminal order, FR1-HCDR1-FR2-HCDR2-FR3-HCDR3-FR4 and a light chain variable (VL) region comprising, in amino-terminal to carboxyl-terminal order, FR1-LCDR1-FR2-LCDR2-FR3-LCDR3-FR4, wherein the HCDR1 is SEQ ID NO:1, the HCDR2 is SEQ ID NO:2, the HCDR3 is SEQ ID NO:3, the LCDR1 is SEQ ID NO:7, the LCDR2 is SEQ ID NO:8 and the LCDR3 is SEQ ID NO:9, wherein the heavy chain FR1, FR2, FR3 and FR4 amino acid sequences are the heavy chain FR1, FR2, FR3 and FR4 amino acid sequences in SEQ ID NO: 89 (see Table 2) and wherein the light chain FR1, FR2, FR3 and FR4 amino acid sequences are the light chain FR1, FR2, FR3 and FR4 amino acid sequences in SEQ ID NO: 92 (see Table 2).

As elaborated herein, the present inventors have succeeded for the first time in generating a number of optimized anti-C-KIT antibody molecules using CDR sequences derived from the murine anti-C-KIT antibody 37M disclosed in WO2014018625A1. In embodiments of the present invention, these antibody molecules have been selected to have binding specificity to both human C-KIT as well as cynomolgus monkey C-KIT (to facilitate in vivo studies in an appropriate animal test species). Further refining of the optimized antibody molecules as described herein has provided improved variable domain stability, higher expression yields, and/or reduced immunogenicity.

Preferred optimized anti-C-KIT antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-C-KIT binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to C-KIT. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-Y-T-F-T-D/N-Y/H/F-Y-M/I-N(SEQ ID NO: 28); the HCDR2 may have the amino acid sequence: M/I-G/A-R-I-Y-P-G/A-S/T/A-G-N-T-Y-Y-A-Q-K-F-Q-G (SEQ ID NO: 29); and the HCDR3 may have the amino acid sequence: G-V-Y/W/F-Y/E/H-F/Y/Q/L-D/G/N/S-Y/A/E/F/GH/I/K/L/M/N/P/Q/R/S/TN (SEQ ID NO: 30).

For example, the HCDR1 may have the amino acid sequence: G-Y-T-F-T-D/N-Y/F-Y-M-N (SEQ ID NO: 31); the HCDR2 may have the amino acid sequence: M/I-G-R-I-Y-P-G/A-S-G-N-T-Y-Y-A-Q-K-F-Q-G (SEQ ID NO: 32); and the HCDR3 may have the amino acid sequence: G-V-Y/W-Y/E/H-Y/Q/L-D-Y/S/T/E (SEQ ID NO: 33).

In the antibody molecule or antigen-binding portion thereof, the LCDR1 may have the amino acid sequence: R-A-S-Q-G-IN-R-T/N-N-L-A (SEQ ID NO: 34); the LCDR2 may have the amino acid sequence: A/S/Y-A-S-S-L-Q-S(SEQ ID NO: 35); and the LCDR3 may have the amino acid sequence: Q-Q-Y-N/A/S/E/T-S/A/N/D-Y-P-R-T (SEQ ID NO: 36).

For example, the LCDR1 may have the amino acid sequence: R-A-S-Q-G-I-R-T/N-N-L-A (SEQ ID NO: 37); the LCDR2 may have the amino acid sequence: A-A-S-S-L-Q-S(SEQ ID NO: 24); and the LCDR3 may have the amino acid sequence: Q-Q-Y-N/A-S/N-Y-P-R-T (SEQ ID NO: 38).

In specific embodiments of the invention, the antibody molecule or antigen-binding portion may comprise:

(a) the amino acid sequences GYTFTDYYMN (HCDR1; SEQ ID NO: 13), MGRIYPGSGNTYYAQKFQG (HCDR2; SEQ ID NO: 14), GVWYFDY (HCDR3; SEQ ID NO: 40), RASQGVRTNVA (LCDR1; SEQ ID NO: 39), SASSLQS (LCDR2; SEQ ID NO: 17), QQYNSYPRT (LCDR3; SEQ ID NO: 12), [Clone E-E10]; or (b) the amino acid sequences GYTFTDYYMN (HCDR1; SEQ ID NO: 13), MGRIYPGSGNTYYAQKFQG (HCDR2; SEQ ID NO: 14), GVYYQDY (HCDR3; SEQ ID NO: 41), RASQGVRTNVA (LCDR1; SEQ ID NO: 39), AASSRQS (LCDR2; SEQ ID NO: 23) and QQYNSYPRT (LCDR3; SEQ ID NO: 12) [Clone F-F2];

(c) the amino acid sequences GYTFTDYYMN (HCDR1; SEQ ID NO: 13), MGRIYPGSGNTYYAQKFQG (HCDR2;

SEQ ID NO: 14), GVYEFDY (HCDR3; SEQ ID NO: 42), RASQGVRNNLA (LCDR1; SEQ ID NO: 43), AASYRQS (LCDR2; SEQ ID NO: 44) and QQYNSYPRT (LCDR3; SEQ ID NO: 12) [Clone C-B12];

(d) the amino acid sequences GYTFTDYYMN (HCDR1; SEQ ID NO: 13), IGRIYPGSGNTYYAQKFQG (HCDR2; SEQ ID NO: 45), GVYYFDS (HCDR3; SEQ ID NO: 46), RASQGVRNNVA (LCDR1; SEQ ID NO: 47), YASSLQS (LCDR2; SEQ ID NO: 48) and QQYNSYPRT (LCDR3; SEQ ID NO: 12) [Clone C-A7];

(e) the amino acid sequences GYTFTDYYMN (HCDR1; SEQ ID NO: 13), MGRIYPGSGNTYYAQKFQG (HCDR2; SEQ ID NO: 14), GVYHFDY (HCDR3; SEQ ID NO: 49), RASQGVRNNVA (LCDR1; SEQ ID NO: 47), AASYLQS (LCDR2; SEQ ID NO: 50) and QQYNSYPRT (LCDR3; SEQ ID NO: 12) [Clone C-A5];

(f) the amino acid sequences GYTFTDYYMN (HCDR1; SEQ ID NO: 13), MGRIYPGSGNTYYAQKFQG (HCDR2; SEQ ID NO: 14), GVYYFDT (HCDR3; SEQ ID NO: 51), RASQGVRTNLA (LCDR1; SEQ ID NO: 22), AASSRQS (LCDR2; SEQ ID NO: 23) and QQYNSYPRT (LCDR3; SEQ ID NO: 12) [Clone D-A10];

(g) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYNSYPRT (LCDR3; SEQ ID NO: 12) [Clone E-C7];

(h) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGVRTNLA (LCDR1; SEQ ID NO: 22), SASSLQS (LCDR2; SEQ ID NO: 17) and QQYNSYPRT (LCDR3; SEQ ID NO: 12) [Clone D-D5];

(i) the amino acid sequences GYTFTDYYMN (HCDR1; SEQ ID NO: 13), MGRIYPGSGNTYYAQKFQG (HCDR2; SEQ ID NO: 14), GVYYLDY (HCDR3; SEQ ID NO: 18), RASQGIRTNVA (LCDR1; SEQ ID NO: 19), SASYRQS (LCDR2; SEQ ID NO: 20) and QQYNSYPRT (LCDR3; SEQ ID NO: 12) [Clone E-C2];

(j) the amino acid sequences GYTFTDYYMN (HCDR1; SEQ ID NO: 13), MGRIYPGSGNTYYAQKFQG (HCDR2; SEQ ID NO: 14), GVYYLDY (HCDR3; SEQ ID NO: 18), RASQGIRTNLA (LCDR1; SEQ ID NO: 16), AASYRQS (LCDR2; SEQ ID NO: 44) and QQYNSYPRT (LCDR3; SEQ ID NO: 12) [Clone F-B11];

(k) the amino acid sequences GYTFTDYYMN (HCDR1; SEQ ID NO: 13), MGRIYPGSGNTYYAQKFQG (HCDR2; SEQ ID NO: 14), GVYYLDY (HCDR3; SEQ ID NO: 18), RASQGVRTNVA (LCDR1; SEQ ID NO: 39), SASSLQS (LCDR2; SEQ ID NO: 17) and QQYNSYPRT (LCDR3; SEQ ID NO: 12) [Clone D-D9];

(l) the amino acid sequences GYTFTDYYMN (HCDR1; SEQ ID NO: 13), MGRIYPGSGNTYYAQKFQG (HCDR2; SEQ ID NO: 14), GVYYFDE (HCDR3; SEQ ID NO: 21), RASQGVRTNVA (LCDR1; SEQ ID NO: 39), SASSRQS (LCDR2; SEQ ID NO: 52) and QQYNSYPRT (LCDR3; SEQ ID NO: 12) [Clone E-G7];

(m) the amino acid sequences GYTFTDYYMN (HCDR1; SEQ ID NO: 13), MGRIYPGSGNTYYAQKFQG (HCDR2; SEQ ID NO: 14), GVYYFDE (HCDR3; SEQ ID NO: 21), RASQGVRTNLA (LCDR1; SEQ ID NO: 22), AASSRQS (LCDR2; SEQ ID NO: 23) and QQYNSYPRT (LCDR3; SEQ ID NO: 12) [Clone F-05];

(n) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), AASSLQS (LCDR2; SEQ ID NO: 24) and QQYNSYPRT (LCDR3; SEQ ID NO: 12) [Clone MH1];

(o) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYASYPRT (LCDR3; SEQ ID NO: 53) [Clone MH2];

(p) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYNAYPRT (LCDR3; SEQ ID NO: 54) [Clone MH3];

(q) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYNDYPRT (LCDR3; SEQ ID NO: 55) [Clone MH4];

(r) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYANYPRT (LCDR3; SEQ ID NO: 25) [Clone MH5];

(s) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYNSYPKT (LCDR3; SEQ ID NO: 56) [Clone MH6];

(t) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYNSYPHT (LCDR3; SEQ ID NO: 57) [Clone MH7];

(u) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYSSYPRT (LCDR3; SEQ ID NO: 58) [Clone MH8];

(v) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYESYPRT (LCDR3; SEQ ID NO: 59) [Clone MH9];

(w) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), SASSLQS (LCDR2; SEQ ID NO: 17) and QQYTSYPRT (LCDR3; SEQ ID NO: 60) [Clone MH10];

(x) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), AASSLQS (LCDR2; SEQ ID NO: 24) and QQYNAYPRT (LCDR3; SEQ ID NO: 54) [Clone MH11];

(y) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGVRTNLA (LCDR1; SEQ ID NO: 22), AASLQS (LCDR2; SEQ ID NO: 24) and QQYNSYPRT (LCDR3; SEQ ID NO: 12) [Clone MH12];

(z) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGVRTNLA (LCDR1; SEQ ID NO: 22), AASSLQS (LCDR2; SEQ ID NO: 24) and QQYNAYPRT (LCDR3; SEQ ID NO: 54) [Clone MH13];

(aa) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGVRTNLA (LCDR1; SEQ ID NO: 22), AASSLQS (LCDR2; SEQ ID NO: 24) and QQYNSYPRT (LCDR3; SEQ ID NO: 12) [Clone MH14];

(bb) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGVRTNLA (LCDR1; SEQ ID NO: 22), AASSLQS (LCDR2; SEQ ID NO: 24) and QQYNAYPRT (LCDR3; SEQ ID NO: 54) [Clone MH15];

(cc) the amino acid sequences GYTFTNYYMN (HCDR1; SEQ ID NO: 181), MGRIYPGTGNTYYAQKFQG (HCDR2; SEQ ID NO: 61), GVWYYDY (HCDR3; SEQ ID NO: 27), RASQGIRTNLA (LCDR1; SEQ ID NO: 16), AASSLQS (LCDR2; SEQ ID NO: 24) and QQYANYPRT (LCDR3; SEQ ID NO: 25) [Clone MH5.1];

(dd) the amino acid sequences GYTFTDFYMN (HCDR1; SEQ ID NO: 180), MGRIYPGTGNTYYAQKFQG (HCDR2; SEQ ID NO: 61), GVWYYDY (HCDR3; SEQ ID NO: 27), RASQGIRTNLA (LCDR1; SEQ ID NO: 16), AASSLQS (LCDR2; SEQ ID NO: 24) and QQYANYPRT (LCDR3; SEQ ID NO: 25) [Clone MH5.2];

(ee) the amino acid sequences GYTFTDFYMN (HCDR1; SEQ ID NO: 180), MGRIYPASGNTYYAQKFQG (HCDR2; SEQ ID NO: 26), GVWYYDY (HCDR3; SEQ ID NO: 27), RASQGIRTNLA (LCDR1; SEQ ID NO: 16), AASSLQS (LCDR2; SEQ ID NO: 24) and QQYANYPRT (LCDR3; SEQ ID NO: 25) [Clone MH5.22];

(ff) the amino acid sequences GYTFTDFYMN (HCDR1; SEQ ID NO: 180), MGRIYPASGNTYYAQKFQG (HCDR2; SEQ ID NO: 26), GVWYFDS (HCDR3; SEQ ID NO: 62), RASQGIRTNLA (LCDR1; SEQ ID NO: 16), AASSLQS (LCDR2; SEQ ID NO: 24) and QQYANYPRT (LCDR3; SEQ ID NO: 25) [Clone MH5.23];

(gg) the amino acid sequences GYTFTDFYMN (HCDR1; SEQ ID NO: 180), MGRIYPASGNTYYAQKFQG (HCDR2; SEQ ID NO: 26), GVWYFDT (HCDR3; SEQ ID NO: 63), RASQGIRTNLA (LCDR1; SEQ ID NO: 16), AASSLQS (LCDR2; SEQ ID NO: 24) and QQYANYPRT (LCDR3; SEQ ID NO: 25) [Clone MH5.24];

(hh) the amino acid sequences GYTFTNYYMN (HCDR1; SEQ ID NO: 181), MGRIYPASGNTYYAQKFQG (HCDR2; SEQ ID NO: 26), GVWYFDS (HCDR3; SEQ ID NO: 62), RASQGIRTNLA (LCDR1; SEQ ID NO: 16), AASSLQS (LCDR2; SEQ ID NO: 24) and QQYANYPRT (LCDR3; SEQ ID NO: 25) [Clone MH5.34];

(ii) the amino acid sequences GYTFTNYYMN (HCDR1; SEQ ID NO: 181), MGRIYPASGNTYYAQKFQG (HCDR2; SEQ ID NO: 26), GVWYFDT (HCDR3; SEQ ID NO: 63), RASQGIRTNLA (LCDR1; SEQ ID NO: 16), AASSLQS (LCDR2; SEQ ID NO: 24) and QQYANYPRT (LCDR3; SEQ ID NO: 25) [Clone MH5.35];

(jj) the amino acid sequences GYTFTDYYMN (HCDR1; SEQ ID NO: 13), MGRIYPGSGNTYYAQKFQG (HCDR2; SEQ ID NO: 14), GVYYYDY (HCDR3; SEQ ID NO: 15), RASQGIRTNLA (LCDR1; SEQ ID NO: 16), AASSLQS (LCDR2; SEQ ID NO: 24) and QQYANYPRT (LCDR3; SEQ ID NO: 25) [Clone MH5-DI].

In some aspects, disclosed herein is an anti-C-KIT antibody or an antigen-binding portion thereof, wherein the antibody comprises a heavy chain variable (VH) region and a light chain variable (VL) region, wherein (a) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of AASSLQS (SEQ ID NO: 24) and LCDR3 of QQYNSYPRT (SEQ ID NO: 12);

(b) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of AASSLQS (SEQ ID NO: 24) and LCDR3 of QQYANYPRT (SEQ ID NO: 25);

(c) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of SASSLQS (SEQ ID NO: 17) and LCDR3 of QQYANYPRT (SEQ ID NO: 25);

(d) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of SASSLQS (SEQ ID NO: 17) and LCDR3 of QQYNSYPRT (SEQ ID NO: 12);

(e) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYLDY (SEQ ID NO: 18); and the VL region amino acid sequence comprises LCDR1 of RASQGIRTNVA (SEQ ID NO: 19), LCDR2 of SASYRQS (SEQ ID NO: 20) and LCDR3 of QQYNSYPRT (SEQ ID NO: 12);

(f) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYFDE (SEQ ID NO: 21); and the VL region amino acid sequence comprises LCDR1 of RASQGVRTNLA (SEQ ID NO: 22), LCDR2 of AASSRQS (SEQ ID NO: 23) and LCDR3 of QQYNSYPRT (SEQ ID NO: 12); or (g) the VH region amino acid sequence comprises HCDR1 of GYTFTDFYMN (SEQ ID NO: 180), HCDR2 of MGRIYPASGNTYYAQKFQG (SEQ ID NO: 26) and HCDR3 of GVWYYDY (SEQ ID NO: 27); and the VL region amino acid sequence comprises LCDR1 of RASQGIRTNLA (SEQ ID NO: 16), LCDR2 of AASSLQS (SEQ ID NO: 24) and LCDR3 of QQYANYPRT (SEQ ID NO: 25).

In some aspects, disclosed herein is an anti-C-KIT antibody or an antigen-binding portion thereof, wherein the antibody comprises a heavy chain variable (VH) region and a light chain variable (VL) region, wherein the VH region comprises any one of the VH region amino acid sequences in Table 12 and the VL region comprises any one of the VL region amino acid sequences in Table 12.

In some aspects, disclosed herein is an anti-C-KIT antibody or an antigen-binding portion thereof, wherein the antibody comprises a heavy chain variable (VH) region and a light chain variable (VL) region, wherein
  (a) the VH region amino acid sequence comprises or consists of SEQ ID NO:185 and the VL region amino acid sequence comprises or consists of SEQ ID NO:186;
  (b) the VH region amino acid sequence comprises or consists of SEQ ID NO:187 and the VL region amino acid sequence comprises or consists of SEQ ID NO:188;
  (c) the VH region amino acid sequence comprises or consists of SEQ ID NO:189 and the VL region amino acid sequence comprises or consists of SEQ ID NO:190;
  (d) the VH region amino acid sequence comprises or consists of SEQ ID NO:191 and the VL region amino acid sequence comprises or consists of SEQ ID NO:192;
  (e) the VH region amino acid sequence comprises or consists of SEQ ID NO:193 and the VL region amino acid sequence comprises or consists of SEQ ID NO:194; or
  (f) the VH region amino acid sequence comprises or consists of SEQ ID NO:195 and the VL region amino acid sequence comprises or consists of SEQ ID NO:196.

In some aspects, disclosed herein is an anti-C-KIT antibody or an antigen-binding portion thereof, wherein the antibody comprises a heavy chain variable (VH) region and a light chain variable (VL) region, wherein
  (a) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:185 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:186;
  (b) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:187 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:188;
  (c) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:189 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:190;
  (d) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:191 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:192;
  (e) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:193 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:194; or
  (f) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:195 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:196. In some aspects, the CDR amino acid sequences of an anti-C-KIT antibody are 100% identical to the CDR amino acid sequences in the recited sequences while the FR amino acid sequences are less than 100% identical to the FR amino acid sequences in the recited sequences.

In some aspects, the antibody or antigen-binding portion as defined herein may be isolated.

The antibody molecule or antigen-binding portion as defined herein may cross-compete for binding to C-KIT with an antibody or antigen-binding portion thereof comprising the sets of CDRs disclosed herein. In some embodiments, the invention provides an isolated anti-C-KIT antibody or an antigen-binding portion thereof, wherein the antibody or antigen-binding portion cross-competes for binding to C-KIT with the antibody or antigen-binding portion comprising the sets of CDRs disclosed herein and (a) comprises fully germline human framework amino acid sequences; and/or (b) does not comprise a deamidation site in the LCDR3; and/or (c) comprises a human germline peptide sequence with high MHC class II binding affinity in HCDR1 and/or LCDR2; and/or (d) comprises a reduced number of immunogenic peptides compared to an anti-C-KIT antibody comprising the variable domain sequences of antibody h37M (Table 2); and/or (e) exhibits reduced immunogenicity compared to an anti-C-KIT antibody comprising the variable domain sequences of antibody h37M (Table 2); and/or (f) exhibits similar potency in receptor internalization to an anti-C-KIT antibody comprising the variable domain sequences of antibody h37M (Table 2) and exhibits reduced potency in C-KIT signalling blockade to an anti-C-KIT antibody comprising the variable domain sequences of antibody h37M (Table 2); and/or (g) is immune effector null.

In some embodiments, an anti-C-KIT antibody or antigen-binding portion has low immunogenicity. In certain cases, an antibody or antigen-binding portion exhibits reduced immunogenicity compared to an anti-C-KIT antibody comprising HCDR1 of GYTFTDYYIN (SEQ ID NO: 4), HCDR2 of IARIYPGSGNTYYNEKFKG (SEQ ID NO: 5), HCDR3 of GVYYFDY (SEQ ID NO: 6), LCDR1 of KASQNVRTNVA (SEQ ID NO: 10), and LCDR2 of SASYRYS (SEQ ID NO: 11). In some examples, immunogenicity risk of an antibody or antigen-binding portion may be determined in silico by identifying the location of T cell epitopes in the antibody or portion (e.g., in the variable regions of the antibody or portion).

For example, T cell epitopes in an antibody or antigen-binding portion may be identified by using iTope™. iTope™ can used to analyse VL and VH region sequences for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class II molecules.

T cell epitopes in an antibody or antigen-binding portion may be identified by analysing VL and VH region sequences using TCED™ (T Cell Epitope Database™) to search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

In some embodiments, an anti-C-KIT antibody or antigen-binding portion may exhibit a low immunogenicity because the antibody or portion has a low number of one or more of the following peptides in its sequences: High Affinity Foreign ('HAF'—high immunogenicity risk), Low Affinity Foreign ('LAF'—lower immunogenicity risk), and/ or TCED+(previously identified epitope in TCED™ database).

In some embodiments, an anti-C-KIT antibody or antigen-binding portion may have high Germline Epitope (GE) content in its sequence. In some examples, an anti-C-KIT antibody or antigen-binding portion has 10, 11, 12, 13, 14, 15, 16, 17, 18, 19 or 20 (or greater than 20) germline epitopes in its sequence. Germline Epitope may be defined as a human germline peptide sequence with high MHC Class II binding affinity. Germline Epitope 9mer peptides are unlikely to have immunogenic potential due to T cell tolerance, as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic and can provide low immunogenicity. In some examples, an anti-C-KIT antibody or antigen-binding portion comprises a human germline peptide sequence with high MHC class II binding affinity (e.g., germline epitope) in the HCDR1 and/or LCDR2.

In certain embodiments, an anti-C-KIT antibody or antigen-binding portion may have a reduced number of HAF, LAF and/or TCED+ epitopes found in the frameworks of both the heavy and light chain variable regions compared to an anti-C-KIT antibody comprising the variable domain sequences of antibody h37M (Table 2). For example, a TCED+ and HAF peptide 'VTITCKASQ' (SEQ ID NO: 64) found in the LCDR-1 of h37M may be eliminated in an anti-C-KIT antibody or antigen-binding portion by the mutation K>R at position 6, converting this sequence to the light chain GE 'VTITCRASQ' (SEQ ID NO: 65; FIG. 11B-H). Similarly, one or both of the HAF peptides 'LIYSASSLQ' (SEQ ID NO: 66) and 'IYSASSLQS' (SEQ ID NO: 67) may be converted to GE sequences by mutation of the LCDR2 sequence to the fully germline sequence 'AASSLQS' (SEQ ID NO: 24).

In one embodiment, an anti-C-KIT antibody or antigen-binding portion comprises the HCDR1 germlining mutation I>M at position 3 of the TCED+ and HAF peptide sequence 'YYINVVVRQA' (SEQ ID NO: 68; spanning the HCDR-1 and FW2).

In some embodiments, an anti-C-KIT antibody or antigen-binding portion comprises the mutation Y>W in the HCDR3 that eliminates two LAF peptide sequences found in antibody h37M.

The terms "cross-compete", "cross-competition", "cross-block", "cross-blocked" and "cross-blocking" are used interchangeably herein to mean the ability of an antibody or portion thereof to interfere with the binding directly or indirectly through allosteric modulation of the anti-C-KIT antibodies of the invention to the target C-KIT (e.g., human C-KIT). The extent to which an antibody or portion thereof is able to interfere with the binding of another to the target, and therefore whether it can be said to cross-block or cross-compete according to the invention, can be determined using competition binding assays. One example of a binding competition assay is Homogeneous Time Resolved Fluorescence (HTRF). One particularly suitable quantitative cross-competition assay uses a FACS- or an AlphaScreen-based approach to measure competition between the labelled (e.g. His tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g. unlabeled) antibody or fragment thereof that needs to be cross-blocked) by the potentially cross-blocking antibody or fragment thereof that is present in a given amount. Preferably, cross-competing antibodies or portions thereof have a recorded displacement that is between 10% and 100%, or between 50% and 100%.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the 37M murine LCDR3 (as defined herein, i.e. the amino acid sequence QQYNSYPRT (SEQ ID NO: 12) has been identified to have a putative deamidation site at residue 4 (N). Removal this site at equivalent positions in an LCDR3 of the invention, for example by substitution (such as to A, S, E or T), is envisaged (as for example in clone MH5 and mutant derivatives of MH5, as in Tables 4 and 6).

The antibody molecule or antigen-binding portion thereof may be human, humanized or chimeric.

The antibody molecule or antigen-binding portion thereof may comprise one or more human variable domain framework scaffolds into which the CDRs have been inserted. For example, the VH region, the VL region, or both the VH and the VL region may comprise one or more human framework region (FR) amino acid sequences.

The antibody molecule or antigen-binding portion thereof may comprise an IGHV1-46 human germline scaffold into which the corresponding HCDR sequences have been inserted. The antibody molecule or antigen-binding portion thereof may comprise a VH region that comprises an IGHV1-46 human germline scaffold amino acid sequence into which a set of corresponding HCDR1, HCDR2 and HCDR3 amino acid sequences have been inserted.

The antibody molecule or antigen-binding portion thereof may comprise an IGKV1-16 human germline scaffold into which the corresponding LCDR sequences have been inserted. The antibody molecule or antigen-binding portion thereof may comprise a VL region that comprises an IGKV1-16 human germline scaffold amino acid sequence into which a set of corresponding LCDR1, LCDR2 and LCDR3 amino acid sequences have been inserted.

The antibody molecule or antigen-binding portion thereof may comprise an IGHV1-46 human germline scaffold into which the corresponding HCDR sequences have been inserted and an IGKV1-16 human germline scaffold into which the corresponding LCDR sequences have been inserted. The antibody molecule or antigen-binding portion thereof may comprise a VH region that comprises an IGHV1-46 human germline scaffold amino acid sequence into which a set of corresponding HCDR1, HCDR2 and HCDR3 amino acid sequences have been inserted and a VL region that comprises an IGKV1-16 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4 or Table 6 (with all six CDR sequences being from the same clone).

In some aspects, the antibody molecule or antigen-binding portion thereof may comprise an immunoglobulin constant region. In some aspects, the immunoglobulin constant region is IgG1, IgG2, IgG3, IgG4, IgA1 or IgA2. In additional aspects, the immunoglobulin constant region is IgG1, IgG2, IgG3, IgG4, IgA1 or IgA2. The antibody molecule or antigen-binding portion thereof may comprise an immunologically inert constant region. In some aspects, an anti-C-KIT antibody or antigen-binding portion thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some aspects, an anti-C-KIT antibody may comprise an immunoglobulin constant region comprising any one of the amino acid sequences in Table 13. The Fc region sequences in Table 13 begin at the CH1 domain. In some aspects, an anti-C-KIT antibody may comprise an immunoglobulin constant region comprising an amino acid sequence of an Fc region of human IgG1, human IgG1-3M or human IgG1-4M. For example, the human IgG1-3M Fc region comprises the following substitutions: L234A, L235A and G237A, while the human IgG1-4M Fc region comprises the following substitutions: L234A, L235A, G237A and P331S. In some aspects, a position of an amino acid residue in a constant region of an immunoglobulin molecule is numbered according to EU nomenclature (Ward et al., 1995 *Therap. Immunol.* 2:77-94). In some aspects, an immunoglobulin constant region may comprise an RDELT (SEQ ID NO:203) motif or an REEM (SEQ ID NO:204) motif (underlined in Table 13). The REEM (SEQ ID NO:204) allotype is found in a smaller human population than the RDELT (SEQ ID NO:203) allotype. In some aspects, an anti-C-KIT antibody may comprise an immunoglobulin constant region comprising any one of SEQ ID NOs:197-202. In some aspects, an anti-C-KIT antibody may comprise the six CDR amino acid sequences of any one of the clones in Table 4 or 6 and any one of the Fc region amino acid sequences in Table 13. In some aspects, an anti-C-KIT antibody may comprise an immunoglobulin heavy chain constant region comprising any one of the Fc region amino acid sequences in Table 13 and an immunoglobulin light chain constant region that is a kappa light chain constant region or a lambda light chain constant region.

In some aspects, disclosed herein is an anti-C-KIT antibody or an antigen-binding portion thereof, wherein the antibody comprises a heavy chain variable (VH) region, a light chain variable (VL) region and a heavy chain constant region, wherein
 (a) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); the VL region amino acid sequence comprises LCDR1 of RASQGIRTNLA (SEQ ID NO: 16), LCDR2 of AASSLQS (SEQ ID NO: 24) and LCDR3 of QQYNSYPRT (SEQ ID NO: 12); and the heavy chain constant region comprises SEQ ID NO:197, SEQ ID NO:198, SEQ ID NO:199, SEQ ID NO:200, SEQ ID NO:201 or SEQ ID NO:202;
 (b) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); the VL region amino acid sequence comprises LCDR1 of RASQGIRTNLA (SEQ ID NO: 16), LCDR2 of AASSLQS (SEQ ID NO: 24) and LCDR3 of QQYANYPRT (SEQ ID NO: 25); and the heavy chain constant region comprises SEQ ID NO:197, SEQ ID NO:198, SEQ ID NO:199, SEQ ID NO:200, SEQ ID NO:201 or SEQ ID NO:202;

(c) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); the VL region amino acid sequence comprises LCDR1 of RASQGIRTNLA (SEQ ID NO: 16), LCDR2 of SASSLQS (SEQ ID NO: 17) and LCDR3 of QQYANYPRT (SEQ ID NO: 25); and the heavy chain constant region comprises SEQ ID NO:197, SEQ ID NO:198, SEQ ID NO:199, SEQ ID NO:200, SEQ ID NO:201 or SEQ ID NO:202;

(d) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); the VL region amino acid sequence comprises LCDR1 of RASQGIRTNLA (SEQ ID NO: 16), LCDR2 of SASSLQS (SEQ ID NO: 17) and LCDR3 of QQYNSYPRT (SEQ ID NO: 12); and the heavy chain constant region comprises SEQ ID NO:197, SEQ ID NO:198, SEQ ID NO:199, SEQ ID NO:200, SEQ ID NO:201 or SEQ ID NO:202;

(e) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYLDY (SEQ ID NO: 18); the VL region amino acid sequence comprises LCDR1 of RASQGIRTNVA (SEQ ID NO: 19), LCDR2 of SASYRQS (SEQ ID NO: 20) and LCDR3 of QQYNSYPRT (SEQ ID NO: 12); and the heavy chain constant region comprises SEQ ID NO:197, SEQ ID NO:198, SEQ ID NO:199, SEQ ID NO:200, SEQ ID NO:201 or SEQ ID NO:202;

(f) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYFDE (SEQ ID NO: 21); the VL region amino acid sequence comprises LCDR1 of RASQGVRTNLA (SEQ ID NO: 22), LCDR2 of AASSRQS (SEQ ID NO: 23) and LCDR3 of QQYNSYPRT (SEQ ID NO: 12); and the heavy chain constant region comprises SEQ ID NO:197, SEQ ID NO:198, SEQ ID NO:199, SEQ ID NO:200, SEQ ID NO:201 or SEQ ID NO:202; or (g) the VH region amino acid sequence comprises HCDR1 of GYTFTDFYMN (SEQ ID NO: 180), HCDR2 of MGRIYPASGNTYYAQKFQG (SEQ ID NO: 26) and HCDR3 of GVWYYDY (SEQ ID NO: 27); the VL region amino acid sequence comprises LCDR1 of RASQGIRTNLA (SEQ ID NO: 16), LCDR2 of AASSLQS (SEQ ID NO: 24) and LCDR3 of QQYANYPRT (SEQ ID NO: 25); and the heavy chain constant region comprises SEQ ID NO:197, SEQ ID NO:198, SEQ ID NO:199, SEQ ID NO:200, SEQ ID NO:201 or SEQ ID NO:202.

In some aspects, disclosed herein is an anti-C-KIT antibody or an antigen-binding portion thereof, wherein the antibody comprises a heavy chain variable (VH) region, a light chain variable (VL) region and a heavy chain constant region, wherein (a) the VH region amino acid sequence comprises or consists of SEQ ID NO:185, the VL region amino acid sequence comprises or consists of SEQ ID NO:186 and the heavy chain constant region comprises a wild-type human IgG1 constant region, a human IgG1 constant region comprising the amino acid substitutions L234A, L235A and G237A or a human IgG1 constant region comprising the amino acid substitutions L234A, L235A, G237A and P331S;

(b) the VH region amino acid sequence comprises or consists of SEQ ID NO:187, the VL region amino acid sequence comprises or consists of SEQ ID NO:188 and the heavy chain constant region comprises a wild-type human IgG1 constant region, a human IgG1 constant region comprising the amino acid substitutions L234A, L235A and G237A or a human IgG1 constant region comprising the amino acid substitutions L234A, L235A, G237A and P331S;

(c) the VH region amino acid sequence comprises or consists of SEQ ID NO:189, the VL region amino acid sequence comprises or consists of SEQ ID NO:190 and the heavy chain constant region comprises a wild-type human IgG1 constant region, a human IgG1 constant region comprising the amino acid substitutions L234A, L235A and G237A or a human IgG1 constant region comprising the amino acid substitutions L234A, L235A, G237A and P331S;

(d) the VH region amino acid sequence comprises or consists of SEQ ID NO:191, the VL region amino acid sequence comprises or consists of SEQ ID NO:192 and the heavy chain constant region comprises a wild-type human IgG1 constant region, a human IgG1 constant region comprising the amino acid substitutions L234A, L235A and G237A or a human IgG1 constant region comprising the amino acid substitutions L234A, L235A, G237A and P331S;

(e) the VH region amino acid sequence comprises or consists of SEQ ID NO:193, the VL region amino acid sequence comprises or consists of SEQ ID NO:194 and the heavy chain constant region comprises a wild-type human IgG1 constant region, a human IgG1 constant region comprising the amino acid substitutions L234A, L235A and G237A or a human IgG1 constant region comprising the amino acid substitutions L234A, L235A, G237A and P331S; or (f) the VH region amino acid sequence comprises or consists of SEQ ID NO:195, the VL region amino acid sequence comprises or consists of SEQ ID NO:196 and the heavy chain constant region comprises a wild-type human IgG1 constant region, a human IgG1 constant region comprising the amino acid substitutions L234A, L235A and G237A or a human IgG1 constant region comprising the amino acid substitutions L234A, L235A, G237A and P331S.

In some aspects, disclosed herein is an anti-C-KIT antibody or an antigen-binding portion thereof, wherein the antibody comprises a heavy chain variable (VH) region, a light chain variable (VL) region and a heavy chain constant region, wherein (a) the VH region amino acid sequence comprises or consists of SEQ ID NO:185, the VL region amino acid sequence comprises or consists of SEQ ID NO:186 and the heavy chain constant region comprises SEQ ID NO:197, SEQ ID NO:198, SEQ ID NO:199, SEQ ID NO:200, SEQ ID NO:201 or SEQ ID NO:202;

(b) the VH region amino acid sequence comprises or consists of SEQ ID NO:187, the VL region amino acid sequence comprises or consists of SEQ ID NO:188 and the heavy chain constant region comprises SEQ ID NO:197, SEQ ID NO:198, SEQ ID NO:199, SEQ ID NO:200, SEQ ID NO:201 or SEQ ID NO:202;

(c) the VH region amino acid sequence comprises or consists of SEQ ID NO:189, the VL region amino acid sequence comprises or consists of SEQ ID NO:190 and the heavy chain constant region comprises SEQ ID NO:197, SEQ ID NO:198, SEQ ID NO:199, SEQ ID NO:200, SEQ ID NO:201 or SEQ ID NO:202;

(d) the VH region amino acid sequence comprises or consists of SEQ ID NO:191, the VL region amino acid sequence comprises or consists of SEQ ID NO:192 and the heavy chain constant region comprises SEQ ID NO:197, SEQ ID NO:198, SEQ ID NO:199, SEQ ID NO:200, SEQ ID NO:201 or SEQ ID NO:202;

(e) the VH region amino acid sequence comprises or consists of SEQ ID NO:193, the VL region amino acid sequence comprises or consists of SEQ ID NO:194 and the heavy chain constant region comprises SEQ ID NO:197, SEQ ID NO:198, SEQ ID NO:199, SEQ ID NO:200, SEQ ID NO:201 or SEQ ID NO:202; or (f) the VH region amino acid sequence comprises or consists of SEQ ID NO:195, the VL region amino acid sequence comprises or consists of SEQ ID NO:196 and the heavy chain constant region comprises SEQ ID NO:197, SEQ ID NO:198, SEQ ID NO:199, SEQ ID NO:200, SEQ ID NO:201 or SEQ ID NO:202.

In some aspects, an anti-C-KIT antibody may be immune effector null. In some aspects, an anti-C-KIT antibody or an antigen-binding portion thereof does not induce immune effector function and, optionally, suppresses immune effector function. In some aspects, an anti-C-KIT antibody may lack measurable binding to human FcγRI, FcγRIIa, FcγRIIIa and FcγRIIIb receptors but maintain binding to human FcγRIIb receptor and optionally maintain binding to human FcRn receptor. FcγRI, FcγRIIa, FcγRIIIa and FcγRIIIb are examples of activating receptors. FcγRIIb is an example of an inhibitory receptor. FcRn is an example of a recycling receptor. In some aspects, binding affinity of an anti-C-KIT antibody or an antigen-binding portion thereof for human Fc receptors may be measured by BIACORE® analysis. In some aspects, Homogeneous Time Resolved Fluorescence (HTRF) can be used to study binding of an anti-C-KIT antibody to human Fc receptors. In one example of HTRF, human IgG1 (wild type) is labelled, as is the full suite of Fc gamma receptors and then antibodies with engineered Fc fragments are used in titration competition. In some aspects, KIT-positive cells may be mixed with human white blood cells and anti-C-KIT antibodies, and cell killing by CDC, ADCC and/or ADCP may be measured. In some aspects, an anti-C-KIT antibody may comprise an amino acid sequence of an Fc region of human IgG1-3M or human IgG1-4M (see Table 13) is effector null. In some aspects, an anti-C-KIT antibody may comprise an amino acid sequence of an Fc region of human IgG1-3M or human IgG1-4M (see Table 13) is not effector null.

The antibody molecule or antigen-binding portion thereof may be a Fab fragment, a F(ab)$_2$ fragment, an Fv fragment, a tetrameric antibody, a tetravalent antibody, a multispecific antibody (for example, a bispecific antibody), a domain-specific antibody, a single domain antibody, a monoclonal antibody or a fusion protein. In one embodiment, an antibody may be a bispecific antibody that binds specifically to a first antigen and a second antigen, wherein the first antigen is C-KIT and the second antigen is not C-KIT. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked to a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the antifolates, *vinca* alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, down-regulate self-antigen expression, or mask MHC antigens.

Also provided is a nucleic acid molecule encoding the antibody molecule or antigen-binding portion thereof of the invention as defined herein. An isolated nucleic acid molecule may encode (a) the VH region amino acid sequence; (b) the VL region amino acid sequence; or (c) both the VH and the VL region amino acid sequences of an anti-C-KIT antibody or an antigen-binding portion thereof described herein.

Further provided is a vector comprising the nucleic acid molecule of the invention as defined herein. The vector may be an expression vector. The vector may further comprise one or more regulatory sequences (e.g., a promoter and/or an enhancer).

Also provided is a host cell comprising the nucleic acid molecule or the vector of the invention as defined herein. The host cell may be a recombinant host cell.

In a further aspect there is provided a method of producing an anti-C-KIT antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

The cancer may for example be selected from the group consisting of: Gastrointestinal Stromal cancer (GIST), pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The autoimmune disease or inflammatory disease may be selected from the group consisting of: arthritis, asthma, multiple sclerosis, psoriasis, Crohn's disease, inflammatory bowel disease, lupus, Grave's disease and Hashimoto's thyroiditis, and ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of a cardiovascular disease or a fibrotic disease.

The cardiovascular disease in any aspect of the invention may for example be coronary heart disease or atherosclerosis.

The fibrotic disease in any aspect of the invention may be selected from the group consisting of myocardial infarction, angina, osteoarthritis, pulmonary fibrosis, asthma, cystic fibrosis and bronchitis.

In one embodiment, the invention provides an anti-C-KIT antibody or an antigen-binding portion thereof comprising the amino acid sequences disclosed herein for use in therapy.

The pharmaceutical composition of the invention may comprise a pharmaceutically acceptable excipient, carrier or diluent. A pharmaceutically acceptable excipient may be a compound or a combination of compounds entering into a pharmaceutical composition which does not provoke secondary reactions and which allows, for example, facilitation of the administration of the anti-C-KIT antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-C-KIT antibody molecule.

In some embodiments, the anti-C-KIT antibody molecule may be provided in a lyophilised form for reconstitution prior to administration. For example, lyophilised antibody molecules may be re-constituted in sterile water and mixed with saline prior to administration to an individual.

The anti-C-KIT antibody molecules will usually be administered in the form of a pharmaceutical composition, which may comprise at least one component in addition to the antibody molecule. Thus pharmaceutical compositions may comprise, in addition to the anti-C-KIT antibody molecule, a pharmaceutically acceptable excipient, carrier, buffer, stabilizer or other materials well known to those skilled in the art. Such materials should be non-toxic and should not interfere with the efficacy of the anti-C-KIT antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-C-KIT antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-C-KIT antibody molecule may be administered alone or in combination with other treatments, either simultaneously or sequentially dependent upon the condition to be treated.

An anti-C-KIT antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-C-KIT antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-C-KIT antibody molecules as described herein may be administered as sub-cutaneous injections. Sub-cutaneous injections may be administered using an auto-injector, for example for long or short-term prophylaxis/treatment.

In some preferred embodiments, the therapeutic effect of the anti-C-KIT antibody molecule may persist for several multiples of the antibody half-life in serum, depending on the dose. For example, the therapeutic effect of a single dose of the anti-C-KIT antibody molecule may persist in an individual for 1 month or more, 2 months or more, 3 months or more, 4 months or more, 5 months or more, or 6 months or more.

The invention also provides a method of producing an antibody molecule which specifically binds to human C-KIT and optionally also to cynomolgus monkey C-KIT or an antigen-binding portion thereof, comprising the steps of:

(1) grafting anti-C-KIT CDRs from a non-human source into a human v-domain framework to produce a humanized anti-C-KIT antibody molecule or antigen-binding portion thereof;

(2) generating a phage library of clones of the humanized anti-C-KIT antibody molecule or antigen-binding portion thereof comprising one or more mutations in the CDRs;

(3) selecting the phage library for binding to human C-KIT and optionally also to cynomolgus monkey C-KIT;

(4) screening clones from the selection step (3) having binding specificity to human C-KIT and optionally also to cynomolgus monkey C-KIT; and (5) producing an antibody molecule which specifically binds to human C-KIT and optionally also to cynomolgus monkey C-KIT, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Refinements applicable to the above method are as described in Example 1 below.

As used herein, the term "C-KIT" refers to CD117 (Cluster of Differentiation 117) and variants thereof that retain at least part of the biological activity of C-KIT. This protein is also known as KIT, PBT, SCFR and KIT proto-oncogene receptor tyrosine kinase. As used herein, C-KIT includes all mammalian species of native sequence C-KIT, including human, rat, mouse and chicken. The term "C-KIT" is used to include variants, isoforms and species homologs of human C-KIT. Examples of human C-KIT sequences are provided in Table 14. Antibodies of the invention may cross-react with C-KIT from species other than human, in particular C-KIT from cynomolgus monkey (*Macaca fascicularis*). In certain embodiments, the antibodies may be completely specific for human C-KIT and do not exhibit non-human cross-reactivity.

As used herein, an "antagonist" as used in the context of the antibody of the invention or an "anti-C-KIT antagonist antibody" (interchangeably termed "anti-C-KIT antibody") refers to an antibody which is able to bind to C-KIT and inhibit C-KIT biological activity and/or downstream pathway(s) mediated by C-KIT signalling. An anti-C-KIT antagonist antibody encompasses antibodies that can block, antagonize, suppress or reduce (including significantly) C-KIT biological activity, including downstream pathways mediated by C-KIT signalling, such as receptor binding and/or elicitation of a cellular response to C-KIT. For the purposes of the present invention, it will be explicitly understood that the term "anti-C-KIT antagonist antibody" encompass all the terms, titles, and functional states and characteristics whereby C-KIT itself, and C-KIT biological activity (including but not limited to its ability to enhance the activation of phagocytosis by cells of the myeloid lineage), or the consequences of the activity or biological activity, are substantially nullified, decreased, or neutralized in any meaningful degree.

The antibody "specifically binds" "specifically interacts", "preferentially binds", "binds" or "interacts" with C-KIT if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen-binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen-binding portion" of an antibody molecule, as used herein, refers to one or more fragments of an intact antibody that retain the ability to specifically bind to C-KIT. Antigen-binding functions of an antibody molecule can be performed by fragments of an intact antibody. Examples of binding fragments encompassed within the term "antigen binding-portion" of an antibody molecule include Fab; Fab'; F(ab')$_2$; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" or "v-domain" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, and contribute to the formation of the antigen binding site of antibodies. When choosing FRs to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (a "Unified" definition) incorporates the lessons of all such prior insights and includes all appropriate loop positions required to sample the full residue landscape that potentially mediates target-binding complementarity.

Table 1 shows the amino acid sequences of the 37M murine anti-C-KIT antibody CDRs as defined herein (a "Unified" scheme), in comparison to well-known alternative systems for defining the same CDRs.

As used herein the term "conservative substitution" refers to replacement of an amino acid with another amino acid which does not significantly deleteriously change the functional activity. A preferred example of a "conservative substitution" is the replacement of one amino acid with another amino acid which has a value ≥0 in the following BLOSUM 62 substitution matrix (see Henikoff & Henikoff, 1992, PNAS 89: 10915-10919):

alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4. |

As used herein, "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage sequence identity is calculated by determining the number of positions at which the identical nucleic acid base or amino acid residue occurs in both sequences to yield the number of identical positions. The number of identical positions is then divided by the total number of positions in the comparison window and multiplied by 100 to yield the percentage of sequence identity. Percentage of sequence identity is determined by comparing two optimally aligned sequences over a comparison window. The comparison window for polynucleotide sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal sequence identity" or "substantial sequence identity" if the two sequences have at least 80%, at least 85%, at least 90%, at least 95%, at least 96%, at least 97%, at least 98%, or at least 99% sequence identity relative to each other.

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding sub-sequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to C-KIT, which is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen-binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a BIA-CORE® system.

The term "potency" is a measurement of biological activity and may be designated as $IC_{50}$, or effective concentration of an antibody or antibody drug conjugate to the antigen C-KIT to inhibit 50% of activity measured in a C-KIT activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to C-KIT.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neo-adjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-C-KIT Therapeutic Antibodies

Introduction

In this example, we successfully generated a panel of antagonistic, optimized anti-C-KIT antibodies. These anti-C-KIT antibodies were well expressed, biophysically stable, highly soluble and of maximized amino acid sequence identity to preferred human germlines.

Materials and Methods

IgG Cloning, Transient Expression, Purification

Antibody v-domain encoding DNA sequences were cloned via restriction-ligation cloning into separate IgG heavy and light-chain expression cassettes in separate plasmid vectors.

Antibodies were expressed in two human IgG1 formats: IgG1 and IgG1null—IgG1 with the lower hinge mutations L234A/L235A/G237A, which minimise Fcγ receptor-driven effector functions. IgGs were expressed in HEK-293expi cells after transient transfection with endotoxin-free IgG expression plasmid preparations, per manufacturer's protocols. IgGs were purified using a single-step protocol: Conditioned media were loaded (neat) onto a 1 ml ProA sepharose column, pre-equilibrated in PBS pH7.4. The column was washed with 5 column volumes of PBS pH7.4, before the protein was eluted with 100 mM glycine, pH 2.7 and subjected to dialysis in PBS pH 7.4 using 30 kDa cutoff dialysis membrane.

IgG Titration Binding ELISAs

To coat Greiner Bio-One High bind ELISA plates, target proteins were diluted to 1 µg/ml in carbonate buffer and added at 100 µl per well, at 4° C., o/n. Coated plates were washed 3× with PBS pH7.4, blocked with 1% BSA in PBS (380 µl/well) for 1 hr at RT, then washed 3× with PBS-Tween 20 (PBST). C-KIT antibodies (100 µl/well; diluted in PBST) were then added and then incubated 1 hr at RT. Plates were then washed 3× with PBST and goat anti-human kappa chain-HRP added (100 µl/well) at RT, for 1 hr. Plates were then washed 3× with PBST and twice with PBS before the addition of 100 µl TMB per well. Reactions were stopped by adding 100 µl 2M $H_2SO_4$/well and OD was read on a plate reader at 450 nm.

Anti-C-KIT antibodies were tested for polyreactivity by ELISA. Purified, recombinant, target and non-target antigens were coated in 96-well Nunc maxisorp plates at 100 ng per well in carbonate buffer, at 4° C. overnight. Plates were then washed 3× with PBS, blocked with 1% BSA in PBS, then washed 3× with PBS-Tween20. A dilution series of primary antibodies was then applied, plates were washed 3× with PBS-Tween20 followed by application of goat anti-human kappa chain-HRP 1:4,000 secondary antibody. Wells were then washed 3× with PBS-Tween20 and 2× with PBS, 100 µl TMB peroxidase substrate was added per well, the reaction was stopped by adding 100 µl 2M $H_2SO_4$ and absorbances were read at 450 nm. IgG binding analysis via ELISA on negatively charged biomolecular surfaces were performed as previously described (see Mouquet et al., 2010, Nature 467: 591-595).

C-KIT Library Generation and Selection

The C-KIT scFv repertoire was assembled by mass oligonucleotide synthesis and PCR. The amplified scFv repertoire was then cloned via restriction-ligation into a phagemid vector, transformed into *E. coli* TG-1 cells, and the phage repertoire rescued essentially as previously described in detail (Finlay et al., 2011, Methods Mol Biol 681: 383-401).

Phage selections were performed by coating streptavidin magnetic microbeads with C-KIT-Fc protein (either human or cyno), washing the beads thrice with PBS and resuspending in PBS pH7.4 plus 5% skim milk protein (MPBS). These beads were coated at 200 nM target protein in round 1 of selection, followed by 100, 50 and 10 nM in subsequent rounds.

HTRF Binding Competition Assay

A competition homogeneous time resolved fluorescence (HTRF) assay was established to examine epitope competition against h37M IgG by grafted and library-derived clones. The purified h37M IgG1 was labelled with terbium using a labelling kit (CisBio) per the manufacturers instructions. The final reaction mix contained biotinylated human C-KIT-Fc, SA-XL665 (CisBio), terbium-labelled parental h37M, and competitor IgG of interest, prepared as described above, in a total reaction volume of 20 µl in 1× assay buffer [50 mM sodium phosphate, pH 7.5, 400 mM potassium fluoride, and 0.1% BSA (w/v)]. Reagents were added sequentially into 384-well low-volume black plates (Nunc). Reactions proceeded for 1 h at room temperature, and plates were subsequently read on a plate reader with excitation at 340 nm and two emission readings at 615 nm (measuring input donor fluorescence from h37M-terbium) and 665 nm (measuring output acceptor fluorescence from SAXL665). Readings were expressed as 665 nm/615 nm ratios.

Antibody v-Domain T Cell Epitope Content: In Silico Analyses

In silico technologies (Abzena, Ltd.), which are based on identifying the location of T cell epitopes in therapeutic antibodies and proteins, were used for assessing potential immunogenicity in antibody v-domains. iTope™ was used to analyse the VL and VH sequences of key leads for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class II molecules.

In addition, the sequences were analysed using TCED™ (T Cell Epitope Database™) search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

BIACORE® Analyses of IgG Affinity for Human Fc Receptors

Interaction affinities for IgGs were determined by surface plasmon resonance using a BIACORE® T200 instrument. For most analyses, His6-tagged FcγRI, FcγRIIa (167R and 167H variants), FcγRIIb, FcγRIIIa (176F and 176 V variants), and FcγRIIIb receptors (all Sino Biological) were captured on a CM5 sensor chip coated with an anti-HIS antibody by standard amine coupling. Receptor-specific formats of analyses were then applied, as below.

FcγRI is a high-affinity receptor for IgG1 monomers, so 1:1 kinetic analysis was performed under the following conditions: 'single cycle' analysis using flow rate 30 µl/min, receptor protein loaded to ~30 RU at 10 µl/min (diluted 0.25 µg/ml in HBS-P+), 5 point three-fold dilution of purified antibodies titrated 0.411 nM to 33.33 nM applied with an association time of 200 s, dissociation time of 300 s. Regeneration with 2× injections glycine pH 1.5 and analysis using 1:1 fit.

The interactions between monomeric IgG and FcγRII and FcγRIII receptors are relatively low affinity interactions, so 'steady state' affinity analyses were performed under the following conditions: flow rate 30 µl/min, receptor protein loaded to ~60 RU at 10 µl/min (diluted 0.25 µg/ml in HBS-P+), 5 point three-fold dilution series of purified antibodies titrated between 33 nM and 24000 nM applied with an association time of 30 s, dissociation time of 25 s. Regeneration with 2× injections glycine pH 1.5 and analysis using steady state affinity calculation.

The interactions between monomeric IgG and FcRn are relatively low affinity and pH-sensitive interactions, so 'steady state' affinity analyses were performed under the following conditions: A CM5 chip was directly coupled with hFcRn in sodium acetate pH 5.5 using standard amine chemistry. Running buffer was PBS 0.05% P20+150 mM NaCl (pH 6.0 or pH 7.4), flow rate 30 µl/min, 5 point three-fold dilutions of purified antibodies from 3000 nM to 37.0 nM applied with an association time of 18s, dissociation time 100 s. Regeneration with 0.1 M Tris pH 8.0 and analysis using steady state affinity calculation.

Antibody v-Domain Specificity Testing: Human Receptor Array Analyses

Human cell membrane receptor proteome arrays were performed at Retrogenix Ltd. Primary screens: IgG1-h37M and IgG1-MH1 antibodies were screened for binding against fixed HEK293 cells/slides expressing 5528 human plasma membrane and cell surface-tethered secreted proteins individually (n=2 slides per slide set). All transfection efficiencies exceeded the minimum threshold. Antibody binding was detected using AF647 fluorescent secondary anti-human IgG1 antibody. Primary hits (duplicate spots) were identified by analysing fluorescence (AF647 and ZsGreen1) on ImageQuant. Vectors encoding all hits were sequenced to confirm their correct identities. Confirmation/specificity screens: Vectors encoding all hits, plus control vectors encoding MS4A1 (CD20), EGFR and other proteins, were spotted in duplicate on new slides, and used to reverse transfect human HEK293 cells as before. All transfection efficiencies exceeded the minimum threshold. Identical fixed slides were treated with 0.5 and 2 µg/ml of each test antibody, 1 µg/ml of the negative control antibody, 1 µg/ml Rituximab biosimilar (positive control), or no test molecule (secondary only; negative control) (n=1 slide per treatment). Slides were analysed as above.

Analyses of Internalisation and Cell-Killing Potential in Armed Antibody Formats CHO cells stably expressing human or cyno c-KIT, grown in Ham's F12 media containing 20% Fetal Bovine Serum, 1 mM L-Glutamine and 1 µg/ml G418 were seeded into 384-well black clear bottomed tissue culture treated assay plates (500 cells in 30 µl per well) and incubated overnight in a $CO_2$ incubator at 37° C. Purified antibodies were serially diluted in media then an equal volume of 120 nM Fab-ZAP added (Advanced Targeting Systems, IT-51). The antibody/Fab-ZAP mixtures were incubated for 30 minutes at 37° C. before being added (10 µl per well) to the cell assay plates. The cells were incubated for 72 hours in $CO_2$ incubator at 37° C. On each plate, background controls (media only) and Fab-ZAP control wells (cells incubated with FAB-ZAP reagent but no c-KIT antibody) were included for the purposes of data normalisation. At the end of the 72-hour incubation, cell viability was determined using the CellTiter-Glo® Cell Viability assay (Promega G7571) according to the manufacturer's instructions. The relative luminescent signal (RLU) for each well was measured using the BMG FLUOstar Omega plate reader. The data was blank corrected by subtraction of the RLU signal of the media only wells and expressed as a % of the blank corrected signal of the Fab-ZAP control wells.

TF-1 cells in RPMI media containing 10% Fetal Bovine Serum, 2 mM L-Glutamine, 10 mM HEPES, 4.5 g/l D-Glucose, penicillin, streptomycin and 2 ng/ml GM-CSF were seeded into 96-well black clear bottomed tissue culture treated assay plates (2500 cells in 75 µl per well). Purified antibodies were serially diluted in media then an equal volume of 40 nM Fab-ZAP added. The antibody/Fab-ZAP mixtures were incubated for 30 minutes at 37° C. before being added (25 µl per well) to the cell assay plates. The cells were incubated for 72 hours in $CO_2$ incubator at 37° C. On each plate, background controls (media only) and Fab-ZAP control wells (cells incubated with FAB-ZAP reagent but no c-KIT antibody) were included for the purposes of data normalisation. At the end of the 72-hour incubation, cell viability was determined using the CellTiter-Glo® Cell Viability assay (Promega G7571) according to the manufacturer's instructions. The relative luminescent signal (RLU) for each well was measured using the BMG FLUOstar Omega plate reader. The data was blank corrected by subtraction of the RLU signal of the media only wells and expressed as a % of the blank corrected signal of the Fab-ZAP control wells.

Analyses of Antibody Potency in C-KIT Receptor Activity Neutralisation

TF-1 cells in RPMI media containing 10% Fetal Bovine Serum, 2 mM L-Glutamine, 10 mM HEPES, 4.5 g/l D-Glucose, penicillin, streptomycin and 2 ng/ml GM-CSF were seeded into 96-well clear bottomed tissue culture treated assay plates. Purified antibodies were serially diluted in media then added to the cell assay plates and incubated for 60 minutes at 37° C. Recombinant h-SCF was then added at 50 ng/ml and the cells were incubated for 72 hours in $CO_2$ incubator at 37° C. On each plate, background controls (media only) were included for the purposes of data normalisation. At the end of the 72-hour incubation, cell viability was determined using the resazurin fluorescence viability assay according to the manufacturer's instructions.

Results and Discussion

CDR Grafting onto Preferred Human Germline v-Genes

The CDRs of an antagonistic murine anti-C-KIT IgG 37M (37M; see WO2014018625A1 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV1-46 and IGKV1-16, which are known to have good solubility, high physical stability and are used at high frequency in the expressed human antibody repertoire.

Those scaffolds and grafted CDR definitions are outlined in Table 2. The heavy and light chain sequences for chimeric anti-C-KIT antibody m37M and humanized h37M are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. Indeed, the inclusion of multiple murine residues in the framework regions of h37M are indicative that full target binding affinity could not be maintained in the direct CDR graft into germline frameworks. The IGHV1-46/IGKV1-16 graft was therefore taken forward as the template for CDR mutagenesis and selection of improved clones.

Library Generation and Screening

The CDR-grafted IGKV1-16/IGHV1-46 v-domain sequences were combined into a VL-VH scFv format and a mutagenesis library cassette was generated by mass oligonucleotide synthesis and assembly. The final scFv library was ligated into a phage display vector and transformed into E. coli via electroporation to generate $1.0 \times 10^9$ independent clones. Library build quality was verified by sequencing 96 clones. This sequencing data showed that the positions encoding either the murine or human germline residue at each position of variance had been effectively sampled at a frequency of approximately 50%. Libraries were rescued using helper phage M13 and selections performed on biotinylated human and cynomolgus monkey C-KIT-Fc proteins in multiple separate branches.

Figure 1B:
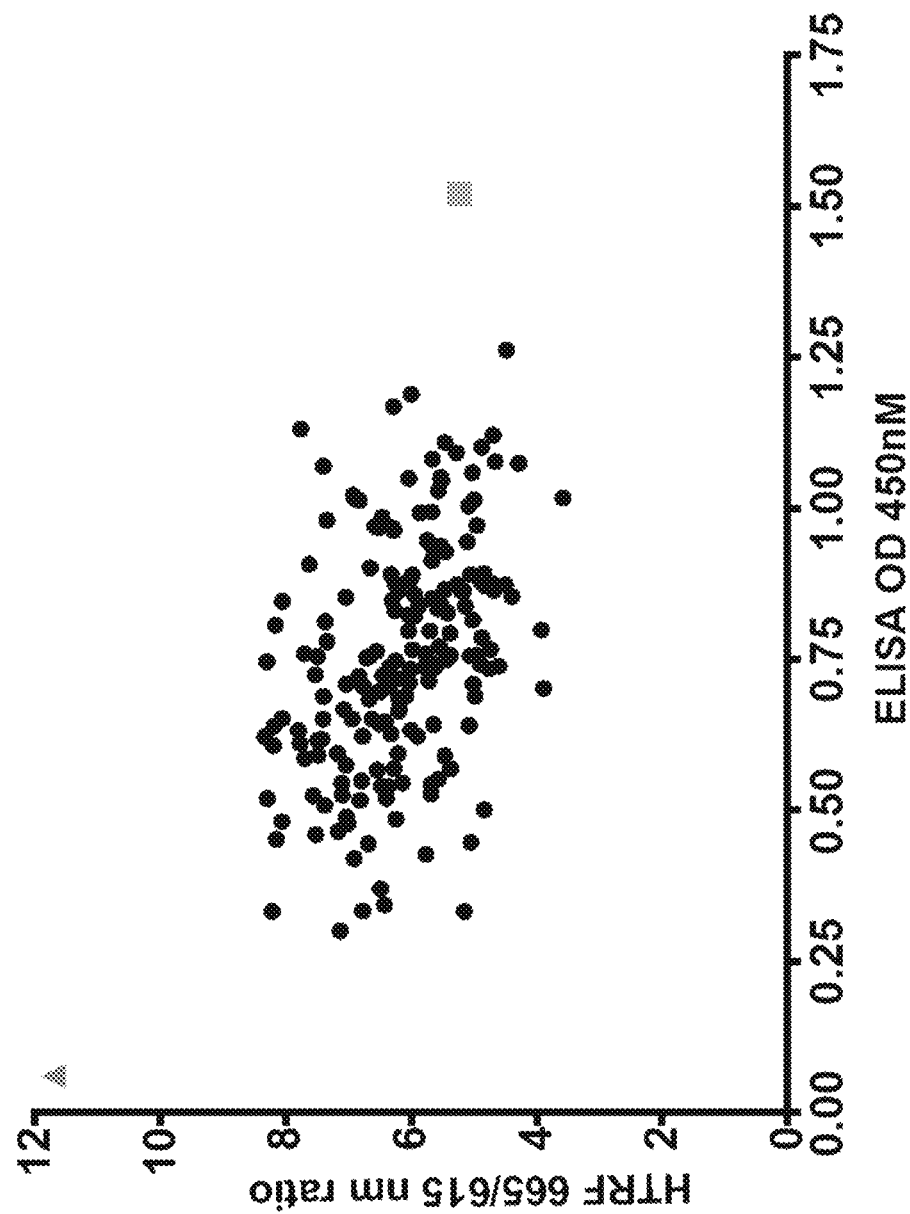

Post-selection screening (as shown in FIG. 1) and DNA sequencing revealed the presence of 219 unique, human and mouse C-KIT-binding scFv clones that retained epitope binding competition with h37M IgG1 and contained significantly increased human content within the CDRs, while the framework sequences remained fully germline. Amongst these 219 clones, germ-lining mutations were observed in all CDRs (Table 3). Lead clones were ranked based on the level of CDR germ-lining versus ELISA and HTRF signals for both human and cyno C-KIT-Fc (FIG. 1). The v-domains of the 13 top clones from this ranking were then sub-cloned into IgG expression vectors for further testing as below (Table 4).

Figure 2A:
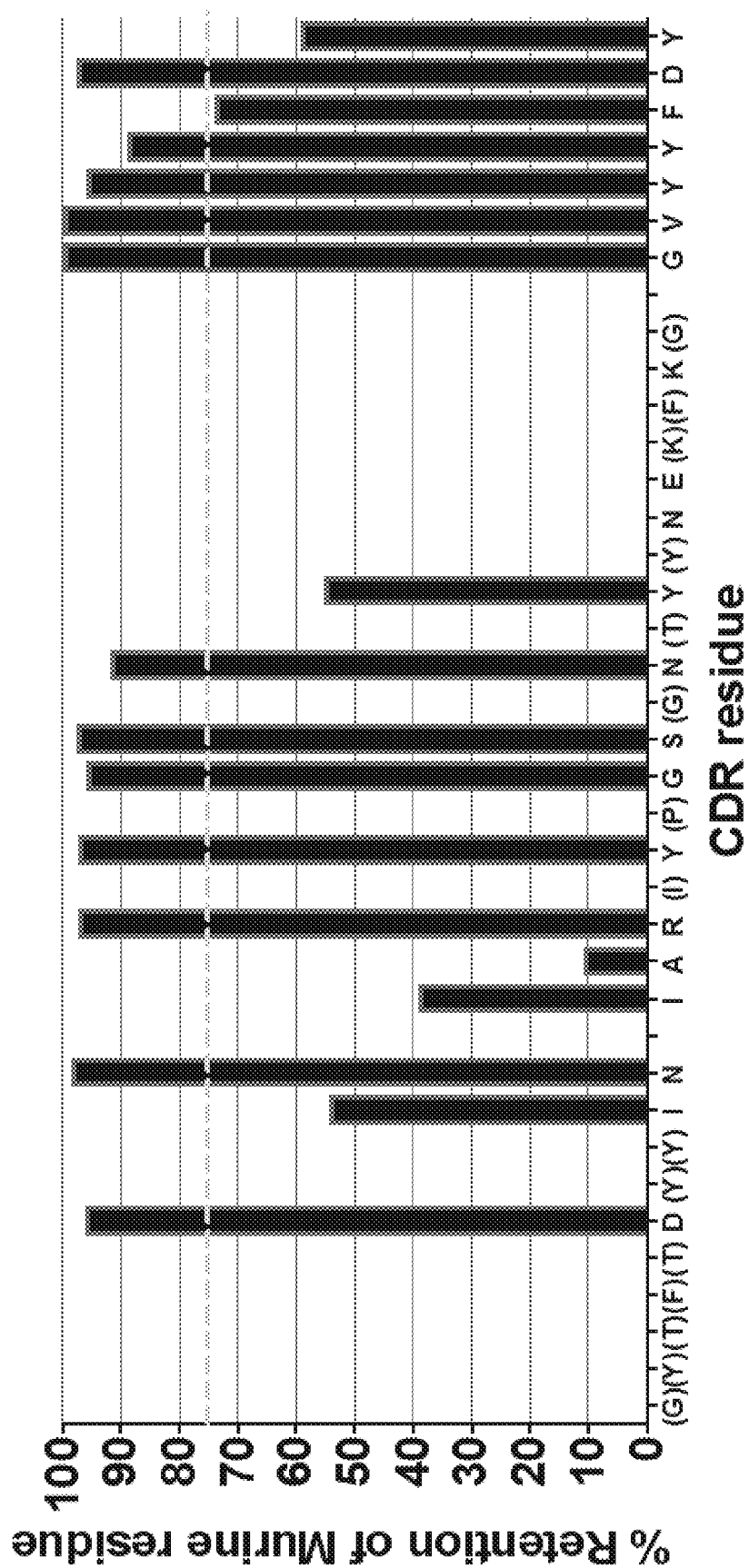
FIG. 2A-FIG. 2B. Analysis of CDR residue tolerance for mutation to germline. A plot of murine amino acid retention frequencies in the CDRs (SEQ ID NOs: 4, 5 and 6) of the ELISA-positive population of 219 unique scFv clones is shown for $V_H$ (FIG. 2A) and $V_L$ (FIG. 2B) domains, respectively. Only those residues targeted for human/murine residue mutagenesis are plotted, other than in the HCDR3. CDR residues noted in parentheses on the X-axes were identical to those found in the human germlines used for grafting (IGKV1-16 and IGHV1-46). Those residues in the HCDR2 that are not in parentheses, but whose values are set at 0, were mutated to human germline during the grafting process. In both plots the dashed line in grey at 75% represents the cut off for tolerance of murine residue replacement by human germline.
Figure 2B:
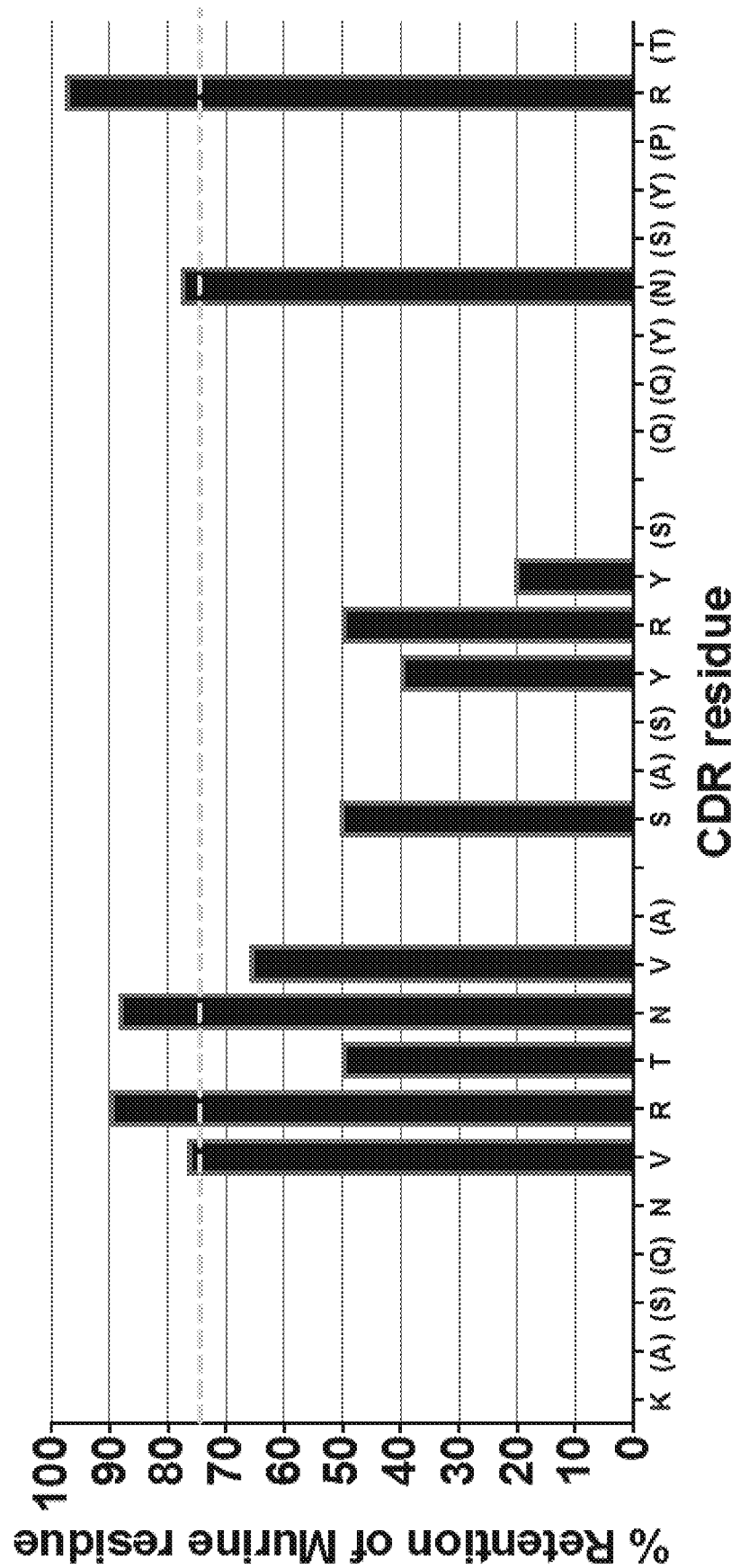

While germ-lining mutations were observed in all CDRs for the lead clones derived directly from library selections, it remained possible that sequence analyses might allow further clones to be designed to have maximal humanization. The 219 sequence-unique hits with binding signals against human and mouse protein were therefore used to analyse the retention frequency for murine amino acids in the CDRs of this functionally characterized population. Positional amino acid retention frequency was expressed as a percentage found in the $V_H$ and $V_L$ domains (FIG. 2A, 2B). Murine residues with RF<75% were regarded as positions that are possibly not essential to the target-binding paratope and are likely to be open to germ-lining, in a series of combinatorial designs.

Fifteen designs containing principally those murine residues with RF>75%, in a number of combinations, were designated "MH1-MH15" (MH=Maximally Humanized). As the LCDR3 of h37M contained a potential deamidation site (NS' at positions 3 and 4 of the CDR), multiple 'MH' clones also sampled possible substitutions such as N/NS/T/E and S/A/N/D, which might remove this development risk motif while maintaining acceptable target binding function. The sole non-human germline residue found in the LCDR3 ('R' at position 8 in the CDR) was also sampled for the tolerance of homologous substitutions R/K/H, to establish if stability or immunogenicity-enhancing mutations might be identified. Another six designer clones "TTP1-6" ('TTP'=Total Theoretically Possible) were also created that combined the most humanized CDRs observed in the high-functioning population of scFv sequences, plus deamidation motif-disrupting mutations (Table 4). The MH and TTP clones were generated by gene synthesis (along with the 13 library-derived clones outlined above, positive controls h37M and m37M, and negative control non-C-KIT-reactive isotype v-domains), then cloned into expression vectors for production as human IgG1. All IgGs were readily expressed and purified from transient transfections of HEK-293 cells.

Lead IgG Specificity and Potency Characteristics

Figure 3A:
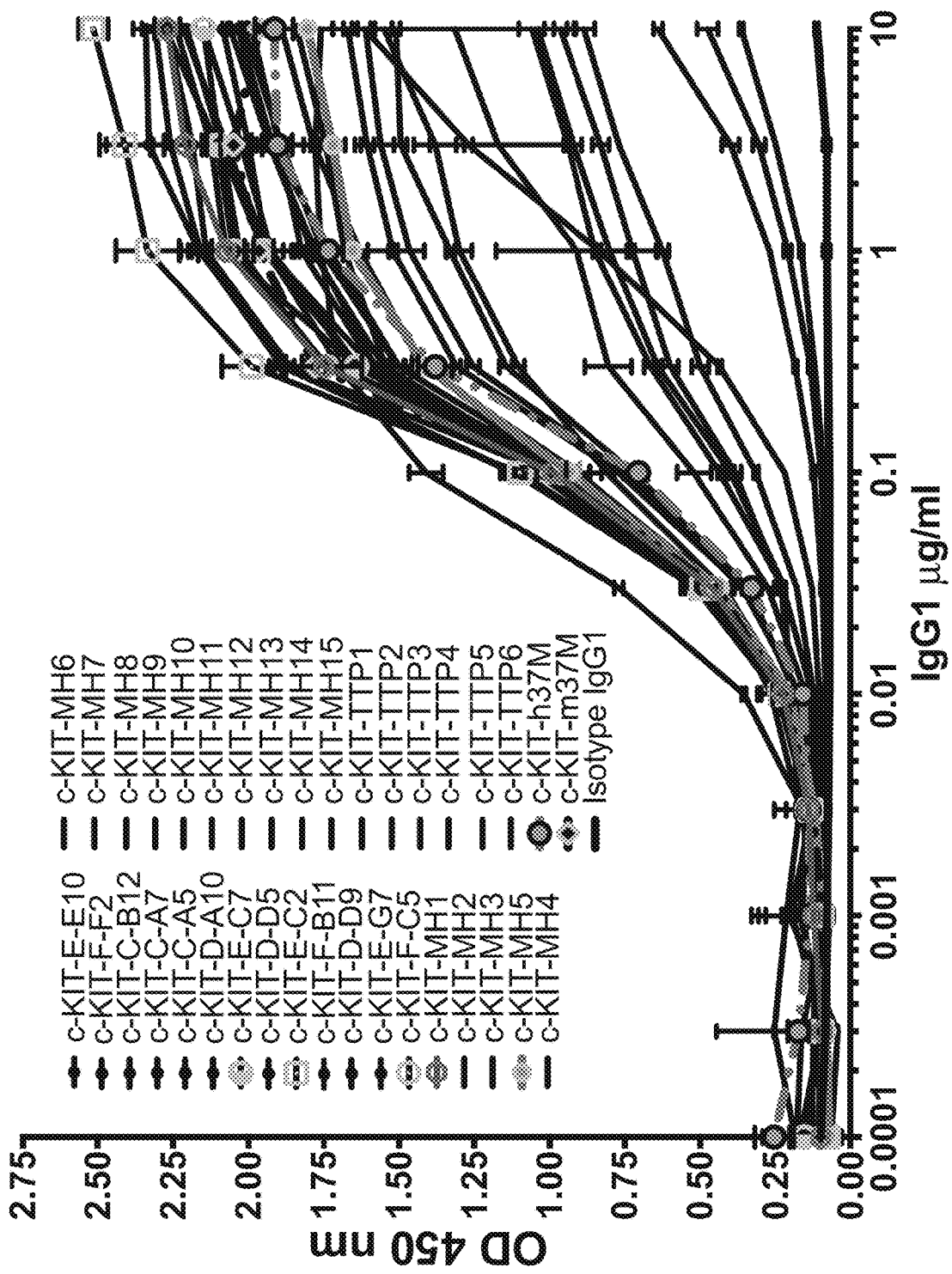
FIG. 3A-FIG. 3B. Direct titration ELISA for IgG binding to human and cyno C-KIT-Fc proteins. Chimeric anti-C-KIT (m37M), humanized h37M, library-derived and designer clones in human IgG1 format were titrated (in µg/ml) in a direct binding ELISA against human (FIG. 3A) and cyno (FIG. 3B) C-KIT-Fc proteins. The 37M, library-derived clones and designer clone MH demonstrated binding activity against both orthologs of C-KIT. All library derived and several designer clones retained approximately equivalent or improved human and cyno C-KIT binding, while all TTP clones and MH clones 4, 6, 7, 9, 13, 14 and 15 all exhibited reduced binding signal on one or both orthologs.
Figure 3B:
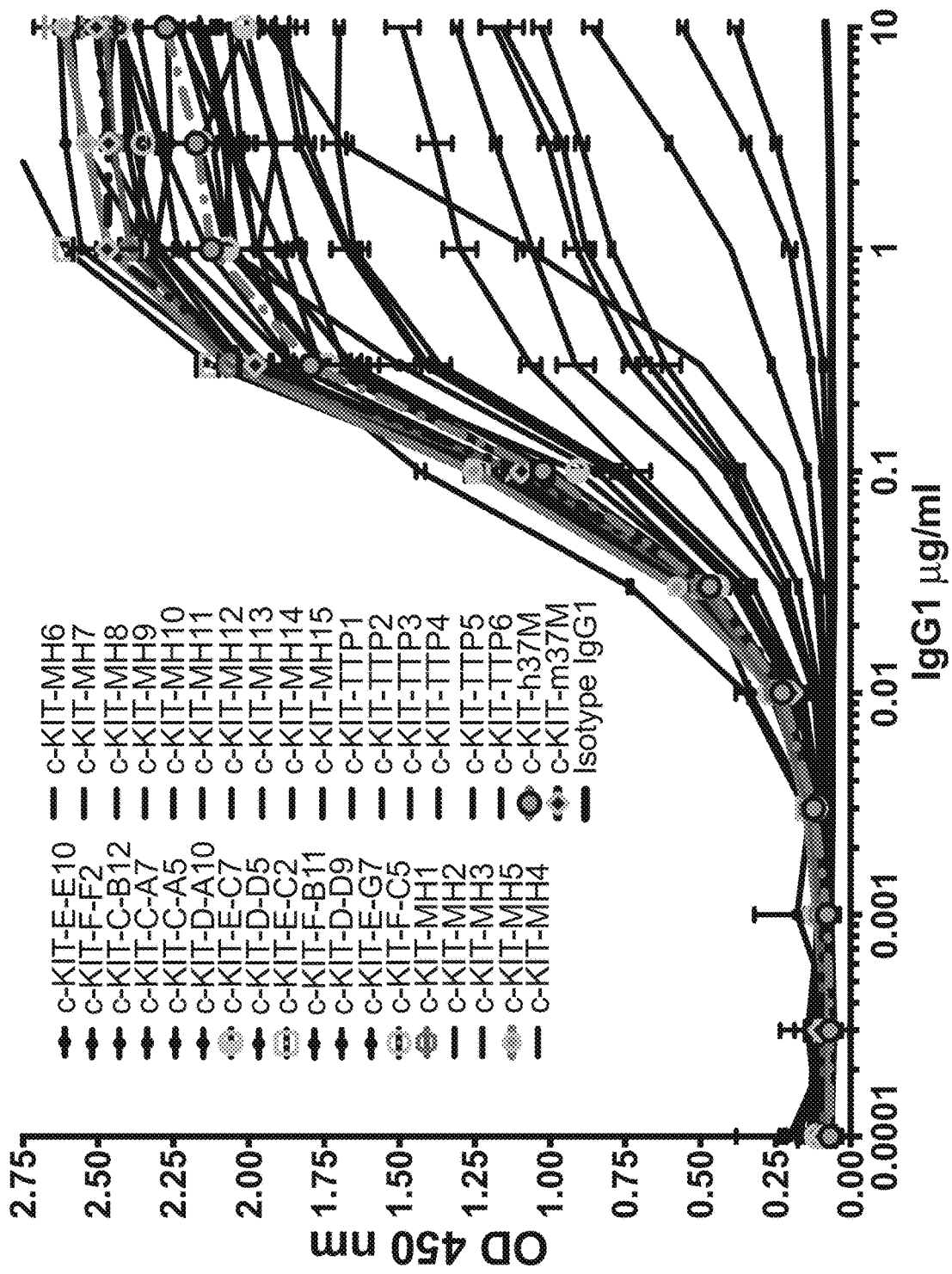

The purified IgGs described above were then tested for binding to human and cyno C-KIT-Fc in direct titration ELISA format (FIG. 3). This analysis demonstrated that while all library derived clones and MH1-3, 5, 10, 11 and 12 designer clones retained binding affinity for human and cyno C-KIT that was comparable to the h37M IgG1, all of the other MH and TTP clones showed reduced binding to both orthologues (FIG. 3).

Figure 4B:
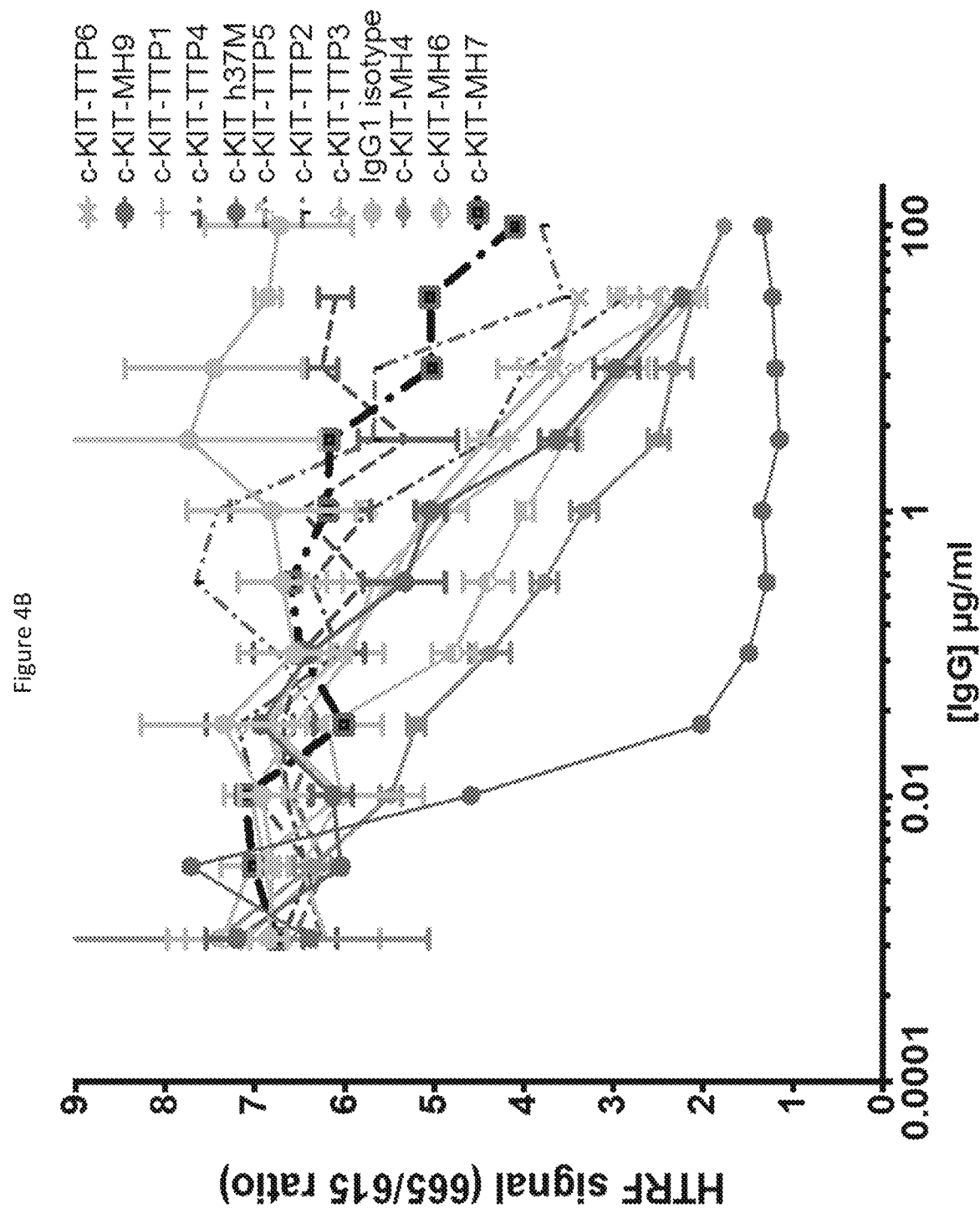
Figure 4C:
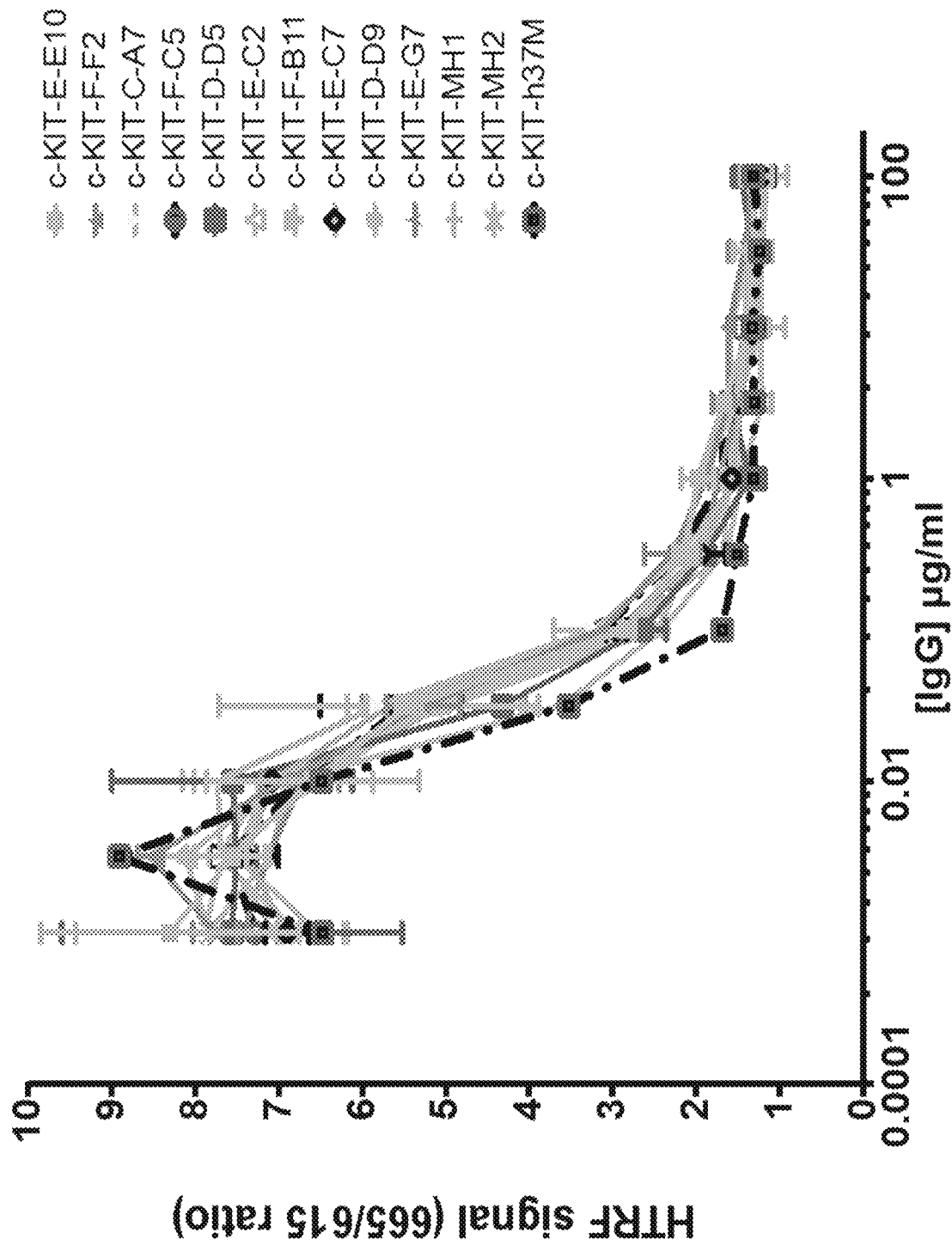
Figure 4D:
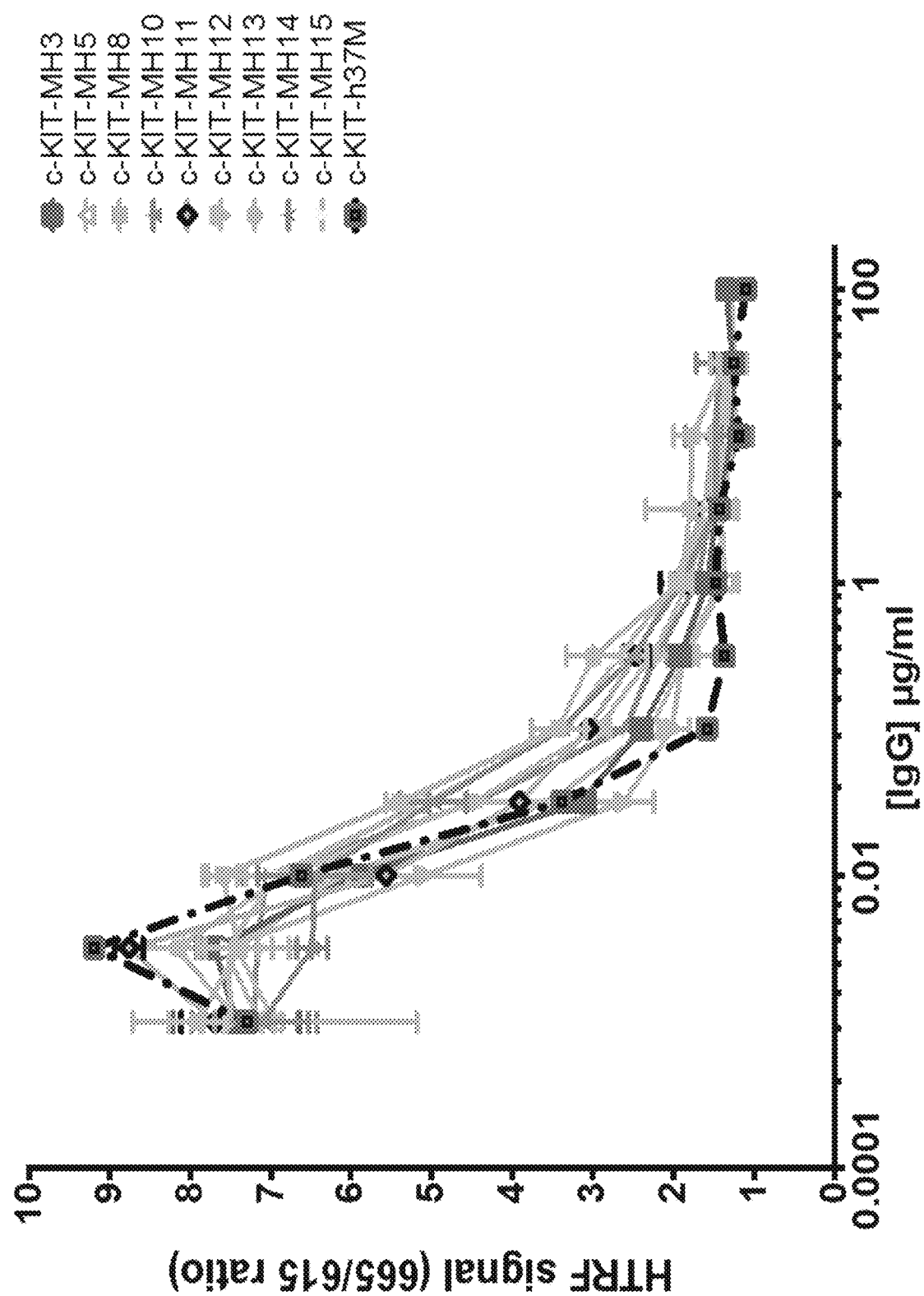

As direct ELISA binding signal is influenced by avidity and does not prove the maintenance a specific epitope, all IgGs were then examined in a solution-phase HTRF competition assay (FIG. 4). All library-derived and multiple designer IgGs exhibited full concentration-dependent inhibition of h37M binding to human (FIG. 4A) and cyno (FIG. 4C, D) c-KIT, with key leads showing highly similar IC50 values to that observed for unlabelled h37M IgG (Table 5). This demonstrated maintenance of a shared epitope and binding affinity in these clones. All TTP clones, plus MH clones 4, 6, 7 and 9 were found not to fully inhibit h37M binding to either human (FIG. 4B) or cyno (FIG. 4E) C-KIT.

Flow Cytometric Analyses of Lead IgG Binding Specificity at the Cell Membrane

Figure 5A:
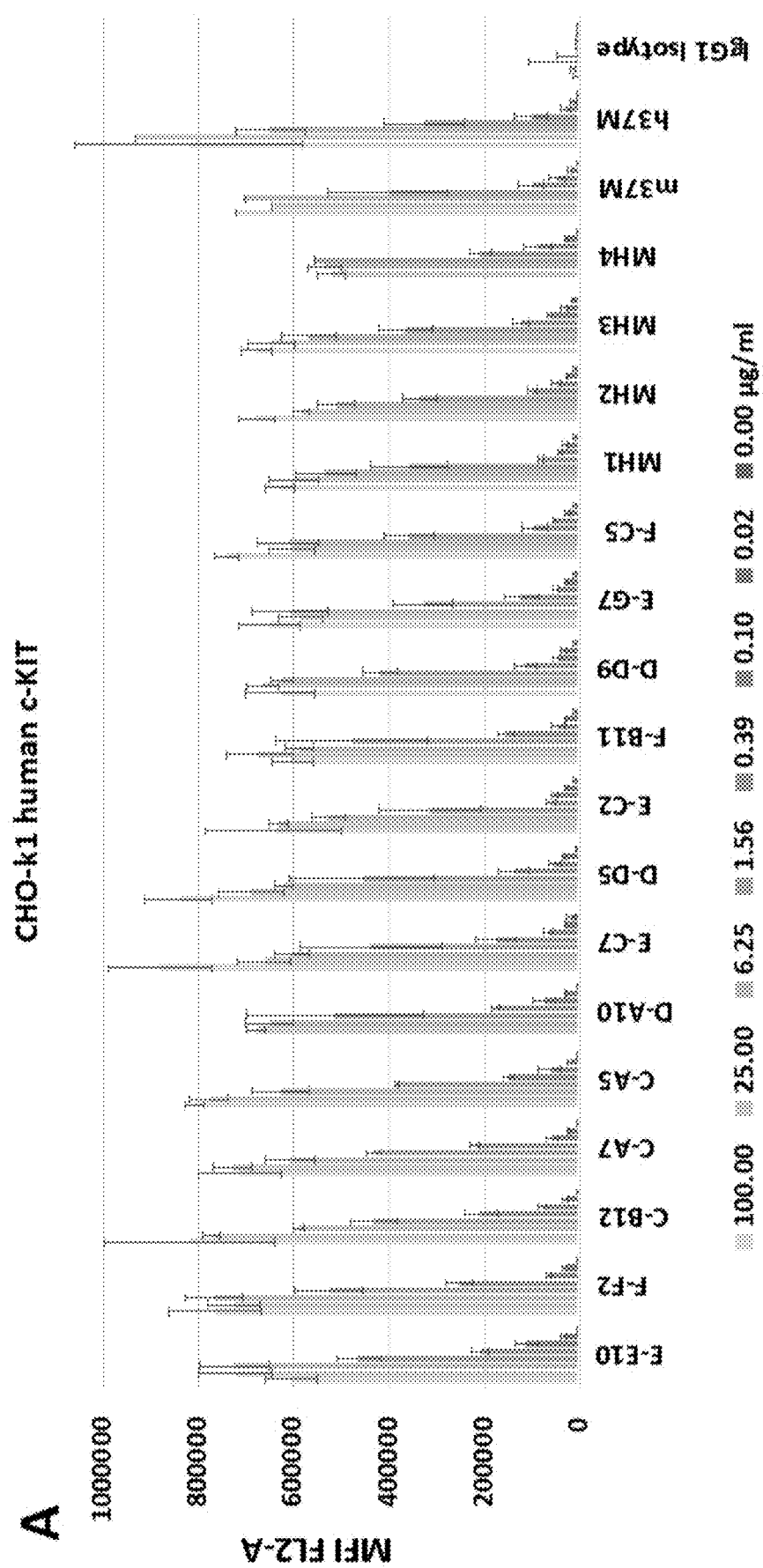
Figure 5B:
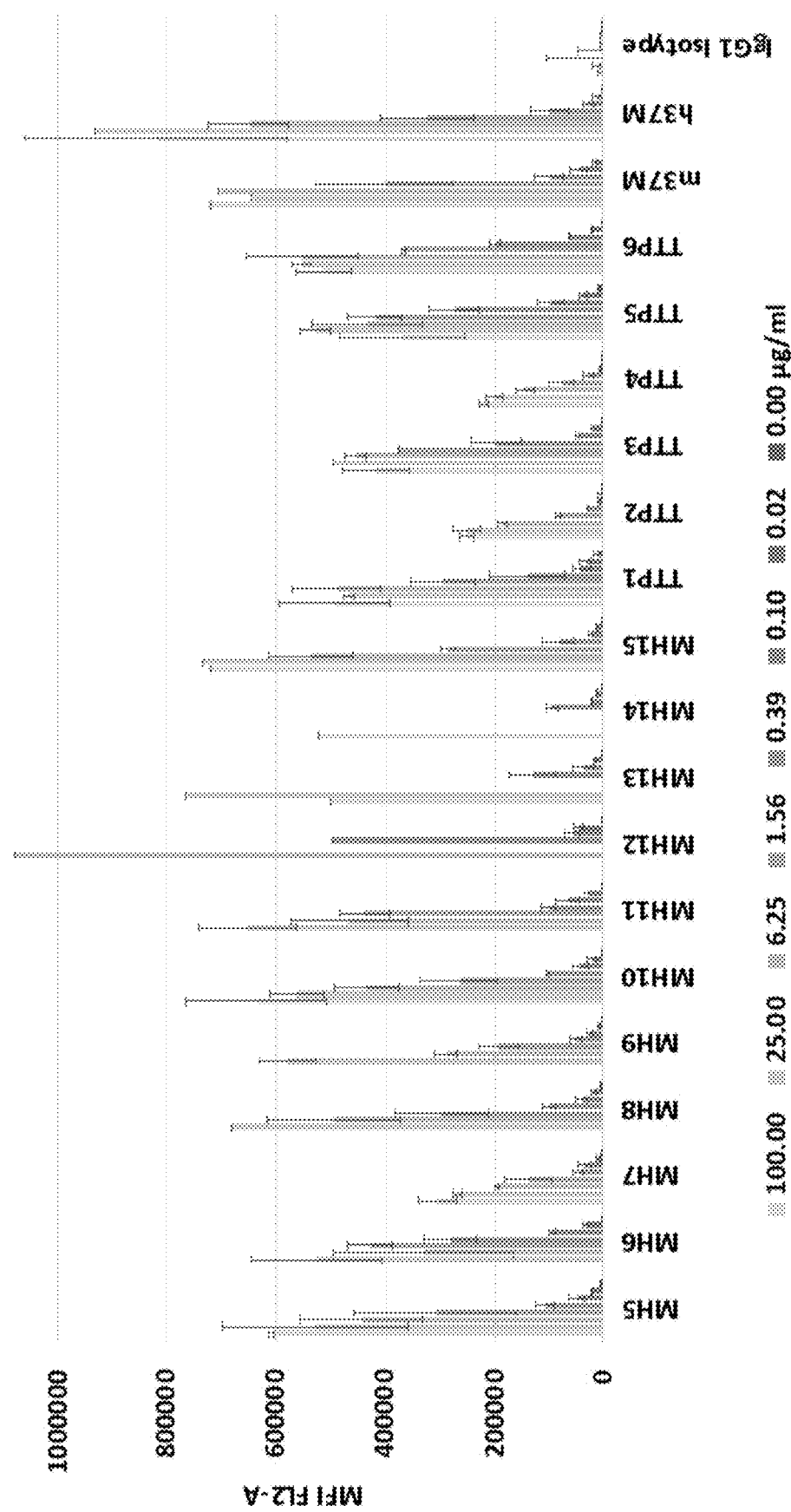
Figure 5D:
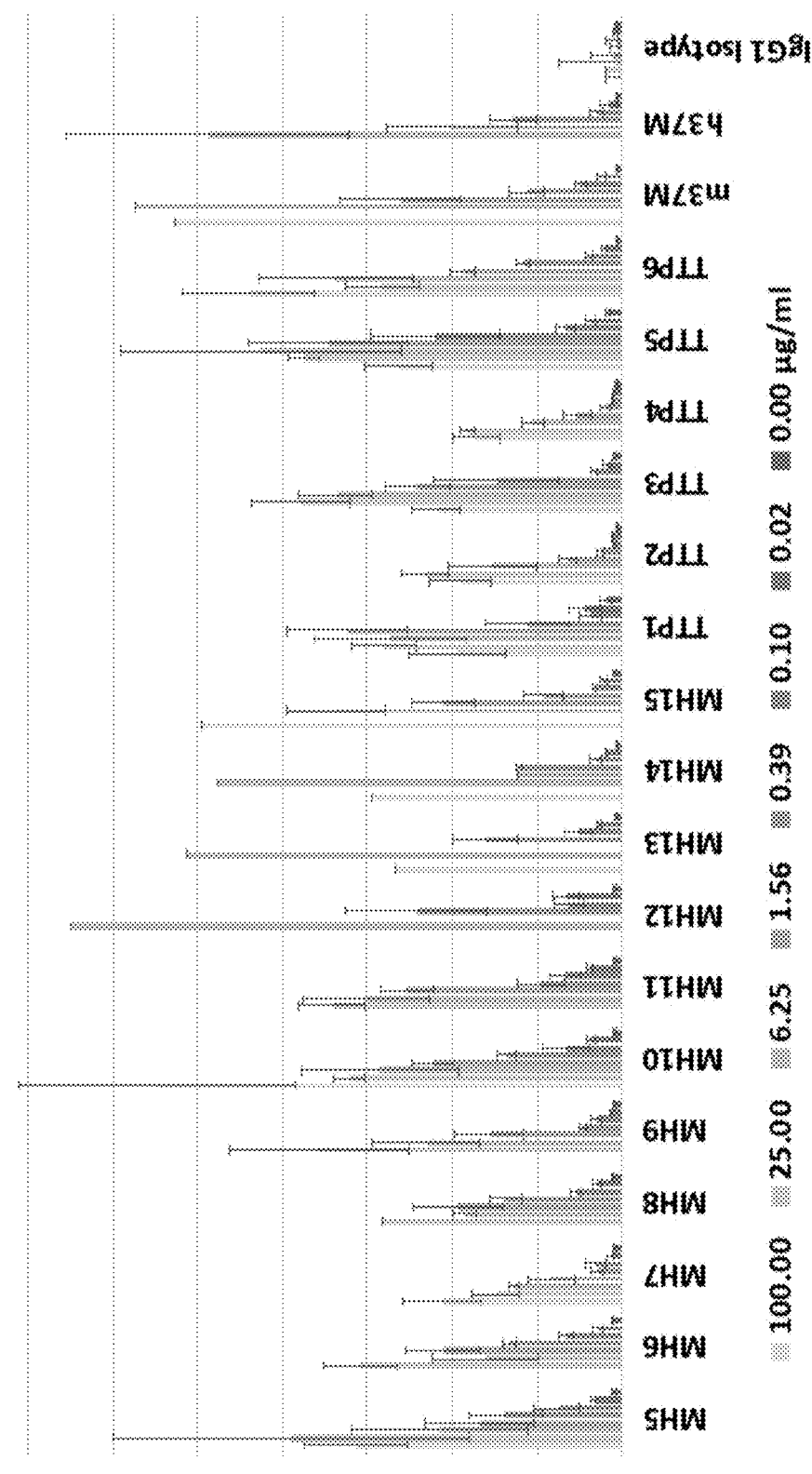
Figure 5E:
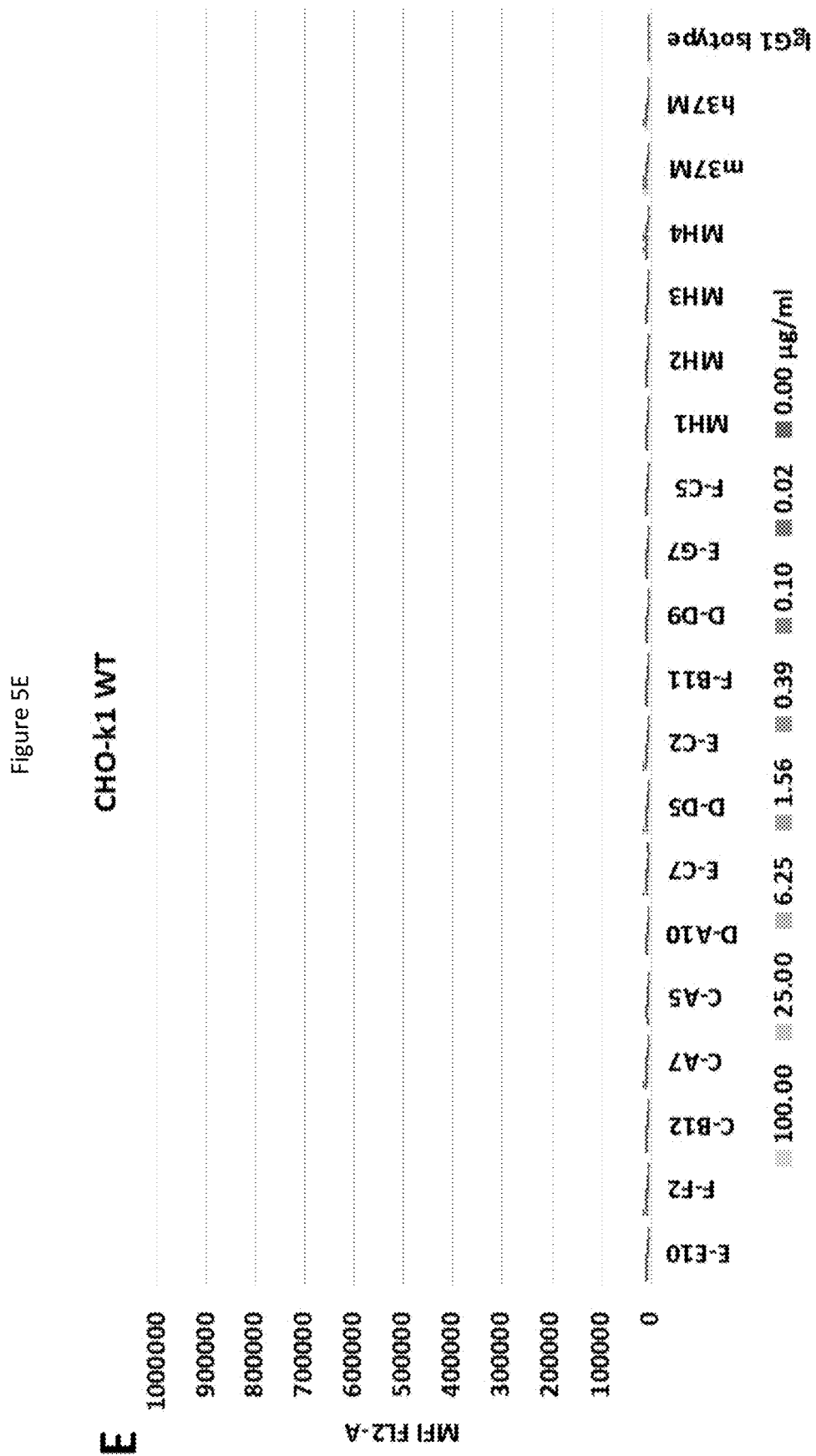
Figure 5F:
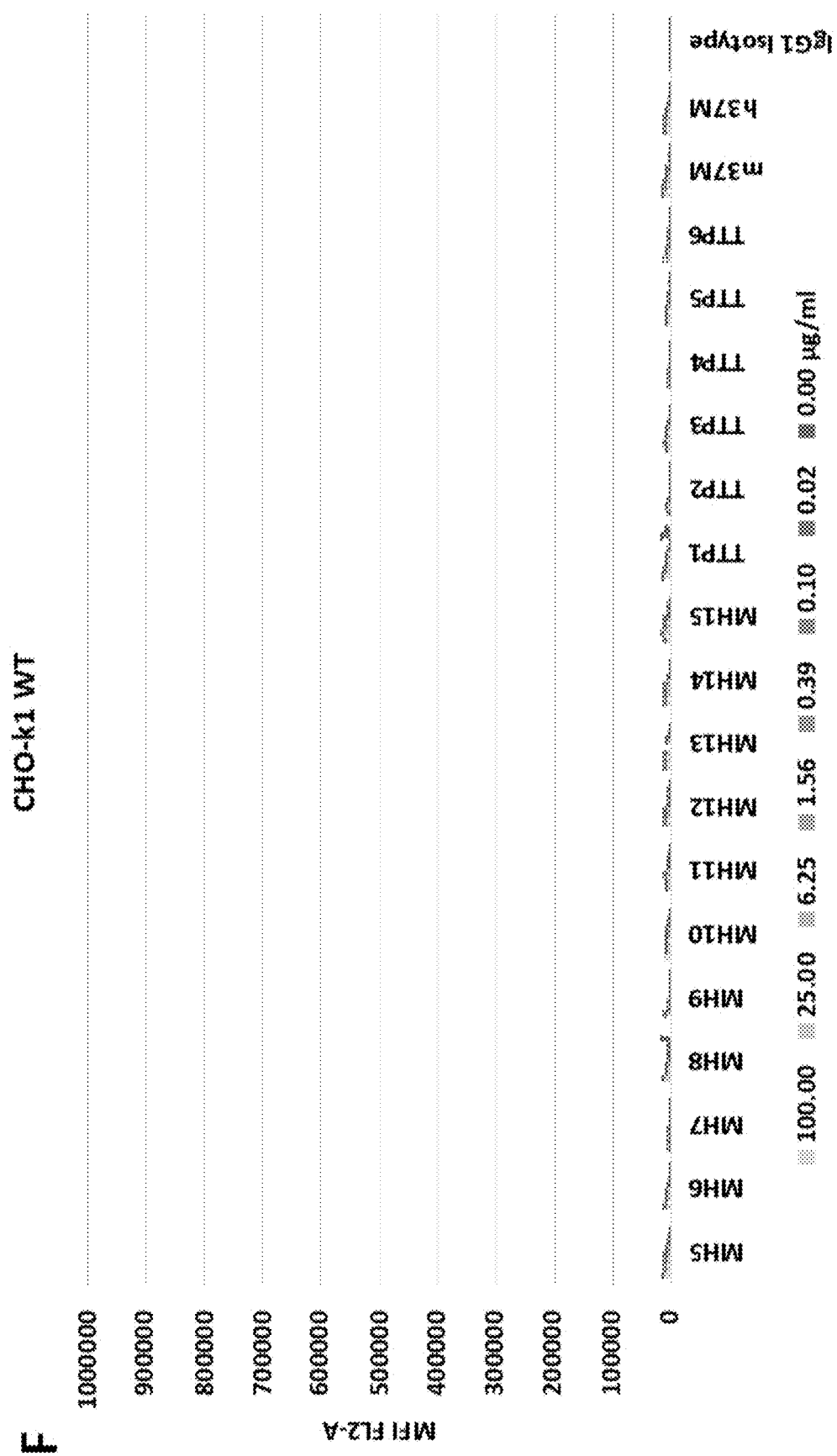

Antibodies to C-KIT were analysed for concentration-dependent binding at the cell surface via flow cytometry. CHO-K1 cells were stably transfected with either human or cyno C-KIT full-length cDNAs. Anti-C-KIT IgGs and an isotype control IgG1 were then all tested in IgG1 format, over a concentration range of 100-0.02 µg/ml for binding to human (FIG. 5A, 5B), cyno (FIG. 5C, 5D) or wild type control ('M', i.e. untransfected) CHO-K1 (FIG. 5E, 5F). All IgGs other than the isotype control showed concentration-dependent binding to human and cyno C-KIT+ cells, with a maximum MFI in each case being>50-fold higher than observed background signals for binding to untransfected CHO-K1. Anti-C-KIT antibodies exhibited no measurable background binding on untransfected CHO-K1 cells, comparable to the Isotype control IgG1 (FIG. 5E, 5F).

Analyses of Designer IgGs Based on the Lead Clone MH5

Figure 6B:
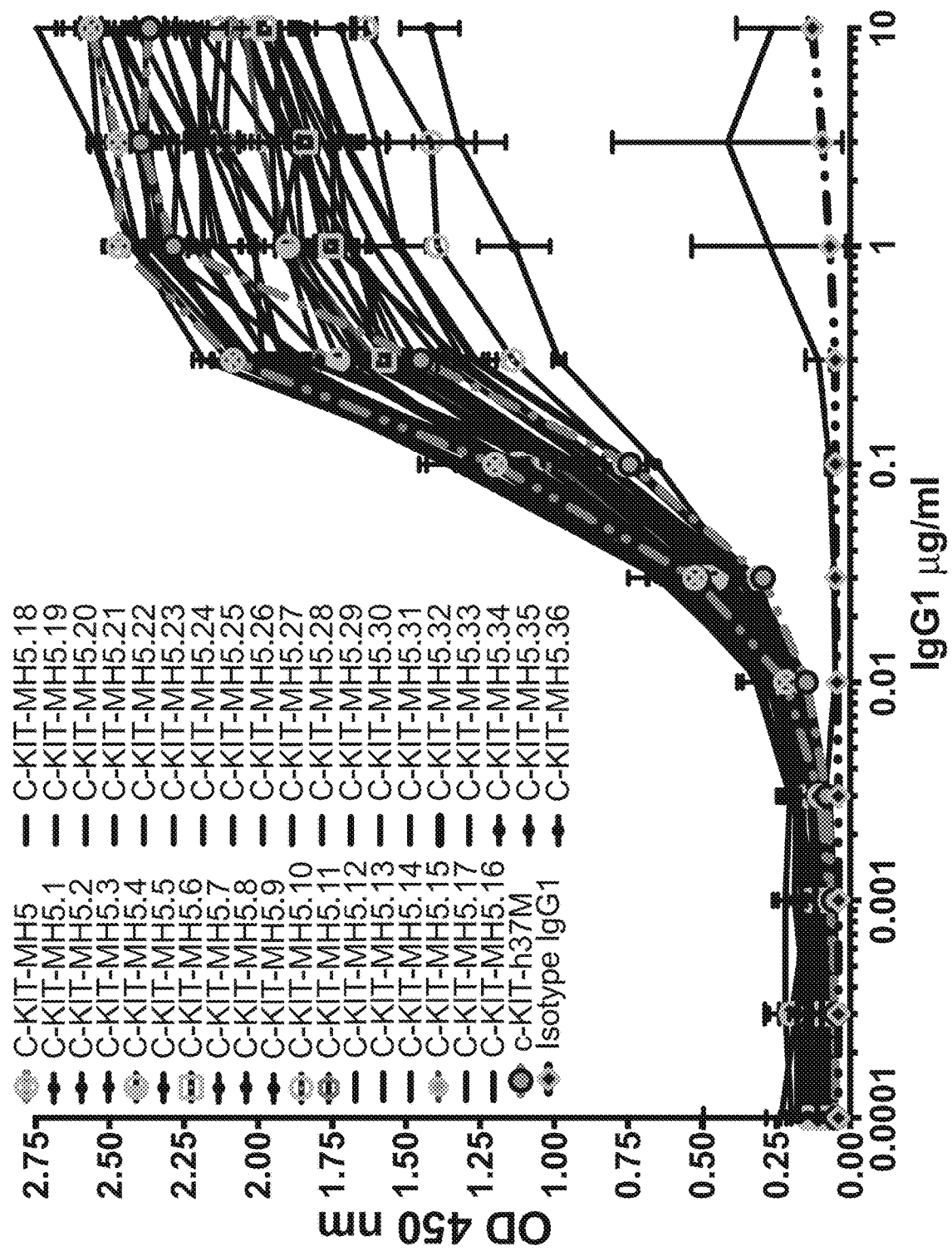
Figure 7B:
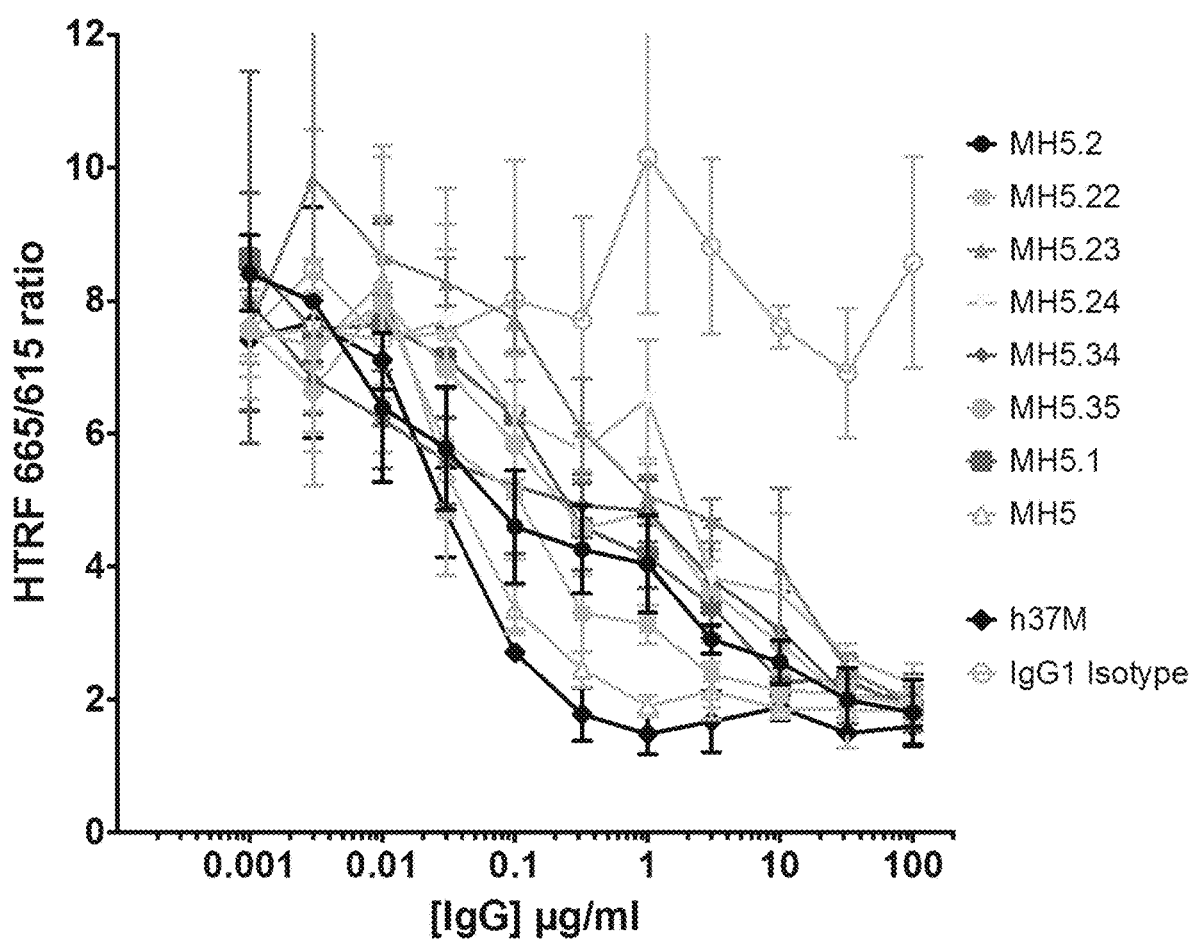

As described above, clone MH5 had proven to have highly specific binding to human and cyno C-KIT, low off-target binding potential, reduced deamidation potential in the CDRs, fully germline framework regions and multiple human germlining mutations in the CDRs. As a first-generation designer clone, however, the MH5 sequence had been targeted for improved human germline content and development qualities in the light chain, but not the heavy chain. The VH domain still retained a number of non-germline (mouse-derived) residues in the CDRs that were suggested to be potentially modifiable by the data found in FIGS. 2A and 2B and observed functional mutant sequences outlined in Table 3. In an attempt to sample further mutations in the VH that might improve expression, stability, immunogenicity or functional characteristics, 36 'second generation' mutants were generated as outlined in Table 6. These clones were expressed and purified in IgG1 format and examined for target binding by ELISA on human and cyno C-KIT orthologs (FIGS. 6A and 6B, respectively) and neutralisation of h37M/C-KIT interaction for both orthologs by HTRF. In this phase, it was found that strong ELISA binding signals for several clones suggested multiple mutations could be tolerated in the CDRs of the majority of the IgGs, but these changes could not always be combined without some changes in potency. In the HTRF analyses (FIG. 7A, 7B) it was found that key second generation leads MH5.1, 5.2, 5.22, 5.23, 5.24, 5.33 and 5.34, in particular, were capable of fully neutralising h37M/C-KIT interaction, albeit with reduced potency by IC50 calculation (Table 7).

Figure 8A:
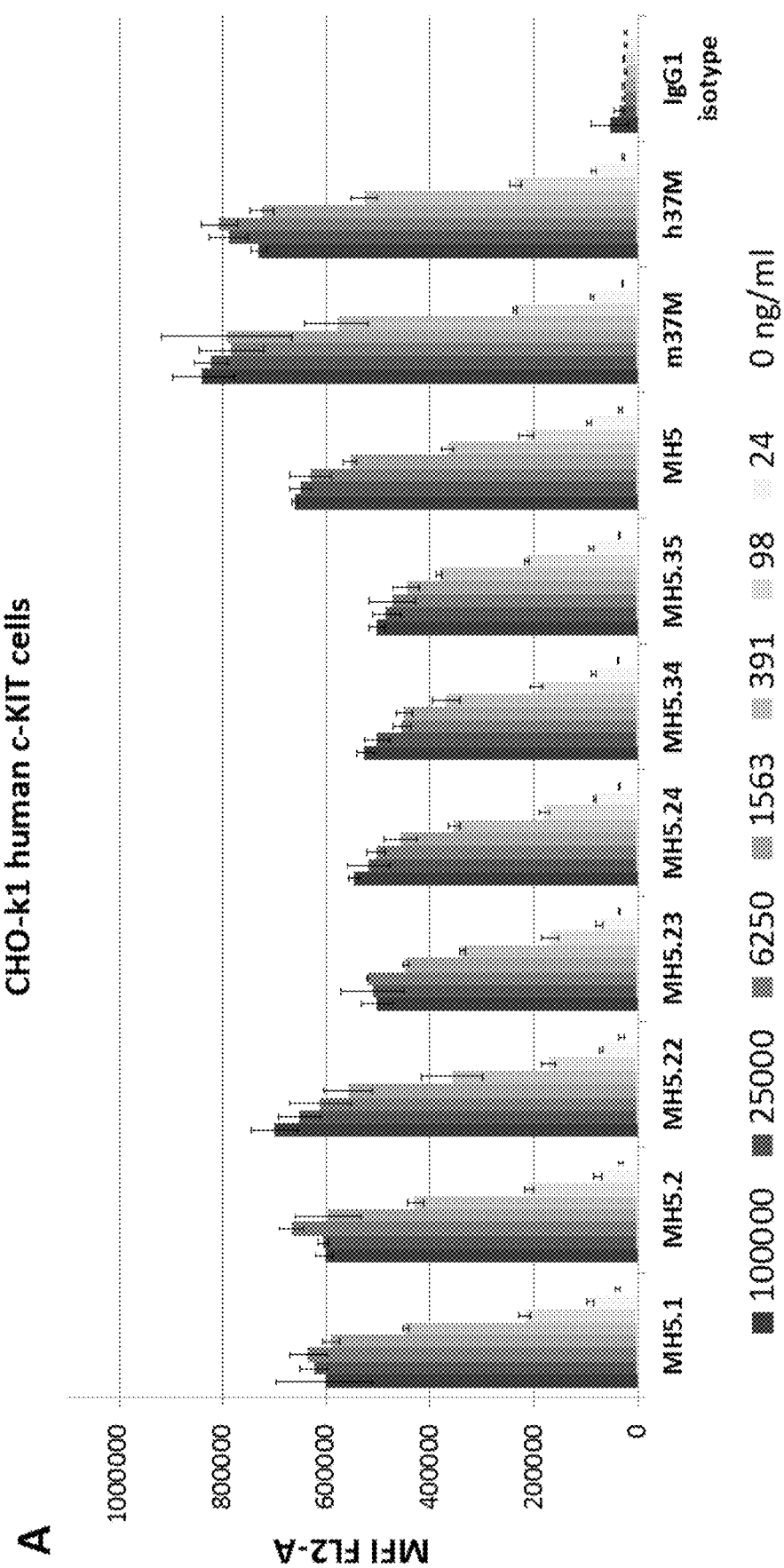
FIG. 8A-FIG. 8C. Flow cytometric binding to human and cyno C-KIT+ CHO-K1 cells for second-generation designer leads. Anti-C-KIT library-derived and designer leads in IgG1 format were examined for specific binding on human C-KIT-transfected CHO-K1 cells (FIG. 8A), cyno C-KIT-transfected CHO-K1 cells (FIG. 8B), and wild type (wt, i.e. untransfected) CHO-K1 cells (FIG. 8C). IgGs were tested at concentrations ranging from 24-100,000 ng/ml. Concentration-dependent binding was observed against both human and cyno cell lines for all C-KIT-specific antibodies but not Isotype controls. No binding signals above background were observed against wild type CHO-K1 cells.
Figure 8B:
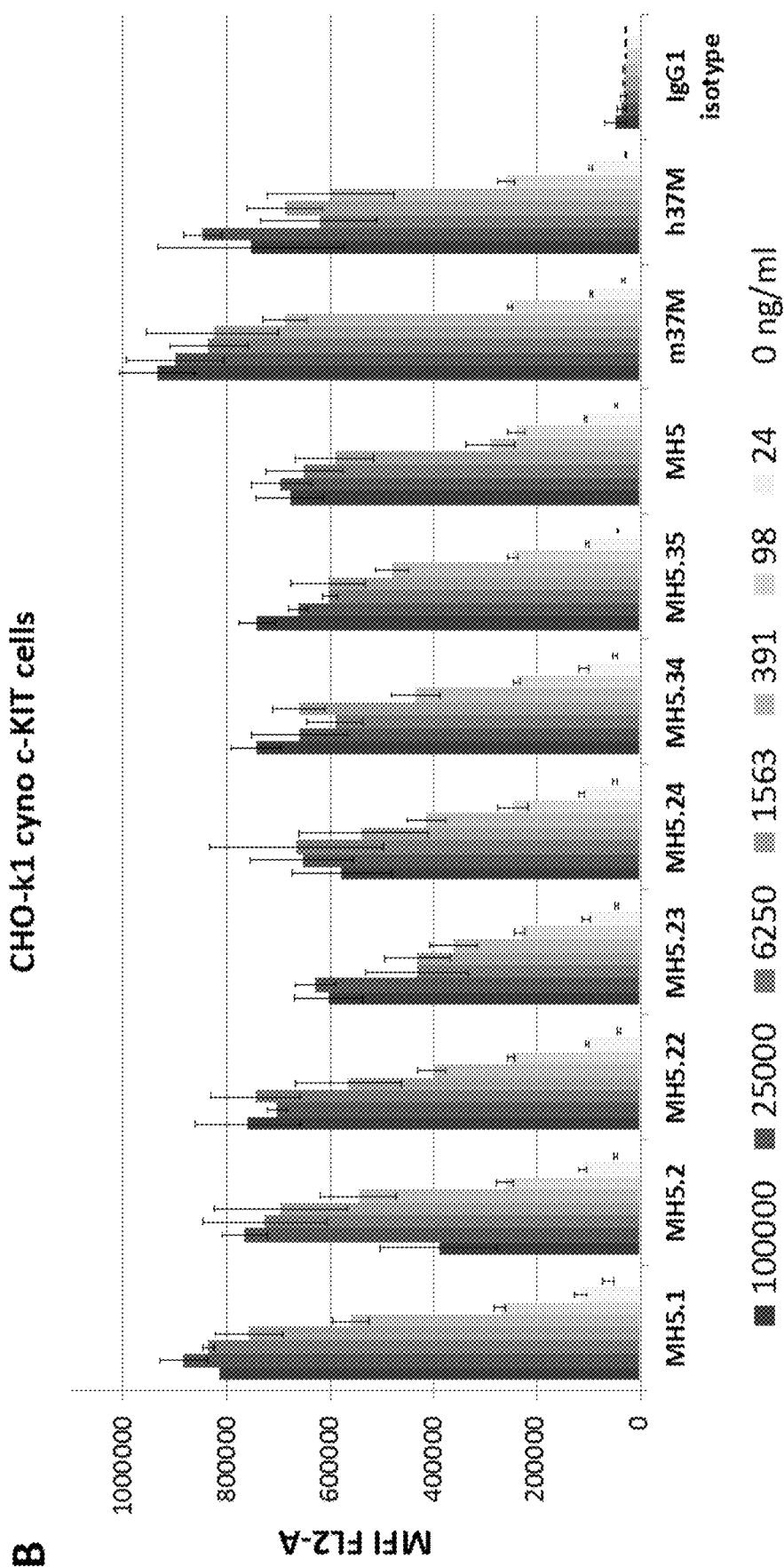
Figure 8C:
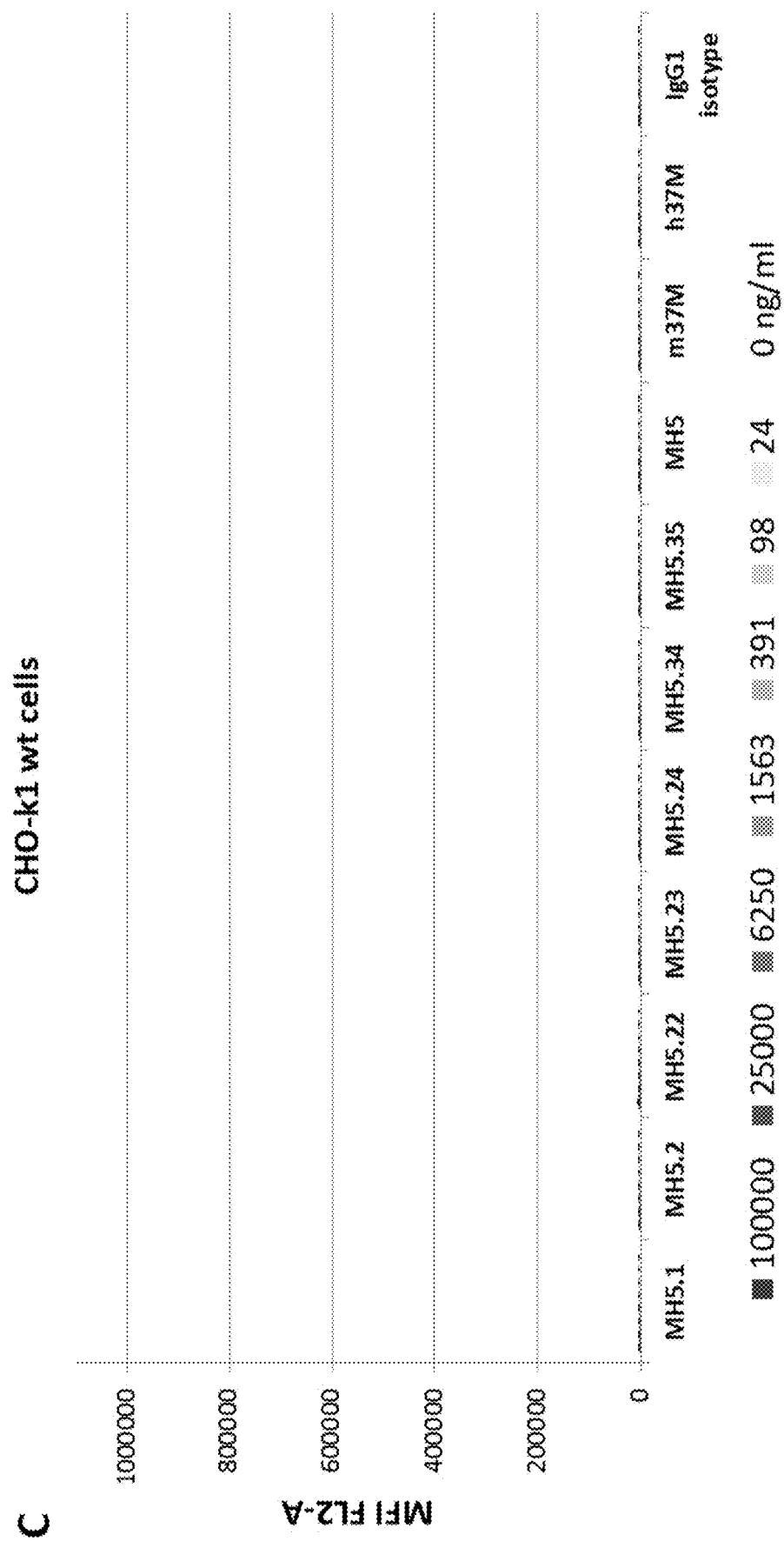
Figure 9A:
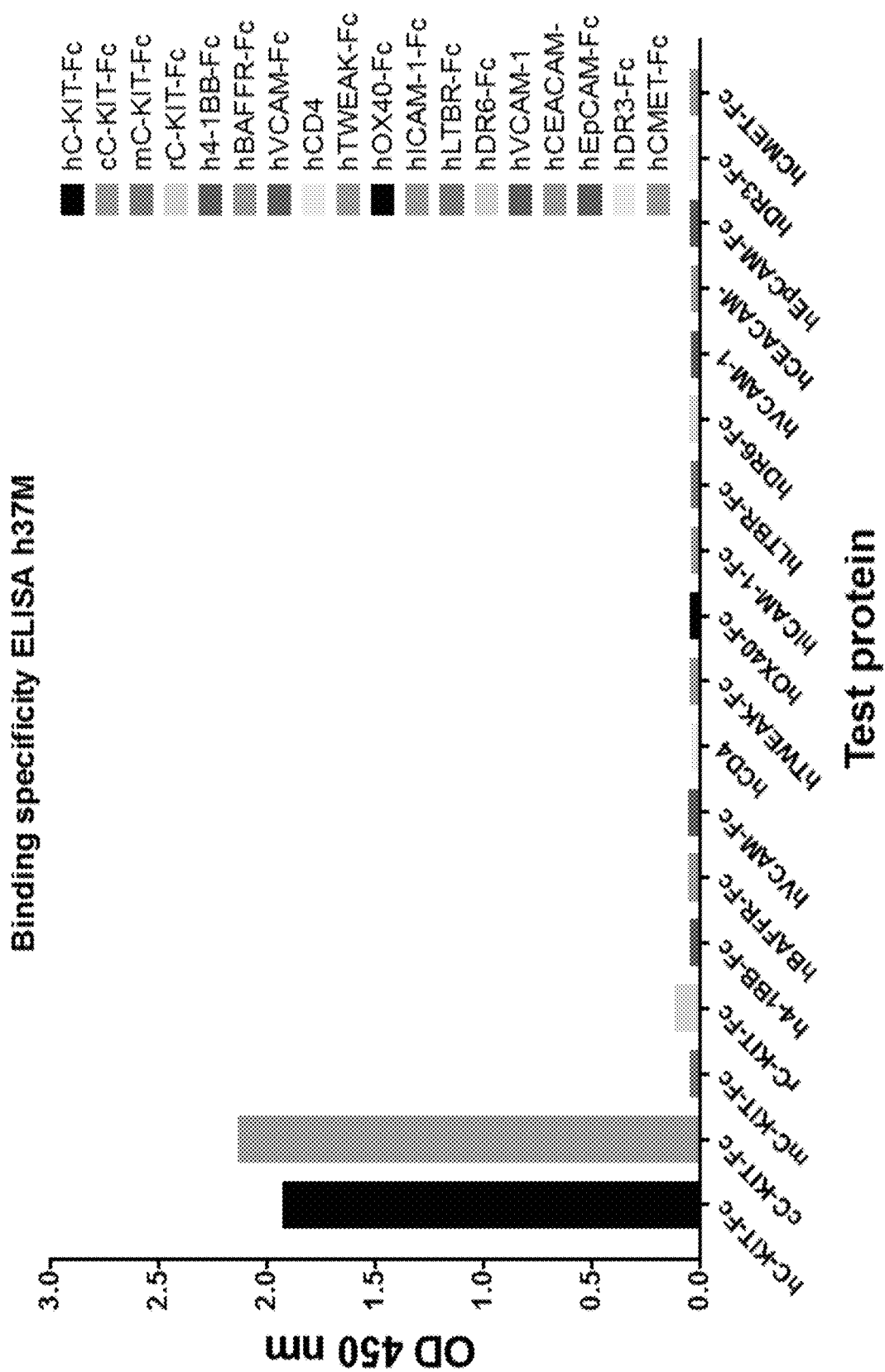
FIG. 9A-FIG. 9F. Binding specificity analyses for prioritized lead clones. Off-target homologue binding risk for h37M and multiple lead antibodies in IgG1 format at 1 µg/ml was examined by direct ELISA on C-KIT-Fc orthologs and a panel of 14 human immunoglobulin superfamily proteins. For all IgGs, binding was observed to human and cyno C-KIT-Fc alone. No binding above background was observed for any other human or ortholog protein.
Figure 9B:
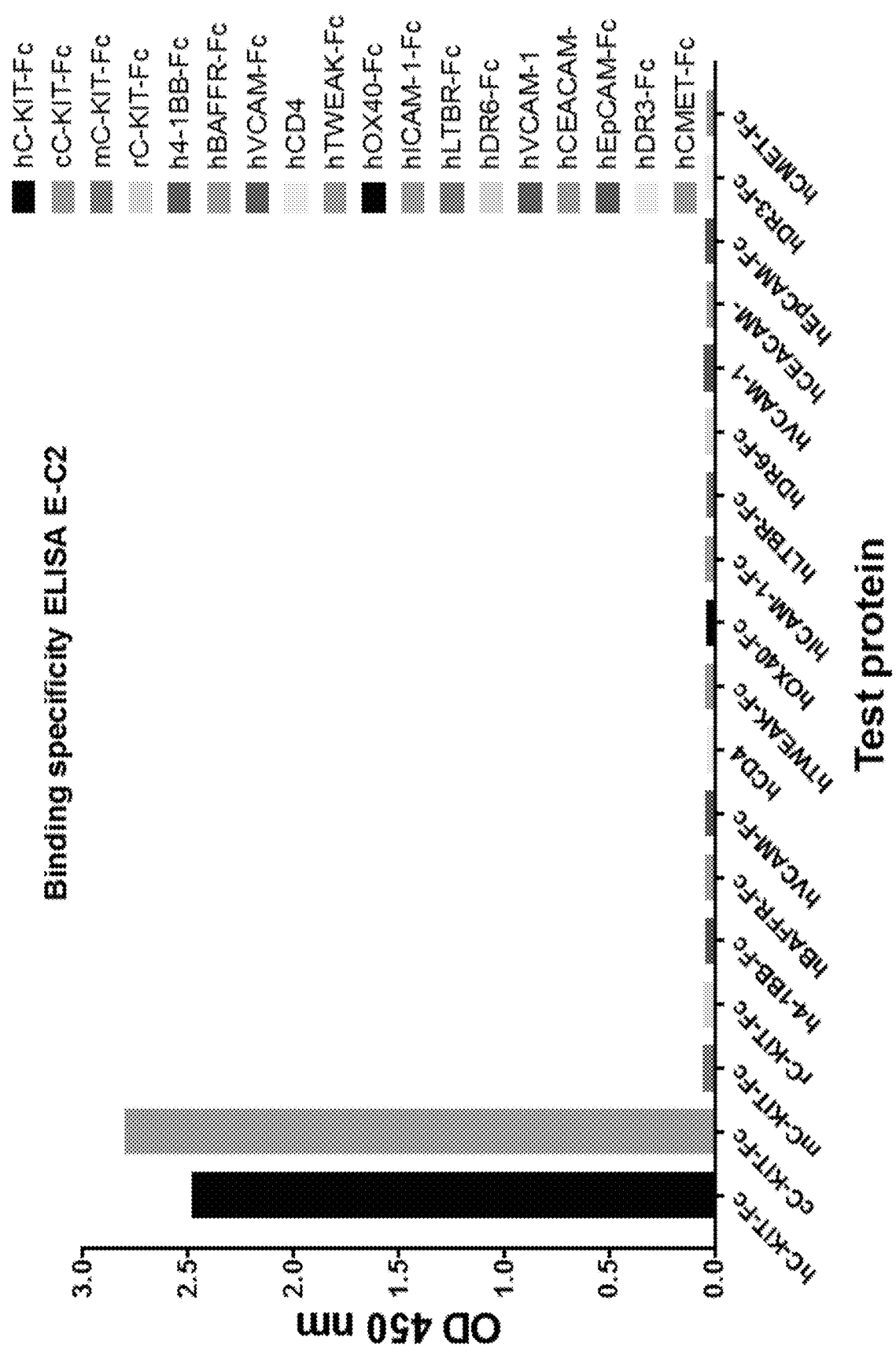
Figure 9C:
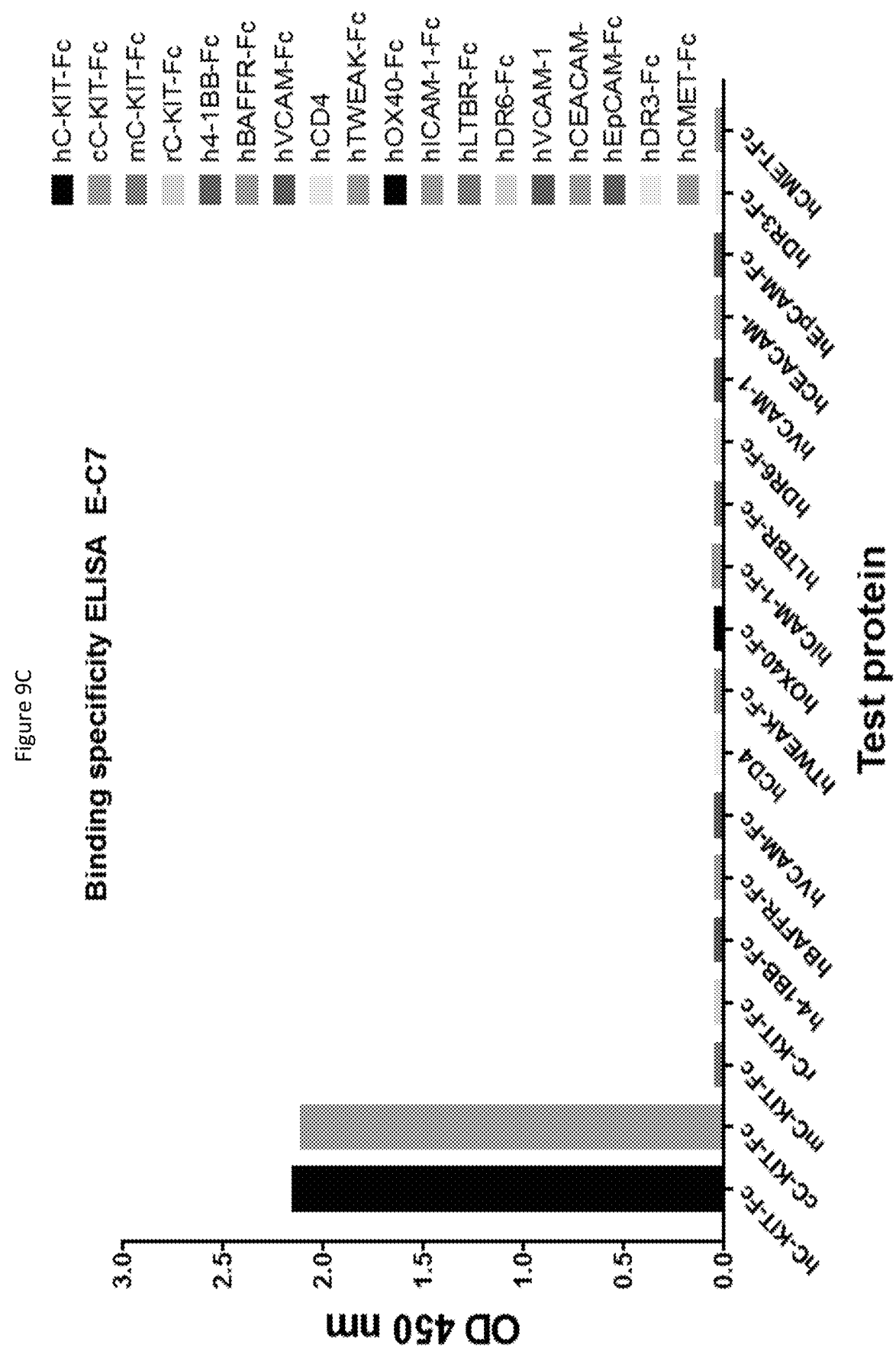
Figure 9D:
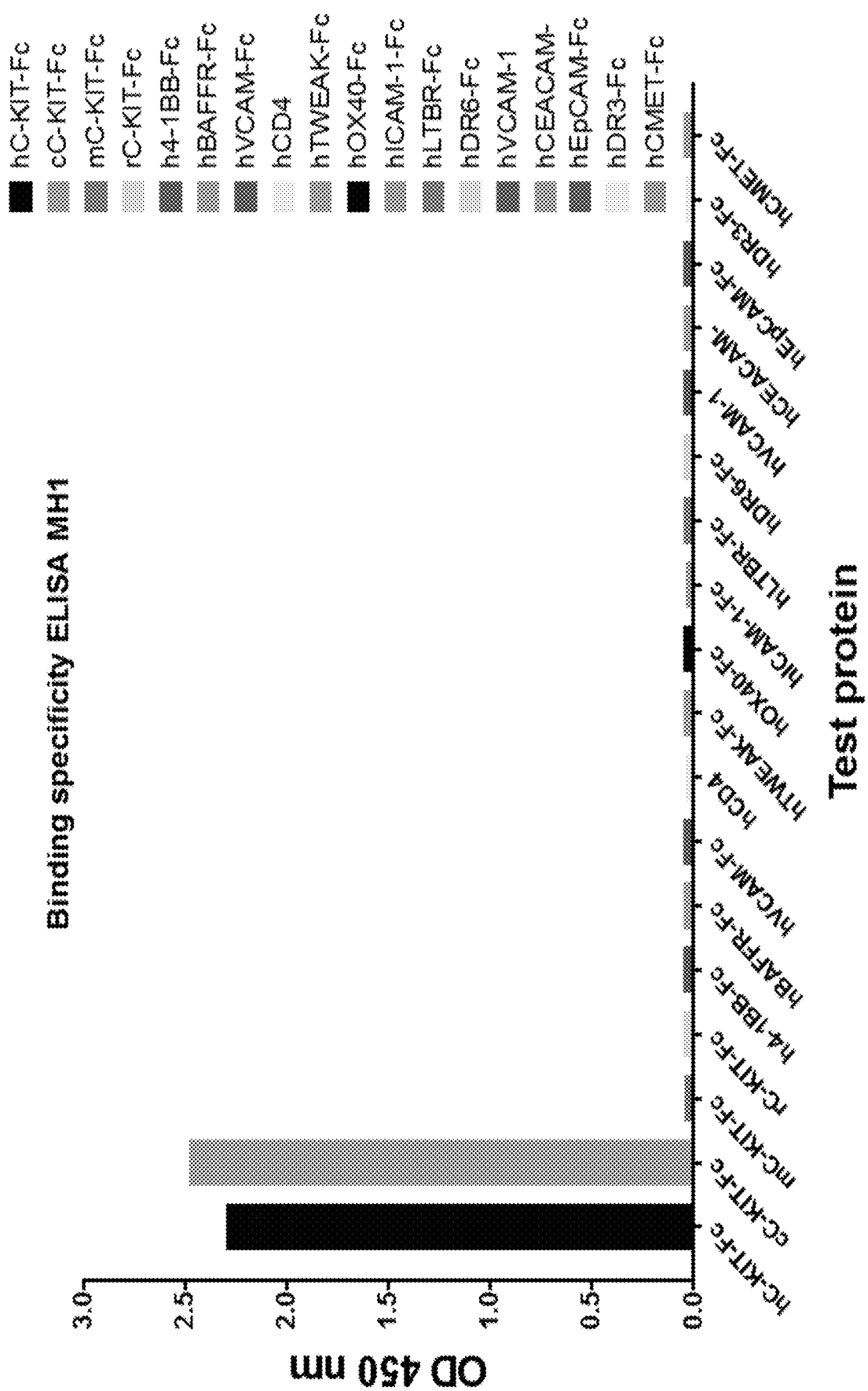
Figure 9E:
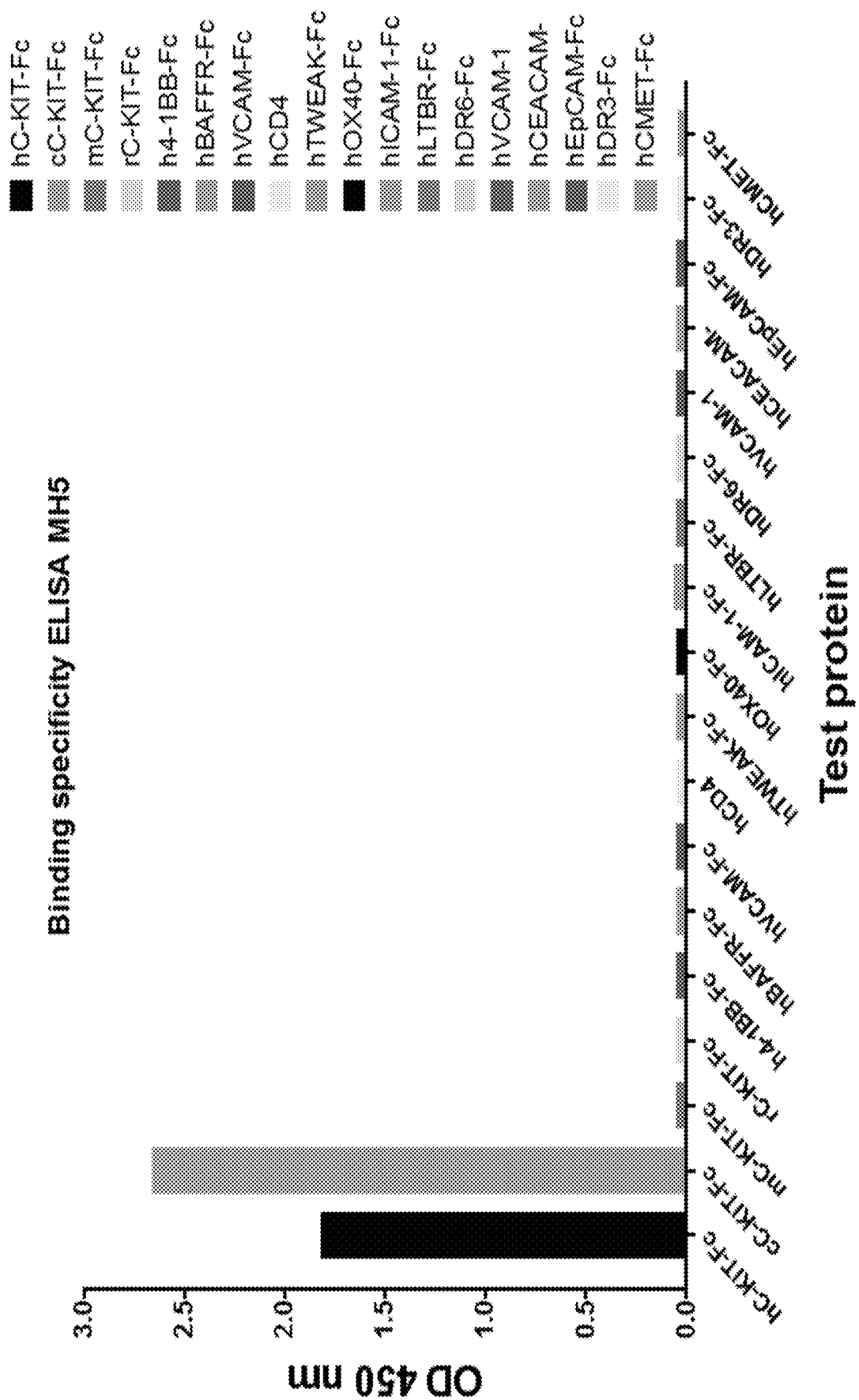
Figure 9F:
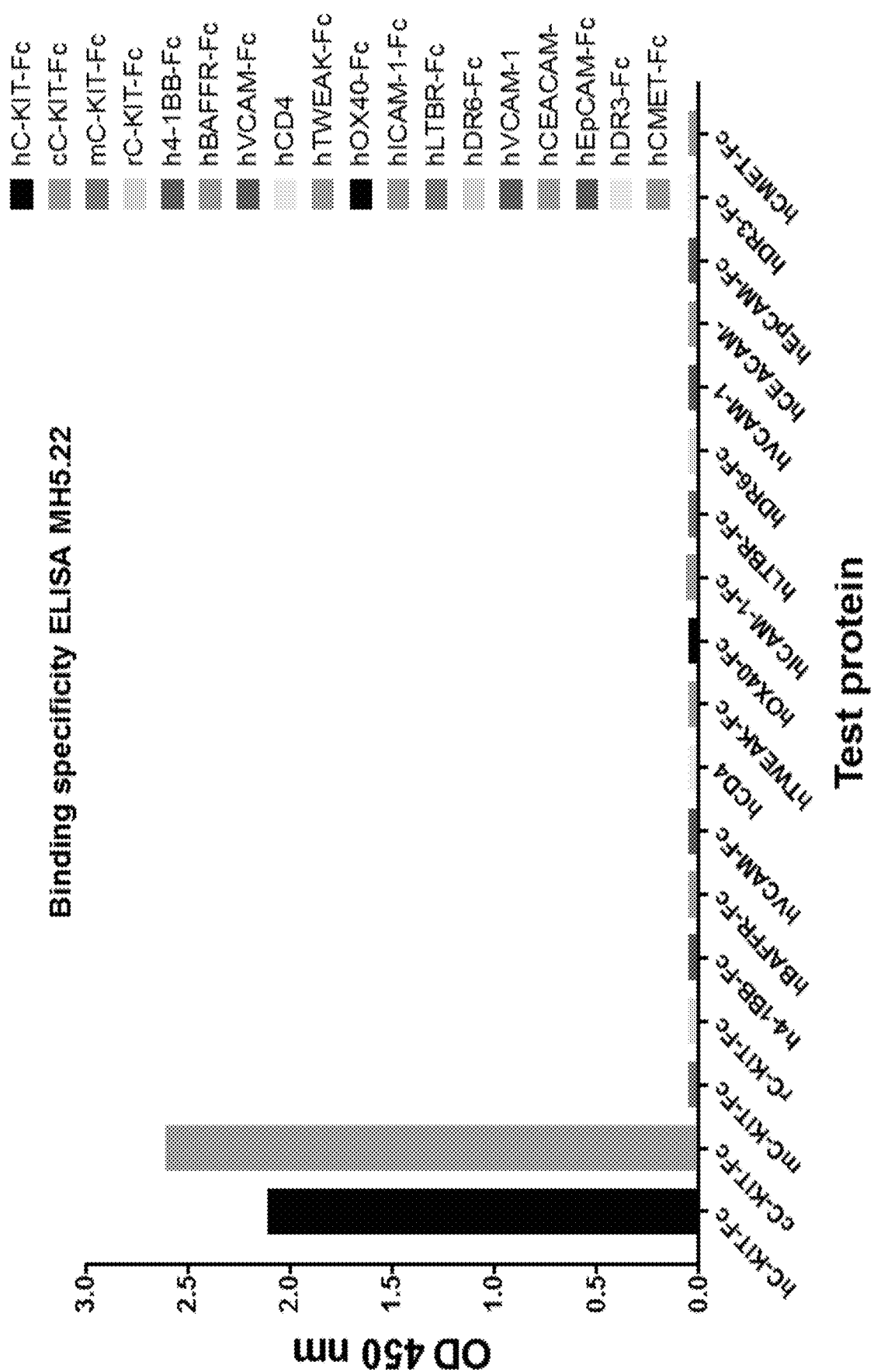
Figure 10A:
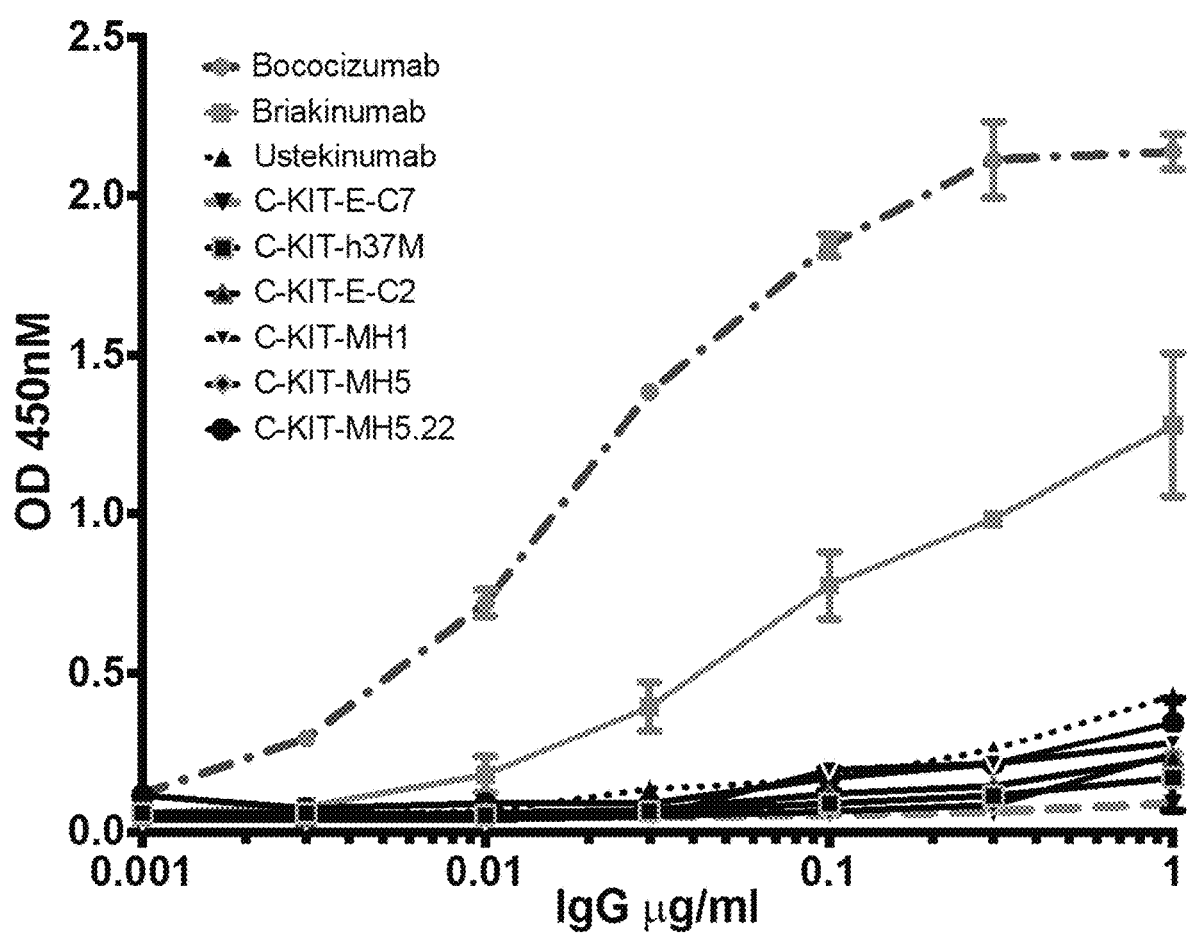
FIG. 10A-FIG. 10C. Development risk ELISAs. This assay showed that the E-C7, E-C3, MH1, MH5, MH5.22 and h37M antibodies in IgG1 form exhibit equivalent or lower binding to the negatively charged biomolecules Insulin (FIG. 10A), double-stranded DNA (dsDNA) (FIG. 10B) and single-stranded DNA (ssDNA) (FIG. 10C) than the negative control IgG1 Ustekinumab analogue. Strong off-target binding to these molecules, as observed for Bococizumab and Briakinumab analogues has been shown to be a high-risk indicator of poor pharmacokinetics of therapeutic antibodies.
Figure 10B:
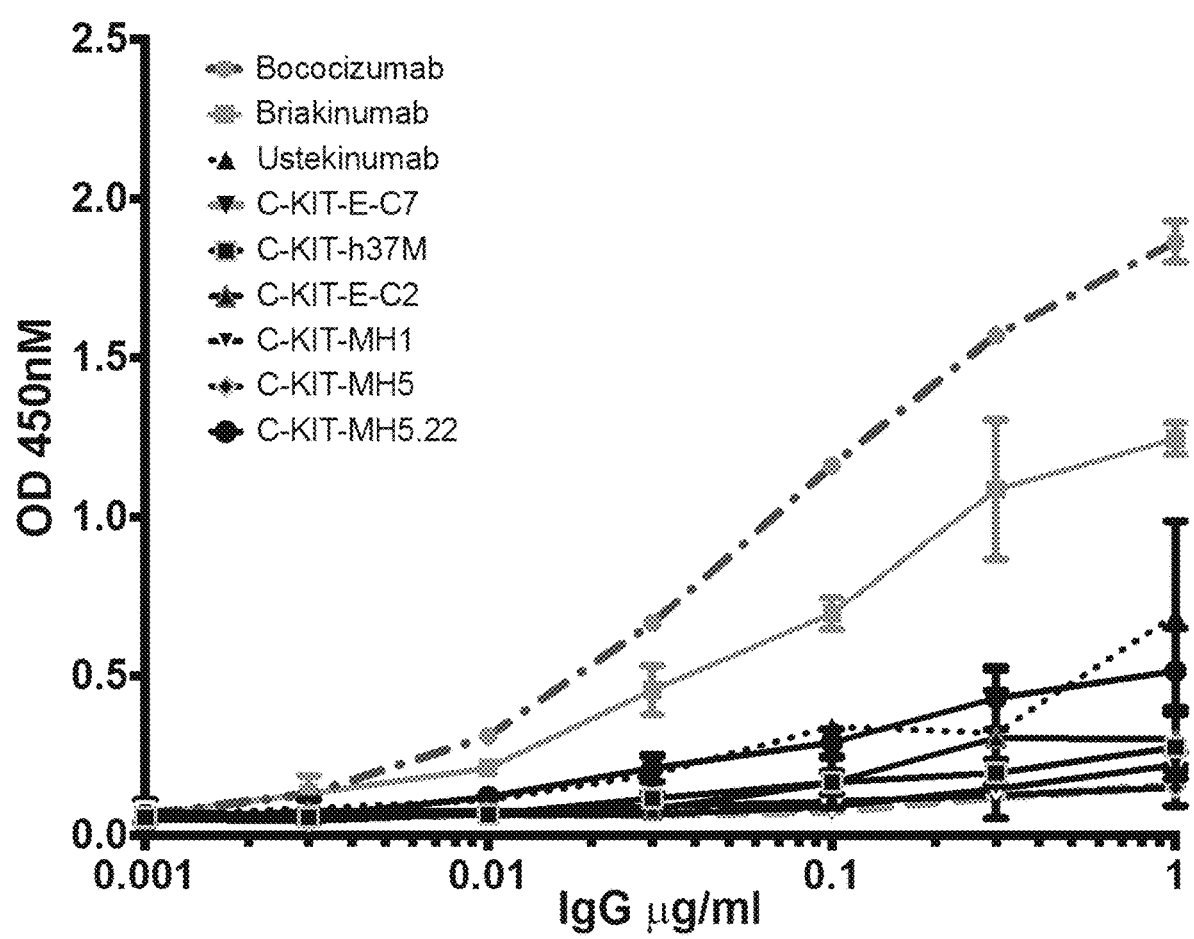
Figure 10C:
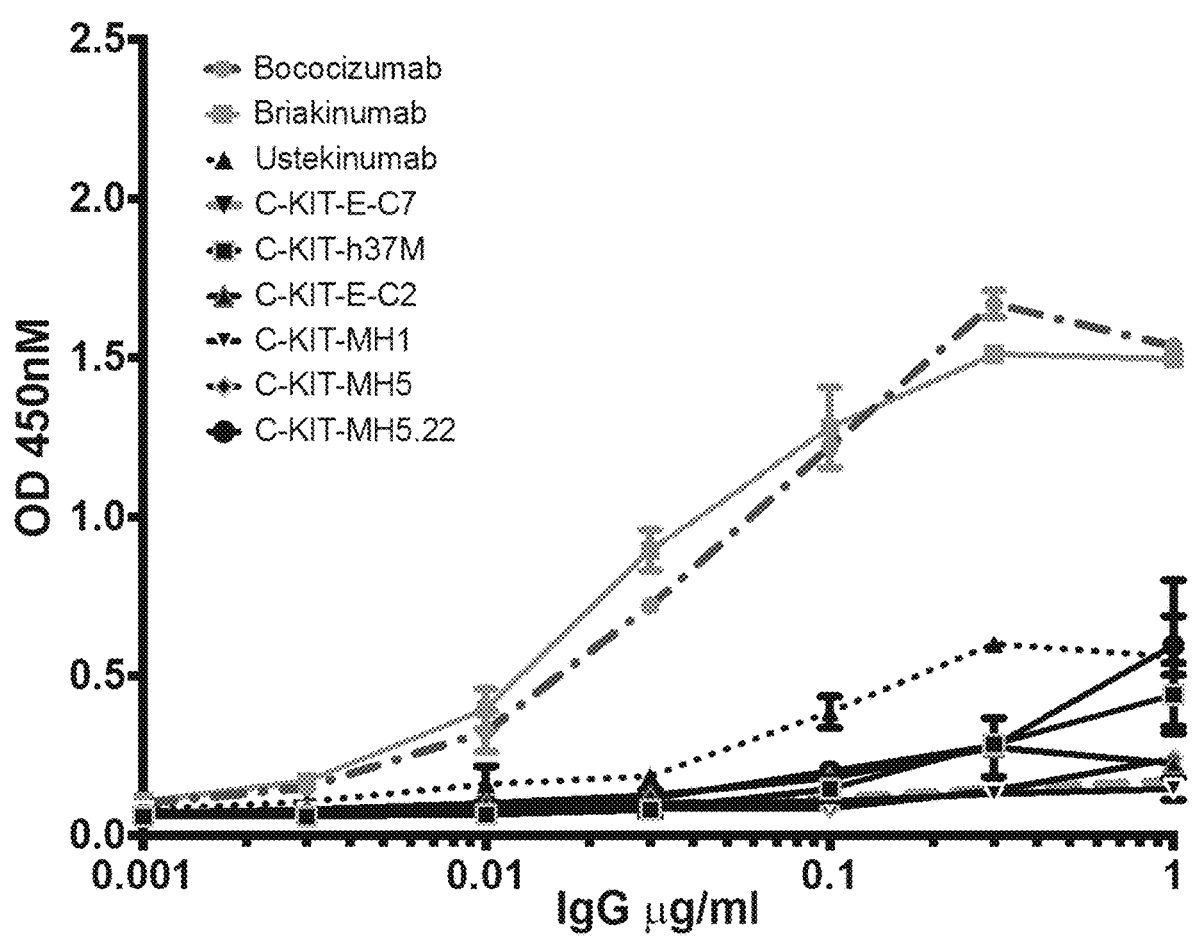
Figure 11A:
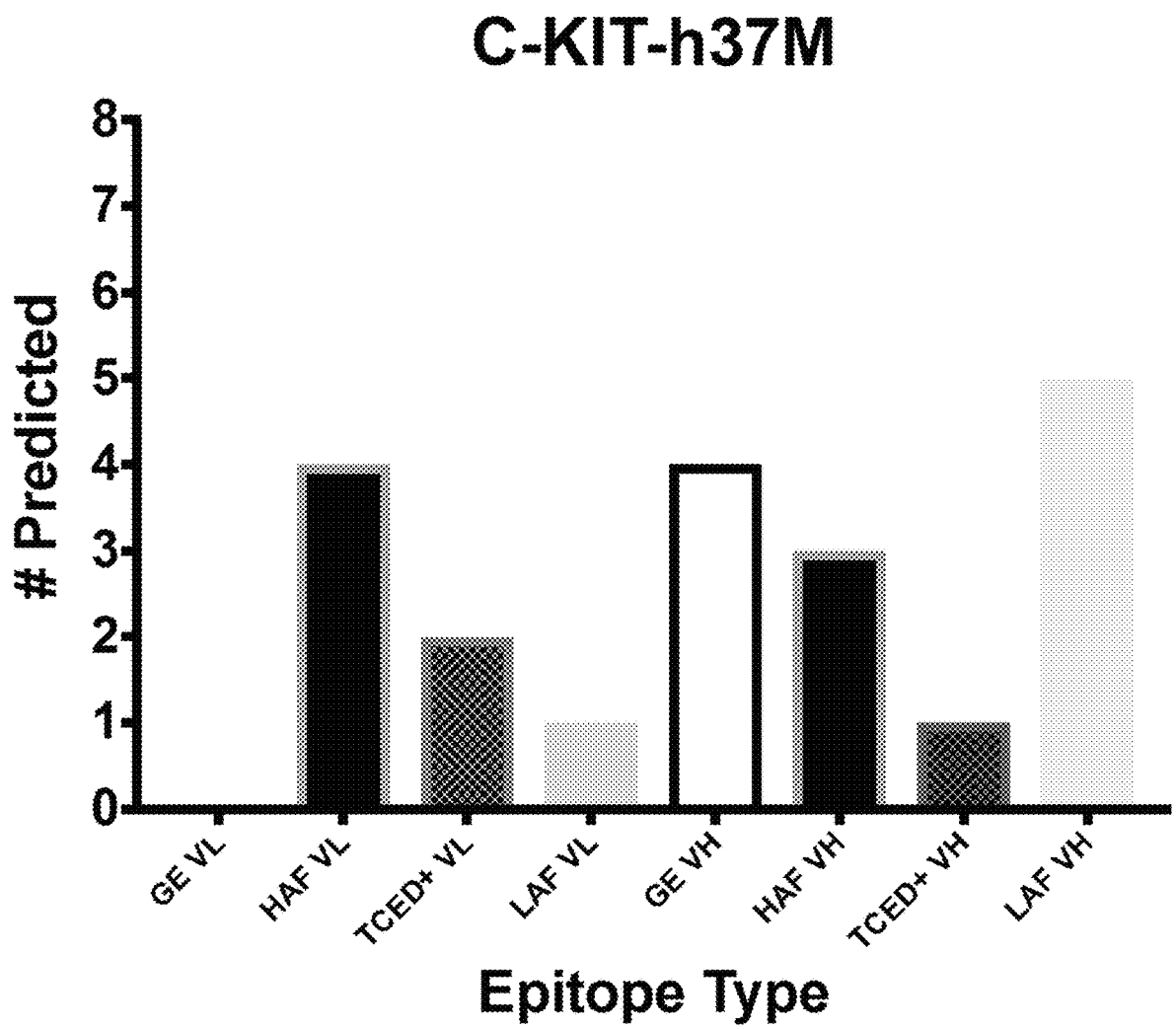
FIG. 11A-FIG. 11H. T cell epitope peptide content in lead antibody v-domains. The v-domains of h37M (FIG. 11A), E-C7 (FIG. 11B), F-05 (FIG. 11C), E-C3 (FIG. 11D), MH1 (FIG. 11E), MH5 (FIG. 11F), MH5.22 (FIG. 11G) and MH5-DI (FIG. 11H) antibodies were examined for the presence of Germline (GE), High Affinity Foreign (HAF), Low Affinity Foreign (LAF) and TCED+ T cell receptor epitopes. Both the VH and VL domains of h37M were found to contain multiple high-risk human T cell epitopes and few germline epitopes. In all lead clones, the high-risk epitope content was significantly reduced and germline epitope content improved.
Figure 11B:
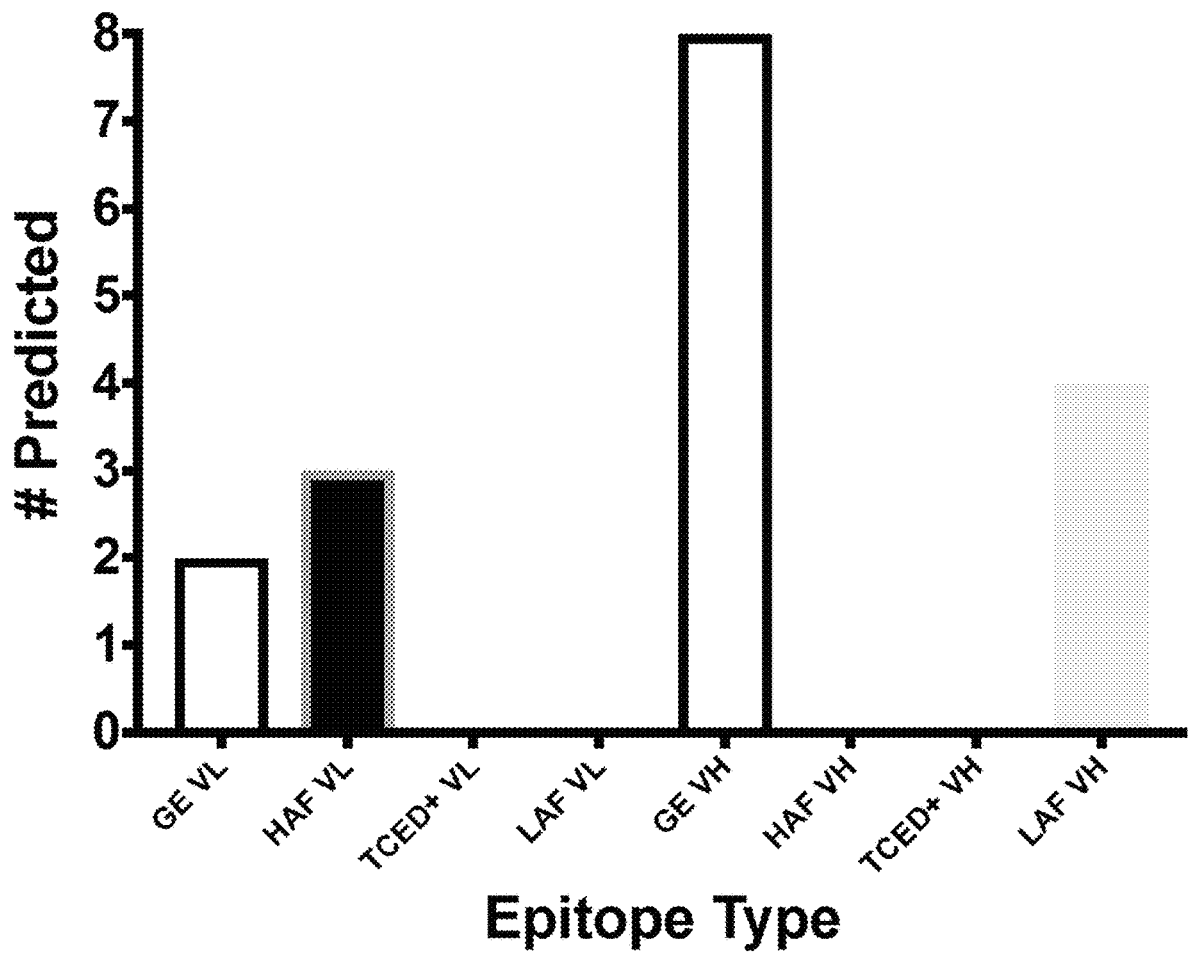
Figure 11C:
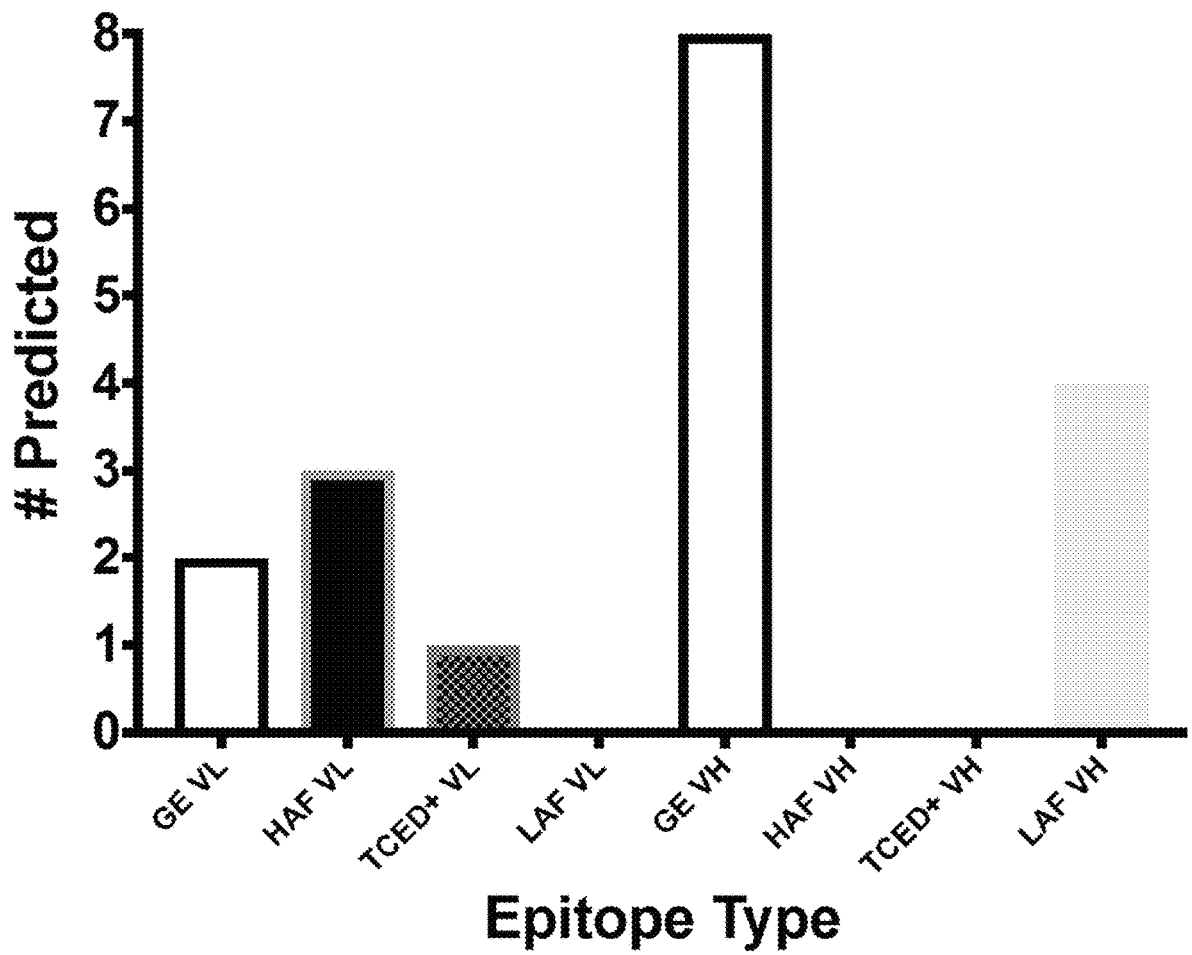
Figure 11D:
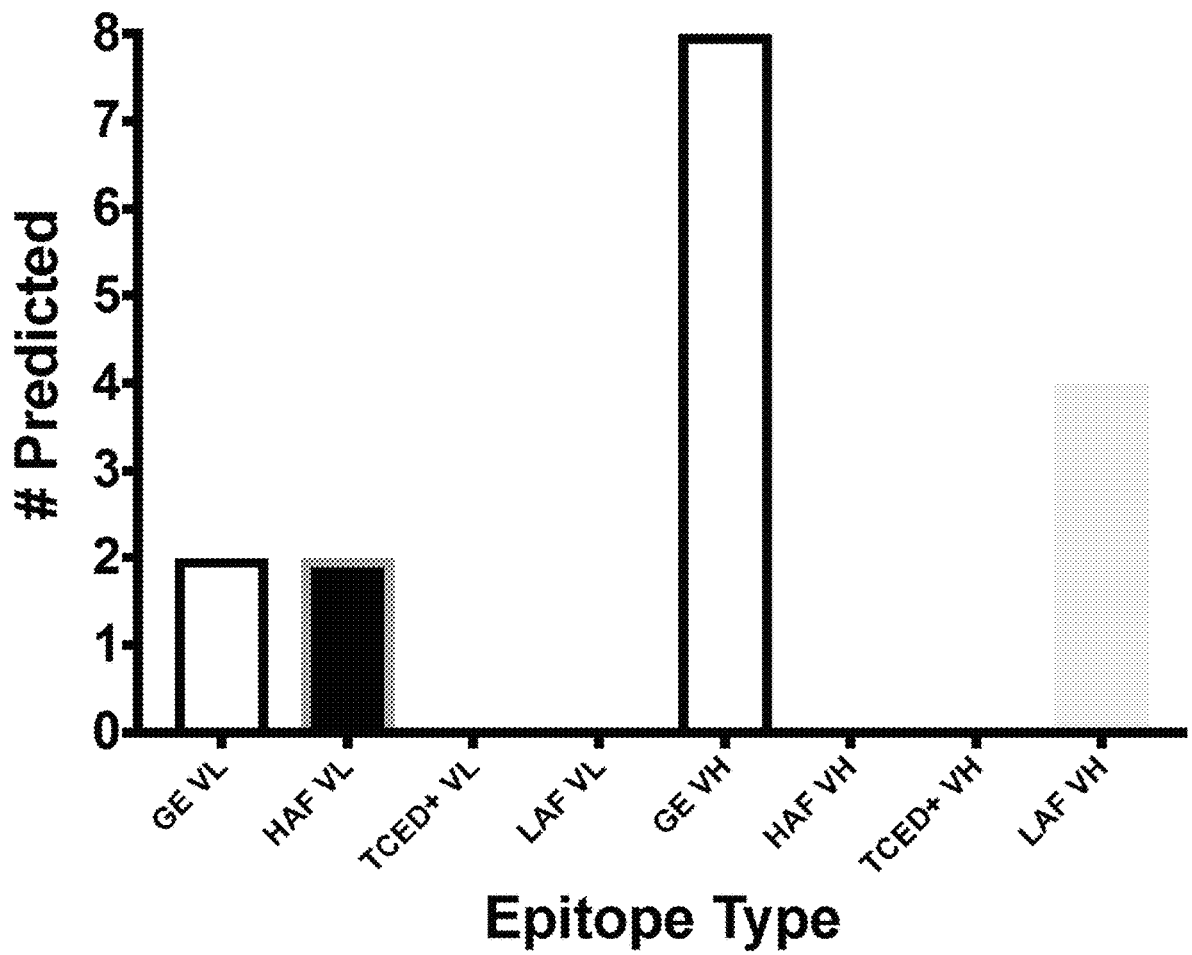
Figure 11E:
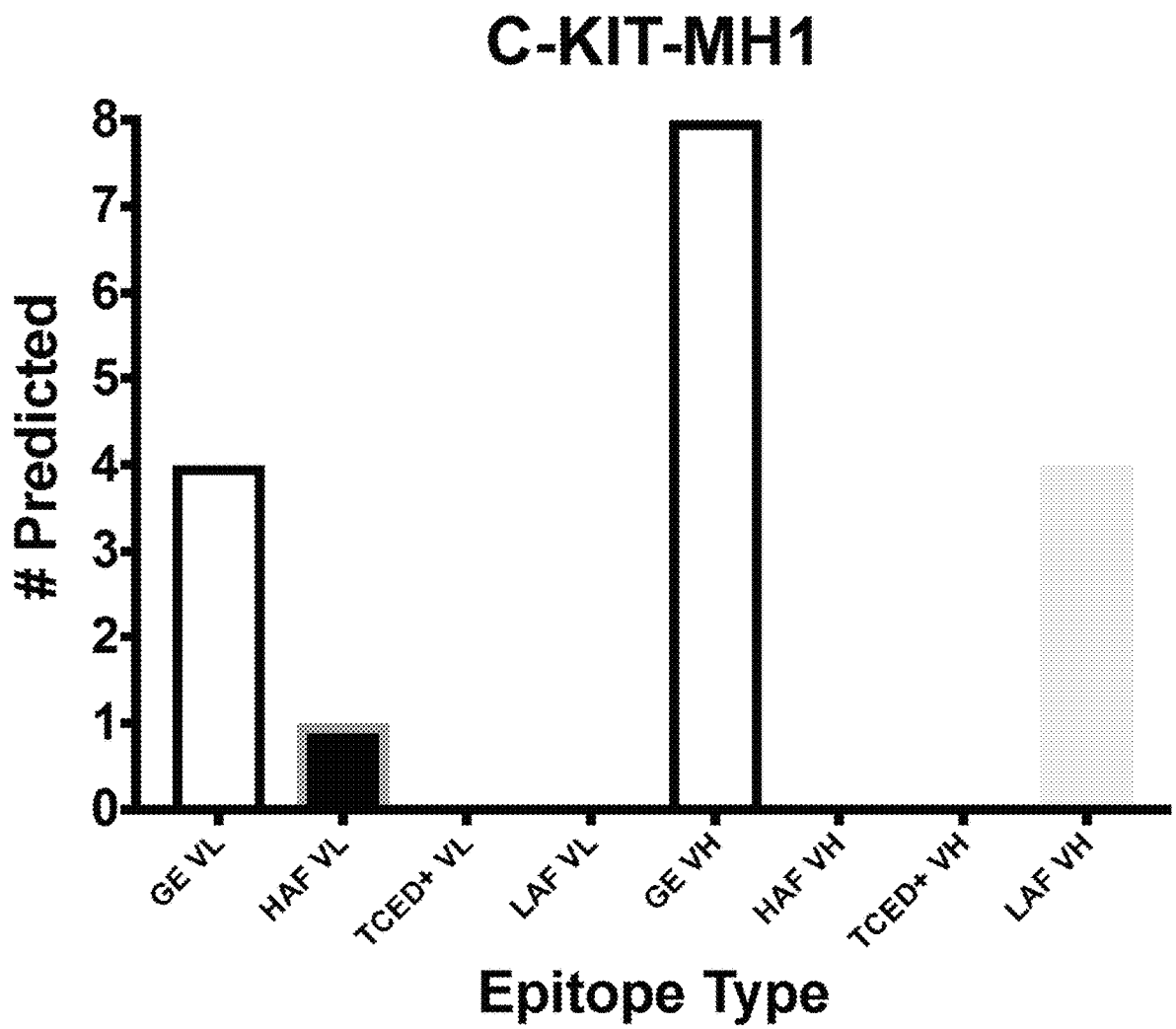
Figure 11F:
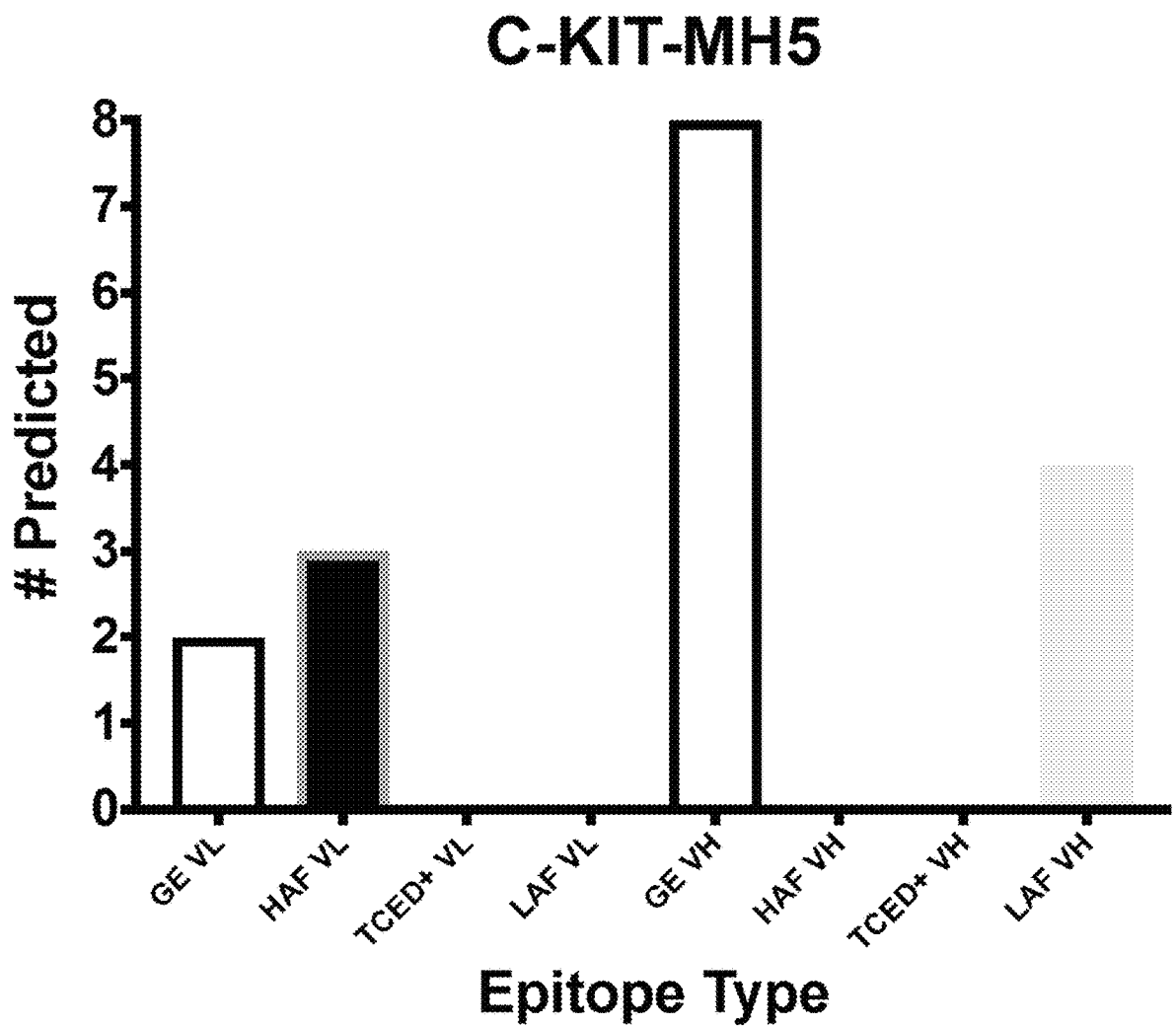
Figure 11G:
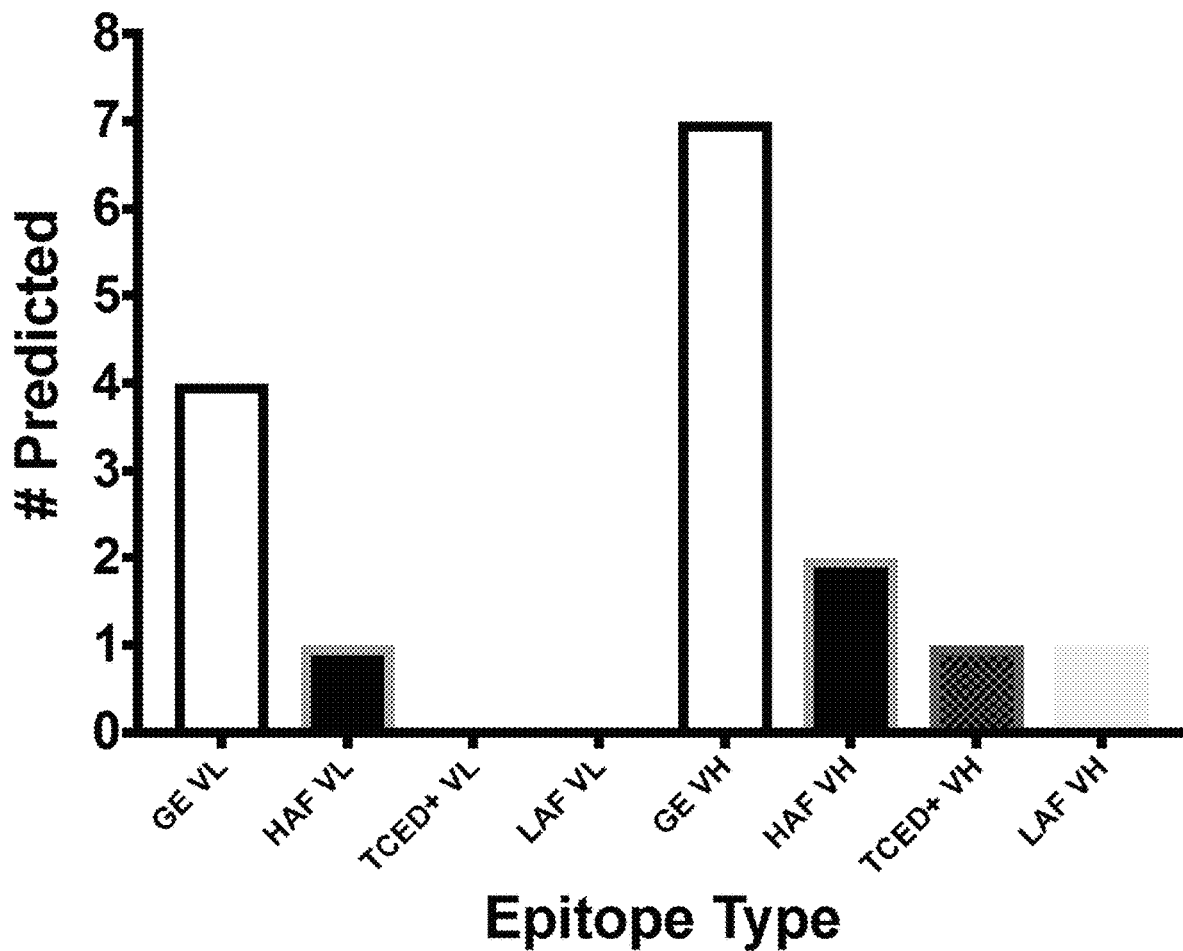
Figure 11H:
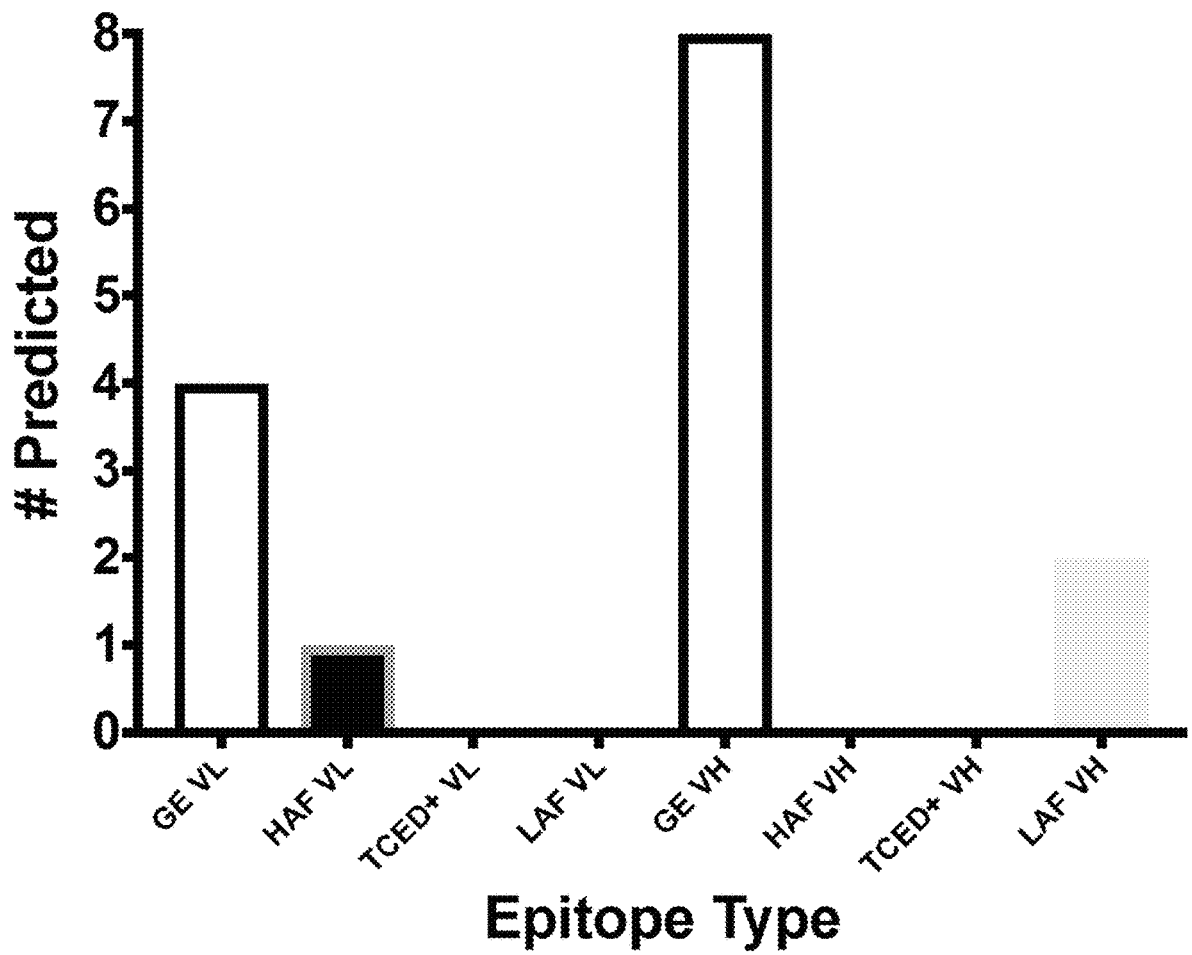
Figure 12B:
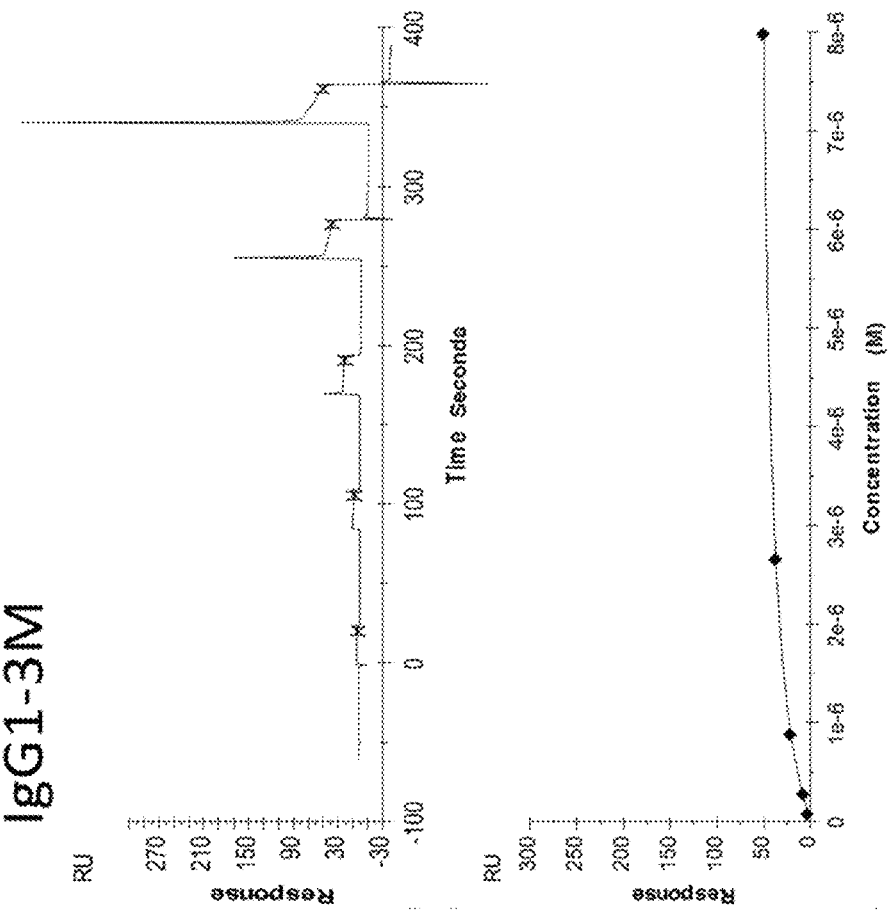
Figure 12C:
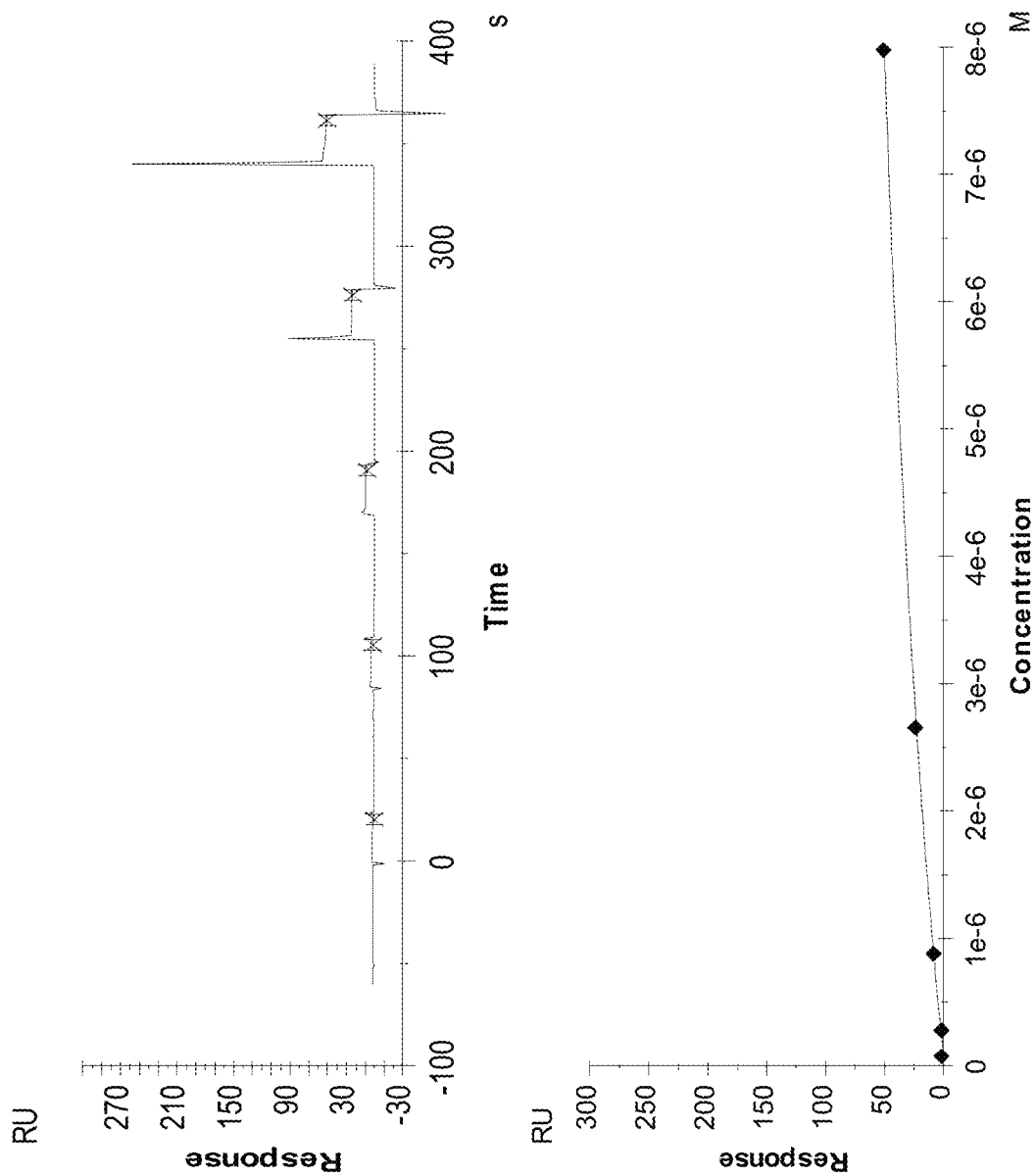
Figure 13A:
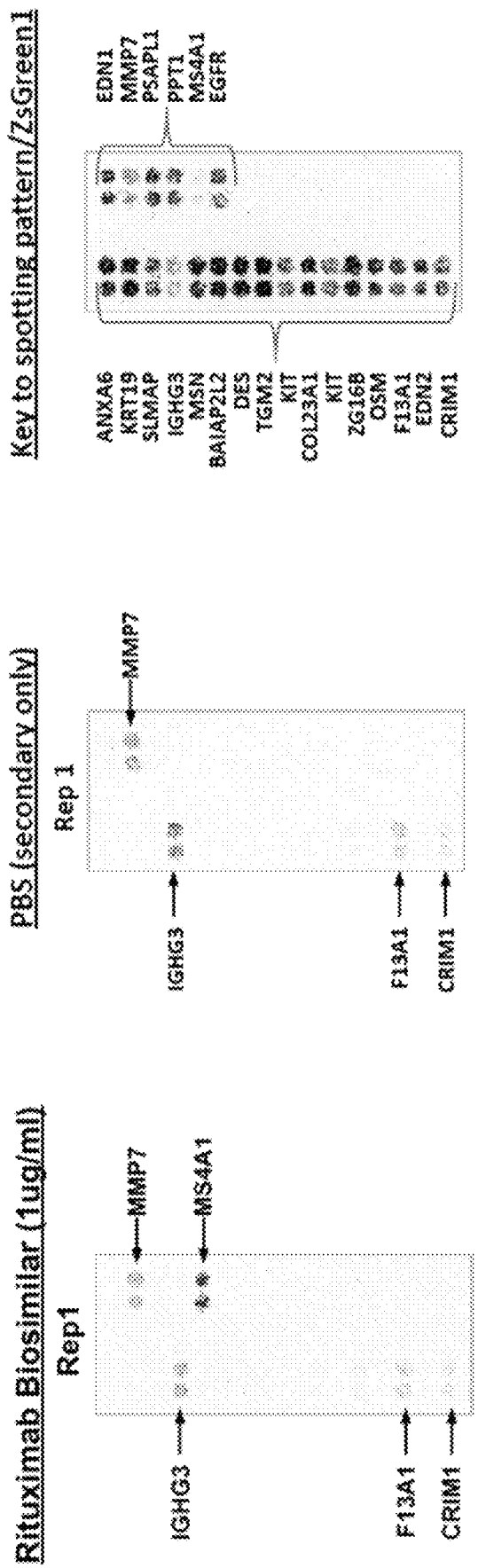
Figure 14A:
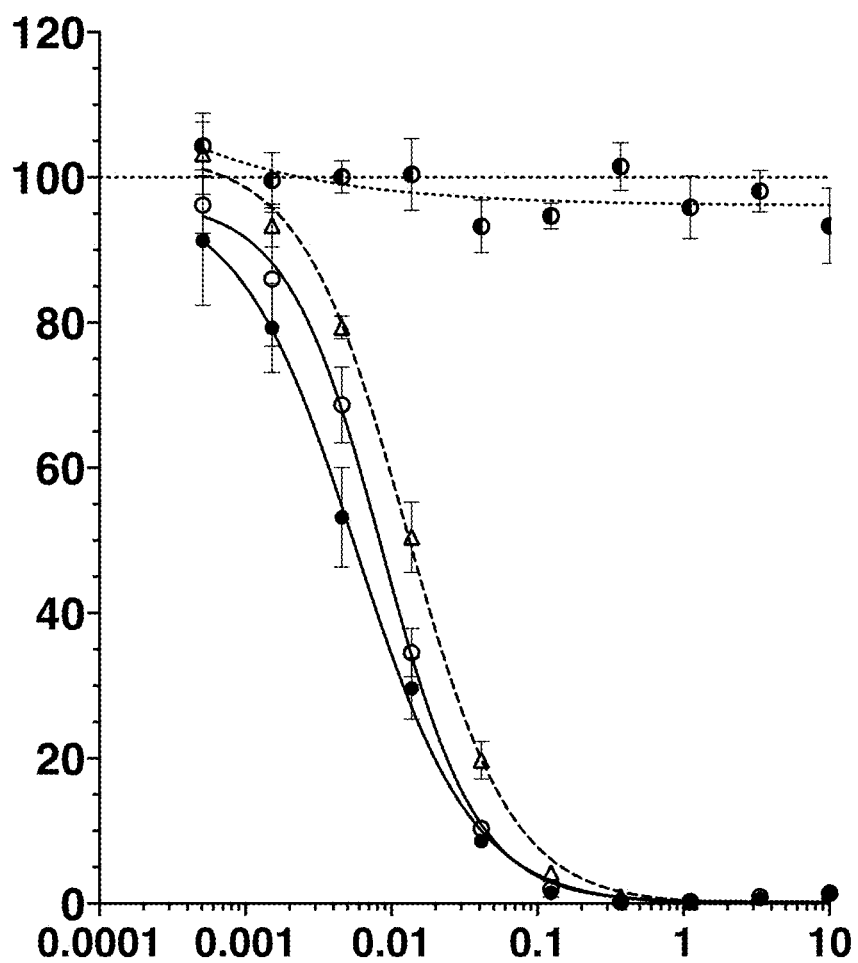
FIG. 14A-FIG. 14C. Anti-C-KIT cell killing assays. Internalisation and toxin delivery was examined on CHO cells transfected with human (FIG. 14A) and cyno (FIG. 14B) C-KIT, and the human erythroleukaemia cell line TF-1 (FIG. 14C), in the presence of FabZAP reagent. Clones h37M, MH1 and MH5-DI in IgG1-3M format all drove highly similar, high-potency cell killing.
Figure 14B:
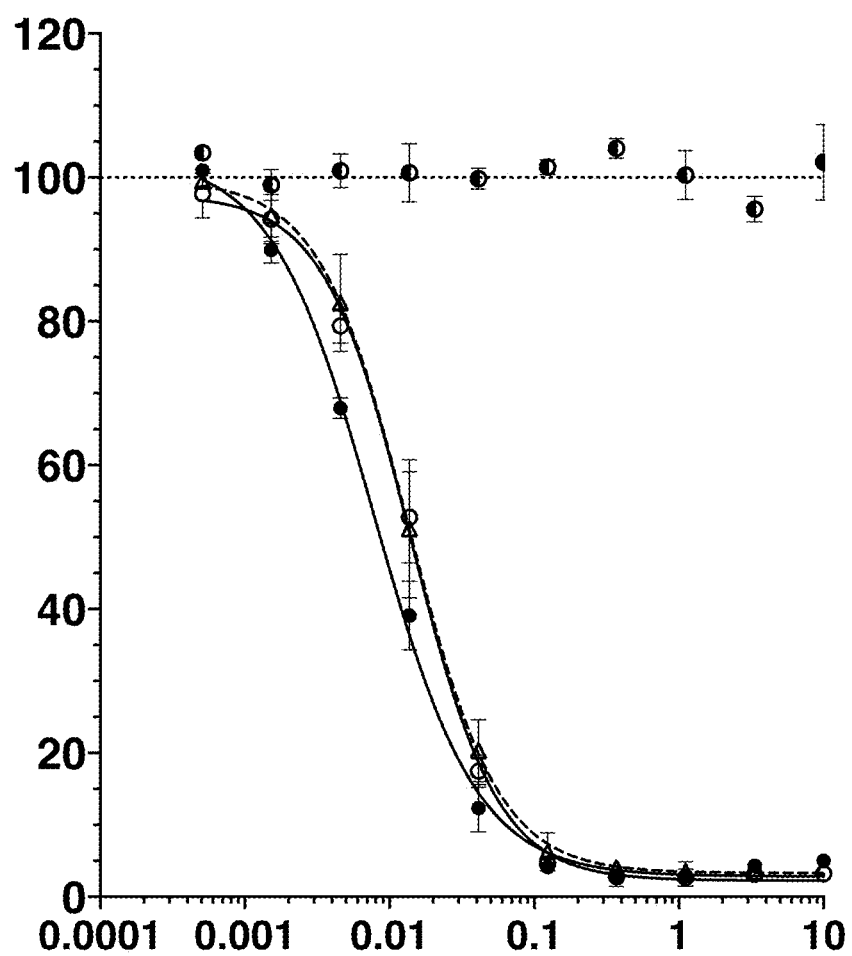
Figure 14C:
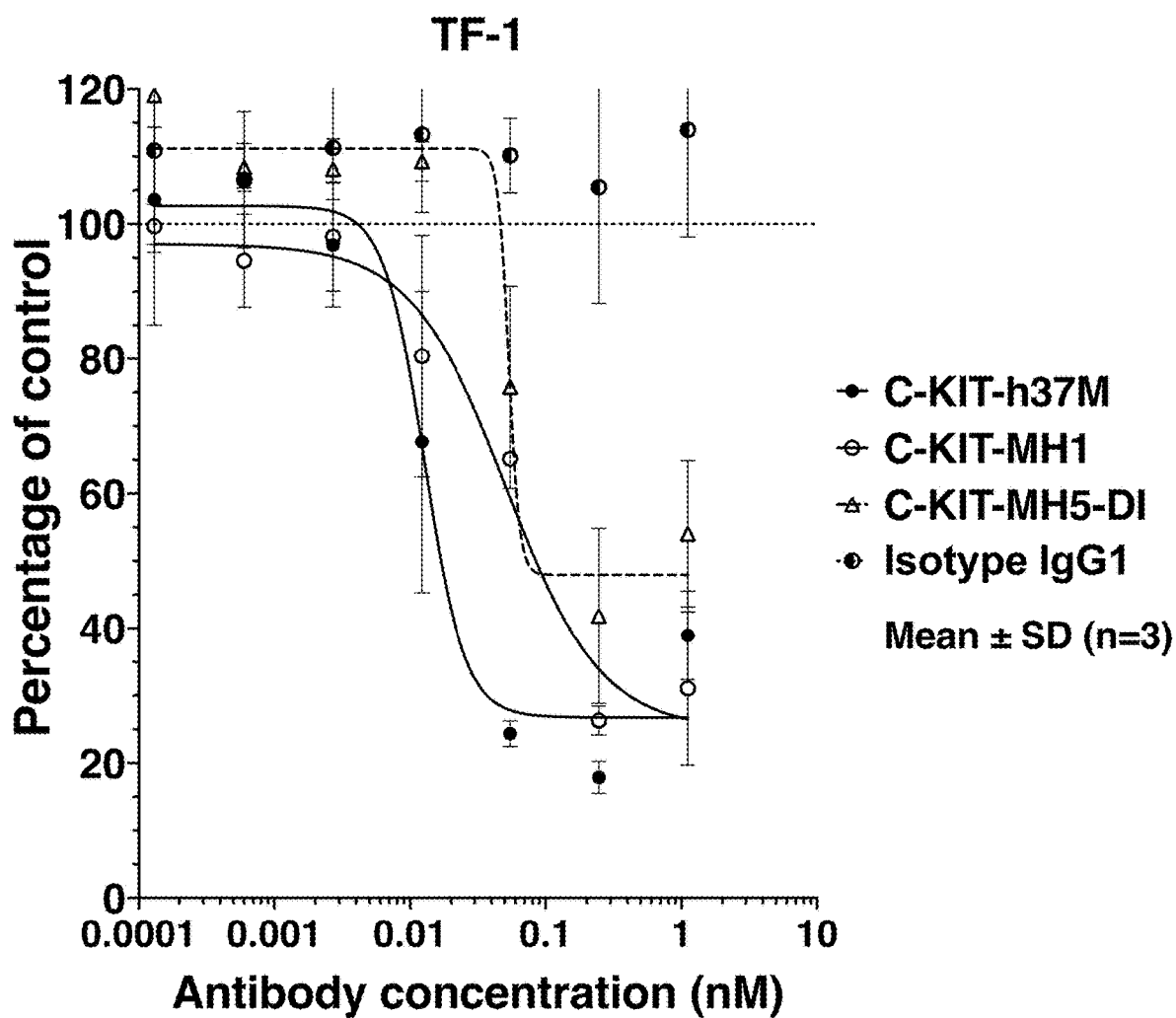
Figure 15A:
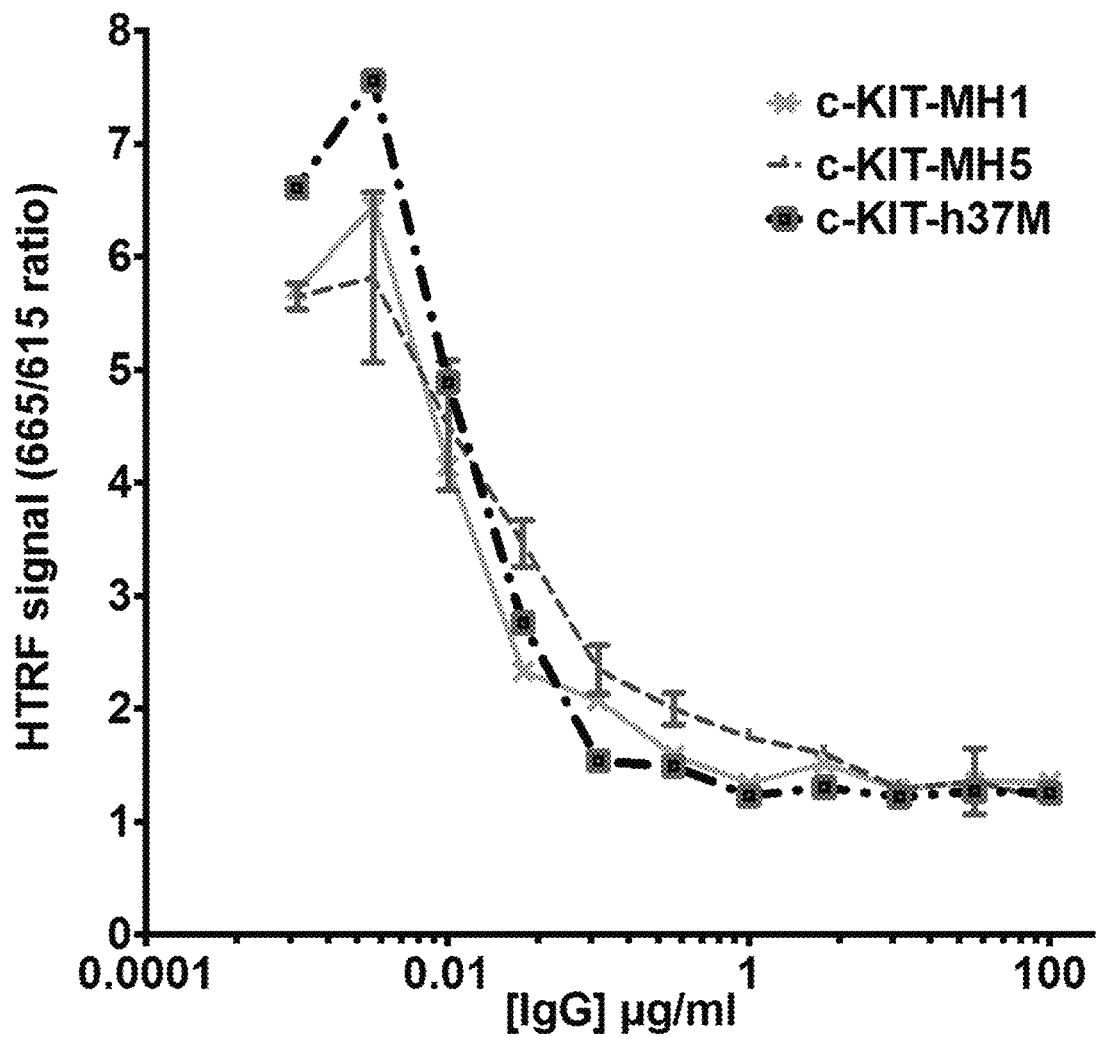
FIG. 15A-FIG. 15B. HTRF-based C-KIT epitope competition assay for h37M, MH1, MH5. HTRF binding signal for the h37M IgG to human or cyno C-KIT was examined in the presence of titrated competitor MH1 and MH5 in IgG1-3M format, plus isotype IgG1 as a negative control and unlabelled h37M IgG1-3M as a positive control. All IgGs (other than the Isotype control IgG1) exhibited full concentration-dependent inhibition of h37M binding to human (FIG. 15A) and cyno (FIG. 15B) C-KIT, overlapping with unlabelled h37M.
Figure 15B:
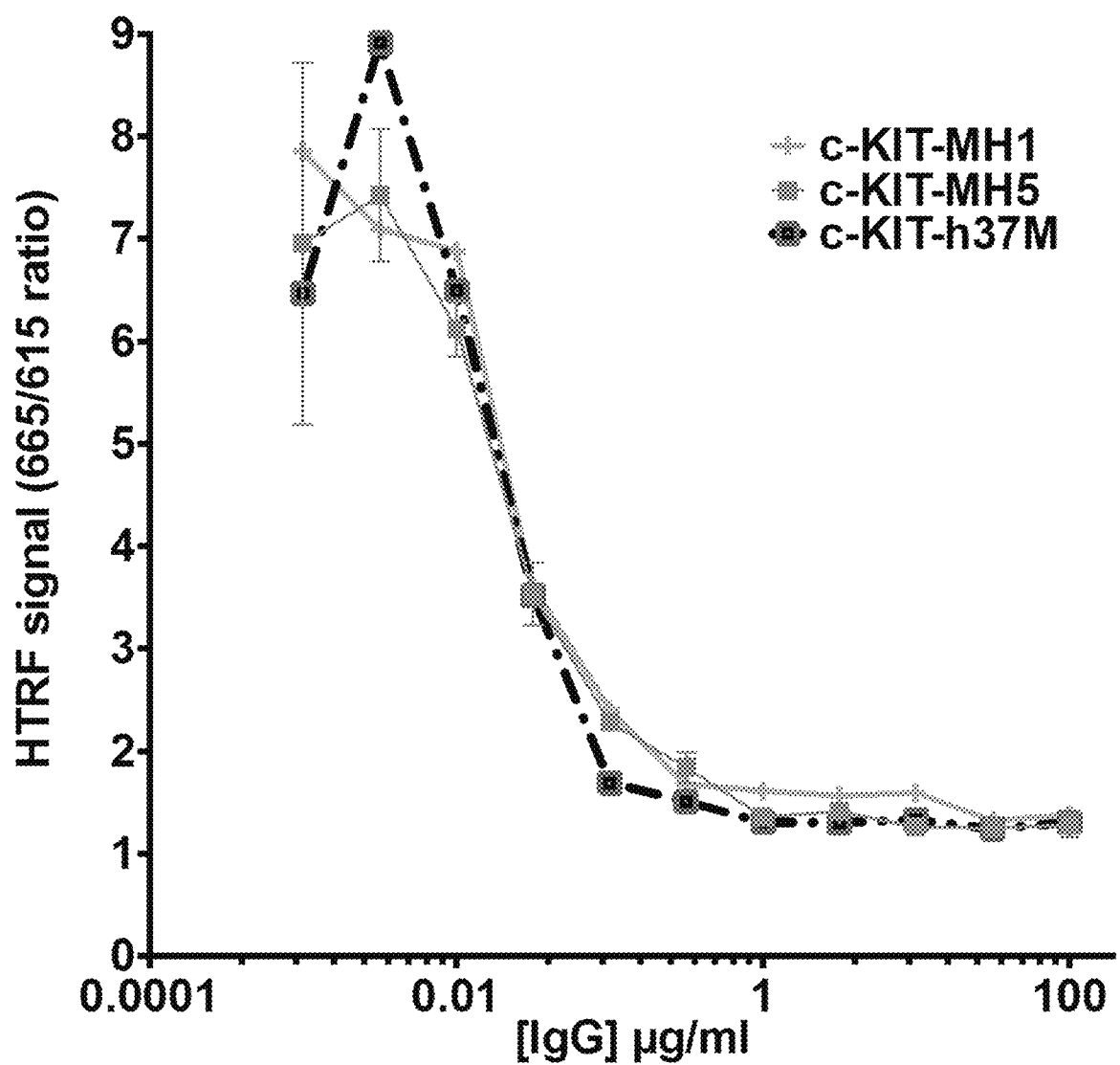
Figure 16:
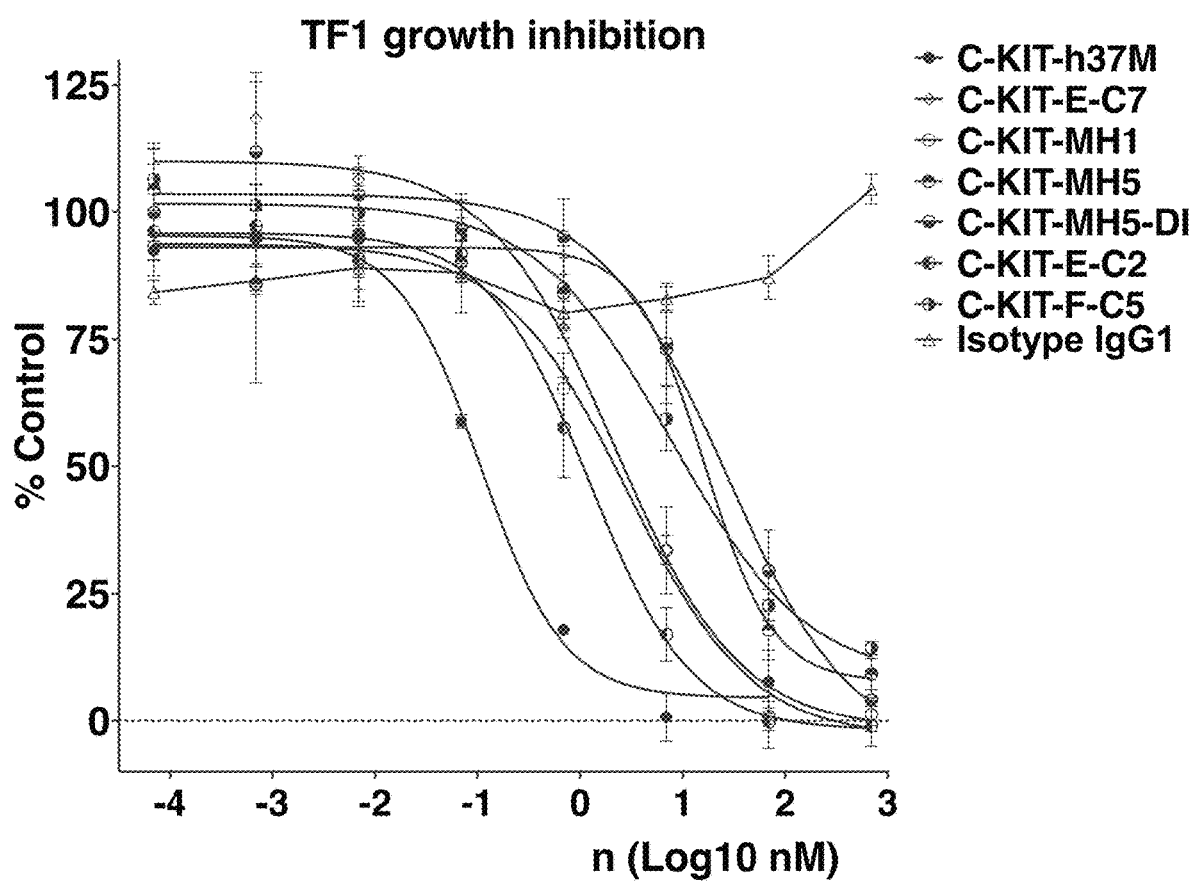
FIG. 16. TF-1 cell-based assay for inhibition of C-KIT/SCF-driven cellular proliferation. Human TF-1 cell line was cultured in the presence of SCF, which promotes cell proliferation through C-KIT. Antibodies were applied for 72 hours and proliferation measured via resazurin fluorescence. h37M was found to be unexpectedly significantly more potent than any other antibody tested.

Finally, the second-generation clones MH5.1, 5.2, 5.22, 5.23, 5.24, 5.33 and 5.34 were examined for their binding to human (FIG. 8A), cyno (FIG. 8B) or wild type control ('wt', i.e. untransfected) CHO-K1 (FIG. 8C) cells by flow cytometry. These analyses confirmed that each of these 7 prioritised second-generation clones still exhibit strong, concentration-dependent binding to human or cyno KIT+ CHO-K1 cells that is near identical to the signals generated by h37M and MH5, but also show no observable binding to untransfected CHO-K1.

Lead IgG Analyses in 'Developability' ELISA Assays

To ensure that high-affinity lead clones had not suffered from loss of target specificity during the mutation and reselection process; clones E-C2, E-C7, MH1, MH5, MH5.22 and h37M were tested for binding to a panel of 14 purified human proteins from the immunoglobulin superfamily (FIG. 9A-F). All six IgGs exhibited strong binding signals at 1 μg/ml to C-KIT-Fc (human OD450 nm>1.8, cyno>2.0), and no detectable binding (OD450 nm<0.1) against any other protein, including the closely-related murine and rat C-KIT-Fc proteins, which demonstrated that target binding specificity had been maintained in these clones.

It is known in the art that the binding of IgGs intended for therapeutic use to several indicative biological substrates is an indicator of high risk for poor performance in patients due to poor bioavailability and short in vivo half-life. Three such biological substrates are Insulin, dsDNA and ssDNA. These three substrates were therefore used to coat ELISA plates and examine the binding of the IgG1null versions of the optimised lead antibodies. Binding signals for these human IgG-based antibodies was compared to 'positive control' human IgG antibodies that have been found to have polyreactivity and poor performance, which stopped their progress in clinical trials (Bococizumab and Briakinumab human IgG1 analogues). For a negative control human IgG1 antibody, an IgG1 Ustekinumab analogue was used as it reacts with the same therapeutic target as Briakinumab, but has longer pK and was successfully approved as a therapeutic product. In the ELISA analyses shown in FIGS. 10A, B and C, the positive control antibodies exhibited the expected strong reactivity to all 3 substrates, while the negative control Ustekinumab showed low reactivity. Importantly, all of the IgG1 lead clones tested showed binding ≤the negative control against all 3 substrates. This finding underlined the maintenance of highly specific, target-driven binding in the optimised clones E-C2, E-C7, MH1, MH5 and MH5.22.

Antibody v-Domain T Cell Epitope Analyses

In silico technologies (Abzena, Ltd.), which are based on identifying the location of T cell epitopes in therapeutic antibodies and proteins, were used for assessing the immunogenicity of both the h37M and lead antibody v-domains. Analysis of the v-domain sequences was performed with overlapping 9mer peptides (with each overlapping the last peptide by 8 residues) which were tested against each of the 34 MHC class II allotypes. Each 9mer was scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e. 17 out of 34 alleles) had a high binding affinity (score>0.6), such peptides were defined as 'high affinity' MHC class II binding peptides which are considered a high risk for containing CD4+ T cell epitopes. Low affinity MHC class II binding peptides bind a high number of alleles (>50%) with a binding score>0.55 (but without a majority>0.6). Further analysis of the sequences was performed using the TCED™. The sequences were used to interrogate the TCED™ by BLAST search in order to identify any high sequence homology between peptides (T cell epitopes) from unrelated proteins/antibodies that stimulated T cell responses in previous in vitro T cell epitope mapping studies performed at Abzena Ltd.

Peptides were grouped into four classes: High Affinity Foreign ('HAF'—high immunogenicity risk), Low Affinity Foreign ('LAF'—lower immunogenicity risk), TCED+(previously identified epitope in TCED™ database), and Germline Epitope (GE'—human germline peptide sequence with high MHC Class II binding affinity). Germline Epitope 9mer peptides are unlikely to have immunogenic potential due to T cell tolerance, as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic.

As shown in FIG. 11 and Table 8, key lead v-domains exhibited significant beneficial changes in peptide epitope content in comparison to h37M. As the v-domain engineering process undertaken here had successfully selected for antibodies that maintained anti-KIT potency without the need for the murine residues included in the frameworks of h37M (Table 2), multiple HAF and LAF epitopes found in the frameworks of both the heavy and light chain v-domains of h37M (FIG. 11A) were absent in all library-derived and designer leads (Table 8). GE epitope content was also found to be significantly increased (from 4 to 10 in all leads), particularly in the VH regions of lead clones (FIGS. 11B-11H), and TCED+ epitopes were reduced or eliminated in all leads (Table 8). Importantly, however, multiple foreign epitopes were also eliminated by germlining mutations found in the CDRs of lead clones. For example, a TCED+ and HAF peptide 'VTITCKASQ' (SEQ ID NO: 64) found in the LCDR-1 of h37M was eliminated in all lead clones by the mutation K>R at position 6, converting this sequence to the light chain GE 'VTITCRASQ' (SEQ ID NO: 65; FIG. 11B-11H). Similarly, for clones MH1 (FIG. 11E) and MH5.22 (FIG. 11G), the HAF peptides 'LIYSASSLQ' (SEQ ID NO: 66) and 'IYSASSLQS' (SEQ ID NO: 67) were both converted to GE sequences by mutation of the LCDR-2 sequence to the fully germline sequence 'AASSLQS' (SEQ ID NO: 24). The stabilising mutations found in the LCDR-3 of clones MH5 and MH5.22 (Tables 4 and 6), which are mutations away from the IGKV1-16 germline, were not found to generate any epitopes.

In the VH region of h37M, the peptide sequence 'YYINWVRQA' (SEQ ID NO: 68; spanning the HCDR-1 and FW2) was found to be both a TCED+ and HAF. The HCDR-1 germlining mutation I>M at position 3, found in all leads other than MH5.22 (Table 6), eliminated this risk and converted the peptide sequence into a GE. For clone MH5.22 however, the mutation Y>W in the HCDR-3 compensated by eliminating two LAF peptide sequences (FIG. 11G, Table 8). The above findings allowed the generation of the fully sequence-optimised clone MH5-DI (by changing the LCDR-2 sequence of MH5 from SASSLQS (SEQ ID NO: 17) to AASSLQS (SEQ ID NO: 24)), which had minimised chemical stability and immunogenicity risk characteristics in its primary sequence (Table 8, FIG. 11H).

BIACORE® Analyses of Affinity of IgG Variants for Human Fc Receptors

Antibodies targeting the KIT receptor have been shown in human clinical studies and in vitro human immunological analyses to have a high risk of injection reactions in patients due to Fc receptor cross-linking during KIT engagement on mast cells (L'Italien et al., Clin Cancer Res 24(14):3465-3474, 2018). In order to examine receptor-engagement potential of Fc-engineered variants of the anti-KIT antibodies, h37M was expressed in IgG1 and IgG1-3M (L234A/L235A/G237A) formats, while clone MH1 was expressed in the novel IgG1-4M format (L234A/L235A/G237A/P331S). Each purified IgG1 variant was then examined for binding affinity to all human Fc receptors via surface plasmon resonance analyses. These analyses demonstrated that both the isotype control human IgG1 and h37M-IgG1 exhibited strong binding affinity for all human Fcγ receptors (Table 9) and normal affinity for FcRn at pH 6.0 but not pH 7.4 (Table 10). In contrast, while h37M-IgG1-3M and MH1 IgG1-4M also demonstrated normal affinity for FcRn at pH 6.0 but not pH 7.4 (Table 10), they both exhibited no measurable binding affinity for any human Fcγ receptors other than the inhibitory receptor FcγRIIb (Table 9). The lowest signals on FcγRIIb were observed for the MH1 IgG-4M (FIG. 12). As demonstrated by the isotype control human IgG4 antibody, use of this isotype reduces the affinity of the antibody to most Fcγ receptors, but is not sufficient to fully ablate activating receptor interaction (Table 9).

Lack of binding to activating FcγRI, FcγRIIa, FcγRIIIa and FcγRIIIb, but maintained binding to inhibitory receptor FcγRIIb and recycling receptor FcRn is an ideal combination of characteristics for an anti-KIT therapeutic antibody in either standard IgG form or as an armed antibody (used in antibody drug conjugate form, or in targeting another immune-activating mechanism such as CD3 ligation, CD16A ligation or CD47 blockade), as this potentially maximises the half-life of the molecule in circulation and simultaneously minimises the risk of mast cell activation-related toxicity in man.

Human Extracellular Proteome Array Analyses of Antibody Specificity

The exquisite specificity of antibody target recognition is one of the primary reasons they are chosen as drug candidates. This specificity is not guaranteed however, and impaired specificity after in vitro engineering of antibodies is a risk. To examine this possibility in the antibodies generated here, in vitro technologies (Retrogenix, Ltd.), which are based on using high-density arrays of cells expressing 5528 unique human plasma membrane and cell surface-tethered secreted proteins, were used to screen for off-target binding specificities in IgG1-h37M and IgG1-MH1. This receptor array binding screen identified that both antibodies exhibited strong binding to membrane-expressed C-KIT, but also had 3 potential off-target binding specificities: MMP7, CRIM1 and F13A1. Analysis of these interactions on re-array slides showed that these interactions were in fact artefactual and were mediated by the secondary antibody (FIG. 13A). For IgG1-h37M and IgG1-MH1 (FIG. 13B, 13C), they therefore showed extreme specificity, both binding only to the 2 known isoforms of C-KIT: accession numbers NM_000222.2 (canonical isoform; SEQ ID NO:209) and NM_001093772 (short isoform; SEQ ID NO:210). Repeat analyses of clones E-C2, E-C7, F-05 and MH5 also exhibited highly specific binding to both C-KIT isoforms.

Cell-Killing Potential in Armed Antibody Formats and Comparison with C-KIT/SCF Neutralisation Potency A key characteristic of antibody drug conjugates is the ability to internalise into cells expressing the antibody's cognate target. Internalisation of anti-c-KIT antibodies was assessed using a goat polyclonal heavy and light chain specific Fab conjugated to saporin toxin. The Fab-ZAP reagent binds to the human IgG1 and if that IgG1 binds to a protein on a cell surface and is internalised, then the Fab-ZAP reagent is also internalised into endosomes. Once in the endosome, the saporin toxin is released from the complex and inactivates ribosomes, eventually resulting in cell death. This method therefore allows direct comparison of the potential potency of IgG1 antibodies as antibody drug conjugates. In these internalisation experiments, all antibodies h37M, MH1 and MH5-DI in IgG1-3M form drove highly potent internalisation and killing of CHO cells expressing human C-KIT (FIG. 14A), cyno C-KIT (FIG. 14B), and the TF-1 human erythroleukaemia line (FIG. 14C), while isotype control human IgG1 did not drive any internalisation or killing of any of the 3 cell types.

Importantly, all 3 clones also generated highly similar potencies, as measured in IC50, with all 3 IC50 values being within ~2-fold on KIT+ CHO cells and within ~4-fold on TF-1 cells (Table 11). These highly similar values for potency in cell-killing experiments were expected, as clones MH1 and MH5 exhibited fully overlapping curves with h37M (and therefore indistinguishable affinities for C-KIT) in high-sensitivity, solution-phase HTRF epitope competition for binding to human C-KIT (FIG. 15A) and cyno C-KIT (FIG. 15B), as above.

As the erythroleukaemia line TF-1 constitutively expresses C-KIT, it is driven to proliferate when the natural ligand for C-KIT, SCF, is added to culture media. This provided an ideal experimental context in which to examine the potency of the anti-C-KIT IgGs in the neutralisation of C-KIT/SCF signalling. TF-1 cells were cultured in the presence of SCF and multiple antibodies tested for their ability to inhibit cellular proliferation. This analysis demonstrated that all antibodies tested were capable of inhibiting cellular proliferation being driven by SCF, but that h37M was significantly more potent than any other clone (FIG. 16). Indeed, when IC50 values were generated, it was found that only h37M exhibited potency in the pM range (0.11 nM), while MH1 and MH5-DI were 26.5-fold and 243.6-fold less potent, respectively (Table 11).

This potency differential in C-KIT/SCF inhibition versus internalisation and toxin delivery is a significant unexpected benefit for clones such as MH1 and MH5-DI. C-KIT is highly expressed on haematopoietic stem cells in the bone marrow, so anti-C-KIT antibody drug conjugates for the treatment of cancer exhibit improved therapeutic index when they efficiently deliver toxins in the pM concentration range but are incapable of blocking C-KIT/SCF signalling when dosed at such low concentrations. This leads to improved tumor targeting, but reduced bone marrow toxicity (L'Italien et al., Clin Cancer Res 24(14):3465-3474, 2018). Reduced potency in C-KIT/SCF signalling inhibition, but retention of high affinity binding to the C-KIT ectodomain may also prove to be beneficial for improving the therapeutic index of other forms of armed anti-C-KIT antibody, for example in immune targeting via CD3 ligation, CD16A ligation, or CD47 blockade. Clones described here, such as MH1 and MH5-DI in IgG1-4M format may therefore have the ideal set of improved characteristics over h37M-IgG1 for development as armed anti-C-KIT antibodies: low immunogenicity, high affinity/high specificity targeting of C-KIT, high potency delivery of toxins via internalisation, lower potency C-KIT/SCF signalling inhibition and no interaction with human Fcγ receptors.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

TABLE 1

Amino acid sequences murine anti-C-KIT CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Unified | GYTFTDYYIN (SEQ ID NO: 4) | IARIYPGSGNTYYNEKFKG (SEQ ID NO: 5) | GVYYFDY (SEQ ID NO: 6) | KASQNVRTNVA (SEQ ID NO: 10) | SASYRYS (SEQ ID NO: 11) | QQYNSYPRT (SEQ ID NO: 12) |
| Kabat | DYYIN (SEQ ID NO: 69) | RIYPGSGNTYYNEKFKG (SEQ ID NO: 73) | GVYYFDY (SEQ ID NO: 6) | KASQNVRTNVA (SEQ ID NO: 10) | SASYRYS (SEQ ID NO: 11) | QQYNSYPRT (SEQ ID NO: 12) |
| Chothia | GYTFTDY (SEQ ID NO: 70) | YPGSGN (SEQ ID NO: 74) | GVYYFDY (SEQ ID NO: 6) | KASQNVRTNVA (SEQ ID NO: 10) | SASYRYS (SEQ ID NO: 11) | QQYNSYPRT (SEQ ID NO: 12) |
| IMGT | GYTFTDYY (SEQ ID NO: 71) | IYPGSGNT (SEQ ID NO: 75) | ARGVYYFDY (SEQ ID NO: 79) | QNVRTN (SEQ ID NO: 82) | SAS | QQYNSYPRT (SEQ ID NO: 12) |
| AHo | GYTFTDYYIN (SEQ ID NO: 4) | IYPGSGNTYYNEKFKG (SEQ ID NO: 76) | GVYYFD (SEQ ID NO: 80) | ASQNVRTN (SEQ ID NO: 83) | SASYRYS (SEQ ID NO: 11) | YNSYPR (SEQ ID NO: 86) |
| AbM | GYTFTDYYIN (SEQ ID NO: 4) | RIYPGSGNTY (SEQ ID NO: 77) | GVYYFDY (SEQ ID NO: 6) | KASQNVRTNVA (SEQ ID NO: 10) | SASYRYS (SEQ ID NO: 11) | QQYNSYPRT (SEQ ID NO: 12) |
| Contact | TDYYIN (SEQ ID NO: 72) | IARIYPGSGNTY (SEQ ID NO: 78) | ARGVYYFD (SEQ ID NO: 81) | VRTNVAWY (SEQ ID NO: 84) | ALIYSASYRY (SEQ ID NO: 85) | QQYNSYPR (SEQ ID NO: 207) |

TABLE 2

Amino acid sequence of 37M murine anti-C-KIT v-domains (m37M) and human germline CDR grafts (h37M).

| V DOMAIN | Human germline[1] | Amino acid sequence[2] |
|---|---|---|
| m37M-VH | n/a | QVQLKQSGAELVRPGASVKLSCKASGYTFTDYYINWVKQRPGQGLEWIARIYPGSGNTYYNEKFKGKATLTAEKSSSTAYM QLSSLTSEDSAVYFCARGVYYFDYWGQGTTLTVSS |

TABLE 2-continued

Amino acid sequence of 37M murine anti-C-KIT v-domains (m37M) and human germline CDR grafts (h37M).

| V DOMAIN | Human germline[1] | Amino acid sequence[2] |
|---|---|---|
| | | (SEQ ID NO: 87) |
| h37M-VH | IGHV1-46[3] | QVQLVQSGAEVKKPGASVKLSCKASGYTFTDYYINWVRQAPG*K*GLEWIARIYPGSGNTYYNEKFKGR*ATLTADKSTST *A*YM*Q*LSSLRSEDTAVY*F*CARGVYYFDYWGQGTTVTVSS (SEQ ID NO: 88) |
| VH graft | IGHV1-46[4] | QVQLVQSGAEVKKPGASVKVSCKASGYTFTDYYINWVRQAPGQGLEWIARTYPGSGNTYYAQKFQGRVTMTRDTSTSTVYMELSSLRSEDTAVYYCARGVYYFDYWGQGTLVTVSS (SEQ ID NO: 89) |
| m37M-VL | n/a | DIVMTQSQKFMSTSVGDRVSVTCKASQNVRTNVAWYQQKPGQSPKALIYSASYRYSGVPDRFTGSGSGTDFTLTISNVQSEDLADYFCQQYNSYPRTFGGGTKLEIKR (SEQ ID NO: 90) |
| h37M-VL | IGKV1-16[3] | DI*V*MTQSPSSLSASVGDRVTITCKASQNVRTNVAW*Y*QQKPGKAPK*A*LIYSASYRYSGVP*D*RF*T*GSGSGTDFTLTISSLQPEDFA*D*YFCQQYNSYPRTFGGGTKVEIK (SEQ ID NO: 91) |
| VL graft | IGKV1-16[4] | DIQMTQSPSSLSASVGDRVTITCRASQGVRTNVAWFQQKPGKAPKSLIYSASYRYSGVPSRFSGSGSGTDFTLTISSLQPEDFATTYCQQYNSYPRTFGGGTKVEIK (SEQ ID NO: 92) |

[1]Human germline definitions used for grafting, based on IMGT system.
[2]CDR residues are in bold and underlined. As noted above, the "Unified" CDR definitions used in this manuscript are an expanded definition in comparison to the classical Kabat definition. Each sequence above shows the framework regions (FRs) and the CDRs in the following order: FR1-CDR1-FR2-CDR2-FR3-CDR3-FR4.
[3]h37M domains contain several murine residues in the framework regions, shown here *italicized*.
[4]Grafts are fully germline in the framework regions, used as the template for CDR mutant library construction.

TABLE 3

Amino acid sequences of unique CDRs from 219 unique anti-C-KIT v-domains.

| LCDR1 | LCDR2 | LCDR3 | HCDR1 | HCDR2 | HCDR3 |
|---|---|---|---|---|---|
| RASQGIRNNLA (SEQ ID NO: 93) | AASSLQS (SEQ ID NO: 24) | QQYASYPLT (SEQ ID NO: 119) | GYTFTDYYMH (SEQ ID NO: 123) | IAIIYPGSGNTYYAQKFQG (SEQ ID NO: 126) | GVYYFDA (SEQ ID NO: 151) |
| RASQGIRNNVA (SEQ ID NO: 94) | AASSLYS (SEQ ID NO: 111) | QQYASYPRT (SEQ ID NO: 53) | GYTFTDYYMN (SEQ ID NO: 13) | IARINPGSGNTSYAQKFQG (SEQ ID NO: 127) | GVYYFDD (SEQ ID NO: 152) |
| RASQGIRNYVA (SEQ ID NO: 95) | AASSRQS (SEQ ID NO: 23) | QQYNSYPLT (SEQ ID NO: 120) | GYTFTSYYIN (SEQ ID NO: 124) | IARINPGSGNTYYAQKFQG (SEQ ID NO: 128) | GVYYFDE (SEQ ID NO: 21) |
| RASQGIRTNLA (SEQ ID NO: 16) | AASSRYS (SEQ ID NO: 112) | QQYQSYPLT (SEQ ID NO: 121) | GYTFTSYYMN (SEQ ID NO: 125) | IARIYPGSGNTSYAQKFQG (SEQ ID NO: 129) | GVYYFDF (SEQ ID NO: 153) |
| RASQGIRTNVA (SEQ ID NO: 19) | AASYLQS (SEQ ID NO: 50) | QQYQSYPRT (SEQ ID NO: 122) | | IARIYPGSGNTYYAQKFQG (SEQ ID NO: 206) | GVYYFDG (SEQ ID NO: 154) |
| RASQGISNYLA (SEQ ID NO: 96) | AASYLYS (SEQ ID NO: 113) | | | IARIYPSSGNTSYAQKFQG (SEQ ID NO: 130) | GVYYFDH (SEQ ID NO: 155) |
| RASQGISNYVA (SEQ ID NO: 97) | AASYRQS (SEQ ID NO: 44) | | | IARIYPSSGNTYYAQKFQG (SEQ ID NO: 131) | GVYYFDI (SEQ ID NO: 156) |
| RASQGISTNLA (SEQ ID NO: 98) | AASYRYS (SEQ ID NO: 114) | | | IGIIYPGSGNTYYAQKFQG (SEQ ID NO: 132) | GVYYFDK (SEQ ID NO: 157) |
| RASQGISTNVA (SEQ ID NO: 99) | SASSLQS (SEQ ID NO: 17) | | | IGRINPGSGNTSYAQKFQG (SEQ ID NO: 133) | GVYYFDL (SEQ ID NO: 205) |
| RASQGISTYLA (SEQ ID NO: 100) | SASSLYS (SEQ ID NO: 115) | | | IGRINPGSGNTYYAQKFQG (SEQ ID NO: 134) | GVYYFDM (SEQ ID NO: 158) |
| RASQGISTYVA (SEQ ID NO: 101) | SASSRQS (SEQ ID NO: 52) | | | IGRIYPGSGNTSYAQKFQG (SEQ ID NO: 135) | GVYYFDN (SEQ ID NO: 159) |
| RASQGVRNNLA (SEQ ID NO: 43) | SASSRYS (SEQ ID NO: 116) | | | IGRIYPGSGNTYYAQKFQG (SEQ ID NO: 45) | GVYYFDP (SEQ ID NO: 160) |
| RASQGVRNNVA (SEQ ID NO: 47) | SASYLQS (SEQ ID NO: 117) | | | IGRIYPSSGNTSYAQKFQG (SEQ ID NO: 136) | GVYYFDQ (SEQ ID NO: 161) |
| RASQGVRNYVA (SEQ ID NO: 102) | SASYLYS (SEQ ID NO: 118) | | | IGRIYPSSGNTYYAQKFQG (SEQ ID NO: 137) | GVYYFDR (SEQ ID NO: 162) |
| RASQGVRTNLA (SEQ ID NO: 22) | SASYRQS (SEQ ID NO: 20) | | | MAIIYPGSGNTYYAQKFQG (SEQ ID NO: 138) | GVYYFDS (SEQ ID NO: 46) |
| RASQGVRTNVA (SEQ ID NO: 39) | YASSLQS (SEQ ID NO: 48) | | | MARINPGSGNTSYAQKFQG (SEQ ID NO: 139) | GVYYFDT (SEQ ID NO: 51) |
| RASQGVSNNLA (SEQ ID NO: 103) | | | | MARINPGSGNTYYAQKFQG (SEQ ID NO: 140) | GVYYFDV (SEQ ID NO: 163) |
| RASQGVSNNVA (SEQ ID NO: 104) | | | | MARIYPGSGNTSYAQKFQG (SEQ ID NO: 141) | GVYYFDW (SEQ ID NO: 164) |
| RASQGVSNYLA (SEQ ID NO: 105) | | | | MARIYPGSGNTYYAQKFQG (SEQ ID NO: 142) | GVYYADY (SEQ ID NO: 165) |

TABLE 3-continued

Amino acid sequences of unique CDRs from 219 unique anti-C-KIT v-domains.

| LCDR1 | LCDR2 | LCDR3 | HCDR1 | HCDR2 | HCDR3 |
|---|---|---|---|---|---|
| RASQGVSNYVA (SEQ ID NO: 106) | | | | MARIYPSSGNTSYAQKFQG (SEQ ID NO: 143) | GVYYGDY (SEQ ID NO: 166) |
| RASQGVSTNLA (SEQ ID NO: 107) | | | | MARIYPSSGNTYYAQKFQG (SEQ ID NO: 144) | GVYYHDY (SEQ ID NO: 167) |
| RASQGVSTNVA (SEQ ID NO: 108) | | | | MGIIYPGSGNTYYAQKFQG (SEQ ID NO: 145) | GVYYQDY (SEQ ID NO: 41) |
| RASQGVSTYLA (SEQ ID NO: 109) | | | | MGRINPGSGNTSYAQKFQG (SEQ ID NO: 146) | GVYYLDY (SEQ ID NO: 18) |
| RASQGVSTYVA (SEQ ID NO: 110) | | | | MGRINPGSGNTYYAQKFQG (SEQ ID NO: 147) | GVYYKDY (SEQ ID NO: 168) |
| | | | | MGRIYPGSGNTSYAQKFQG (SEQ ID NO: 148) | GVYYNDY (SEQ ID NO: 169) |
| | | | | MGRIYPGSGNTYYAQKFQG (SEQ ID NO: 14) | GVYYMDY (SEQ ID NO: 170) |
| | | | | MGRIYPSSGNTSYAQKFQG (SEQ ID NO: 149) | GVYYYDY (SEQ ID NO: 15) |
| | | | | MGRIYPSSGNTYYAQKFQG (SEQ ID NO: 150) | GVYYWDY (SEQ ID NO: 171) |
| | | | | | GVYAFDY (SEQ ID NO: 172) |
| | | | | | GVYQFDY (SEQ ID NO: 173) |
| | | | | | GVYHFDY (SEQ ID NO: 49) |
| | | | | | GVYWFDY (SEQ ID NO: 174) |
| | | | | | GVYNFDY (SEQ ID NO: 175) |
| | | | | | GVYEFDY (SEQ ID NO: 42) |
| | | | | | GVYTFDY (SEQ ID NO: 176) |
| | | | | | GVYDFDY (SEQ ID NO: 177) |
| | | | | | GVWYFDY (SEQ ID NO: 40) |

TABLE 4

Amino acid sequences of CDRs of unique, library-derived and designer, human/cyno cross-reactive anti-C-KIT antibodies.

| Clone Name | LCDR1 | LCDR2 | LCDR3 | HCDR1 | HCDR2 | HCDR3 |
|---|---|---|---|---|---|---|
| E-E10 | RASQGVRTNVA (SEQ ID NO: 39) | SASSLQS (SEQ ID NO: 17) | QQYNSYPRT (SEQ ID NO: 12) | GYTFTDYYMN (SEQ ID NO: 13) | MGRIYPGSGNTYYAQKFQG (SEQ ID NO: 14) | GVWYFDY (SEQ ID NO: 40) |
| F-F2 | RASQGVRTNVA (SEQ ID NO: 39) | AASSRQS (SEQ ID NO: 23) | QQYNSYPRT (SEQ ID NO: 12) | GYTFTDYYMN (SEQ ID NO: 13) | MGRIYPGSGNTYYAQKFQG (SEQ ID NO: 14) | GVYYQDY (SEQ ID NO: 41) |
| C-B12 | RASQGVRNNLA (SEQ ID NO: 43) | AASYRQS (SEQ ID NO: 44) | QQYNSYPRT (SEQ ID NO: 12) | GYTFTDYYMN (SEQ ID NO: 13) | MGRIYPGSGNTYYAQKFQG (SEQ ID NO: 14) | GVYEFDY (SEQ ID NO: 42) |
| C-A7 | RASQGVRNNVA (SEQ ID NO: 47) | YASSLQS (SEQ ID NO: 48) | QQYNSYPRT (SEQ ID NO: 12) | GYTFTDYYMN (SEQ ID NO: 13) | IGRIYPGSGNTYYAQKFQG (SEQ ID NO: 45) | GVYYFDS (SEQ ID NO: 46) |
| C-A5 | RASQGVRNNVA (SEQ ID NO: 47) | AASYLQS (SEQ ID NO: 50) | QQYNSYPRT (SEQ ID NO: 12) | GYTFTDYYMN (SEQ ID NO: 13) | MGRIYPGSGNTYYAQKFQG (SEQ ID NO: 14) | GVYHFDY (SEQ ID NO: 49) |
| D-A10 | RASQGVRTNLA (SEQ ID NO: 22) | AASSRQS (SEQ ID NO: 23) | QQYNSYPRT (SEQ ID NO: 12) | GYTFTDYYMN (SEQ ID NO: 13) | MGRIYPGSGNTYYAQKFQG (SEQ ID NO: 14) | GVYYFDT (SEQ ID NO: 51) |
| E-C7 | RASQGIRTNLA (SEQ ID NO: 16) | SASSLQS (SEQ ID NO: 17) | QQYNSYPRT (SEQ ID NO: 12) | GYTFTDYYMN (SEQ ID NO: 13) | MGRIYPGSGNTYYAQKFQG (SEQ ID NO: 14) | GVYYYDY (SEQ ID NO: 15) |
| D-D5 | RASQGVRTNLA (SEQ ID NO: 22) | SASSLQS (SEQ ID NO: 17) | QQYNSYPRT (SEQ ID NO: 12) | GYTFTDYYMN (SEQ ID NO: 13) | MGRIYPGSGNTYYAQKFQG (SEQ ID NO: 14) | GVYYYDY (SEQ ID NO: 15) |
| E-C2 | RASQGIRTNVA (SEQ ID NO: 19) | SASYRQS (SEQ ID NO: 20) | QQYNSYPRT (SEQ ID NO: 12) | GYTFTDYYMN (SEQ ID NO: 13) | MGRIYPGSGNTYYAQKFQG (SEQ ID NO: 14) | GVYYLDY (SEQ ID NO: 18) |
| F-B11 | RASQGIRTNLA (SEQ ID NO: 16) | AASYRQS (SEQ ID NO: 44) | QQYNSYPRT (SEQ ID NO: 12) | GYTFTDYYMN (SEQ ID NO: 13) | MGRIYPGSGNTYYAQKFQG (SEQ ID NO: 14) | GVYYLDY (SEQ ID NO: 18) |
| D-D9 | RASQGVRTNVA (SEQ ID NO: 39) | SASSLQS (SEQ ID NO: 17) | QQYNSYPRT (SEQ ID NO: 12) | GYTFTDYYMN (SEQ ID NO: 13) | MGRIYPGSGNTYYAQKFQG (SEQ ID NO: 14) | GVYYLDY (SEQ ID NO: 18) |
| E-G7 | RASQGVRTNVA (SEQ ID NO: 39) | SASSRQS (SEQ ID NO: 52) | QQYNSYPRT (SEQ ID NO: 12) | GYTFTDYYMN (SEQ ID NO: 13) | MGRIYPGSGNTYYAQKFQG (SEQ ID NO: 14) | GVYYFDE (SEQ ID NO: 21) |
| F-C5 | RASQGVRTNLA (SEQ ID NO: 22) | AASSRQS (SEQ ID NO: 23) | QQYNSYPRT (SEQ ID NO: 12) | GYTFTDYYMN (SEQ ID NO: 13) | MGRIYPGSGNTYYAQKFQG (SEQ ID NO: 14) | GVYYFDE (SEQ ID NO: 21) |
| MH1 | RASQGIRTNLA (SEQ ID NO: 16) | AASSLQS (SEQ ID NO: 24) | QQYNSYPRT (SEQ ID NO: 12) | GYTFTDYYMN (SEQ ID NO: 13) | MGRIYPGSGNTYYAQKFQG (SEQ ID NO: 14) | GVYYYDY (SEQ ID NO: 15) |
| MH2 | RASQGIRTNLA (SEQ ID NO: 16) | SASSLQS (SEQ ID NO: 17) | QQYASYPRT (SEQ ID NO: 53) | GYTFTDYYMN (SEQ ID NO: 13) | MGRIYPGSGNTYYAQKFQG (SEQ ID NO: 14) | GVYYYDY (SEQ ID NO: 15) |
| MH3 | RASQGIRTNLA (SEQ ID NO: 16) | SASSLQS (SEQ ID NO: 17) | QQYNAYPRT (SEQ ID NO: 54) | GYTFTDYYMN (SEQ ID NO: 13) | MGRIYPGSGNTYYAQKFQG (SEQ ID NO: 14) | GVYYYDY (SEQ ID NO: 15) |
| MH4 | RASQGIRTNLA (SEQ ID NO: 16) | SASSLQS (SEQ ID NO: 17) | QQYNDYPRT (SEQ ID NO: 55) | GYTFTDYYMN (SEQ ID NO: 13) | MGRIYPGSGNTYYAQKFQG (SEQ ID NO: 14) | GVYYYDY (SEQ ID NO: 15) |
| MH5 | RASQGIRTNLA (SEQ ID NO: 16) | SASSLQS (SEQ ID NO: 17) | QQYANYPRT (SEQ ID NO: 25) | GYTFTDYYMN (SEQ ID NO: 13) | MGRIYPGSGNTYYAQKFQG (SEQ ID NO: 14) | GVYYYDY (SEQ ID NO: 15) |
| MH6 | RASQGIRTNLA (SEQ ID | SASSLQS (SEQ ID | QQYNSYPKT (SEQ ID | GYTFTDYYMN (SEQ ID | MGRIYPGSGNTYYAQKFQG (SEQ ID NO: 14) | GVYYYDY (SEQ ID |

TABLE 4-continued

Amino acid sequences of CDRs of unique, library-derived and designer, human/cyno cross-reactive anti-C-KIT antibodies.

| Clone Name | LCDR1 | LCDR2 | LCDR3 | HCDR1 | HCDR2 | HCDR3 |
|---|---|---|---|---|---|---|
| | 16) | NO: 17) | NO: 56) | NO: 13) | | NO: 15) |
| MH7 | RASQGIRTNLA (SEQ ID NO: 16) | SASSLQS (SEQ ID NO: 17) | QQYNSYPHT (SEQ ID NO: 57) | GYTFTDYYMN (SEQ ID NO: 13) | MGRIYPGSGNTYYAQKFQG (SEQ ID NO: 14) | GVYYYDY (SEQ ID NO: 15) |
| MH8 | RASQGIRTNLA (SEQ ID NO: 16) | SASSLQS (SEQ ID NO: 17) | QQYSSYPRT (SEQ ID NO: 58) | GYTFTDYYMN (SEQ ID NO: 13) | MGRIYPGSGNTYYAQKFQG (SEQ ID NO: 14) | GVYYYDY (SEQ ID NO: 15) |
| MH9 | RASQGIRTNLA (SEQ ID NO: 16) | SASSLQS (SEQ ID NO: 17) | QQYESYPRT (SEQ ID NO: 59) | GYTFTDYYMN (SEQ ID NO: 13) | MGRIYPGSGNTYYAQKFQG (SEQ ID NO: 14) | GVYYYDY (SEQ ID NO: 15) |
| MH10 | RASQGIRTNLA (SEQ ID NO: 16) | SASSLQS (SEQ ID NO: 17) | QQYTSYPRT (SEQ ID NO: 60) | GYTFTDYYMN (SEQ ID NO: 13) | MGRIYPGSGNTYYAQKFQG (SEQ ID NO: 14) | GVYYYDY (SEQ ID NO: 15) |
| MH11 | RASQGIRTNLA (SEQ ID NO: 16) | AASSLQS (SEQ ID NO: 24) | QQYNAYPRT (SEQ ID NO: 54) | GYTFTDYYMN (SEQ ID NO: 13) | MGRIYPGSGNTYYAQKFQG (SEQ ID NO: 14) | GVYYYDY (SEQ ID NO: 15) |
| MH12 | RASQGVRTNLA (SEQ ID NO: 22) | AASSLQS (SEQ ID NO: 24) | QQYNSYPRT (SEQ ID NO: 12) | GYTFTDYYMN (SEQ ID NO: 13) | MGRIYPGSGNTYYAQKFQG (SEQ ID NO: 14) | GVYYYDY (SEQ ID NO: 15) |
| MH13 | RASQGVRTNLA (SEQ ID NO: 22) | AASSLQS (SEQ ID NO: 24) | QQYNAYPRT (SEQ ID NO: 54) | GYTFTDYYMN (SEQ ID NO: 13) | MGRIYPGSGNTYYAQKFQG (SEQ ID NO: 14) | GVYYYDY (SEQ ID NO: 15) |
| MH14 | RASQGVRTNLA (SEQ ID NO: 22) | AASSLQS (SEQ ID NO: 24) | QQYNSYPRT (SEQ ID NO: 12) | GYTFTDYYMN (SEQ ID NO: 13) | MGRIYPGSGNTYYAQKFQG (SEQ ID NO: 14) | GVYYLDY (SEQ ID NO: 18) |
| MH15 | RASQGVRTNLA (SEQ ID NO: 22) | AASSLQS (SEQ ID NO: 24) | QQYNAYPRT (SEQ ID NO: 54) | GYTFTDYYMN (SEQ ID NO: 13) | MGRIYPGSGNTYYAQKFQG (SEQ ID NO: 14) | GVYYLDY (SEQ ID NO: 18) |
| TTP1 | RASQGIRTNLA (SEQ ID NO: 16) | AASSLQS (SEQ ID NO: 24) | QQYNSYPKT (SEQ ID NO: 56) | GYTFTDYYMN (SEQ ID NO: 13) | MGRIYPGSGNTYYAQKFQG (SEQ ID NO: 14) | GVYYLDY (SEQ ID NO: 18) |
| TTP2 | RASQGIRTNLA (SEQ ID NO: 16) | AASSLQS (SEQ ID NO: 24) | QQYNSYPHT (SEQ ID NO: 57) | GYTFTDYYMN (SEQ ID NO: 13) | MGRIYPGSGNTYYAQKFQG (SEQ ID NO: 14) | GVYYYDY (SEQ ID NO: 15) |
| TTP3 | RASQGVRTNLA (SEQ ID NO: 22) | SASSLQS (SEQ ID NO: 17) | QQYNAYPKT (SEQ ID NO: 178) | GYTFTDYYMN (SEQ ID NO: 13) | MGRIYPGSGNTYYAQKFQG (SEQ ID NO: 14) | GVYYLDY (SEQ ID NO: 18) |
| TTP4 | RASQGVRTNLA (SEQ ID NO: 22) | SASSLQS (SEQ ID NO: 17) | QQYNAYPHT (SEQ ID NO: 179) | GYTFTDYYMN (SEQ ID NO: 13) | MGRIYPGSGNTYYAQKFQG (SEQ ID NO: 14) | GVYYYDY (SEQ ID NO: 15) |
| TTP5 | RASQGVRTNLA (SEQ ID NO: 22) | AASSLQS (SEQ ID NO: 24) | QQYNAYPKT (SEQ ID NO: 178) | GYTFTDYYMN (SEQ ID NO: 13) | MGRIYPGSGNTYYAQKFQG (SEQ ID NO: 14) | GVYYLDY (SEQ ID NO: 18) |
| TTP6 | RASQGVRTNLA (SEQ ID NO: 22) | AASSLQS (SEQ ID NO: 24) | QQYNAYPHT (SEQ ID NO: 179) | GYTFTDYYMN (SEQ ID NO: 13) | MGRIYPGSGNTYYAQKFQG (SEQ ID NO: 14) | GVYYYDY (SEQ ID NO: 15) |

TABLE 5

HTRF epitope competition IC50 values for key library derived and designer lead anti-C-KIT antibodies in IgG1 format.

| Clone Name | Human IC50 (µg/ml) | Cyno IC50 (µg/ml) |
|---|---|---|
| C-KIT-h37M | 0.025 | 0.035 |
| C-KIT-D-A10 | 0.027 | 0.059 |

TABLE 5-continued

HTRF epitope competition IC50 values for key library derived and designer lead anti-C-KIT antibodies in IgG1 format.

| Clone Name | Human IC50 (μg/ml) | Cyno IC50 (μg/ml) |
|---|---|---|
| C-KIT-E-C7 | 0.028 | 0.051 |
| C-KIT-E-E10 | 0.031 | 0.097 |
| C-KIT-F-C5 | 0.031 | 0.079 |
| C-KIT-C-A7 | 0.037 | 0.081 |
| C-KIT-F-F2 | 0.046 | 0.121 |
| C-KIT-MH11 | 0.051 | 0.101 |
| C-KIT-MH5 | 0.063 | 0.036 |
| C-KIT-C-B12 | 0.066 | 0.166 |

TABLE 6

Amino acid sequences of CDRs of second generation, designer, human/cyno cross-reactive anti-C-KIT antibodies.

| Clone Name | LCDR1 | LCDR2 | LCDR3 | HCDR1 | HCDR2 | HCDR3 |
|---|---|---|---|---|---|---|
| MH5.1 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPGTGNTYYAQKFQG (SEQ ID NO: 61) | GVWYYDY (SEQ ID NO: 27) |
| MH5.2 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPGTGNTYYAQKFQG (SEQ ID NO: 61) | GVWYYDY (SEQ ID NO: 27) |
| MH5.3 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPGTGNTYYAQKFQG (SEQ ID NO: 61) | GVWYYDY (SEQ ID NO: 27) |
| MH5.4 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPGTGNTYYAQXFQG (SEQ ID NO: 61) | GVWYFDS (SEQ ID NO: 62) |
| MH5.5 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPGTGNTYYAQKFQG (SEQ ID NO: 61) | GVWYFDT (SEQ ID NO: 63) |
| MH5.6 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPGTGNTYYAQKFQG (SEQ ID NO: 61) | GVWYFDS (SEQ ID NO: 184) |
| MH5.7 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPGAGNTYYAQKFQG (SEQ ID NO: 183) | GVWYYDY (SEQ ID NO: 27) |
| MH5.8 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPGAGNTYYAQKFQG (SEQ ID NO: 183) | GVWYFDS (SEQ ID NO: 62) |
| MH5.9 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPGAGNTYYAQKFQG (SEQ ID NO: 183) | GVWYFDT (SEQ ID NO: 63) |
| MH5.10 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPGAGNTYYAQKFQG (SEQ ID NO: 183) | GVWYFDS (SEQ ID NO: 184) |
| MH5.11 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPASGNTYYAQKFQG (SEQ ID NO: 26) | GVWYYDY (SEQ ID NO: 27) |
| MH5.12 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPASGNTYYAQKFQG (SEQ ID NO: 26) | GVWYFDS (SEQ ID NO: 62) |
| MH5.13 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPASGNTYYAQKFQG (SEQ ID NO: 26) | GVWYFDT (SEQ ID NO: 63) |
| MH5.14 | RASQGIRTNLA (SEQ ID NO: 16) | AASSLQS (SEQ ID NO: 24) | QQYANYPRT (SEQ ID NO: 25) | GYTFTDHYMN (SEQ ID NO: 182) | MGRIYPASGNTYYAQKFQG (SEQ ID NO: 26) | GVWYFDE (SEQ ID NO: 184) |
| MH5.15 | RASQGIRTNLA (SEQ ID | AASSLQS (SEQ ID | QQYANYPRT (SEQ ID | GYTFTDFYMN (SEQ ID | MGRIYPGTGNTYYAQKFQG (SEQ ID NO: 61) | GVWYFDS (SEQ ID |

TABLE 6-continued

Amino acid sequences of CDRs of second generation, designer, human/cyno cross-reactive anti-C-KIT antibodies.

| Clone Name | LCDR1 | LCDR2 | LCDR3 | HCDR1 | HCDR2 | HCDR3 |
|---|---|---|---|---|---|---|
| | 16) | NO: 24) | NO: 25) | NO: 180) | | NO: 62) |
| MH5.16 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPGTGNTYYAQKFQG (SEQ ID NO: 61) | GVWYFDT (SEQ ID NO: 63) |
| MH5.17 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPGTGNTYYAQKFQG (SEQ ID NO: 61) | GVWYFDE (SEQ ID NO: 184) |
| MH5.18 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPGAGNTYYAQKFQG (SEQ ID NO: 183) | GVWYYDY (SEQ ID NO: 27) |
| MH5.19 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPGAGNTYYAQKFQG (SEQ ID NO: 183) | GVWYFDS (SEQ ID NO: 62) |
| MH5.20 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPGAGNTYYAQKFQG (SEQ ID NO: 183) | GVWYFDT (SEQ ID NO: 63) |
| MH5.21 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPGAGNTYYAQKFQG (SEQ ID NO: 183) | GVWYFDE (SEQ ID NO: 184) |
| MH5.22 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPASGNTYYAQKFQG (SEQ ID NO: 26) | GVWYYDY (SEQ ID NO: 27) |
| MH5.23 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPASGNTYYAQKFQG (SEQ ID NO: 26) | GVWYFDS (SEQ ID NO: 62) |
| MH5.24 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPASGNTYYAQKFQG (SEQ ID NO: 26) | GVWYFDT (SEQ ID NO: 63) |
| MH5.25 | RASQGIRTNLA (SEQ ID NO: 16) | AASSLQS (SEQ ID NO: 24) | QQYANYPRT (SEQ ID NO: 25) | GYTFTDFYMN (SEQ ID NO: 180) | MGRIYPASGNTYYAQKFQG (SEQ ID NO: 26) | GVWYFDE (SEQ ID NO: 184) |
| MH5.26 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPGTGNTYYAQKFQG (SEQ ID NO: 61) | GVWYFDS (SEQ ID NO: 62) |
| MH5.27 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPGTGNTYYAQKFQG (SEQ ID NO: 61) | GVWYFDT (SEQ ID NO: 63) |
| MH5.28 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPGTGNTYYAQKFQG (SEQ ID NO: 61) | GVWYFDE (SEQ ID NO: 184) |
| MH5.29 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPGAGNTYYAQKFQG (SEQ ID NO: 183) | GVWYYDY (SEQ ID NO: 27) |
| MH5.30 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPGAGNTYYAQKFQG (SEQ ID NO: 183) | GVWYFDS (SEQ ID NO: 62) |
| MH5.31 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPGAGNTYYAQKFQG (SEQ ID NO: 183) | GVWYFDT (SEQ ID NO: 63) |
| MH5.32 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPGAGNTYYAQKFQG (SEQ ID NO: 183) | GVWYFDE (SEQ ID NO: 184) |
| MH5.33 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPASGNTYYAQKFQG (SEQ ID NO: 26) | GVWYYDY (SEQ ID NO: 27) |

TABLE 6-continued

Amino acid sequences of CDRs of second generation, designer, human/cyno cross-reactive anti-C-KIT antibodies.

| Clone Name | LCDR1 | LCDR2 | LCDR3 | HCDR1 | HCDR2 | HCDR3 |
|---|---|---|---|---|---|---|
| MH5.34 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPASGNTYYAQKFQG (SEQ ID NO: 26) | GVWYFDS (SEQ ID NO: 62) |
| MH5.35 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPASGNTYYAQKFQG (SEQ ID NO: 26) | GVWYFDT (SEQ ID NO: 63) |
| MH5.36 | RASQGIRTNLA (SEQ ID NO: 16) | AASSLQS (SEQ ID NO: 24) | QQYANYPRT (SEQ ID NO: 25) | GYTFTNYYMN (SEQ ID NO: 181) | MGRIYPASGNTYYAQKFQG (SEQ ID NO: 26) | GVWYFDE (SEQ ID NO: 184) |

TABLE 7

HTRF epitope competition IC50 values for second generation designer anti-C-KIT antibodies in IgG1 format.

| Clone Name | Human IC50 (μg/ml) | Cyno IC50 (μg/ml) |
|---|---|---|
| C-KIT-h37M | 0.016 | 0.036 |
| C-KIT-MH5 | 0.067 | 0.058 |
| C-KIT-MH5.1 | 0.684 | 0.633 |
| C-KIT-MH5.2 | 0.272 | 0.254 |
| C-KIT-MH5.22 | 0.134 | 0.164 |
| C-KIT-MH5.23 | 2.024 | 3.256 |
| C-KIT-MH5.24 | 2.201 | 2.743 |
| C-KIT-MH5.34 | 0.839 | 0.532 |
| C-KIT-MH5.35 | 2.047 | 0.785 |

TABLE 8

Human T cell epitope content in v-domains predicted by iTOPE ™ and TCED ™.

| Clone Name | Germline epitopes | High Affinity Foreign | Low Affinity Foreign | TCED+ |
|---|---|---|---|---|
| C-KIT-h37M | 4 | 7 | 6 | 3 |
| C-KIT-E-C7 | 10 | 3 | 4 | 0 |
| C-KIT-F-C5 | 10 | 3 | 4 | 1 |
| C-KIT-E-C2 | 10 | 2 | 4 | 0 |
| C-KIT-MH1 | 12 | 1 | 4 | 0 |
| C-KIT-MH5 | 10 | 3 | 4 | 0 |
| C-KIT-MH5.22 | 11 | 3 | 1 | 1 |
| C-KIT-MH5-DI | 12 | 1 | 2 | 0 |

TABLE 9

BIACORE ® analyses of affinity of IgG variants for human Fc receptors.

| Receptor | Antibody | KD (M) | Chi2 |
|---|---|---|---|
| FcG RI | Isotype IgG1 | 3.44E−09 | 0.0289 |
| FcG RI | Isotype IgG4 | 9.25E−09 | 0.016 |
| FcG RI | h37M-IgG1 | 1.06E−09 | 0.573 |
| FcG RI | h37M-IgG1-3M | NS | NS |
| FcG RI | MH1-IgG1-4M | NS | NS |
| FcG RIIa (167R) | Isotype IgG1 | 3.71E−06 | 3.57 |
| FcG RIIa (167R) | Isotype IgG4 | Low | Low |
| FcG RIIa (167R) | h37M-IgG1 | 4.47E−07 | 23.7 |
| FcG RIIa (167R) | h37M-IgG1-3M | NS | NS |
| FcG RIIa (167R) | MH1-IgG1-4M | NS | NS |
| FcG RIIa (167H) | Isotype IgG1 | 6.14E−06 | 2.09 |
| FcG RIIa (167H) | Isotype IgG4 | Low | Low |
| FcG RIIa (167H) | h37M-IgG1 | 5.12E−07 | 4.16 |
| FcG RIIa (167H) | h37M-IgG1-3M | NS | NS |
| FcG RIIa (167H) | MH1-IgG1-4M | NS | NS |
| FcG RIIb | Isotype IgG1 | 1.72E−05 | 1.55 |
| FcG RIIb | Isotype IgG4 | 2.31E−05 | 0.431 |
| FcG RIIb | h37M-IgG1 | 1.44E−06 | 2.58 |
| FcG RIIb | h37M-IgG1-3M | Low | Low |
| FcG RIIb | MH1-IgG1-4M | Low | Low |
| FcG RIIIa (176F) | Isotype IgG1 | 3.53E−06 | 0.0343 |
| FcG RIIIa (176F) | Isotype IgG4 | NS | NS |
| FcG RIIIa (176F) | h37M-IgG1 | 8.20E−08 | 0.205 |
| FcG RIIIa (176F) | h37M-IgG1-3M | NS | NS |
| FcG RIIIa (176F) | MH1-IgG1-4M | NS | NS |
| FcG RIIIa (176V) | Isotype IgG1 | 1.40E−06 | 0.448 |
| FcG RIIIa (176V) | Isotype IgG4 | Low | Low |
| FcG RIIIa (176V) | h37M-IgG1 | 4.11E−08 | 3.36 |
| FcG RIIIa (176V) | h37M-IgG1-3M | NS | NS |
| FcG RIIIa (176V) | MH1-IgG1-4M | NS | NS |
| FcG RIIIb | Isotype IgG1 | 9.9E−06 | 1.85 |
| FcG RIIIb | Isotype IgG4 | NS | NS |
| FcG RIIIb | h37M-IgG1 | 2.49E−07 | 5.6 |
| FcG RIIIb | h37M-IgG1-3M | NS | NS |
| FcG RIIIb | MH1-IgG1-4M | NS | NS |

NS = No Signal observed at any concentration of IgG
Low = Signal observed at high IgG concentrations

TABLE 10

BIACORE ® analyses of affinity of IgG variants for human FcRn.

| pH | Antibody | KD (M) | Chi2 |
|---|---|---|---|
| 6 | Isotype IgG1 | 1.18E−06 | 0.756 |
| 7.4 | Isotype IgG1 | NS | NS |
| 6 | Isotype IgG4 | 2.6E−06 | 0.213 |
| 7.4 | Isotype IgG4 | NS | NS |
| 6 | h37M-IgG1 | 1.24E−06 | 8.75 |
| 7.4 | h37M-IgG1 | NS | NS |
| 6 | h37M-IgG1-3M | 1.32E−06 | 6.58 |
| 7.4 | h37M-IgG1-3M | NS | NS |
| 6 | MH1-IgG1-4M | 1.59E−06 | 3 |
| 7.4 | MH1-IgG1-4M | NS | NS |

NS = No Signal observed at any concentration of IgG

TABLE 11

Potency values for anti-C-KIT antibodies
in IgG format in cell-based assays.

| Clone Name | TF-1 proliferation IC50 (nM) | TF-1 FabZAP IC50 (pM) | Human C-KIT CHO FabZAP IC50 (pM) | Cyno C-KIT CHO FabZAP IC50 (pM) |
|---|---|---|---|---|
| C-KIT-h37M | 0.11 | 12.76 | 5.7 | 7.823 |
| C-KIT-MH1 | 2.86 | 51.09 | 8.7 | 13.96 |
| C-KIT-MH5-DI | 26.31 | 53.68 | 12.6 | 13.54 |

TABLE 12

Examples of antibody variable region amino acid sequences.

Antibody MH1 heavy chain variable (VH) region
QVQLVQSGAEVKKPGASVKVSCKASGYTFTDYYMNWVRQAPGQGLEWMGRIYPGSGNT

YYAQKFQGRVTMTRDTSTSTVYMELSSLRSEDTAVYYCARGVYYYDYWGQGTLVTVSS
(SEQ ID NO: 185)

Antibody MH1 VL light chain variable (VL) region
DIQMTQSPSSLSASVGDRVTITCRASQGIRTNLAWFQQKPGKAPKSLIYAASSLQSGV

PSRFSGSGSGTDFTLTISSLQPEDFATYYCQQYNSYPRTFGGGTKVEIK
(SEQ ID NO: 186)

Antibody MH5-DI heavy chain variable (VH) region
QVQLVQSGAEVKKPGASVKVSCKASGYTFTDYYMNWVRQAPGQGLEWMGRIYPGSGNT

YYAQKFQGRVTMTRDTSTSTVYMELSSLRSEDTAVYYCARGVYYYDYWGQGTLVTVSS
(SEQ ID NO: 187)

Antibody MH5-DI light chain variable (VL) region
DIQMTQSPSSLSASVGDRVTITCRASQGIRTNLAWFQQKPGKAPKSLIYAASSLQSGV

PSRFSGSGSGTDFTLTISSLQPEDFATYYCQQYANYPRTFGGGTKVEIK
(SEQ ID NO: 188)

Antibody MH5 heavy chain variable (VH) region
QVQLVQSGAEVKKPGASVKVSCKASGYTFTDYYMNWVRQAPGQGLEWMGRIYPGSGNT

YYAQKFQGRVTMTRDTSTSTVYMELSSLRSEDTAVYYCARGVYYYDYWGQGTLVTVSS
(SEQ ID NO: 189)

Antibody MH5 light chain variable (VL) region
DIQMTQSPSSLSASVGDRVTITCRASQGIRTNLAWFQQKPGKAPKSLIYSASSLQSGV

PSRFSGSGSGTDFTLTISSLQPEDFATYYCQQYANYPRTFGGGTKVEIKM
(SEQ ID NO: 190)

Antibody EC7 heavy chain variable (VH) region
QVQLVQSGAEVKKPGASVKVSCKASGYTFTDYYMNWVRQAPGQGLEWMGRIYPGSGNT

YYAQKFQGRVTMTRDTSTSTVYMELSSLRSEDTAVYYCARGVYYYDYWGQGTLVTVSS
(SEQ ID NO: 191)

Antibody EC7 light chain variable (VL) region
DIQMTQSPSSLSASVGDRVTITCRASQGIRTNLAWFQQKPGKAPKSLIYSASSLQSGV

PSRFSGSGSGTDFTLTISSLQPEDFATYYCQQYNSYPRTFGGGTKVEIK
(SEQ ID NO: 192)

Antibody EC2 heavy chain variable (VH) region
QVQLVQSGAEVKKPGASVKVSCKASGYTFTDYYMNWVRQAPGQGLEWMGRIYPGSGNT

YYAQKFQGRVTMTRDTSTSTVYMELSSLRSEDTAVYYCARGVYYLDYWGQGTLVTVSS
(SEQ ID NO: 193)

Antibody EC2 light chain variable (VL) region
DIQMTQSPSSLSASVGDRVTITCRASQGIRTNVAWLQQKPGKAPKSLIYSASYRQSGV

PSRFSGSGSGTDFTLTISSLQPEDFATYYCQQYNSYPRTFGGGTKVEIK
(SEQ ID NO: 194)

Antibody F-C5 heavy chain variable (VH) region
QVQLVQSGAEVKKPGASVKVSCKASGYTFTDYYMNWVRQAPGQGLEWMGRIYPGSGNT

TABLE 12-continued

Examples of antibody variable region amino acid sequences.

YYAQKFQGRVTMTRDTSISTVYMELSSLRSEDTAVYYCARGVYYFDEWGQGTLVTVSS
(SEQ ID NO: 195)

Antibody F-C5 light chain variable (VL) region
DIQMTQSPSSLSASVGDRVTITCRASQGVRTNLAWFQQKPGKAPKSLIYAASSRQSGV

PSRFSGSGSGTDFTLTISSLQPEDFATYYCQQYNSYPRTFGGGTKVEIK
(SEQ ID NO: 196)

TABLE 13

Examples of antibody Fc region amino acid sequences.

Human IgG1 wild type
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK (SEQ ID NO: 197)

Human IgG1-3M
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK (SEQ ID NO: 198)

Human IgG1-4M
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPASIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK (SEQ ID NO: 199)

Human IgG1 wild type "REEM" allotype
ASTKGPSVFPLAPSSKSISGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSREEMKNQVSLTCLVKGF

YPSDIAVEWESNGQPENNYKTTPPVLDSDGSFFLYSKLTVDKSRWQQGNVF

SCSVMHEALHNHYTQKSLSLSPGK (SEQ ID NO: 200)

Human IgG1-3M "REEM" allotype
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSREEMKNQVSLTCLVKGF

YPSDIAVEWESNGQPENNYKTTPPVLDSDGSFFLYSKLTVDKSRWQQGNVF

SCSVMHEALHNHYTQKSLSLSPGK (SEQ ID NO: 201)

Human IgG1-4M "REEM" allotype
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPASIEKTISKAKGQPREPQVYTLPPSREEMKNQVSLTCLVKGF

YPSDIAVEWESNGQPENNYKTTPPVLDSDGSFFLYSKLTVDKSRWQQGNVF

SCSVMHEALHNHYTQKSLSLSPGK (SEQ ID NO: 202)

TABLE 14

Examples of human C-KIT amino acid and nucleotide sequences.

Human C-KIT protein
MRGARGAWDFLCVLLLLLRVQTGSSQPSVSPGEPSPPSIHPGKSDLIVRVGDEIRLLCTDPGFVKWTFEI

LDETNENKQNEWITEKAEATNTGKYTCTNKHGLSNSIYVFVRDPAKLFLVDRSLYGKEDNDTLVRCPLTD

PEVTNYSLKGCQGKPLPKDLRFIPDPKAGIMIKSVKRAYHRLCLHCSVDQEGKSVLSEKFILKVRPAFKA

VPVVSVSKASYLLREGEEFTVTCTIKDVSSSVYSTWKRENSQTKLQEKYNSWHHGDFNYERQATLTISSA

RVNDSGVFMCYANNTFGSANVTTTLEVVDKGFINIFPMINTTVFVNDGENVDLIVEYEAFPKPEHQQWIY

TABLE 14-continued

Examples of human C-KIT amino acid and nucleotide sequences.

```
MNRTFTDKWEDYPKSENESNIRYVSELHLTRLKGTEGGTYTFLVSNSDVNAAIAFNVYVNTKPEILTYDR
LVNGMLQCVAAGFPEPTIDWYFCPGTEQRCSASVLPVDVQTLNSSGPPFGKLVVQSSIDSSAFKHNGTVE
CKAYNDVGKTSAYFNFAFKGNNKEQIHPHTLFTPLLIGFVIVAGMMCIIVMILTYKYLQKPMYEVQWKVV
EEINGNNYVYIDPTQLPYDHKWEFPRNRLSFGKTLGAGAFGKVVEATAYGLIKSDAAMTVAVKMLKPSAH
LTEREALMSELKVLSYLGNHMNIVNLLGACTIGGPTLVITEYCCYGDLLNFLRRKRDSFICSKQEDHAEA
ALYKNLLHSKESSCSDSTNEYMDMKPGVSYVVPTKADKRRSVRIGSYIERDVTPAIMEDDELAIDLEDLL
SFSYQVAKGMAFLASKNCIHRDLAARNILLTHGRITKICDFGLARDIKNDSNYVVKGNARLPVKWMAHES
IFNCVYTFESDVWSYGIFLWELFSLGSSPYPGMPVDSKFYKMIKEGFRMLSPEHAPAEMYDIMKTCWDAD
PLKRPTFKQIVQLIEKQISESTNHIYSNLANCSPNRQKPVVDHSVRINSVGSTASSSQPLLVHDDV
(SEQ ID NO: 208)
Human C-KIT protein, transcript variant 1
TCTGGGGGCTCGGCTTTGCCGCGCTCGCTGCACTTGGGCGAGAGCTGGAACGTGGACCAGAGCTCGGATC
CCATCGCAGCTACCGCGATGAGAGGCGCTCGCGGCGCCTGGGATTTTCTCTGCGTTCTGCTCCTACTGCT
TCGCGTCCAGACAGGCTCTTCTCAACCATCTGTGAGTCCAGGGGAACCGTCTCCACCATCCATCCATCCA
GGAAAATCAGACTTAATAGTCCGCGTGGGCGACGAGATTAGGCTGTTATGCACTGATCCGGGCTTTGTCA
AATGGACTTTTGAGATCCTGGATGAAACGAATGAGAATAAGCAGAATGAATGGATCACGGAAAAGGCAGA
AGCCACCAACACCGGCAAATACACGTGCACCAACAAACACGGCTTAAGCAATTCCATTTATGTGTTTGTT
AGAGATCCTGCCAAGCTTTTCCTTGTTGACCGCTCCTTGTATGGGAAAGAAGACAACGACACGCTGGTCC
GCTGTCCTCTCACAGACCCAGAAGTGACCAATTATTCCCTCAAGGGGTGCCAGGGGAAGCCTCTTCCCAA
GGACTTGAGGTTTATTCCTGACCCCAAGGCGGGCATCATGATCAAAAGTGTGAAACGCGCCTACCATCGG
CTCTGTCTGCATTGTTCTGTGGACCAGGAGGGCAAGTCAGTGCTGTCGGAAAAATTCATCCTGAAAGTGA
GGCCAGCCTTCAAAGCTGTGCCTGTTGTGTCTGTGTCCAAAGCAAGCTATCTTCTTAGGGAAGGGGAAGA
ATTCACAGTGACGTGCACAATAAAAGATGTGTCTAGTTCTGTGTACTCAACGTGGAAAAGAGAAAACAGT
CAGACTAAACTACAGGAGAAATATAATAGCTGGCATCACGGTGACTTCAATTATGAACGTCAGGCAACGT
TGACTATCAGTTCAGCGAGAGTTAATGATTCTGGAGTGTTCATGTGTTATGCCAATAATACTTTTGGATC
AGCAAATGTCACAACAACCTTGGAAGTAGTAGATAAAGGATTCATTAATATCTTCCCCATGATAAACACT
ACAGTATTTGTAAACGATGGAGAAAATGTAGATTTGATTGTTGAATATGAAGCATTCCCCAAACCTGAAC
ACCAGCAGTGGATCTATATGAACAGAACCTTCACTGATAAATGGGAAGATTATCCCAAGTCTGAGAATGA
AAGTAATATCAGATACGTAAGTGAACTTCATCTAACGAGATTAAAAGGCACCGAAGGAGGCACTTACACA
TTCCTAGTGTCCAATTCTGACGTCAATGCTGCCATAGCATTTAATGTTTATGTGAATACAAAACCAGAAA
TCCTGACTTACGACAGGCTCGTGAATGGCATGCTCCAATGTGTGGCAGCAGGATTCCCAGAGCCCACAAT
AGATTGGTATTTTTGTCCAGGAACTGAGCAGAGATGCTCTGCTTCTGTACTGCCAGTGGATGTGCAGACA
CTAAACTCATCTGGGCCACCGTTTGGAAAGCTAGTGGTTCAGAGTTCTATAGATTCTAGTGCATTCAAGC
ACAATGGCACGGTTGAATGTAAGGCTTACAACGATGTGGGCAAGACTTCTGCCTATTTTAACTTTGCATT
TAAAGGTAACAACAAAGAGCAAATCCATCCCCACACCCTGTTCACTCCTTTGCTGATTGGTTTCGTAATC
GTAGCTGGCATGATGTGCATTATTGTGATGATTCTGACCTACAAATATTTACAGAAACCCATGTATGAAG
TACAGTGGAAGGTTGTTGAGGAGATAAATGGAAACAATTATGTTTACATAGACCCAACACAACTTCCTTA
TGATCACAAATGGGAGTTTCCCAGAAACAGGCTGAGTTTTGGGAAAACCCTGGGTGCTGGAGCTTTCGGG
AAGGTTGTTGAGGCAACTGCTTATGGCTTAATTAAGTCAGATGCGGCCATGACTGTCGCTGTAAAGATGC
TCAAGCCGAGTGCCCATTTGACAGAACGGGAAGCCCTCATGTCTGAACTCAAAGTCCTGAGTTACCTTGG
```

TABLE 14-continued

Examples of human C-KIT amino acid and nucleotide sequences.

TAATCACATGAATATTGTGAATCTACTTGGAGCCTGCACCATTGGAGGGCCCACCCTGGTCATTACAGAA

TATTGTTGCTATGGTGATCTTTTGAATTTTTTGAGAAGAAAACGTGATTCATTTATTTGTTCAAAGCAGG

AAGATCATGCAGAAGCTGCACTTTATAAGAATCTTCTGCATTCAAAGGAGTCTTCCTGCAGCGATAGTAC

TAATGAGTACATGGACATGAAACCTGGAGTTTCTTATGTTGTCCCAACCAAGGCCGACAAAAGGAGATCT

GTGAGAATAGGCTCATACATAGAAAGAGATGTGACTCCCGCCATCATGGAGGATGACGAGTTGGCCCTAG

ACTTAGAAGACTTGCTGAGCTTTTCTTACCAGGTGGCAAAGGGCATGGCTTTCCTCGCCTCCAAGAATTG

TATTCACAGAGACTTGGCAGCCAGAAATATCCTCCTTACTCATGGTCGGATCACAAAGATTTGTGATTTT

GGTCTAGCCAGAGACATCAAGAATGATTCTAATTATGTGGTTAAAGGAAACGCTCGACTACCTGTGAAGT

GGATGGCACCTGAAAGCATTTTCAACTGTGTATACACGTTTGAAAGTGACGTCTGGTCCTATGGGATTTT

TCTTTGGGAGCTGTTCTCTTTAGGAAGCAGCCCCTATCCTGGAATGCCGGTCGATTCTAAGTTCTACAAG

ATGATCAAGGAAGGCTTCCGGATGCTCAGCCCTGAACACGCACCTGCTGAAATGTATGACATAATGAAGA

CTTGCTGGGATGCAGATCCCCTAAAAAGACCAACATTCAAGCAAATTGTTCAGCTAATTGAGAAGCAGAT

TTCAGAGAGCACCAATCATATTTACTCCAACTTAGCAAACTGCAGCCCCAACCGACAGAAGCCCGTGGTA

GACCATTCTGTGCGGATCAATTCTGTCGGCAGCACCGCTTCCTCCTCCCAGCCTCTGCTTGTGCACGACG

ATGTCTGAGCAGAATCAGTGTTTGGGTCACCCCTCCAGGAATGATCTCTTCTTTTGGCTTCCATGATGGT

TATTTTCTTTTCTTTCAACTTGCATCCAACTCCAGGATAGTGGGCACCCCACTGCAATCCTGTCTTTCTG

AGCACACTTTAGTGGCCGATGATTTTTGTCATCAGCCACCATCCTATTGCAAAGGTTCCAACTGTATATA

TTCCCAATAGCAACGTAGCTTCTACCATGAACAGAAAACATTCTGATTTGGAAAAAGAGAGGGAGGTATG

GACTGGGGGCCAGAGTCCTTTCCAAGGCTTCTCCAATTCTGCCCAAAAATATGGTTGATAGTTTACCTGA

ATAAATGGTAGTAATCACAGTTGGCCTTCAGAACCATCCATAGTAGTATGATGATACAAGATTAGAAGCT

GAAAACCTAAGTCCTTTATGTGGAAAACAGAACATCATTAGAACAAAGGACAGAGTATGAACACCTGGGC

TTAAGAAATCTAGTATTTCATGCTGGGAATGAGACATAGGCCATGAAAAAAATGATCCCCAAGTGTGAAC

AAAAGATGCTCTTCTGTGGACCACTGCATGAGCTTTTATACTACCGACCTGGTTTTTAAATAGAGTTTGC

TATTAGAGCATTGAATTGGAGAGAAGGCCTCCCTAGCCAGCACTTGTATATACGCATCTATAAATTGTCC

GTGTTCATACATTTGAGGGGAAAACACCATAAGGTTTCGTTTCTGTATACAACCCTGGCATTATGTCCAC

TGTGTATAGAAGTAGATTAAGAGCCATATAAGTTTGAAGGAAACAGTTAATACCATTTTTTAAGGAAACA

ATATAACCACAAAGCACAGTTTGAACAAAATCTCCTCTTTTAGCTGATGAACTTATTCTGTAGATTCTGT

GGAACAAGCCTATCAGCTTCAGAATGGCATTGTACTCAATGGATTTGATGCTGTTTGACAAAGTTACTGA

TTCACTGCATGGCTCCCACAGGAGTGGGAAAACACTGCCATCTTAGTTTGGATTCTTATGTAGCAGGAAA

TAAAGTATAGGTTTAGCCTCCTTCGCAGGCATGTCCTGGACACCGGGCCAGTATCTATATATGTGTATGT

ACGTTTGTATGTGTGTAGACAAATATTTGGAGGGGTATTTTTGCCCTGAGTCCAAGAGGGTCCTTTAGTA

CCTGAAAAGTAACTTGGCTTTCATTATTAGTACTGCTCTTGTTTCTTTTCACATAGCTGTCTAGAGTAGC

TTACCAGAAGCTTCCATAGTGGTGCAGAGGAAGTGGAAGGCATCAGTCCCTATGTATTTGCAGTTCACCT

GCACTTAAGGCACTCTGTTATTTAGACTCATCTTACTGTACCTGTTCCTTAGACCTTCCATAATGCTACT

GTCTCACTGAAACATTTAAATTTTACCCTTTAGACTGTAGCCTGGATATTATTCTTGTAGTTTACCTCTT

TAAAAACAAAACAAAACAAAACAAAAAACTCCCCTTCCTCACTGCCCAATATAAAAGGCAAATGTGTACA

TGGCAGAGTTTGTGTGTTGTCTTGAAAGATTCAGGTATGTTGCCTTTATGGTTTCCCCCTTCTACATTTC

TTAGACTACATTTAGAGAACTGTGGCCGTTATCTGGAAGTAACCATTTGCACTGGAGTTCTATGCTCTCG

CACCTTTCCAAAGTTAACAGATTTTGGGGTTGTGTTGTCACCCAAGAGATTGTTGTTTGCCATACTTTGT

TABLE 14-continued

Examples of human C-KIT amino acid and nucleotide sequences.

```
CTGAAAAATTCCTTTGTGTTTCTATTGACTTCAATGATAGTAAGAAAAGTGGTTGTTAGTTATAGATGTC

TAGGTACTTCAGGGGCACTTCATTGAGAGTTTTGTCTTGGATATTCTTGAAAGTTTATATTTTTATAATT

TTTTCTTACATCAGATGTTTCTTTGCAGTGGCTTAATGTTTGAAATTATTTTGTGGCTTTTTTTGTAAAT

ATTGAAATGTAGCAATAATGTCTTTTGAATATTCCCAAGCCCATGAGTCCTTGAAAATATTTTTATATA

TACAGTAACTTTATGTGTAAATACATAAGCGGCGTAAGTTTAAAGGATGTTGGTGTTCCACGTGTTTTAT

TCCTGTATGTTGTCCAATTGTTGACAGTTCTGAAGAATTCTAATAAAATGTACATATATAAATCAAAAAA

AAAAAAAAA
(SEQ ID NO: 209)

Human C-KIT protein, transcript variant 2
TCTGGGGGCTCGGCTTTGCCGCGCTCGCTGCACTTGGGCGAGAGCTGGAACGTGGACCAGAGCTCGGATC

CCATCGCAGCTACCGCGATGAGAGGCGCTCGCGGCGCCTGGGATTTTCTCTGCGTTCTGCTCCTACTGCT

TCGCGTCCAGACAGGCTCTTCTCAACCATCTGTGAGTCCAGGGGAACCGTCTCCACCATCCATCCATCCA

GGAAAATCAGACTTAATAGTCCGCGTGGGCGACGAGATTAGGCTGTTATGCACTGATCCGGGCTTTGTCA

AATGGACTTTTGAGATCCTGGATGAAACGAATGAGAATAAGCAGAATGAATGGATCACGGAAAAGGCAGA

AGCCACCAACACCGGCAAATACACGTGCACCAACAAACACGGCTTAAGCAATTCCATTTATGTGTTTGTT

AGAGATCCTGCCAAGCTTTTCCTTGTTGACCGCTCCTTGTATGGGAAAGAAGACAACGACACGCTGGTCC

GCTGTCCTCTCACAGACCCAGAAGTGACCAATTATTCCCTCAAGGGGTGCCAGGGGAAGCCTCTTCCCAA

GGACTTGAGGTTTATTCCTGACCCCAAGGCGGGCATCATGATCAAAAGTGTGAAACGCGCCTACCATCGG

CTCTGTCTGCATTGTTCTGTGGACCAGGAGGGCAAGTCAGTGCTGTCGGAAAAATTCATCCTGAAAGTGA

GGCCAGCCTTCAAAGCTGTGCCTGTTGTGTCTGTGTCCAAAGCAAGCTATCTTCTTAGGGAAGGGGAAGA

ATTCACAGTGACGTGCACAATAAAAGATGTGTCTAGTTCTGTGTACTCAACGTGGAAAAGAGAAAACAGT

CAGACTAAACTACAGGAGAAATATAATAGCTGGCATCACGGTGACTTCAATTATGAACGTCAGGCAACGT

TGACTATCAGTTCAGCGAGAGTTAATGATTCTGGAGTGTTCATGTGTTATGCCAATAATACTTTTGGATC

AGCAAATGTCACAACAACCTTGGAAGTAGTAGATAAAGGATTCATTAATATCTTCCCCATGATAAACACT

ACAGTATTTGTAAACGATGGAGAAAATGTAGATTTGATTGTTGAATATGAAGCATTCCCCAAACCTGAAC

ACCAGCAGTGGATCTATATGAACAGAACCTTCACTGATAAATGGGAAGATTATCCCAAGTCTGAGAATGA

AAGTAATATCAGATACGTAAGTGAACTTCATCTAACGAGATTAAAAGGCACCGAAGGAGGCACTTACACA

TTCCTAGTGTCCAATTCTGACGTCAATGCTGCCATAGCATTTAATGTTTATGTGAATACAAAACCAGAAA

TCCTGACTTACGACAGGCTCGTGAATGGCATGCTCCAATGTGTGGCAGCAGGATTCCCAGAGCCCACAAT

AGATTGGTATTTTTGTCCAGGAACTGAGCAGAGATGCTCTGCTTCTGTACTGCCAGTGGATGTGCAGACA

CTAAACTCATCTGGGCCACCGTTTGGAAAGCTAGTGGTTCAGAGTTCTATAGATTCTAGTGCATTCAAGC

ACAATGGCACGGTTGAATGTAAGGCTTACAACGATGTGGGCAAGACTTCTGCCTATTTTAACTTTGCATT

TAAAGAGCAAATCCATCCCCACACCCTGTTCACTCCTTTGCTGATTGGTTTCGTAATCGTAGCTGGCATG

ATGTGCATTATTGTGATGATTCTGACCTACAAATATTTACAGAAACCCATGTATGAAGTACAGTGGAAGG

TTGTTGAGGAGATAAATGGAAACAATTATGTTTACATAGACCCAACACAACTTCCTTATGATCACAAATG

GGAGTTTCCCAGAAACAGGCTGAGTTTTGGGAAAACCCTGGGTGCTGGAGCTTTCGGGAAGGTTGTTGAG

GCAACTGCTTATGGCTTAATTAAGTCAGATGCGGCCATGACTGTCGCTGTAAAGATGCTCAAGCCGAGTG

CCCATTTGACAGAACGGGAAGCCCTCATGTCTGAACTCAAAGTCCTGAGTTACCTTGGTAATCACATGAA

TATTGTGAATCTACTTGGAGCCTGCACCATTGGAGGGCCCACCCTGGTCATTACAGAATATTGTTGCTAT

GGTGATCTTTTGAATTTTTTGAGAAGAAAACGTGATTCATTTATTTGTTCAAAGCAGGAAGATCATGCAG
```

TABLE 14-continued

Examples of human C-KIT amino acid and nucleotide sequences.

AAGCTGCACTTTATAAGAATCTTCTGCATTCAAAGGAGTCTTCCTGCAGCGATAGTACTAATGAGTACAT
GGACATGAAACCTGGAGTTTCTTATGTTGTCCCAACCAAGGCCGACAAAAGGAGATCTGTGAGAATAGGC
TCATACATAGAAAGAGATGTGACTCCCGCCATCATGGAGGATGACGAGTTGGCCCTAGACTTAGAAGACT
TGCTGAGCTTTTCTTACCAGGTGGCAAAGGGCATGGCTTTCCTCGCCTCCAAGAATTGTATTCACAGAGA
CTTGGCAGCCAGAAATATCCTCCTTACTCATGGTCGGATCACAAAGATTTGTGATTTTGGTCTAGCCAGA
GACATCAAGAATGATTCTAATTATGTGGTTAAAGGAAACGCTCGACTACCTGTGAAGTGGATGGCACCTG
AAAGCATTTTCAACTGTGTATACACGTTTGAAAGTGACGTCTGGTCCTATGGGATTTTTCTTTGGGAGCT
GTTCTCTTTAGGAAGCAGCCCCTATCCTGGAATGCCGGTCGATTCTAAGTTCTACAAGATGATCAAGGAA
GGCTTCCGGATGCTCAGCCCTGAACACGCACCTGCTGAAATGTATGACATAATGAAGACTTGCTGGGATG
CAGATCCCCTAAAAAGACCAACATTCAAGCAAATTGTTCAGCTAATTGAGAAGCAGATTTCAGAGAGCAC
CAATCATATTTACTCCAACTTAGCAAACTGCAGCCCCAACCGACAGAAGCCCGTGGTAGACCATTCTGTG
CGGATCAATTCTGTCGGCAGCACCGCTTCCTCCTCCCAGCCTCTGCTTGTGCACGACGATGTCTGAGCAG
AATCAGTGTTTGGGTCACCCCTCCAGGAATGATCTCTTCTTTTGGCTTCCATGATGGTTATTTTCTTTTC
TTTCAACTTGCATCCAACTCCAGGATAGTGGGCACCCCACTGCAATCCTGTCTTTCTGAGCACACTTTAG
TGGCCGATGATTTTTGTCATCAGCCACCATCCTATTGCAAAGGTTCCAACTGTATATATTCCCAATAGCA
ACGTAGCTTCTACCATGAACAGAAAACATTCTGATTTGGAAAAAGAGAGGGAGGTATGGACTGGGGGCCA
GAGTCCTTTCCAAGGCTTCTCCAATTCTGCCCAAAAATATGGTTGATAGTTTACCTGAATAAATGGTAGT
AATCACAGTTGGCCTTCAGAACCATCCATAGTAGTATGATGATACAAGATTAGAAGCTGAAAACCTAAGT
CCTTTATGTGGAAAACAGAACATCATTAGAACAAAGGACAGAGTATGAACACCTGGGCTTAAGAAATCTA
GTATTTCATGCTGGGAATGAGACATAGGCCATGAAAAAAATGATCCCCAAGTGTGAACAAAAGATGCTCT
TCTGTGGACCACTGCATGAGCTTTTATACTACCGACCTGGTTTTTAAATAGAGTTTGCTATTAGAGCATT
GAATTGGAGAGAAGGCCTCCCTAGCCAGCACTTGTATATACGCATCTATAAATTGTCCGTGTTCATACAT
TTGAGGGGAAAACACCATAAGGTTTCGTTTCTGTATACAACCCTGGCATTATGTCCACTGTGTATAGAAG
TAGATTAAGAGCCATATAAGTTTGAAGGAAACAGTTAATACCATTTTTTAAGGAAACAATATAACCACAA
AGCACAGTTTGAACAAAATCTCCTCTTTTAGCTGATGAACTTATTCTGTAGATTCTGTGGAACAAGCCTA
TCAGCTTCAGAATGGCATTGTACTCAATGGATTTGATGCTGTTTGACAAAGTTACTGATTCACTGCATGG
CTCCCACAGGAGTGGGAAAACACTGCCATCTTAGTTTGGATTCTTATGTAGCAGGAAATAAAGTATAGGT
TTAGCCTCCTTCGCAGGCATGTCCTGGACACCGGGCCAGTATCTATATATGTGTATGTACGTTTGTATGT
GTGTAGACAAATATTTGGAGGGGTATTTTTGCCCTGAGTCCAAGAGGGTCCTTTAGTACCTGAAAAGTAA
CTTGGCTTTCATTATTAGTACTGCTCTTGTTTCTTTTCACATAGCTGTCTAGAGTAGCTTACCAGAAGCT
TCCATAGTGGTGCAGAGGAAGTGGAAGGCATCAGTCCCTATGTATTTGCAGTTCACCTGCACTTAAGGCA
CTCTGTTATTTAGACTCATCTTACTGTACCTGTTCCTTAGACCTTCCATAATGCTACTGTCTCACTGAAA
CATTTAAATTTTACCCTTTAGACTGTAGCCTGGATATTATTCTTGTAGTTTACCTCTTTAAAAACAAAAC
AAAACAAAACAAAAAACTCCCCTTCCTCACTGCCCAATATAAAAGGCAAATGTGTACATGGCAGAGTTTG
TGTGTTGTCTTGAAAGATTCAGGTATGTTGCCTTTATGGTTTCCCCCTTCTACATTTCTTAGACTACATT
TAGAGAACTGTGGCCGTTATCTGGAAGTAACCATTTGCACTGGAGTTCTATGCTCTCGCACCTTTCCAAA
GTTAACAGATTTTGGGGTTGTGTTGTCACCCAAGAGATTGTTGTTTGCCATACTTTGTCTGAAAAATTCC
TTTGTGTTTCTATTGACTTCAATGATAGTAAGAAAAGTGGTTGTTAGTTATAGATGTCTAGGTACTTCAG
GGGCACTTCATTGAGAGTTTTGTCTTGGATATTCTTGAAAGTTTATATTTTTATAATTTTTTCTTACATC

TABLE 14-continued

Examples of human C-KIT amino acid and nucleotide sequences.

AGATGTTTCTTTGCAGTGGCTTAATGTTTGAAATTATTTTGTGGCTTTTTTTGTAAATATTGAAATGTAG

CAATAATGTCTTTTGAATATTCCCAAGCCCATGAGTCCTTGAAAATATTTTTTATATATACAGTAACTTT

ATGTGTAAATACATAAGCGGCGTAAGTTTAAAGGATGTTGGTGTTCCACGTGTTTTATTCCTGTATGTTG

TCCAATTGTTGACAGTTCTGAAGAATTCTAATAAAATGTACATATATAAATCAAAAAAAAAAAAAAAA
(SEQ ID NO: 210)

The invention claimed is:

1. An anti-C-KIT antibody or an antigen-binding portion thereof, wherein the antibody comprises a heavy chain variable (VH) region and a light chain variable (VL) region, wherein
  (a) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of AASSLQS (SEQ ID NO: 24) and LCDR3 of QQYNSYPRT (SEQ ID NO: 12); or
  (b) the VH region amino acid sequence comprises HCDR1 of GYTFTDYYMN (SEQ ID NO: 13), HCDR2 of MGRIYPGSGNTYYAQKFQG (SEQ ID NO: 14) and HCDR3 of GVYYYDY (SEQ ID NO: 15); and the VL region amino acid sequence comprises LCDR1 of RASQGIRTNLA (SEQ ID NO: 16), LCDR2 of AASSLQS (SEQ ID NO: 24) and LCDR3 of QQYANYPRT (SEQ ID NO: 25).

2. The antibody or antigen-binding portion of claim 1, wherein
  (a) the VH region amino acid sequence comprises SEQ ID NO:185 and the VL region amino acid sequence comprises SEQ ID NO:186; or
  (b) the VH region amino acid sequence comprises SEQ ID NO:187 and the VL region amino acid sequence comprises SEQ ID NO:188.

3. The antibody or antigen-binding portion of claim 1, wherein the antibody is human, humanized or chimeric.

4. The antibody or antigen-binding portion of claim 1, wherein the VH region, the VL region, or both the VH and the VL region comprise one or more human framework region amino acid sequences.

5. The antibody or antigen-binding portion of claim 1, wherein the VH region, the VL region, or both the VH and the VL region comprise a human variable region framework scaffold amino acid sequence into which the CDRs have been inserted.

6. The antibody or antigen-binding portion of claim 1, wherein the VH region comprises an IGHV1-46 human germline scaffold amino acid sequence into which the HCDR1, HCDR2 and HCDR3 amino acid sequences have been inserted.

7. The antibody or antigen-binding portion of claim 1, wherein the VL region comprises an IGKV1-16 human germline scaffold amino acid sequence into which the LCDR1, LCDR2 and LCDR3 amino acid sequences have been inserted.

8. The antibody or antigen-binding portion of claim 1, wherein the antibody comprises an immunoglobulin constant region.

9. The antibody or antigen-binding portion of claim 8, wherein the immunoglobulin constant region is IgG, IgE, IgM, IgD, IgA or IgY.

10. The antibody or antigen-binding portion of claim 9, wherein the immunoglobulin constant region is IgG1, IgG2, IgG3, IgG4, IgA1 or IgA2.

11. The antibody or antigen-binding portion of claim 8, wherein the immunoglobulin constant region is immunologically inert.

12. The antibody or antigen-binding portion of claim 8, wherein the immunoglobulin constant region is a wild-type human IgG1 constant region, a human IgG1 constant region comprising the amino acid substitutions L234A, L235A and G237A or a human IgG1 constant region comprising the amino acid substitutions L234A, L235A, G237A and P331S.

13. The antibody or antigen-binding portion of claim 8, wherein the immunoglobulin constant region comprises SEQ ID NO:197, SEQ ID NO:198, SEQ ID NO:199, SEQ ID NO:200, SEQ ID NO:201 or SEQ ID NO:202.

14. The antigen-binding portion of claim 1, wherein the antibody or antigen-binding portion is an Fab, an Fab', an F(ab')$_2$, an Fd, an Fv, an scFv, a single domain antibody (dAb), a maxibody, a minibody, an intrabody, a diabody, a triabody, a tetrabody, a v-NAR or a bis-scFv.

15. The antibody or antigen-binding portion of claim 1, wherein the antibody is monoclonal.

16. The antibody or antigen-binding portion of claim 1, wherein the antibody or antigen-binding portion binds specifically to (a) human C-KIT or (b) human C-KIT and cynomolgus C-KIT.

17. A pharmaceutical composition comprising the antibody or antigen-binding portion of claim 1, and a pharmaceutically acceptable carrier, diluent or excipient.

18. An immunoconjugate comprising the antibody or antigen-binding portion of claim 1 linked to a therapeutic agent.

19. The immunoconjugate of claim 18, wherein the therapeutic agent is a cytotoxin, a radioisotope, a chemotherapeutic agent, an immunomodulatory agent, an anti-angiogenic agent, an antiproliferative agent, a pro-apoptotic agent, a cytostatic enzyme, a cytolytic enzymes, a therapeutic nucleic acid, an anti-angiogenic agent, an anti-proliferative agent, or a pro-apoptotic agent.

20. A pharmaceutical composition comprising the immunoconjugate of claim 18 and a pharmaceutically acceptable carrier, diluent or excipient.

21. An isolated nucleic acid molecule encoding
the VH amino acid sequence and the VL region amino acid sequence of the antibody or antigen-binding portion of claim 1.

22. An expression vector comprising the nucleic acid molecule of claim 21.

23. A recombinant host cell comprising the nucleic acid molecule of claim 21.

24. A recombinant host cell comprising the expression vector of claim 22.

* * * * *

SEQUENCE LISTING

<160> NUMBER OF SEQ ID NOS: 210

<210> SEQ ID NO 1
<211> LENGTH: 10
<212> TYPE: PRT
<213> ORGANISM: Artificial Sequence
<220> FEATURE:
<223> OTHER INFORMATION: anti-C-KIT HCDR1
<220> FEATURE:
<221> NAME/KEY: MISC_FEATURE
<222> LOCATION: (6)..(6)
<223> OTHER INFORMATION: Xaa is Asp or a conservative substitution of
      Asp
<220> FEATURE:
<221> NAME/KEY: MISC_FEATURE
<222> LOCATION: (7)..(7)
<223> OTHER INFORMATION: Xaa is Tyr or a conservative substitution of
      Tyr
<220> FEATURE:
<221> NAME/KEY: MISC_FEATURE
<222> LOCATION: (9)..(9)
<223> OTHER INFORMATION: Xaa is Met or a conservative substitution of
      Met

<400> SEQUENCE: 1

Gly Tyr Thr Phe Thr Xaa Xaa Tyr Xaa Asn
1               5                   10

<210> SEQ ID NO 2
<211> LENGTH: 19
<212> TYPE: PRT
<213> ORGANISM: Artificial Sequence
<220> FEATURE:
<223> OTHER INFORMATION: anti-C-KIT HCDR2
<220> FEATURE:
<221> NAME/KEY: MISC_FEATURE
<222> LOCATION: (1)..(1)
<223> OTHER INFORMATION: Xaa is Met or a conservative substitution of
      Met
<220> FEATURE:
<221> NAME/KEY: MISC_FEATURE
<222> LOCATION: (2)..(2)
<223> OTHER INFORMATION: Xaa is Gly or a conservative substitution of
      Gly
<220> FEATURE:
<221> NAME/KEY: MISC_FEATURE
<222> LOCATION: (7)..(7)
<223> OTHER INFORMATION: Xaa is Gly or a conservative substitution of
      Gly
<220> FEATURE:
<221> NAME/KEY: MISC_FEATURE
<222> LOCATION: (8)..(8)
<223> OTHER INFORMATION: Xaa is Ser or a conservative substitution of
      Ser

<400> SEQUENCE: 2

Xaa Xaa Arg Ile Tyr Pro Xaa Xaa Gly Asn Thr Tyr Tyr Ala Gln Lys
1               5                   10                  15

Phe Gln Gly

```
<210> SEQ ID NO 3
<211> LENGTH: 7
<212> TYPE: PRT
<213> ORGANISM: Artificial Sequence
<220> FEATURE:
<223> OTHER INFORMATION: anti-C-KIT HCDR3
<220> FEATURE:
<221> NAME/KEY: MISC_FEATURE
<222> LOCATION: (3)..(4)
<223> OTHER INFORMATION: Xaa is Tyr or any other amino acid
<220> FEATURE:
<221> NAME/KEY: MISC_FEATURE
<222> LOCATION: (5)..(5)
<223> OTHER INFORMATION: Xaa is Phe or any other amino acid
<220> FEATURE:
<221> NAME/KEY: MISC_FEATURE
<222> LOCATION: (6)..(6)
<223> OTHER INFORMATION: Xaa is Asp or any other amino acid
<220> FEATURE:
<221> NAME/KEY: MISC_FEATURE
<222> LOCATION: (7)..(7)
<223> OTHER INFORMATION: Xaa is Tyr or any other amino acid

<400> SEQUENCE: 3
```

Gly Val Xaa Xaa Xaa Xaa Xaa
1               5

```
<210> SEQ ID NO 4
<211> LENGTH: 10
<212> TYPE: PRT
<213> ORGANISM: Artificial Sequence
<220> FEATURE:
<223> OTHER INFORMATION: 37M murine/humanized antibody HCDR1

<400> SEQUENCE: 4
```

Gly Tyr Thr Phe Thr Asp Tyr Tyr Ile Asn
1               5                   10

```
<210> SEQ ID NO 5
<211> LENGTH: 19
<212> TYPE: PRT
<213> ORGANISM: Artificial Sequence
<220> FEATURE:
<223> OTHER INFORMATION: 37M murine/humanized antibody HCDR2

<400> SEQUENCE: 5
```

Ile Ala Arg Ile Tyr Pro Gly Ser Gly Asn Thr Tyr Tyr Asn Glu Lys
1               5                   10                  15

Phe Lys Gly

```
<210> SEQ ID NO 6
<211> LENGTH: 7
<212> TYPE: PRT
<213> ORGANISM: Artificial Sequence
<220> FEATURE:
<223> OTHER INFORMATION: 37M murine/humanized antibody HCDR3

<400> SEQUENCE: 6
```

Gly Val Tyr Tyr Phe Asp Tyr
1               5

```
<210> SEQ ID NO 7
<211> LENGTH: 11
<212> TYPE: PRT
<213> ORGANISM: Artificial Sequence
<220> FEATURE:
```

```
<223> OTHER INFORMATION: anti-C-KIT LCDR1
<220> FEATURE:
<221> NAME/KEY: MISC_FEATURE
<222> LOCATION: (6)..(6)
<223> OTHER INFORMATION: Xaa is Ile or a conservative substitution of
      Ile
<220> FEATURE:
<221> NAME/KEY: MISC_FEATURE
<222> LOCATION: (7)..(7)
<223> OTHER INFORMATION: Xaa is Arg or a conservative substitution of
      Arg
<220> FEATURE:
<221> NAME/KEY: MISC_FEATURE
<222> LOCATION: (8)..(8)
<223> OTHER INFORMATION: Xaa is Thr or any other amino acid
<220> FEATURE:
<221> NAME/KEY: MISC_FEATURE
<222> LOCATION: (9)..(9)
<223> OTHER INFORMATION: Xaa is Asn or any other amino acid

<400> SEQUENCE: 7

Arg Ala Ser Gln Gly Xaa Xaa Xaa Xaa Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: anti-C-KIT LCDR2
<220> FEATURE:
<221> NAME/KEY: MISC_FEATURE
<222> LOCATION: (1)..(1)
<223> OTHER INFORMATION: Xaa is Ala or any other amino acid
<220> FEATURE:
<221> NAME/KEY: MISC_FEATURE
<222> LOCATION: (4)..(4)
<223> OTHER INFORMATION: Xaa is Ser or any other amino acid
<220> FEATURE:
<221> NAME/KEY: MISC_FEATURE
<222> LOCATION: (5)..(5)
<223> OTHER INFORMATION: Xaa is Leu or any other amino acid
<220> FEATURE:
<221> NAME/KEY: MISC_FEATURE
<222> LOCATION: (6)..(6)
<223> OTHER INFORMATION: Xaa is Gln or any other amino acid

<400> SEQUENCE: 8

Xaa Ala Ser Xaa Xaa Xaa Ser
1               5

<210> SEQ ID NO 9
<211> LENGTH: 9
<212> TYPE: PRT
<213> ORGANISM: Artificial Sequence
<220> FEATURE:
<223> OTHER INFORMATION: anti-C-KIT LCDR3
<220> FEATURE:
<221> NAME/KEY: MISC_FEATURE
<222> LOCATION: (4)..(4)
<223> OTHER INFORMATION: Xaa is Asn or any other amino acid
<220> FEATURE:
<221> NAME/KEY: MISC_FEATURE
<222> LOCATION: (5)..(5)
<223> OTHER INFORMATION: Xaa is Ser or any other amino acid

<400> SEQUENCE: 9

Gln Gln Tyr Xaa Xaa Tyr Pro Arg Thr
1               5

<210> SEQ ID NO 10
<211> LENGTH: 11
<212> TYPE: PRT
```

<213> ORGANISM: Artificial Sequence
<220> FEATURE:
<223> OTHER INFORMATION: 37M murine/humanized antibody LCDR1

<400> SEQUENCE: 10

Lys Ala Ser Gln Asn Val Arg Thr Asn Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: 37M murine/humanized antibody LCDR2

<400> SEQUENCE: 11

Ser Ala Ser Tyr Arg Tyr Ser
1               5

<210> SEQ ID NO 12
<211> LENGTH: 9
<212> TYPE: PRT
<213> ORGANISM: Artificial Sequence
<220> FEATURE:
<223> OTHER INFORMATION: 37M murine/humanized antibody LCDR3

<400> SEQUENCE: 12

Gln Gln Tyr Asn Ser Tyr Pro Arg Thr
1               5

<210> SEQ ID NO 13
<211> LENGTH: 10
<212> TYPE: PRT
<213> ORGANISM: Artificial Sequence
<220> FEATURE:
<223> OTHER INFORMATION: anti-C-KIT HCDR1

<400> SEQUENCE: 13

Gly Tyr Thr Phe Thr Asp Tyr Tyr Met Asn
1               5                   10

<210> SEQ ID NO 14
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 14

Met Gly Arg Ile Tyr Pro Gly Ser Gly Asn Thr Tyr Tyr Ala Gln Lys
1               5                   10                  15

Phe Gln Gly

<210> SEQ ID NO 15
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 15

Gly Val Tyr Tyr Tyr Asp Tyr
1               5

<210> SEQ ID NO 16
<211> LENGTH: 11

```
<212> TYPE: PRT
<213> ORGANISM: Artificial Sequence
<220> FEATURE:
<223> OTHER INFORMATION: anti-C-KIT LCDR1

<400> SEQUENCE: 16

Arg Ala Ser Gln Gly Ile Arg Thr Asn Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 17

Ser Ala Ser Ser Leu Gln Ser
1               5

<210> SEQ ID NO 18
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 18

Gly Val Tyr Tyr Leu Asp Tyr
1               5

<210> SEQ ID NO 19
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 19

Arg Ala Ser Gln Gly Ile Arg Thr Asn Val Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 20

Ser Ala Ser Tyr Arg Gln Ser
1               5

<210> SEQ ID NO 21
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 21

Gly Val Tyr Tyr Phe Asp Glu
1               5

<210> SEQ ID NO 22
<211> LENGTH: 11
<212> TYPE: PRT
```

<213> ORGANISM: Artificial Sequence
<220> FEATURE:
<223> OTHER INFORMATION: anti-C-KIT LCDR1

<400> SEQUENCE: 22

Arg Ala Ser Gln Gly Val Arg Thr Asn Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 23

Ala Ala Ser Ser Arg Gln Ser
1               5

<210> SEQ ID NO 24
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 24

Ala Ala Ser Ser Leu Gln Ser
1               5

<210> SEQ ID NO 25
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 25

Gln Gln Tyr Ala Asn Tyr Pro Arg Thr
1               5

<210> SEQ ID NO 26
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 26

Met Gly Arg Ile Tyr Pro Ala Ser Gly Asn Thr Tyr Tyr Ala Gln Lys
1               5                   10                  15

Phe Gln Gly

<210> SEQ ID NO 27
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 27

Gly Val Trp Tyr Tyr Asp Tyr
1               5

<210> SEQ ID NO 28
<211> LENGTH: 10

```
<212> TYPE: PRT
<213> ORGANISM: Artificial Sequence
<220> FEATURE:
<223> OTHER INFORMATION: anti-C-KIT HCDR1
<220> FEATURE:
<221> NAME/KEY: MISC_FEATURE
<222> LOCATION: (6)..(6)
<223> OTHER INFORMATION: Xaa is Asp or Asn
<220> FEATURE:
<221> NAME/KEY: MISC_FEATURE
<222> LOCATION: (7)..(7)
<223> OTHER INFORMATION: Xaa is Tyr, His or Phe
<220> FEATURE:
<221> NAME/KEY: MISC_FEATURE
<222> LOCATION: (9)..(9)
<223> OTHER INFORMATION: Xaa is Met or Ile

<400> SEQUENCE: 28

Gly Tyr Thr Phe Thr Xaa Xaa Tyr Xaa Asn
1               5                   10

<210> SEQ ID NO 29
<211> LENGTH: 19
<212> TYPE: PRT
<213> ORGANISM: Artificial Sequence
<220> FEATURE:
<223> OTHER INFORMATION: anti-C-KIT HCDR2
<220> FEATURE:
<221> NAME/KEY: MISC_FEATURE
<222> LOCATION: (1)..(1)
<223> OTHER INFORMATION: Xaa is Met or Ile
<220> FEATURE:
<221> NAME/KEY: MISC_FEATURE
<222> LOCATION: (2)..(2)
<223> OTHER INFORMATION: Xaa is Gly or Ala
<220> FEATURE:
<221> NAME/KEY: MISC_FEATURE
<222> LOCATION: (7)..(7)
<223> OTHER INFORMATION: Xaa is Gly or Ala
<220> FEATURE:
<221> NAME/KEY: MISC_FEATURE
<222> LOCATION: (8)..(8)
<223> OTHER INFORMATION: Xaa is Ser, Thr or Ala

<400> SEQUENCE: 29

Xaa Xaa Arg Ile Tyr Pro Xaa Xaa Gly Asn Thr Tyr Tyr Ala Gln Lys
1               5                   10                  15

Phe Gln Gly

<210> SEQ ID NO 30
<211> LENGTH: 7
<212> TYPE: PRT
<213> ORGANISM: Artificial Sequence
<220> FEATURE:
<223> OTHER INFORMATION: anti-C-KIT HCDR3
<220> FEATURE:
<221> NAME/KEY: MISC_FEATURE
<222> LOCATION: (3)..(3)
<223> OTHER INFORMATION: Xaa is Tyr, Trp or Phe
<220> FEATURE:
<221> NAME/KEY: MISC_FEATURE
<222> LOCATION: (4)..(4)
<223> OTHER INFORMATION: Xaa is Tyr, Glu or His
<220> FEATURE:
<221> NAME/KEY: MISC_FEATURE
<222> LOCATION: (5)..(5)
<223> OTHER INFORMATION: Xaa is Phe, Tyr, Gln or Leu
<220> FEATURE:
<221> NAME/KEY: MISC_FEATURE
<222> LOCATION: (6)..(6)
<223> OTHER INFORMATION: Xaa is Asp, Gly, Asn or Ser
<220> FEATURE:
<221> NAME/KEY: MISC_FEATURE
<222> LOCATION: (7)..(7)
```

```
<223> OTHER INFORMATION: Xaa is Tyr, Ala, Glu, Phe, Gly, His, Ile, Lys,
      Leu, Met, Asn, Pro, Gln, Arg, Ser, Thr or Val

<400> SEQUENCE: 30

Gly Val Xaa Xaa Xaa Xaa Xaa
1               5

<210> SEQ ID NO 31
<211> LENGTH: 10
<212> TYPE: PRT
<213> ORGANISM: Artificial Sequence
<220> FEATURE:
<223> OTHER INFORMATION: anti-C-KIT HCDR1
<220> FEATURE:
<221> NAME/KEY: MISC_FEATURE
<222> LOCATION: (6)..(6)
<223> OTHER INFORMATION: Xaa is Asp or Asn
<220> FEATURE:
<221> NAME/KEY: MISC_FEATURE
<222> LOCATION: (7)..(7)
<223> OTHER INFORMATION: Xaa is Tyr or Phe

<400> SEQUENCE: 31

Gly Tyr Thr Phe Thr Xaa Xaa Tyr Met Asn
1               5                   10

<210> SEQ ID NO 32
<211> LENGTH: 19
<212> TYPE: PRT
<213> ORGANISM: Artificial Sequence
<220> FEATURE:
<223> OTHER INFORMATION: anti-C-KIT HCDR2
<220> FEATURE:
<221> NAME/KEY: MISC_FEATURE
<222> LOCATION: (1)..(1)
<223> OTHER INFORMATION: Xaa is Met or Ile
<220> FEATURE:
<221> NAME/KEY: MISC_FEATURE
<222> LOCATION: (7)..(7)
<223> OTHER INFORMATION: Xaa is Gly or Ala

<400> SEQUENCE: 32

Xaa Gly Arg Ile Tyr Pro Xaa Ser Gly Asn Thr Tyr Tyr Ala Gln Lys
1               5                   10                  15

Phe Gln Gly

<210> SEQ ID NO 33
<211> LENGTH: 7
<212> TYPE: PRT
<213> ORGANISM: Artificial Sequence
<220> FEATURE:
<223> OTHER INFORMATION: anti-C-KIT HCDR3
<220> FEATURE:
<221> NAME/KEY: MISC_FEATURE
<222> LOCATION: (3)..(3)
<223> OTHER INFORMATION: Xaa is Tyr or Trp
<220> FEATURE:
<221> NAME/KEY: MISC_FEATURE
<222> LOCATION: (4)..(4)
<223> OTHER INFORMATION: Xaa is Tyr, Glu or His
<220> FEATURE:
<221> NAME/KEY: MISC_FEATURE
<222> LOCATION: (5)..(5)
<223> OTHER INFORMATION: Xaa is Tyr, Gln or Leu
<220> FEATURE:
<221> NAME/KEY: MISC_FEATURE
<222> LOCATION: (7)..(7)
<223> OTHER INFORMATION: Xaa is Tyr, Ser, Thr or Glu

<400> SEQUENCE: 33

Gly Val Xaa Xaa Xaa Asp Xaa
```

```
<210> SEQ ID NO 34
<211> LENGTH: 11
<212> TYPE: PRT
<213> ORGANISM: Artificial Sequence
<220> FEATURE:
<223> OTHER INFORMATION: anti-C-KIT LCDR1
<220> FEATURE:
<221> NAME/KEY: MISC_FEATURE
<222> LOCATION: (6)..(6)
<223> OTHER INFORMATION: Xaa is Ile or Val
<220> FEATURE:
<221> NAME/KEY: MISC_FEATURE
<222> LOCATION: (8)..(8)
<223> OTHER INFORMATION: Xaa is Thr or Asn

<400> SEQUENCE: 34

Arg Ala Ser Gln Gly Xaa Arg Xaa Asn Leu Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: anti-C-KIT LCDR2
<220> FEATURE:
<221> NAME/KEY: MISC_FEATURE
<222> LOCATION: (1)..(1)
<223> OTHER INFORMATION: Xaa is Ala, Ser or Tyr

<400> SEQUENCE: 35

Xaa Ala Ser Ser Leu Gln Ser
1               5

<210> SEQ ID NO 36
<211> LENGTH: 9
<212> TYPE: PRT
<213> ORGANISM: Artificial Sequence
<220> FEATURE:
<223> OTHER INFORMATION: anti-C-KIT LCDR3
<220> FEATURE:
<221> NAME/KEY: MISC_FEATURE
<222> LOCATION: (4)..(4)
<223> OTHER INFORMATION: Xaa is Asn, Ala, Ser, Glu or Thr
<220> FEATURE:
<221> NAME/KEY: MISC_FEATURE
<222> LOCATION: (5)..(5)
<223> OTHER INFORMATION: Xaa is Ser, Ala, Asn or Asp

<400> SEQUENCE: 36

Gln Gln Tyr Xaa Xaa Tyr Pro Arg Thr
1               5

<210> SEQ ID NO 37
<211> LENGTH: 11
<212> TYPE: PRT
<213> ORGANISM: Artificial Sequence
<220> FEATURE:
<223> OTHER INFORMATION: anti-C-KIT LCDR1
<220> FEATURE:
<221> NAME/KEY: MISC_FEATURE
<222> LOCATION: (8)..(8)
<223> OTHER INFORMATION: Xaa is Thr or Asn

<400> SEQUENCE: 37

Arg Ala Ser Gln Gly Ile Arg Xaa Asn Leu Ala
1               5                   10
```

```
<210> SEQ ID NO 38
<211> LENGTH: 9
<212> TYPE: PRT
<213> ORGANISM: Artificial Sequence
<220> FEATURE:
<223> OTHER INFORMATION: anti-C-KIT LCDR3
<220> FEATURE:
<221> NAME/KEY: MISC_FEATURE
<222> LOCATION: (4)..(4)
<223> OTHER INFORMATION: Xaa is Asn or Ala
<220> FEATURE:
<221> NAME/KEY: MISC_FEATURE
<222> LOCATION: (5)..(5)
<223> OTHER INFORMATION: Xaa is Ser or Asn

<400> SEQUENCE: 38

Gln Gln Tyr Xaa Xaa Tyr Pro Arg Thr
1               5

<210> SEQ ID NO 39
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 39

Arg Ala Ser Gln Gly Val Arg Thr Asn Val Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 40

Gly Val Trp Tyr Phe Asp Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 41

Gly Val Tyr Tyr Gln Asp Tyr
1               5

<210> SEQ ID NO 42
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 42

Gly Val Tyr Glu Phe Asp Tyr
1               5

<210> SEQ ID NO 43
<211> LENGTH: 11
<212> TYPE: PRT
<213> ORGANISM: Artificial Sequence
<220> FEATURE:
<223> OTHER INFORMATION: anti-C-KIT LCDR1
```

```
<400> SEQUENCE: 43

Arg Ala Ser Gln Gly Val Arg Asn Asn Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 44

Ala Ala Ser Tyr Arg Gln Ser
1               5

<210> SEQ ID NO 45
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 45

Ile Gly Arg Ile Tyr Pro Gly Ser Gly Asn Thr Tyr Tyr Ala Gln Lys
1               5                   10                  15

Phe Gln Gly

<210> SEQ ID NO 46
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 46

Gly Val Tyr Tyr Phe Asp Ser
1               5

<210> SEQ ID NO 47
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 47

Arg Ala Ser Gln Gly Val Arg Asn Asn Val Ala
1               5                   10

<210> SEQ ID NO 48
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 48

Tyr Ala Ser Ser Leu Gln Ser
1               5

<210> SEQ ID NO 49
<211> LENGTH: 7
<212> TYPE: PRT
<213> ORGANISM: Artificial Sequence
<220> FEATURE:
```

```
<223> OTHER INFORMATION: anti-C-KIT HCDR3

<400> SEQUENCE: 49

Gly Val Tyr His Phe Asp Tyr
1               5

<210> SEQ ID NO 50
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 50

Ala Ala Ser Tyr Leu Gln Ser
1               5

<210> SEQ ID NO 51
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 51

Gly Val Tyr Tyr Phe Asp Thr
1               5

<210> SEQ ID NO 52
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 52

Ser Ala Ser Ser Arg Gln Ser
1               5

<210> SEQ ID NO 53
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 53

Gln Gln Tyr Ala Ser Tyr Pro Arg Thr
1               5

<210> SEQ ID NO 54
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 54

Gln Gln Tyr Asn Ala Tyr Pro Arg Thr
1               5

<210> SEQ ID NO 55
<211> LENGTH: 9
<212> TYPE: PRT
<213> ORGANISM: Artificial Sequence
<220> FEATURE:
<223> OTHER INFORMATION: anti-C-KIT LCDR3
```

<400> SEQUENCE: 55

Gln Gln Tyr Asn Asp Tyr Pro Arg Thr
1               5

<210> SEQ ID NO 56
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 56

Gln Gln Tyr Asn Ser Tyr Pro Lys Thr
1               5

<210> SEQ ID NO 57
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 57

Gln Gln Tyr Asn Ser Tyr Pro His Thr
1               5

<210> SEQ ID NO 58
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 58

Gln Gln Tyr Ser Ser Tyr Pro Arg Thr
1               5

<210> SEQ ID NO 59
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 59

Gln Gln Tyr Glu Ser Tyr Pro Arg Thr
1               5

<210> SEQ ID NO 60
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 60

Gln Gln Tyr Thr Ser Tyr Pro Arg Thr
1               5

<210> SEQ ID NO 61
<211> LENGTH: 19
<212> TYPE: PRT
<213> ORGANISM: Artificial Sequence
<220> FEATURE:
<223> OTHER INFORMATION: anti-C-KIT HCDR2

```
<400> SEQUENCE: 61

Met Gly Arg Ile Tyr Pro Gly Thr Gly Asn Thr Tyr Tyr Ala Gln Lys
1               5                   10                  15

Phe Gln Gly

<210> SEQ ID NO 62
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 62

Gly Val Trp Tyr Phe Asp Ser
1               5

<210> SEQ ID NO 63
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 63

Gly Val Trp Tyr Phe Asp Thr
1               5

<210> SEQ ID NO 64
<211> LENGTH: 9
<212> TYPE: PRT
<213> ORGANISM: Artificial Sequence
<220> FEATURE:
<223> OTHER INFORMATION: TCED+ and HAF peptide

<400> SEQUENCE: 64

Val Thr Ile Thr Cys Lys Ala Ser Gln
1               5

<210> SEQ ID NO 65
<211> LENGTH: 9
<212> TYPE: PRT
<213> ORGANISM: Artificial Sequence
<220> FEATURE:
<223> OTHER INFORMATION: light chain GE

<400> SEQUENCE: 65

Val Thr Ile Thr Cys Arg Ala Ser Gln
1               5

<210> SEQ ID NO 66
<211> LENGTH: 9
<212> TYPE: PRT
<213> ORGANISM: Artificial Sequence
<220> FEATURE:
<223> OTHER INFORMATION: HAF peptide

<400> SEQUENCE: 66

Leu Ile Tyr Ser Ala Ser Ser Leu Gln
1               5

<210> SEQ ID NO 67
<211> LENGTH: 9
<212> TYPE: PRT
<213> ORGANISM: Artificial Sequence
<220> FEATURE:
<223> OTHER INFORMATION: HAF peptide
```

<400> SEQUENCE: 67

Ile Tyr Ser Ala Ser Ser Leu Gln Ser
1               5

<210> SEQ ID NO 68
<211> LENGTH: 9
<212> TYPE: PRT
<213> ORGANISM: Artificial Sequence
<220> FEATURE:
<223> OTHER INFORMATION: TCED+ and HAF peptide

<400> SEQUENCE: 68

Tyr Tyr Ile Asn Trp Val Arg Gln Ala
1               5

<210> SEQ ID NO 69
<211> LENGTH: 5
<212> TYPE: PRT
<213> ORGANISM: Artificial Sequence
<220> FEATURE:
<223> OTHER INFORMATION: anti-C-KIT HCDR1

<400> SEQUENCE: 69

Asp Tyr Tyr Ile Asn
1               5

<210> SEQ ID NO 70
<211> LENGTH: 7
<212> TYPE: PRT
<213> ORGANISM: Artificial Sequence
<220> FEATURE:
<223> OTHER INFORMATION: anti-C-KIT HCDR1

<400> SEQUENCE: 70

Gly Tyr Thr Phe Thr Asp Tyr
1               5

<210> SEQ ID NO 71
<211> LENGTH: 8
<212> TYPE: PRT
<213> ORGANISM: Artificial Sequence
<220> FEATURE:
<223> OTHER INFORMATION: anti-C-KIT HCDR1

<400> SEQUENCE: 71

Gly Tyr Thr Phe Thr Asp Tyr Tyr
1               5

<210> SEQ ID NO 72
<211> LENGTH: 6
<212> TYPE: PRT
<213> ORGANISM: Artificial Sequence
<220> FEATURE:
<223> OTHER INFORMATION: anti-C-KIT HCDR1

<400> SEQUENCE: 72

Thr Asp Tyr Tyr Ile Asn
1               5

<210> SEQ ID NO 73
<211> LENGTH: 17
<212> TYPE: PRT
<213> ORGANISM: Artificial Sequence
<220> FEATURE:
<223> OTHER INFORMATION: anti-C-KIT HCDR2

<400> SEQUENCE: 73

Arg Ile Tyr Pro Gly Ser Gly Asn Thr Tyr Tyr Asn Glu Lys Phe Lys
1               5                   10                  15
Gly

<210> SEQ ID NO 74
<211> LENGTH: 6
<212> TYPE: PRT
<213> ORGANISM: Artificial Sequence
<220> FEATURE:
<223> OTHER INFORMATION: anti-C-KIT HCDR2

<400> SEQUENCE: 74

Tyr Pro Gly Ser Gly Asn
1               5

<210> SEQ ID NO 75
<211> LENGTH: 8
<212> TYPE: PRT
<213> ORGANISM: Artificial Sequence
<220> FEATURE:
<223> OTHER INFORMATION: anti-C-KIT HCDR2

<400> SEQUENCE: 75

Ile Tyr Pro Gly Ser Gly Asn Thr
1               5

<210> SEQ ID NO 76
<211> LENGTH: 16
<212> TYPE: PRT
<213> ORGANISM: Artificial Sequence
<220> FEATURE:
<223> OTHER INFORMATION: anti-C-KIT HCDR2

<400> SEQUENCE: 76

Ile Tyr Pro Gly Ser Gly Asn Thr Tyr Tyr Asn Glu Lys Phe Lys Gly
1               5                   10                  15

<210> SEQ ID NO 77
<211> LENGTH: 10
<212> TYPE: PRT
<213> ORGANISM: Artificial Sequence
<220> FEATURE:
<223> OTHER INFORMATION: anti-C-KIT HCDR2

<400> SEQUENCE: 77

Arg Ile Tyr Pro Gly Ser Gly Asn Thr Tyr
1               5                   10

<210> SEQ ID NO 78
<211> LENGTH: 12
<212> TYPE: PRT
<213> ORGANISM: Artificial Sequence
<220> FEATURE:
<223> OTHER INFORMATION: anti-C-KIT HCDR2

<400> SEQUENCE: 78

Ile Ala Arg Ile Tyr Pro Gly Ser Gly Asn Thr Tyr
1               5                   10

<210> SEQ ID NO 79
<211> LENGTH: 9
<212> TYPE: PRT
<213> ORGANISM: Artificial Sequence
<220> FEATURE:
<223> OTHER INFORMATION: anti-C-KIT HCDR3

```
<400> SEQUENCE: 79

Ala Arg Gly Val Tyr Tyr Phe Asp Tyr
1               5

<210> SEQ ID NO 80
<211> LENGTH: 6
<212> TYPE: PRT
<213> ORGANISM: Artificial Sequence
<220> FEATURE:
<223> OTHER INFORMATION: anti-C-KIT HCDR3

<400> SEQUENCE: 80

Gly Val Tyr Tyr Phe Asp
1               5

<210> SEQ ID NO 81
<211> LENGTH: 8
<212> TYPE: PRT
<213> ORGANISM: Artificial Sequence
<220> FEATURE:
<223> OTHER INFORMATION: anti-C-KIT HCDR3

<400> SEQUENCE: 81

Ala Arg Gly Val Tyr Tyr Phe Asp
1               5

<210> SEQ ID NO 82
<211> LENGTH: 6
<212> TYPE: PRT
<213> ORGANISM: Artificial Sequence
<220> FEATURE:
<223> OTHER INFORMATION: anti-C-KIT LCDR1

<400> SEQUENCE: 82

Gln Asn Val Arg Thr Asn
1               5

<210> SEQ ID NO 83
<211> LENGTH: 8
<212> TYPE: PRT
<213> ORGANISM: Artificial Sequence
<220> FEATURE:
<223> OTHER INFORMATION: anti-C-KIT LCDR1

<400> SEQUENCE: 83

Ala Ser Gln Asn Val Arg Thr Asn
1               5

<210> SEQ ID NO 84
<211> LENGTH: 8
<212> TYPE: PRT
<213> ORGANISM: Artificial Sequence
<220> FEATURE:
<223> OTHER INFORMATION: anti-C-KIT LCDR1

<400> SEQUENCE: 84

Val Arg Thr Asn Val Ala Trp Tyr
1               5

<210> SEQ ID NO 85
<211> LENGTH: 10
<212> TYPE: PRT
<213> ORGANISM: Artificial Sequence
<220> FEATURE:
<223> OTHER INFORMATION: anti-C-KIT LCDR2
```

```
<400> SEQUENCE: 85

Ala Leu Ile Tyr Ser Ala Ser Tyr Arg Tyr
1               5                   10

<210> SEQ ID NO 86
<211> LENGTH: 6
<212> TYPE: PRT
<213> ORGANISM: Artificial Sequence
<220> FEATURE:
<223> OTHER INFORMATION: anti-C-KIT LCDR3

<400> SEQUENCE: 86

Tyr Asn Ser Tyr Pro Arg
1               5

<210> SEQ ID NO 87
<211> LENGTH: 116
<212> TYPE: PRT
<213> ORGANISM: Mus musculus

<400> SEQUENCE: 87

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Ala Arg Ile Tyr Pro Gly Ser Gly Asn Thr Tyr Tyr Asn Glu Lys Phe
        50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Tyr Tyr Phe Asp Tyr Trp Gly Gln Gly Thr Thr Leu
            100                 105                 110

Thr Val Ser Ser
        115

<210> SEQ ID NO 88
<211> LENGTH: 116
<212> TYPE: PRT
<213> ORGANISM: Artificial Sequence
<220> FEATURE:
<223> OTHER INFORMATION: h37M-VH

<400> SEQUENCE: 88

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Arg Gln Ala Pro Gly Lys Gly Leu Glu Trp Ile
            35                  40                  45

Ala Arg Ile Tyr Pro Gly Ser Gly Asn Thr Tyr Tyr Asn Glu Lys Phe
        50                  55                  60

Lys Gly Arg Ala Thr Leu Thr Ala Asp Lys Ser Thr Ser Thr Ala Tyr
65                  70                  75                  80

Met Gln Leu Ser Ser Leu Arg Ser Glu Asp Thr Ala Val Tyr Phe Cys
                85                  90                  95

Ala Arg Gly Val Tyr Tyr Phe Asp Tyr Trp Gly Gln Gly Thr Thr Val
```

Thr Val Ser Ser
        115

<210> SEQ ID NO 89
<211> LENGTH: 116
<212> TYPE: PRT
<213> ORGANISM: Artificial Sequence
<220> FEATURE:
<223> OTHER INFORMATION: VH graft

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Asn Trp Val Arg Gln Ala Pro Gly Gln Gly Leu Glu Trp Ile
            35                  40                  45

Ala Arg Ile Tyr Pro Gly Ser Gly Asn Thr Tyr Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Tyr Phe Asp Tyr Trp Gly Gln Gly Thr Leu Val
            100                 105                 110

Thr Val Ser Ser
        115

<210> SEQ ID NO 90
<211> LENGTH: 108
<212> TYPE: PRT
<213> ORGANISM: Mus musculus

<400> SEQUENCE: 90

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Arg Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Arg
                85                  90                  95

Thr Phe Gly Gly Gly Thr Lys Leu Glu Ile Lys Arg
            100                 105

<210> SEQ ID NO 91
<211> LENGTH: 107
<212> TYPE: PRT
<213> ORGANISM: Artificial Sequence
<220> FEATURE:
<223> OTHER INFORMATION: h37M-VL

<400> SEQUENCE: 91

Asp Ile Val Met Thr Gln Ser Pro Ser Ser Leu Ser Ala Ser Val Gly

```
                1               5                  10                  15
Asp Arg Val Thr Ile Thr Cys Lys Ala Ser Gln Asn Val Arg Thr Asn
                    20                  25                  30

Val Ala Trp Tyr Gln Gln Lys Pro Gly Lys Ala Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Arg
                    85                  90                  95

Thr Phe Gly Gly Gly Thr Lys Val Glu Ile Lys
                100                 105

<210> SEQ ID NO 92
<211> LENGTH: 107
<212> TYPE: PRT
<213> ORGANISM: Artificial Sequence
<220> FEATURE:
<223> OTHER INFORMATION: VL graft

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Arg Thr Asn
                    20                  25                  30

Val Ala Trp Phe Gln Gln Lys Pro Gly Lys Ala Pro Lys Ser Leu Ile
            35                  40                  45

Tyr Ser Ala Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                    85                  90                  95

Thr Phe Gly Gly Gly Thr Lys Val Glu Ile Lys
                100                 105

<210> SEQ ID NO 93
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 93

Arg Ala Ser Gln Gly Ile Arg Asn Asn Leu Ala
1               5                   10

<210> SEQ ID NO 94
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 94

Arg Ala Ser Gln Gly Ile Arg Asn Asn Val Ala
1               5                   10

<210> SEQ ID NO 95
```

```
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 95

Arg Ala Ser Gln Gly Ile Arg Asn Tyr Val Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 96

Arg Ala Ser Gln Gly Ile Ser Asn Tyr Leu Ala
1               5                   10

<210> SEQ ID NO 97
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 97

Arg Ala Ser Gln Gly Ile Ser Asn Tyr Val Ala
1               5                   10

<210> SEQ ID NO 98
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 98

Arg Ala Ser Gln Gly Ile Ser Thr Asn Leu Ala
1               5                   10

<210> SEQ ID NO 99
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 99

Arg Ala Ser Gln Gly Ile Ser Thr Asn Val Ala
1               5                   10

<210> SEQ ID NO 100
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 100

Arg Ala Ser Gln Gly Ile Ser Thr Tyr Leu Ala
1               5                   10

<210> SEQ ID NO 101
<211> LENGTH: 11
```

```
<212> TYPE: PRT
<213> ORGANISM: Artificial Sequence
<220> FEATURE:
<223> OTHER INFORMATION: anti-C-KIT LCDR1

<400> SEQUENCE: 101

Arg Ala Ser Gln Gly Ile Ser Thr Tyr Val Ala
1               5                   10

<210> SEQ ID NO 102
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 102

Arg Ala Ser Gln Gly Val Arg Asn Tyr Val Ala
1               5                   10

<210> SEQ ID NO 103
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 103

Arg Ala Ser Gln Gly Val Ser Asn Asn Leu Ala
1               5                   10

<210> SEQ ID NO 104
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 104

Arg Ala Ser Gln Gly Val Ser Asn Asn Val Ala
1               5                   10

<210> SEQ ID NO 105
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 105

Arg Ala Ser Gln Gly Val Ser Asn Tyr Leu Ala
1               5                   10

<210> SEQ ID NO 106
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 106

Arg Ala Ser Gln Gly Val Ser Asn Tyr Val Ala
1               5                   10

<210> SEQ ID NO 107
<211> LENGTH: 11
<212> TYPE: PRT
```

```
<213> ORGANISM: Artificial Sequence
<220> FEATURE:
<223> OTHER INFORMATION: anti-C-KIT LCDR1

<400> SEQUENCE: 107

Arg Ala Ser Gln Gly Val Ser Thr Asn Leu Ala
1               5                   10

<210> SEQ ID NO 108
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 108

Arg Ala Ser Gln Gly Val Ser Thr Asn Val Ala
1               5                   10

<210> SEQ ID NO 109
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 109

Arg Ala Ser Gln Gly Val Ser Thr Tyr Leu Ala
1               5                   10

<210> SEQ ID NO 110
<211> LENGTH: 11
<212> TYPE: PRT
<213> ORGANISM: Artificial Sequence
<220> FEATURE:
<223> OTHER INFORMATION: anti-C-KIT LCDR1

<400> SEQUENCE: 110

Arg Ala Ser Gln Gly Val Ser Thr Tyr Val Ala
1               5                   10

<210> SEQ ID NO 111
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 111

Ala Ala Ser Ser Leu Tyr Ser
1               5

<210> SEQ ID NO 112
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 112

Ala Ala Ser Ser Arg Tyr Ser
1               5

<210> SEQ ID NO 113
<211> LENGTH: 7
<212> TYPE: PRT
<213> ORGANISM: Artificial Sequence
```

```
<220> FEATURE:
<223> OTHER INFORMATION: anti-C-KIT LCDR2

<400> SEQUENCE: 113

Ala Ala Ser Tyr Leu Tyr Ser
1               5

<210> SEQ ID NO 114
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 114

Ala Ala Ser Tyr Arg Tyr Ser
1               5

<210> SEQ ID NO 115
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 115

Ser Ala Ser Ser Leu Tyr Ser
1               5

<210> SEQ ID NO 116
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 116

Ser Ala Ser Ser Arg Tyr Ser
1               5

<210> SEQ ID NO 117
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 117

Ser Ala Ser Tyr Leu Gln Ser
1               5

<210> SEQ ID NO 118
<211> LENGTH: 7
<212> TYPE: PRT
<213> ORGANISM: Artificial Sequence
<220> FEATURE:
<223> OTHER INFORMATION: anti-C-KIT LCDR2

<400> SEQUENCE: 118

Ser Ala Ser Tyr Leu Tyr Ser
1               5

<210> SEQ ID NO 119
<211> LENGTH: 9
<212> TYPE: PRT
<213> ORGANISM: Artificial Sequence
<220> FEATURE:
```

<223> OTHER INFORMATION: anti-C-KIT LCDR3

<400> SEQUENCE: 119

Gln Gln Tyr Ala Ser Tyr Pro Leu Thr
1               5

<210> SEQ ID NO 120
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 120

Gln Gln Tyr Asn Ser Tyr Pro Leu Thr
1               5

<210> SEQ ID NO 121
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 121

Gln Gln Tyr Gln Ser Tyr Pro Leu Thr
1               5

<210> SEQ ID NO 122
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 122

Gln Gln Tyr Gln Ser Tyr Pro Arg Thr
1               5

<210> SEQ ID NO 123
<211> LENGTH: 10
<212> TYPE: PRT
<213> ORGANISM: Artificial Sequence
<220> FEATURE:
<223> OTHER INFORMATION: anti-C-KIT HCDR1

<400> SEQUENCE: 123

Gly Tyr Thr Phe Thr Asp Tyr Tyr Met His
1               5                   10

<210> SEQ ID NO 124
<211> LENGTH: 10
<212> TYPE: PRT
<213> ORGANISM: Artificial Sequence
<220> FEATURE:
<223> OTHER INFORMATION: anti-C-KIT HCDR1

<400> SEQUENCE: 124

Gly Tyr Thr Phe Thr Ser Tyr Tyr Ile Asn
1               5                   10

<210> SEQ ID NO 125
<211> LENGTH: 10
<212> TYPE: PRT
<213> ORGANISM: Artificial Sequence
<220> FEATURE:
<223> OTHER INFORMATION: anti-C-KIT HCDR1

<400> SEQUENCE: 125

Gly Tyr Thr Phe Thr Ser Tyr Tyr Met Asn
1               5                   10

<210> SEQ ID NO 126
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 126

Ile Ala Ile Ile Tyr Pro Gly Ser Gly Asn Thr Tyr Tyr Ala Gln Lys
1               5                   10                  15

Phe Gln Gly

<210> SEQ ID NO 127
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 127

Ile Ala Arg Ile Asn Pro Gly Ser Gly Asn Thr Ser Tyr Ala Gln Lys
1               5                   10                  15

Phe Gln Gly

<210> SEQ ID NO 128
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 128

Ile Ala Arg Ile Asn Pro Gly Ser Gly Asn Thr Tyr Tyr Ala Gln Lys
1               5                   10                  15

Phe Gln Gly

<210> SEQ ID NO 129
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 129

Ile Ala Arg Ile Tyr Pro Gly Ser Gly Asn Thr Ser Tyr Ala Gln Lys
1               5                   10                  15

Phe Gln Gly

<210> SEQ ID NO 130
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 130

Ile Ala Arg Ile Tyr Pro Ser Ser Gly Asn Thr Ser Tyr Ala Gln Lys
1               5                   10                  15

Phe Gln Gly

<210> SEQ ID NO 131
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 131

Ile Ala Arg Ile Tyr Pro Ser Ser Gly Asn Thr Tyr Tyr Ala Gln Lys
1               5                   10                  15

Phe Gln Gly

<210> SEQ ID NO 132
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 132

Ile Gly Ile Ile Tyr Pro Gly Ser Gly Asn Thr Tyr Tyr Ala Gln Lys
1               5                   10                  15

Phe Gln Gly

<210> SEQ ID NO 133
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 133

Ile Gly Arg Ile Asn Pro Gly Ser Gly Asn Thr Ser Tyr Ala Gln Lys
1               5                   10                  15

Phe Gln Gly

<210> SEQ ID NO 134
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 134

Ile Gly Arg Ile Asn Pro Gly Ser Gly Asn Thr Tyr Tyr Ala Gln Lys
1               5                   10                  15

Phe Gln Gly

<210> SEQ ID NO 135
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 135

Ile Gly Arg Ile Tyr Pro Gly Ser Gly Asn Thr Ser Tyr Ala Gln Lys
1               5                   10                  15

Phe Gln Gly

<210> SEQ ID NO 136

```
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 136

Ile Gly Arg Ile Tyr Pro Ser Ser Gly Asn Thr Ser Tyr Ala Gln Lys
1               5                   10                  15

Phe Gln Gly

<210> SEQ ID NO 137
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 137

Ile Gly Arg Ile Tyr Pro Ser Ser Gly Asn Thr Tyr Tyr Ala Gln Lys
1               5                   10                  15

Phe Gln Gly

<210> SEQ ID NO 138
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 138

Met Ala Ile Ile Tyr Pro Gly Ser Gly Asn Thr Tyr Tyr Ala Gln Lys
1               5                   10                  15

Phe Gln Gly

<210> SEQ ID NO 139
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 139

Met Ala Arg Ile Asn Pro Gly Ser Gly Asn Thr Ser Tyr Ala Gln Lys
1               5                   10                  15

Phe Gln Gly

<210> SEQ ID NO 140
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 140

Met Ala Arg Ile Asn Pro Gly Ser Gly Asn Thr Tyr Tyr Ala Gln Lys
1               5                   10                  15

Phe Gln Gly

<210> SEQ ID NO 141
<211> LENGTH: 19
<212> TYPE: PRT
<213> ORGANISM: Artificial Sequence
<220> FEATURE:
```

<223> OTHER INFORMATION: anti-C-KIT HCDR2

<400> SEQUENCE: 141

Met Ala Arg Ile Tyr Pro Gly Ser Gly Asn Thr Ser Tyr Ala Gln Lys
1               5                   10                  15

Phe Gln Gly

<210> SEQ ID NO 142
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 142

Met Ala Arg Ile Tyr Pro Gly Ser Gly Asn Thr Tyr Tyr Ala Gln Lys
1               5                   10                  15

Phe Gln Gly

<210> SEQ ID NO 143
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 143

Met Ala Arg Ile Tyr Pro Ser Ser Gly Asn Thr Ser Tyr Ala Gln Lys
1               5                   10                  15

Phe Gln Gly

<210> SEQ ID NO 144
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 144

Met Ala Arg Ile Tyr Pro Ser Ser Gly Asn Thr Tyr Tyr Ala Gln Lys
1               5                   10                  15

Phe Gln Gly

<210> SEQ ID NO 145
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 145

Met Gly Ile Ile Tyr Pro Gly Ser Gly Asn Thr Tyr Tyr Ala Gln Lys
1               5                   10                  15

Phe Gln Gly

<210> SEQ ID NO 146
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 146

```
Met Gly Arg Ile Asn Pro Gly Ser Gly Asn Thr Ser Tyr Ala Gln Lys
1               5                   10                  15

Phe Gln Gly

<210> SEQ ID NO 147
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 147

Met Gly Arg Ile Asn Pro Gly Ser Gly Asn Thr Tyr Tyr Ala Gln Lys
1               5                   10                  15

Phe Gln Gly

<210> SEQ ID NO 148
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 148

Met Gly Arg Ile Tyr Pro Gly Ser Gly Asn Thr Ser Tyr Ala Gln Lys
1               5                   10                  15

Phe Gln Gly

<210> SEQ ID NO 149
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 149

Met Gly Arg Ile Tyr Pro Ser Ser Gly Asn Thr Ser Tyr Ala Gln Lys
1               5                   10                  15

Phe Gln Gly

<210> SEQ ID NO 150
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 150

Met Gly Arg Ile Tyr Pro Ser Ser Gly Asn Thr Tyr Tyr Ala Gln Lys
1               5                   10                  15

Phe Gln Gly

<210> SEQ ID NO 151
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 151

Gly Val Tyr Tyr Phe Asp Ala
1               5
```

```
<210> SEQ ID NO 152
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 152

Gly Val Tyr Tyr Phe Asp Asp
1               5

<210> SEQ ID NO 153
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 153

Gly Val Tyr Tyr Phe Asp Phe
1               5

<210> SEQ ID NO 154
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 154

Gly Val Tyr Tyr Phe Asp Gly
1               5

<210> SEQ ID NO 155
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 155

Gly Val Tyr Tyr Phe Asp His
1               5

<210> SEQ ID NO 156
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 156

Gly Val Tyr Tyr Phe Asp Ile
1               5

<210> SEQ ID NO 157
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 157

Gly Val Tyr Tyr Phe Asp Lys
1               5

<210> SEQ ID NO 158
```

```
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 158

Gly Val Tyr Tyr Phe Asp Met
1               5

<210> SEQ ID NO 159
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 159

Gly Val Tyr Tyr Phe Asp Asn
1               5

<210> SEQ ID NO 160
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 160

Gly Val Tyr Tyr Phe Asp Pro
1               5

<210> SEQ ID NO 161
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 161

Gly Val Tyr Tyr Phe Asp Gln
1               5

<210> SEQ ID NO 162
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 162

Gly Val Tyr Tyr Phe Asp Arg
1               5

<210> SEQ ID NO 163
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 163

Gly Val Tyr Tyr Phe Asp Val
1               5

<210> SEQ ID NO 164
<211> LENGTH: 7
```

```
<212> TYPE: PRT
<213> ORGANISM: Artificial Sequence
<220> FEATURE:
<223> OTHER INFORMATION: anti-C-KIT HCDR3

<400> SEQUENCE: 164

Gly Val Tyr Tyr Phe Asp Trp
1               5

<210> SEQ ID NO 165
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 165

Gly Val Tyr Tyr Ala Asp Tyr
1               5

<210> SEQ ID NO 166
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 166

Gly Val Tyr Tyr Gly Asp Tyr
1               5

<210> SEQ ID NO 167
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 167

Gly Val Tyr Tyr His Asp Tyr
1               5

<210> SEQ ID NO 168
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 168

Gly Val Tyr Tyr Lys Asp Tyr
1               5

<210> SEQ ID NO 169
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 169

Gly Val Tyr Tyr Asn Asp Tyr
1               5

<210> SEQ ID NO 170
<211> LENGTH: 7
<212> TYPE: PRT
```

```
<213> ORGANISM: Artificial Sequence
<220> FEATURE:
<223> OTHER INFORMATION: anti-C-KIT HCDR3

<400> SEQUENCE: 170

Gly Val Tyr Tyr Met Asp Tyr
1               5

<210> SEQ ID NO 171
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 171

Gly Val Tyr Tyr Trp Asp Tyr
1               5

<210> SEQ ID NO 172
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 172

Gly Val Tyr Ala Phe Asp Tyr
1               5

<210> SEQ ID NO 173
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 173

Gly Val Tyr Gln Phe Asp Tyr
1               5

<210> SEQ ID NO 174
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 174

Gly Val Tyr Trp Phe Asp Tyr
1               5

<210> SEQ ID NO 175
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 175

Gly Val Tyr Asn Phe Asp Tyr
1               5

<210> SEQ ID NO 176
<211> LENGTH: 7
<212> TYPE: PRT
<213> ORGANISM: Artificial Sequence
```

```
<220> FEATURE:
<223> OTHER INFORMATION: anti-C-KIT HCDR3

<400> SEQUENCE: 176

Gly Val Tyr Thr Phe Asp Tyr
1               5

<210> SEQ ID NO 177
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 177

Gly Val Tyr Asp Phe Asp Tyr
1               5

<210> SEQ ID NO 178
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 178

Gln Gln Tyr Asn Ala Tyr Pro Lys Thr
1               5

<210> SEQ ID NO 179
<211> LENGTH: 9
<212> TYPE: PRT
<213> ORGANISM: Artificial Sequence
<220> FEATURE:
<223> OTHER INFORMATION: anti-C-KIT LCDR3

<400> SEQUENCE: 179

Gln Gln Tyr Asn Ala Tyr Pro His Thr
1               5

<210> SEQ ID NO 180
<211> LENGTH: 10
<212> TYPE: PRT
<213> ORGANISM: Artificial Sequence
<220> FEATURE:
<223> OTHER INFORMATION: anti-C-KIT HCDR1

<400> SEQUENCE: 180

Gly Tyr Thr Phe Thr Asp Phe Tyr Met Asn
1               5                   10

<210> SEQ ID NO 181
<211> LENGTH: 10
<212> TYPE: PRT
<213> ORGANISM: Artificial Sequence
<220> FEATURE:
<223> OTHER INFORMATION: anti-C-KIT HCDR1

<400> SEQUENCE: 181

Gly Tyr Thr Phe Thr Asn Tyr Tyr Met Asn
1               5                   10

<210> SEQ ID NO 182
<211> LENGTH: 10
<212> TYPE: PRT
<213> ORGANISM: Artificial Sequence
<220> FEATURE:
```

```
<223> OTHER INFORMATION: anti-C-KIT HCDR1

<400> SEQUENCE: 182

Gly Tyr Thr Phe Thr Asp His Tyr Met Asn
1               5                   10

<210> SEQ ID NO 183
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 183

Met Gly Arg Ile Tyr Pro Gly Ala Gly Asn Thr Tyr Tyr Ala Gln Lys
1               5                   10                  15

Phe Gln Gly

<210> SEQ ID NO 184
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 184

Gly Val Trp Tyr Phe Asp Glu
1               5

<210> SEQ ID NO 185
<211> LENGTH: 116
<212> TYPE: PRT
<213> ORGANISM: Artificial Sequence
<220> FEATURE:
<223> OTHER INFORMATION: Antibody MH1 heavy chain variable (VH) region

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Met
            35                  40                  45

Gly Arg Ile Tyr Pro Gly Ser Gly Asn Thr Tyr Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Tyr Tyr Asp Tyr Trp Gly Gln Gly Thr Leu Val
            100                 105                 110

Thr Val Ser Ser
        115

<210> SEQ ID NO 186
<211> LENGTH: 107
<212> TYPE: PRT
<213> ORGANISM: Artificial Sequence
<220> FEATURE:
<223> OTHER INFORMATION: Antibody MH1 VL light chain variable (VL)
      region

<400> SEQUENCE: 186
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Thr Asn
            20                  25                  30

Leu Ala Trp Phe Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gly Gly Thr Lys Val Glu Ile Lys
            100                 105
```

<210> SEQ ID NO 187
<211> LENGTH: 116
<212> TYPE: PRT
<213> ORGANISM: Artificial Sequence
<220> FEATURE:
<223> OTHER INFORMATION: Antibody MH5-DI heavy chain variable (VH)
      region

<400> SEQUENCE: 187

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
            35                  40                  45

Gly Arg Ile Tyr Pro Gly Ser Gly Asn Thr Tyr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Tyr Tyr Asp Tyr Trp Gly Gln Gly Thr Leu Val
            100                 105                 110

Thr Val Ser Ser
        115
```

<210> SEQ ID NO 188
<211> LENGTH: 107
<212> TYPE: PRT
<213> ORGANISM: Artificial Sequence
<220> FEATURE:
<223> OTHER INFORMATION: Antibody MH5-DI light chain variable (VL)
      region

<400> SEQUENCE: 188

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Thr Asn
            20                  25                  30

Leu Ala Trp Phe Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Asn Tyr Pro Arg
                85                  90                  95

Thr Phe Gly Gly Gly Thr Lys Val Glu Ile Lys
            100                 105

<210> SEQ ID NO 189
<211> LENGTH: 116
<212> TYPE: PRT
<213> ORGANISM: Artificial Sequence
<220> FEATURE:
<223> OTHER INFORMATION: Antibody MH5 heavy chain variable (VH) region

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Met
            35                  40                  45

Gly Arg Ile Tyr Pro Gly Ser Gly Asn Thr Tyr Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Tyr Asp Tyr Trp Gly Gln Gly Thr Leu Val
            100                 105                 110

Thr Val Ser Ser
        115

<210> SEQ ID NO 190
<211> LENGTH: 107
<212> TYPE: PRT
<213> ORGANISM: Artificial Sequence
<220> FEATURE:
<223> OTHER INFORMATION: Antibody MH5 light chain variable (VL) region

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Thr Asn
                20                  25                  30

Leu Ala Trp Phe Gln Gln Lys Pro Gly Lys Ala Pro Lys Ser Leu Ile
            35                  40                  45

Tyr Ser Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Asn Tyr Pro Arg
                85                  90                  95

Thr Phe Gly Gly Gly Thr Lys Val Glu Ile Lys
            100                 105

<210> SEQ ID NO 191
<211> LENGTH: 116
<212> TYPE: PRT

```
<213> ORGANISM: Artificial Sequence
<220> FEATURE:
<223> OTHER INFORMATION: Antibody EC7 heavy chain variable (VH) region

<400> SEQUENCE: 191

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Ile Tyr Pro Gly Ser Gly Asn Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Tyr Tyr Asp Tyr Trp Gly Gln Gly Thr Leu Val
            100                 105                 110

Thr Val Ser Ser
        115

<210> SEQ ID NO 192
<211> LENGTH: 107
<212> TYPE: PRT
<213> ORGANISM: Artificial Sequence
<220> FEATURE:
<223> OTHER INFORMATION: Antibody EC7 light chain variable (VL) region

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Thr Asn
            20                  25                  30

Leu Ala Trp Phe Gln Gln Lys Pro Gly Lys Ala Pro Lys Ser Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 193
<211> LENGTH: 116
<212> TYPE: PRT
<213> ORGANISM: Artificial Sequence
<220> FEATURE:
<223> OTHER INFORMATION: Antibody EC2 heavy chain variable (VH) region

<400> SEQUENCE: 193

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45
```

```
Gly Arg Ile Tyr Pro Gly Ser Gly Asn Thr Tyr Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Val Tyr Tyr Leu Asp Tyr Trp Gly Gln Gly Thr Leu Val
               100                 105                 110

Thr Val Ser Ser
            115

<210> SEQ ID NO 194
<211> LENGTH: 107
<212> TYPE: PRT
<213> ORGANISM: Artificial Sequence
<220> FEATURE:
<223> OTHER INFORMATION: Antibody EC2 light chain variable (VL) region

<400> SEQUENCE: 194

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Thr Asn
                20                  25                  30

Val Ala Trp Leu Gln Gln Lys Pro Gly Lys Ala Pro Lys Ser Leu Ile
            35                  40                  45

Tyr Ser Ala Ser Tyr Arg Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                85                  90                  95

Thr Phe Gly Gly Gly Thr Lys Val Glu Ile Lys
               100                 105

<210> SEQ ID NO 195
<211> LENGTH: 116
<212> TYPE: PRT
<213> ORGANISM: Artificial Sequence
<220> FEATURE:
<223> OTHER INFORMATION: Antibody F-C5 heavy chain variable (VH) region

<400> SEQUENCE: 195

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Met
            35                  40                  45

Gly Arg Ile Tyr Pro Gly Ser Gly Asn Thr Tyr Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Val Tyr Tyr Phe Asp Glu Trp Gly Gln Gly Thr Leu Val
               100                 105                 110

Thr Val Ser Ser
```

```
<210> SEQ ID NO 196
<211> LENGTH: 107
<212> TYPE: PRT
<213> ORGANISM: Artificial Sequence
<220> FEATURE:
<223> OTHER INFORMATION: Antibody F-C5 light chain variable (VL) region

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Arg Thr Asn
            20                  25                  30

Leu Ala Trp Phe Gln Gln Lys Pro Gly Lys Ala Pro Lys Ser Leu Ile
        35                  40                  45

Tyr Ala Ala Ser Ser Arg Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 197
<211> LENGTH: 330
<212> TYPE: PRT
<213> ORGANISM: Homo sapiens

<400> SEQUENCE: 197

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 198
<211> LENGTH: 330
<212> TYPE: PRT
<213> ORGANISM: Homo sapiens

<400> SEQUENCE: 198

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                        245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 199
<211> LENGTH: 330
<212> TYPE: PRT
<213> ORGANISM: Homo sapiens

<400> SEQUENCE: 199

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 200
<211> LENGTH: 330
<212> TYPE: PRT
<213> ORGANISM: Homo sapiens

<400> SEQUENCE: 200

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 201
<211> LENGTH: 330
<212> TYPE: PRT
<213> ORGANISM: Homo sapiens

<400> SEQUENCE: 201

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 202
<211> LENGTH: 330
<212> TYPE: PRT
<213> ORGANISM: Homo sapiens

<400> SEQUENCE: 202

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 203
<211> LENGTH: 5
<212> TYPE: PRT
<213> ORGANISM: Homo sapiens

<400> SEQUENCE: 203

```
Arg Asp Glu Leu Thr
1               5
```

<210> SEQ ID NO 204
<211> LENGTH: 4
<212> TYPE: PRT

```
<213> ORGANISM: Homo sapiens

<400> SEQUENCE: 204

Arg Glu Glu Met
1

<210> SEQ ID NO 205
<211> LENGTH: 7
<212> TYPE: PRT
<213> ORGANISM: Artificial Sequence
<220> FEATURE:
<223> OTHER INFORMATION: anti-C-KIT HCDR3

<400> SEQUENCE: 205

Gly Val Tyr Tyr Phe Asp Leu
1               5

<210> SEQ ID NO 206
<211> LENGTH: 19
<212> TYPE: PRT
<213> ORGANISM: Artificial Sequence
<220> FEATURE:
<223> OTHER INFORMATION: anti-C-KIT HCDR2

<400> SEQUENCE: 206

Ile Ala Arg Ile Tyr Pro Gly Ser Gly Asn Thr Tyr Ala Gln Lys
1               5                   10                  15

Phe Gln Gly

<210> SEQ ID NO 207
<211> LENGTH: 8
<212> TYPE: PRT
<213> ORGANISM: Artificial Sequence
<220> FEATURE:
<223> OTHER INFORMATION: anti-C-KIT LCDR3

<400> SEQUENCE: 207

Gln Gln Tyr Asn Ser Tyr Pro Arg
1               5

<210> SEQ ID NO 208
<211> LENGTH: 976
<212> TYPE: PRT
<213> ORGANISM: Homo sapiens

<400> SEQUENCE: 208

Met Arg Gly Ala Arg Gly Ala Trp Asp Phe Leu Cys Val Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125
```

-continued

Asp Asn Asp Thr Leu Val Arg Cys Pro Leu Thr Asp Pro Glu Val Thr
        130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
530                 535                 540

```
Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
    610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680                 685

Phe Ile Cys Ser Lys Gln Glu Asp His Ala Glu Ala Leu Tyr Lys
    690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Glu Leu Ala Ile Asp Leu Glu Asp
        755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala His Glu Ser Ile Phe Asn Cys Val Tyr Thr Phe
        835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
```

<210> SEQ ID NO 209
<211> LENGTH: 5190
<212> TYPE: DNA
<213> ORGANISM: Homo sapiens

<400> SEQUENCE: 209

```
tctgggggct cggctttgcc gcgctcgctg cacttgggcg agagctggaa cgtggaccag      60
agctcggatc ccatcgcagc taccgcgatg agaggcgctc gcggcgcctg ggattttctc     120
tgcgttctgc tcctactgct tcgcgtccag acaggctctt ctcaaccatc tgtgagtcca     180
ggggaaccgt ctccaccatc catccatcca ggaaaatcag acttaatagt ccgcgtgggc     240
gacgagatta ggctgttatg cactgatccg ggctttgtca aatggacttt tgagatcctg     300
gatgaaacga atgagaataa gcagaatgaa tggatcacgg aaaaggcaga agccaccaac     360
accggcaaat acacgtgcac caacaaacac ggcttaagca attccattta tgtgtttgtt     420
agagatcctg ccaagctttt ccttgttgac cgctccttgt atgggaaaga agacaacgac     480
acgctggtcc gctgtcctct cacagaccca gaagtgacca attattccct caaggggtgc     540
caggggaagc ctcttcccaa ggacttgagg tttattcctg accccaaggc gggcatcatg     600
atcaaaagtg tgaaacgcgc ctaccatcgg ctctgtctgc attgttctgt ggaccaggag     660
ggcaagtcag tgctgtcgga aaaattcatc ctgaaagtga ggccagcctt caaagctgtg     720
cctgttgtgt ctgtgtccaa agcaagctat cttcttaggg aaggggaaga attcacagtg     780
acgtgcacaa taaagatgt gtctagttct gtgtactcaa cgtggaaaag agaaacagt      840
cagactaaac tacaggagaa atataatagc tggcatcacg gtgacttcaa ttatgaacgt     900
caggcaacgt tgactatcag ttcagcgaga gttaatgatt ctggagtgtt catgtgttat     960
gccaataata cttttggatc agcaaatgtc acaacaacct tggaagtagt agataaagga    1020
ttcattaata tcttccccat gataaacact acagtatttg taaacgatgg agaaaatgta    1080
gatttgattg ttgaatatga agcattcccc aaacctgaac accagcagtg gatctatatg    1140
aacagaacct tcactgataa atgggaagat tatcccaagt ctgagaatga agtaatatc      1200
agatacgtaa gtgaacttca tctaacgaga ttaaaaggca ccgaaggagg cacttacaca    1260
ttcctagtgt ccaattctga cgtcaatgct gccatagcat ttaatgttta tgtgaataca    1320
aaaccagaaa tcctgactta cgacaggctc gtgaatggca tgctccaatg tgtggcagca    1380
ggattcccag agcccacaat agattggtat ttttgtccag aactgagca gagatgctct     1440
gcttctgtac tgccagtgga tgtgcagaca ctaaactcat ctgggccacc gtttggaaag    1500
ctagtggttc agagttctat agattctagt gcattcaagc acaatggcac ggttgaatgt    1560
aaggcttaca acgatgtggg caagacttct gcctatttta actttgcatt taaaggtaac    1620
aacaaagagc aaatccatcc ccacacccctg ttcactcctt tgctgattgg tttcgtaatc    1680
gtagctggca tgatgtgcat tatgtgatg attctgacct acaaatattt acagaaaccc    1740
atgtatgaag tacagtggaa ggttgttgag gagataaatg gaaacaatta tgtttacata    1800
gacccaacac aacttcctta tgatcacaaa tgggagtttc cagaaacag gctgagtttt    1860
gggaaaaccc tgggtgctgg agcttcgggg aaggttgttg aggcaactgc ttatggctta    1920
attaagtcag atgcggccat gactgtcgct gtaaagatgc tcaagccgag tgcccatttg    1980
acagaacggg aagccctcat gtctgaactc aaagtcctga gttaccttgg taatcacatg    2040
aatattgtga atctacttgg agcctgcacc attggagggc ccaccctggt cattacagaa    2100
```

```
tattgttgct atggtgatct tttgaatttt ttgagaagaa aacgtgattc atttatttgt    2160
tcaaagcagg aagatcatgc agaagctgca ctttataaga atcttctgca ttcaaaggag    2220
tcttcctgca gcgatagtac taatgagtac atggacatga aacctggagt ttcttatgtt    2280
gtcccaacca aggccgacaa aaggagatct gtgagaatag gctcatacat agaaagagat    2340
gtgactcccg ccatcatgga ggatgacgag ttggccctag acttagaaga cttgctgagc    2400
ttttcttacc aggtggcaaa gggcatggct ttcctcgcct ccaagaattg tattcacaga    2460
gacttggcag ccagaaatat cctccttact catggtcgga tcacaaagat ttgtgatttt    2520
ggtctagcca gagacatcaa gaatgattct aattatgtgg ttaaaggaaa cgctcgacta    2580
cctgtgaagt ggatggcacc tgaaagcatt ttcaactgtg tatacacgtt tgaaagtgac    2640
gtctggtcct atgggatttt tctttgggag ctgttctctt taggaagcag ccccatcct    2700 ggaatgccgg tcgattctaa gttctacaag atgatcaagg aaggcttccg gatgctcagc    2760
cctgaacacg cacctgctga atgtatgac ataatgaaga cttgctggga tgcagatccc    2820
ctaaaaagac caacattcaa gcaaattgtt cagctaattg agaagcagat ttcagagagc    2880
accaatcata tttactccaa cttagcaaac tgcagcccca accgacagaa gcccgtggta    2940
gaccattctg tgcggatcaa ttctgtcggc agcaccgctt cctcctccca gcctctgctt    3000
gtgcacgacg atgtctgagc agaatcagtg tttgggtcac ccctccagga tgatctctt    3060 cttttggctt ccatgatggt tatttttctt tctttcaact tgcatccaac tccaggatag    3120
tgggcacccc actgcaatcc tgtctttctg agcacacttt agtggccgat gatttttgtc    3180
atcagccacc atcctattgc aaaggttcca actgtatata ttcccaatag caacgtagct    3240
tctaccatga acagaaaaca ttctgatttg gaaaagaga gggaggtatg gactggggc    3300 cagagtcctt tccaaggctt ctccaattct gcccaaaaat atggttgata gtttacctga    3360
ataaatggta gtaatcacag ttggccttca gaaccatcca tagtagtatg atgatacaag    3420
attagaagct gaaaacctaa gtcctttatg tggaaaacag aacatcatta gaacaaagga    3480
cagagtatga acacctgggc ttaagaaatc tagtatttca tgctgggaat gagacatagg    3540
ccatgaaaaa aatgatcccc aagtgtgaac aaaagatgct cttctgtgga ccactgcatg    3600
agcttttata ctaccgacct ggttttttaaa tagagtttgc tattagagca ttgaattgga    3660
gagaaggcct ccctagccag cacttgtata tacgcatcta taaattgtcc gtgttcatac    3720
atttgagggg aaaacaccat aaggtttcgt ttctgtatac aaccctggca ttatgtccac    3780
tgtgtataga agtagattaa gagccatata agtttgaagg aaacagttaa taccatttt    3840 taaggaaaca atataaccac aaagcacagt ttgaacaaaa tctcctcttt tagctgatga    3900
acttattctg tagattctgt ggaacaagcc tatcagcttc agaatggcat tgtactcaat    3960
ggatttgatg ctgtttgaca aagttactga ttcactgcat ggctcccaca ggagtgggaa    4020
aacactgcca tcttagtttg gattcttatg tagcaggaaa taaagtatag gtttagcctc    4080
cttcgcaggc atgtcctgga caccgggcca gtatctatat atgtgtatgt acgtttgtat    4140
gtgtgtagac aaatatttgg agggtattt ttgccctgag tccaagaggg tcctttagta    4200
cctgaaaagt aacttggctt tcattattag tactgctctt gtttcttttc acatagctgt    4260
ctagagtagc ttaccagaag cttccatagt ggtgcagagg aagtggaagg catcagtccc    4320
tatgtatttg cagttcacct gcacttaagg cactctgtta tttagactca tcttactgta    4380
cctgttcctt agaccttcca taatgctact gtctcactga aacatttaaa ttttacccct    4440
```

```
tagactgtag cctggatatt attcttgtag tttacctctt taaaaacaaa acaaaacaaa    4500
acaaaaaact cccctttcctc actgcccaat ataaaaggca aatgtgtaca tggcagagtt   4560
tgtgtgttgt cttgaaagat tcaggtatgt tgcctttatg gtttccccct tctacatttc    4620
ttagactaca tttagagaac tgtggccgtt atctggaagt aaccatttgc actggagttc    4680
tatgctctcg cacctttcca aagttaacag attttggggt tgtgttgtca cccaagagat    4740
tgttgtttgc catactttgt ctgaaaaatt cctttgtgtt tctattgact caatgatag     4800 taagaaaagt ggttgttagt tatagatgtc taggtacttc aggggcactt cattgagagt   4860
tttgtcttgg atattcttga aagtttatat ttttataatt ttttcttaca tcagatgttt    4920
ctttgcagtg gcttaatgtt tgaaattatt ttgtggcttt ttttgtaaat attgaaatgt     4980
agcaataatg tcttttgaat attcccaagc ccatgagtcc ttgaaaatat tttttatata   5040
tacagtaact ttatgtgtaa atacataagc ggcgtaagtt taaaggatgt tggtgttcca    5100
cgtgttttat tcctgtatgt tgtccaattg ttgacagttc tgaagaattc taataaaatg   5160
tacatatata aatcaaaaaa aaaaaaaaaa                                      5190

<210> SEQ ID NO 210
<211> LENGTH: 5178
<212> TYPE: DNA
<213> ORGANISM: Homo sapiens

<400> SEQUENCE: 210
tctgggggct cggctttgcc gcgctcgctg cacttgggcg agagctggaa cgtggaccag      60
agctcggatc ccatcgcagc taccgcgatg agaggcgctc gcggcgcctg ggattttctc    120
tgcgttctgc tcctactgct tcgcgtccag acaggctctt ctcaaccatc tgtgagtcca    180
ggggaaccgt ctccaccatc catccatcca ggaaaatcag acttaatagt ccgcgtgggc    240
gacgagatta ggctgttatg cactgatccg ggctttgtca aatggacttt tgagatcctg    300
gatgaaacga atgagaataa gcagaatgaa tggatcacgg aaaaggcaga agccaccaac    360
accggcaaat acacgtgcac caacaaacac ggcttaagca attccattta tgtgtttgtt    420
agagatcctg ccaagctttt ccttgttgac cgctccttgt atgggaaaga agacaacgac    480
acgctggtcc gctgtcctct cacagaccca gaagtgacca attattccct caaggggtgc    540
caggggaagc tcttcccaa ggacttgagg tttattcctg accccaaggc gggcatcatg     600 atcaaagtg tgaaacgcgc ctaccatcgg ctctgtctgc attgttctgt ggaccaggag     660
ggcaagtcag tgctgtcgga aaaattcatc ctgaaagtga ggccagcctt caaagctgtg    720
cctgttgtgt ctgtgtccaa agcaagctat cttcttaggg aaggggaaga attcacagtg    780
acgtgcacaa taaagatgt gtctagttct gtgtactcaa cgtggaaaag agaaaacagt    840
cagactaaac tacaggagaa atataatagc tggcatcacg gtgacttcaa ttatgaacgt    900
caggcaacgt tgactatcag ttcagcgaga gttaatgatt ctggagtgtt catgtgttat    960
gccaataata cttttggatc agcaaatgtc acaacaacct tggaagtagt agataaagga   1020
ttcattaata tcttccccat gataaacact acagtatttg taaacgatgg agaaaatgta    1080
gatttgattg ttgaatatga agcattcccc aaacctgaac accagcagtg gatctatatg    1140
aacagaacct tcactgataa atgggaagat tatcccaagt ctgagaatga agtaatatc     1200 agatacgtaa gtgaacttca tctaacgaga ttaaaaggca ccgaaggagg cacttacaca    1260
ttcctagtgt ccaattctga cgtcaatgct gccatagcat ttaatgttta tgtgaataca    1320
aaaccagaaa tcctgactta cgacaggctc gtgaatggca tgctccaatg tgtggcagca    1380
```

```
ggattcccag agcccacaat agattggtat ttttgtccag gaactgagca gagatgctct    1440
gcttctgtac tgccagtgga tgtgcagaca ctaaactcat ctgggccacc gtttggaaag    1500
ctagtggttc agagttctat agattctagt gcattcaagc acaatggcac ggttgaatgt    1560
aaggcttaca acgatgtggg caagacttct gcctatttta actttgcatt taaagagcaa    1620
atccatcccc acaccctgtt cactcctttg ctgattggtt tcgtaatcgt agctggcatg    1680
atgtgcatta ttgtgatgat tctgacctac aaatatttac agaaacccat gtatgaagta    1740
cagtggaagg ttgttgagga gataaatgga aacaattatg tttacataga cccaacacaa    1800
cttccttatg atcacaaatg ggagtttccc agaaacaggc tgagttttgg gaaaaccctg    1860
ggtgctggag ctttcgggaa ggttgttgag gcaactgctt atggcttaat taagtcagat    1920
gcggccatga ctgtcgctgt aaagatgctc aagccgagtg cccatttgac agaacgggaa    1980
gccctcatgt ctgaactcaa agtcctgagt taccttggta atcacatgaa tattgtgaat    2040
ctacttggag cctgcaccat tggagggccc accctggtca ttacagaata ttgttgctat    2100
ggtgatcttt tgaattttt gagaagaaaa cgtgattcat ttatttgttc aaagcaggaa    2160
gatcatgcag aagctgcact ttataagaat cttctgcatt caaaggagtc ttcctgcagc    2220
gatagtacta atgagtacat ggacatgaaa cctggagttt cttatgttgt cccaaccaag    2280
gccgacaaaa ggagatctgt gagaataggc tcatacatag aaagagatgt gactcccgcc    2340
atcatggagg atgacgagtt ggccctagac ttagaagact tgctgagctt ttcttaccag    2400
gtggcaaagg gcatggcttt cctcgcctcc aagaattgta ttcacagaga cttggcagcc    2460
agaaatatcc tccttactca tggtcggatc acaaagattt gtgattttgg tctagccaga    2520
gacatcaaga atgattctaa ttatgtggtt aaaggaaacg ctcgactacc tgtgaagtgg    2580
atggcacctg aaagcatttt caactgtgta tacacgtttg aaagtgacgt ctggtcctat    2640 gggattttc tttgggagct gttctcttta ggaagcagcc cctatcctgg aatgccggtc    2700
gattctaagt tctacaagat gatcaaggaa ggcttccgga tgctcagccc tgaacacgca    2760
cctgctgaaa tgtatgacat aatgaagact tgctgggatg cagatcccct aaaaagacca    2820
acattcaagc aaattgttca gctaattgag aagcagattt cagagagcac caatcatatt    2880
tactccaact tagcaaactg cagccccaac cgacagaagc ccgtggtaga ccattctgtg    2940
cggatcaatt ctgtcggcag caccgcttcc tcctcccagc ctctgcttgt gcacgacgat    3000
gtctgagcag aatcagtgtt tgggtcaccc ctccaggaat gatctcttct tttggcttcc    3060
atgatggtta ttttctttc tttcaacttg catccaactc caggatagtg ggcaccccac    3120
tgcaatcctg tctttctgag cacactttag tggccgatga tttttgtcat cagccaccat    3180
cctattgcaa aggttccaac tgtatatatt cccaatagca acgtagcttc taccatgaac    3240
agaaaacatt ctgatttgga aaaagagagg gaggtatgga ctgggggcca gagtcctttc    3300
caaggcttct ccaattctgc ccaaaaatat ggttgatagt ttacctgaat aaatggtagt    3360
aatcacagtt ggccttcaga accatccata gtagtatgat gatacaagat tagaagctga    3420
aaacctaagt cctttatgtg gaaaacagaa catcattaga acaaaggaca gagtatgaac    3480
acctgggctt aagaaatcta gtatttcatg ctgggaatga acataggcc atgaaaaaaa    3540 tgatccccaa gtgtgaacaa agatgctct tctgtggacc actgcatgag ctttatact    3600 accgacctgg ttttaaaata gagtttgcta ttagagcatt gaattggaga gaaggcctcc    3660
ctagccagca cttgtatata cgcatctata aattgtccgt gttcatacat ttgaggggaa    3720
```

```
aacaccataa ggtttcgttt ctgtatacaa ccctggcatt atgtccactg tgtatagaag    3780
tagattaaga gccatataag tttgaaggaa acagttaata ccatttttta aggaaacaat    3840
ataaccacaa agcacagttt gaacaaaatc tcctctttta gctgatgaac ttattctgta    3900
gattctgtgg aacaagccta tcagcttcag aatggcattg tactcaatgg atttgatgct    3960
gtttgacaaa gttactgatt cactgcatgg ctcccacagg agtgggaaaa cactgccatc    4020
ttagtttgga ttcttatgta gcaggaaata aagtataggt ttagcctcct tcgcaggcat    4080
gtcctggaca ccgggccagt atctatatat gtgtatgtac gtttgtatgt gtgtagacaa    4140
atatttggag gggtattttt gccctgagtc caagagggtc ctttagtacc tgaaaagtaa    4200
cttggctttc attattagta ctgctcttgt ttcttttcac atagctgtct agagtagctt    4260
accagaagct tccatagtgg tgcagaggaa gtggaaggca tcagtcccta tgtatttgca    4320
gttcacctgc acttaaggca ctctgttatt tagactcatc ttactgtacc tgttccttag    4380
accttccata atgctactgt ctcactgaaa catttaaatt ttacccttta gactgtagcc    4440
tggatattat tcttgtagtt tacctcttta aaaacaaaac aaaacaaaac aaaaaactcc    4500
ccttcctcac tgcccaatat aaaaggcaaa tgtgtacatg gcagagtttg tgtgttgtct    4560
tgaaagattc aggtatgttg cctttatggt ttccccttc tacattttctt agactacatt    4620 tagagaactg tggccgttat ctggaagtaa ccatttgcac tggagttcta tgctctcgca    4680
cctttccaaa gttaacagat tttgggggttg tgttgtcacc caagagattg ttgtttgcca    4740
tactttgtct gaaaaattcc tttgtgtttc tattgacttc aatgatagta agaaaagtgg    4800
ttgttagtta tagatgtcta ggtacttcag gggcacttca ttgagagttt tgtcttggat    4860
attcttgaaa gtttatattt ttataattt ttcttacatc agatgtttct ttgcagtggc    4920
ttaatgtttg aaattatttt gtggcttttt ttgtaaatat tgaaatgtag caataatgtc    4980
ttttgaatat tcccaagccc atgagtcctt gaaaatattt tttatatata cagtaacttt    5040
atgtgtaaat acataagcgg cgtaagttta aaggatgttg gtgttccacg tgttttattc    5100
ctgtatgttg tccaattgtt gacagttctg aagaattcta ataaaatgta catatataaa    5160
tcaaaaaaaa aaaaaaaa                                                  5178
```